(12) United States Patent
Brun et al.

(10) Patent No.: US 10,577,362 B2
(45) Date of Patent: Mar. 3, 2020

(54) SUBSTITUTED 2, 4-DIAMINO-QUINOLINE DERIVATIVES FOR USE IN THE TREATMENT OF PROLIFERATIVE DISEASES

(71) Applicant: GENOSCIENCE PHARMA, Marseilles (FR)

(72) Inventors: Sonia Brun, Aix-en-Provence (FR); Antoine Beret, Marseilles (FR); Firas Bassissi, Marseilles (FR); Philippe Halfon, Marseilles (FR); Jérôme Courcambeck, Marseilles (FR)

(73) Assignee: GENOSCIENCE PHARMA, Marseilles (FR)

(*) Notice: Subject to any disclaimer, the term of this patent is extended or adjusted under 35 U.S.C. 154(b) by 0 days.

(21) Appl. No.: 16/098,546

(22) PCT Filed: May 4, 2017

(86) PCT No.: PCT/IB2017/052614
§ 371 (c)(1),
(2) Date: Nov. 2, 2018

(87) PCT Pub. No.: WO2017/191599
PCT Pub. Date: Nov. 9, 2017

(65) Prior Publication Data
US 2019/0144437 A1 May 16, 2019

Related U.S. Application Data

(60) Provisional application No. 62/331,844, filed on May 4, 2016.

(51) Int. Cl.
| | | |
|---|---|---|
| *C07D 413/14* | (2006.01) | |
| *C07D 401/14* | (2006.01) | |
| *C07D 405/14* | (2006.01) | |
| *C07D 401/04* | (2006.01) | |
| *A61P 35/00* | (2006.01) | |
| *A61K 45/06* | (2006.01) | |

(52) U.S. Cl.
CPC ............ *C07D 413/14* (2013.01); *A61P 35/00* (2018.01); *C07D 401/04* (2013.01); *C07D 401/14* (2013.01); *C07D 405/14* (2013.01); *A61K 45/06* (2013.01)

(58) Field of Classification Search
CPC .. C07D 413/14; C07D 401/04; C07D 401/14; C07D 405/14; A61P 35/00; A61K 45/06
See application file for complete search history.

(56) References Cited

U.S. PATENT DOCUMENTS

| | | | |
|---|---|---|---|
| 4,169,846 A | 10/1979 | Inagaki et al. | |
| 4,235,871 A | 11/1980 | Papahadjopoulos et al. | |
| 4,261,989 A | 4/1981 | Sasaki et al. | |
| 4,737,323 A | 4/1988 | Martin et al. | |
| 5,266,573 A | 11/1993 | Croci et al. | |
| 5,621,002 A | 4/1997 | Bosslet et al. | |
| 5,693,652 A * | 12/1997 | Takase ................. | C07D 215/42 514/322 |
| 6,262,059 B1 * | 7/2001 | Pamukcu ............. | A61K 31/517 514/266.22 |
| 6,339,093 B1 * | 1/2002 | Alanine ............... | C07D 401/04 514/307 |
| 6,743,799 B2 * | 6/2004 | Westbrook .......... | A61K 31/404 514/258.1 |
| 6,780,996 B2 | 8/2004 | Boschelli et al. | |
| 7,160,900 B2 * | 1/2007 | Nakazato ............. | C07D 401/04 514/260.1 |
| 8,044,068 B2 * | 10/2011 | Okubo ................. | C07D 401/12 514/314 |
| 8,680,089 B2 * | 3/2014 | Huang ................. | C07D 471/04 514/210.21 |
| 8,765,940 B2 * | 7/2014 | Brown ................. | C07D 401/14 540/362 |
| 2003/0158179 A1 * | 8/2003 | Klug .................... | C04B 35/632 514/217.07 |

(Continued)

FOREIGN PATENT DOCUMENTS

| | | | |
|---|---|---|---|
| WO | 1996/014057 A1 | 5/1996 | |
| WO | 2001/002369 A2 | 1/2001 | |

(Continued)

OTHER PUBLICATIONS

R.J. Kok, 25 Pharmaceutical Research, 2413-2415 (2008) (Year: 2008).*
Z. Ghiassi-Nejad et al. 2 Expert Review of Gastroenterology & Hepatology, 803-816 (2008) (Year: 2008).*
International Search Report and Written Opinion of the International Search Authority dated Jul. 17, 2017 of corresponding International application No. PCT/IB2017/052614; 13 pages including Partial English-Language Translation Attached.
Ge et al., "Controlling First-Row Catalysts: Amination of Aryl and Heteroaryl Chlorides and Bromides with Primary Aliphatic Amines Catalyzed by a BINAP-Ligated Single-Component Ni(0) Complex", Journal of the American Chemical Society, 2014, pp. 1617-1627.

(Continued)

*Primary Examiner* — Alexander R Pagano
(74) *Attorney, Agent, or Firm* — Maier & Maier, PLLC

(57) ABSTRACT

This application discloses compounds according to generic Formula I: wherein all variables are defined as described herein which exhibit strong inhibition effects on various cancer cell lines. The compounds disclosed herein are useful for the treatment of proliferative diseases, including neoplastic diseases such as cancer and non-neoplastic disorders such as rheumatoid arthritis. Also disclosed are pharmaceutical compositions containing compounds of Formula I and at least one carrier, diluent or excipient and optionally one or more additional therapeutically active agents, including anticancer agents. This application also discloses methods for treating a proliferative disease, including neoplastic diseases such as cancer and non-neoplastic disorders such as rheumatoid arthritis.

31 Claims, No Drawings

(56) References Cited

U.S. PATENT DOCUMENTS

2008/0119515 A1* 5/2008 Siddiqui ............... C07D 401/06
514/312

FOREIGN PATENT DOCUMENTS

| WO | 2002/010192 | A2 | 2/2002 | |
|---|---|---|---|---|
| WO | 2002/066470 | A1 | 8/2002 | |
| WO | 2003/064383 | A2 | 8/2003 | |
| WO | 2003/075836 | A2 | 9/2003 | |
| WO | 2004/002960 | A1 | 1/2004 | |
| WO | 2004/020431 | A2 | 3/2004 | |
| WO | 2004/080463 | A1 | 9/2004 | |
| WO | 2005/028443 | A2 | 3/2005 | |
| WO | 2006/028958 | A2 | 3/2006 | |
| WO | 2006/122806 | A2 | 11/2006 | |
| WO | 2007/005643 | A2 | 1/2007 | |
| WO | 2007/005644 | A2 | 1/2007 | |
| WO | 2007/016361 | A2 | 2/2007 | |
| WO | 2007/016431 | A2 | 2/2007 | |
| WO | 2009/036082 | A2 | 3/2009 | |
| WO | 2009/055730 | A1 | 4/2009 | |
| WO | 2009/155386 | A2 | 12/2009 | |
| WO | 2010/151737 | A2 | 12/2010 | |
| WO | 2016/067112 | A1 | 5/2016 | |
| WO | WO-2016067112 | A1 * | 5/2016 | ........... C07D 401/04 |

OTHER PUBLICATIONS

Ali et al., "An Improved Method for the Palladium-Catalyzed Amination of Aryl Iodides", J. Org. Chem., Mar. 24, 2001, pp. 2560-2565.

Dordunoo et al., "Preformulation Studies on Solid Dispersions Containing Triamterene or Temazepam in Polyethylene Glycols or Gelucire 44/14 for Liquid Filling of Hard Gelatin Capsules", Drug Development and Industrial Pharmacy, 1991, pp. 1685-1713.

Druker et al., "Five-Year Follow-up of Patients Receiving Imatinib for Chronic Myeloid Leukemia", The new England Journal of Medicine, Dec. 7, 2006, pp. 2408-2417.

Hashimoto et al., "Cancer stem-like sphere cells induced from de-differentiated hepatocellular carcinoma-derived cell lines possess the resistance to anti-cancer drugs", BMC Cancer, 2014, pp. 1-14:722.

Heller, "Electrical Wiring of Redox Enzymes", Acc. Chem. Res., 1990, pp. 128-134.

Schmidt et al., "Pyrazolo[3,4-d]pyrimidine mit Koffein-ahnlicher Struktur und Wirkung", Helvetica Chimica Acta, 1958, pp. 1052-1060 including Partial English-Language Translation Attached.

Sheen et al., "Bioavailability of a Poorly Water-Soluble Drug from Tablet and Solid Dispersion in Humans", J. Pharm. Sci., 1991, pp. 712-714.

Surry et al., "Dialkylbiaryl phosphines in Pd-catalyzed amination: a user's guide", Chemical Science, 2011, pp. 27-50.

Tovar et al., "Tumour initiating cells and IGF/FGF signalling contribute to sorafenib resistance in hepatocellular carcinoma", Gut, Mar. 2017, pp. 530-540.

Uden et al., "Cyclodextrins as a useful tool for bioconversions in plant cell biotechnology", Plant Cell Tiss. Org. Cult., 1994, pp. 103-113.

Wamhoff et al., "Synthesis of 1H-Pyrazolo[3,4-d]pyrimidines", Liebigs Annalen der Chemie, 1985, pp. 1910-1916.

Wenz, "Cyclodextrins as Building Blocks for Supramolecular Structures and Functional Units", Agnew. Chem. Int. Ed. Engl., 1994, pp. 803-822.

Ferroni et al.; "Cyclic Guanidines: Synthesis and Antiplatelet Activity of 4,6,7,8-Tetrahydro-1H-imidazo[1,2-a]pyrazolo[3,4-d]pyrimidin-7-ones and 1,4,6,7,8,9-Hexahydropyrazolo[3',4':4,5]pyrimido[2,1-c] [1,2,4]triazin-7-ones"; Anticoagulants—Antithrombotics—Antivaricosis Drugs—Blood Flow Stimulants; Arzneim.-Forsch./Drug Res.; vol. 40 (II); No. 12; 1990; pp. 1328-1331.

* cited by examiner

SUBSTITUTED 2, 4-DIAMINO-QUINOLINE DERIVATIVES FOR USE IN THE TREATMENT OF PROLIFERATIVE DISEASES

FILED OF THE INVENTION

The present invention relates to novel substituted 2,4-amino-quinoline derivatives, their manufacture, pharmaceutical compositions containing them, and their use as medicament.

The novel substituted 2,4-amino-quinoline derivatives according the present invention are useful for the treatment of proliferative disorders, including cancer.

The invention pertains generally to the field of treating proliferative diseases, in particular cancer.

BACKGROUND OF THE INVENTION

Cancer is a disorder characterized by uncontrolled proliferation and spread of abnormal cells. These abnormal cells can create expansive masses, spread to vital organs and eventually cause patient death. Cancer affects people worldwide.

Traditional approaches to treatment of abnormal cells proliferation include surgery, chemotherapy, radiotherapy, and the like, as well as combinations thereof. Surgery is not always an option due to tumor size or location, and/or advanced metastasis. Additionally, surgery might not completely remove the neoplastic tissue. Radiation therapy can often elicit serious side effects. Chemotherapy typically involves use of one or more compounds that inhibit cancer cell growth. Unfortunately, most known anticancer drugs have limited selectivity for cancer and are inherently toxic to both cancer and normal tissues. They also can cause significant side effects, including hair loss, suppression of hematopoesis, and nausea, etc. Depending on the general health of a patient, such side effects can preclude the administration of chemotherapy, or, at least, be extremely unpleasant and uncomfortable for the patient and severely decrease quality of the remaining life of cancer patients.

The drug discovery of new anticancer agents has recently moved from cell-based assay to a more focused in vitro approach on well characterized, isolated and transfection assisted expressed proteins of druggable targets. The transition from cytotoxic chemotherapy to molecularly targeted cancer drug discovery and development has resulted in an increasing number of successful therapies that have impacted the lives of a large number of cancer patients. The ABL inhibitor imatinib is generally regarded as a trail blazer drug that most impressively validated the concept of designing small molecule therapeutics to treat a defined patient population in this case chronic myeloid leukaemia in which the malignancy is driven by the BCR-ABL translocation and for which the improvement in survival has been dramatic (Druker, S. et al., N. Engl. J. Med. 2006 (355) 2408-2417). However, despite the considerable progress made with the new molecularly targeted therapies, several cancers seem to remain naturally resistant to the clinical use of kinase inhibitors or the molecularly targeted therapies are not really relevant (e.g. hepatocellular carcinoma and pancreas cancer). Moreover, the molecular understanding and the molecular description of cellular transformation, cancer growth, cancer microenvironment and metastasis evolution is still remain in constant development, with for example the description of the cancer stem cells (CSCs) concept or tumor initiating cells (TICs).

In 2013, the estimated number of liver cancers was 559,000 in men and 233,000 in women, which is comprehensive of the dominant hepatocarcinoma (HCC); hepatoblastoma and sarcoma. The estimated number of deaths due to this tumor was 554,000 and 254,000 respectively. Worldwide liver cancer stands at the second leading cause of cancer in men and the fifth in women with a median survival of 7.2 month (Global burden of cancer 2013 JAMA Oncol 2015 (1) 505-527). In spite of successful approval and wide application of sorafenib (SOC), the prognosis for patients with advanced hepatocellular carcinoma (HCC) remains poor. In recent years, highly tumorigenic sub-populations of cancer cells named Cancer Stem Cells (CSCs) have been implicated in post-treatment tumor recurrence. Indeed, CSCs are resistant to chemotherapy, and they have the ability to regenerate all the cell type within the tumor. For this reason, innovative drugs with original mechanism of action and could tackle CSCs would likely improve cancer treatment of patients.

In this context, we decided to take into account the whole cell compartment and a cellular culture environment with the development of an unbiased phenotypic cellular screening assay.

Accordingly, in view of the above considerations, it is seen that a constant need exists for active compounds that could help preventing and treating neoplastic and non-neoplastic proliferative diseases, such as cancer with either improved effect or reduced side effects.

In particular, a need exists for such active compounds that could help addressing the problems of cancer resistance.

DISCLOSURE OF THE INVENTION

It has now been unexpectedly discovered that certain substituted 2-amino-4-secondary amino-quinoline derivatives surprisingly exhibit potent antiproliferative and cytotoxic effects against several cancer cell lines. The Applicant has indeed demonstrated in experiments that the compounds of the present invention exhibit marked antiproliferative and cytotoxicity effects on at least seven human cancer lines. This antiproliferative activity suggests that compounds of the invention are useful in the treatment of a wide variety of disorders associated with abnormal cell proliferation. These disorders or diseases can be of oncological nature, such as malignant neoplasias, or non-oncological nature, such as benign tumors, psoriasis, etc. The compounds of the present invention and compositions containing them can thus be used for the treatment and prevention of any disorder of cell proliferation or cell differentiation (malignant or nonmalignant). They also can be used for the treatment of cancer, metastatic cancer, drug-resistant cancer or radiation-resistant cancer. Furthermore, the compounds of the present invention and the compositions containing them can also be used to sensitize a subject to other therapies, such as radiation therapy, or can be used as maintenance therapy of cancer patients. Moreover, this class of compounds shows equally an additional activity against human cancer stem cells (CSCs) which are widely incriminated in the recurrence and the relapse of cancers after anti-cancer therapy. Tumor sphere formation assays were used as cancer stem cell functional marker to describe the activity against CSCs (Tovar, V. et al. Gut 2015 (0) 1-11, Hashimoto, N. et al. BMC Cancer 2014 (14) 722). It is another object of the present invention to provide a method for inhibiting the growth or differentiation of a Cancer Stem Cell (CSC), a tumor initiating cell, a mesenchymal-like cell associated with cancer, a mesenchymal cancerous cell, or a mesenchymal cell.

Accordingly, in one aspect, the present invention relates to a group of substituted 2-amino-4-secondary amino-quinoline compounds represented by the structural formula (I)

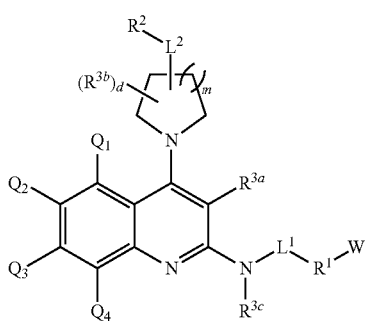

(I)

Wherein $L^1$ is a single bond, or substituted or unsubstituted alkylene, substituted or unsubstituted alkenylene, or substituted or unsubstituted alkynylene $L^2$ is a single bond, carbonyl, substituted or unsubstituted alkylene, substituted or unsubstituted alkenylene, or substituted or unsubstituted alkynylene;

$R^1$ is substituted or unsubstituted aryl, substituted or unsubstituted heteroaryl, substituted or unsubstituted arylene, or substituted or unsubstituted heteroarylene;

$R^2$ is hydroxyl, substituted or unsubstituted alkoxy, substituted or unsubstituted aryloxy, substituted or unsubstituted heteroaryloxy, substituted or unsubstituted alkoxycarbonylamino, substituted or unsubstituted aryloxycarbonylamino, substituted or unsubstituted heteroaryloxycarbonylamino, substituted or unsubstituted alkylaminocarbonylamino, substituted or unsubstituted arylaminocarbonylamino, substituted or unsubstituted heteroarylaminocarbonylamino, or $NR^5R^6$ wherein each $R^5$ and $R^6$ is independently H, substituted or unsubstituted alkyl, substituted or unsubstituted cycloalkyl, substituted or unsubstituted aryl, substituted or unsubstituted heteroaryl, or substituted or unsubstituted heterocycloalkyl, or $R^5$ and $R^6$ together with the nitrogen atom to which they are attached are combined to form a substituted or unsubstituted heterocyclic ring;

$Q_1$, $Q_2$, $Q_3$ and $Q_4$ are each independently H, hydroxyl, halo, amino, nitro, thiol, carboxyl, cyano, azido, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted arylalkyl, substituted or unsubstituted heterocycloalkyl, substituted or unsubstituted aryl, substituted or unsubstituted heteroaryl, substituted or unsubstituted alkoxy, substituted or unsubstituted aryloxy, substituted or unsubstituted heteroaryloxy, substituted or unsubstituted sulfanyl, substituted or unsubstituted alkylamino, substituted or unsubstituted dialkylamino, substituted or unsubstituted arylamino, substituted or unsubstituted heteroarylamino, substituted or unsubstituted acyl, substituted or unsubstituted acylamino, substituted or unsubstituted aminocarbonyl, substituted or unsubstituted alkoxycarbonyl, substituted or unsubstituted aryloxycarbonyl, substituted or unsubstituted heteroaryloxycarbonyl, substituted sulfo, substituted sulfonyl, substituted sulfinyl, substituted or unsubstituted aminosulfonyl, substituted or unsubstituted sulfonylamino, substituted or unsubstituted aminocarbonylamino, substituted or unsubstituted aminocarbonyloxy, substituted or unsubstituted alkoxycarbonylamino, substituted or unsubstituted aryloxycarbonylamino, or substituted or unsubstituted heteroaryloxycarbonylamino;

$R^{3a}$ is H, halo, cyano, substituted or unsubstituted alkyl, substituted or unsubstituted aryl, substituted or unsubstituted heteroaryl, substituted or unsubstituted cycloalkyl, substituted or unsubstituted heterocycloalkyl, substituted or unsubstituted alkoxy, substituted or unsubstituted alkoxycarbonyl, substituted or unsubstituted aryloxycarbonyl, substituted or unsubstituted heteroaryloxycarbonyl, or substituted or unsubstituted aminocarbonyl;

each $R^{3b}$ is independently H, hydroxyl, halo, azido, amino, nitro, thiol, cyano, carboxyl, substituted or unsubstituted alkyl, substituted or unsubstituted alkenyl, substituted or unsubstituted alkynyl, substituted or unsubstituted arylalkyl, substituted or unsubstituted aryl, substituted or unsubstituted heteroaryl, substituted or unsubstituted cycloalkyl, substituted or unsubstituted cycloalkenyl, or substituted or unsubstituted heterocycloalkyl;

$R^{3c}$ is H, substituted or unsubstituted alkyl, substituted or unsubstituted alkenyl, substituted or unsubstituted alkynyl, substituted or unsubstituted cycloalkyl, substituted or unsubstituted cycloalkenyl, or substituted or unsubstituted heterocycloalkyl, provided that when $R^{3c}$ is H, $L^2$ is other than a single bond or $R^2$ is other than $NR^5R^6$ or $R^{3a}$ is other than H or at least two of $Q_1$, $Q_2$, $Q_3$ and $Q_4$ are other than H and are distinct;

W is optionally present and if present is H, hydroxyl, halo, azido, amino, nitro, thiol, cyano, carboxyl, substituted or unsubstituted alkyl, substituted or unsubstituted alkenyl, substituted or unsubstituted alkynyl, substituted or unsubstituted arylalkyl, substituted or unsubstituted aryl, substituted or unsubstituted heteroaryl, substituted or unsubstituted cycloalkyl, substituted or unsubstituted cycloalkenyl, substituted or unsubstituted heterocycloalkyl, substituted or unsubstituted alkoxy, substituted or unsubstituted aryloxy, substituted or unsubstituted heteroaryloxy, substituted or unsubstituted sulfanyl, substituted or unsubstituted alkylamino, substituted or unsubstituted dialkylamino, substituted or unsubstituted arylamino, substituted or unsubstituted heteroarylamino, substituted or unsubstituted acyl, substituted or unsubstituted acylamino, substituted or unsubstituted aminocarbonyl, substituted or unsubstituted alkoxycarbonyl, substituted or unsubstituted aryloxycarbonyl, substituted or unsubstituted heteroaryloxycarbonyl, substituted sulfo, substituted sulfonyl, substituted sulfinyl, substituted or unsubstituted aminosulfonyl, substituted or unsubstituted sulfonylamino, substituted or unsubstituted alkylsulfonyl, substituted or unsubstituted arylsulfonyl, substituted or unsubstituted aminocarbonylamino, substituted or unsubstituted aminocarbonyloxy, substituted or unsubstituted alkoxycarbonylamino, substituted or unsubstituted aryloxycarbonylamino, or substituted or unsubstituted heteroaryloxycarbonylamino;

m is 0, 1, 2, 3, or 4;

if m is 0, then d is independently 0, 1 or 2; if m is 1, then d is independently 0, 1, 2 or 3; if m is 2, then d is independently 0, 1, 2, 3 or 4; if m is 3, then d is independently 0, 1, 2, 3, 4 or 5 or if m is 4 then d is independently 0, 1, 2, 3, 4, 5 or 6;

or a pharmaceutically acceptable salt, hydrate, solvate, or prodrug thereof, or an isotopic variant, tautomer, or stereoisomer thereof.

Other preferred embodiments of the invention are presented hereafter, any combination of two or more of these embodiments being considered within the scope of the present invention:

A preferred embodiment provides a compound of Formula (I), wherein $L^1$ is a single bond, or substituted or unsubstituted alkylene.

Another preferred embodiment provides a compound of Formula (I), wherein $L^2$ is a single bond, carbonyl, substituted or unsubstituted alkylene.

Yet another preferred embodiment of the present invention provides a compound of formula (I), wherein $R^2$ is hydroxyl, substituted or unsubstituted alkoxy, substituted or unsubstituted aryloxy, substituted or unsubstituted heteroaryloxy, or $NR^5R^6$ wherein each $R^5$ and $R^6$ is independently H, substituted or unsubstituted alkyl, substituted or unsubstituted cycloalkyl, substituted or unsubstituted aryl, substituted or unsubstituted heteroaryl, or substituted or unsubstituted heterocycloalkyl, or $R^5$ and $R^6$ together with the nitrogen atom to which they are attached are combined to form a substituted or unsubstituted heterocyclic ring. In another preferred embodiment, the present invention provides a compound of formula (I), wherein m is 0, 1, or 2.

Yet in another preferred embodiment, the present invention provides a compound of formula (I), wherein: $R^{3a}$ is H, halo, cyano, substituted or unsubstituted alkyl or substituted or unsubstituted alkoxycarbonyl; and each $R^{3b}$ is independently H.

Yet in another preferred embodiment, the present invention provides a compound of formula (I), wherein: $R^{3c}$ is H, substituted or unsubstituted alkyl or substituted or unsubstituted cycloalkyl.

In a particular embodiment, the present invention provides a compound of formula (I), wherein: $Q_1$, $Q_2$, $Q_3$ and $Q_4$ are each independently H, halo, cyano, or substituted or unsubstituted alkyl.

Another particular embodiment of the present invention provides a compound of formula (I), wherein: $L^2$ is a single bond and $R^2$ is $NR^5R^6$.

In another embodiment, the present invention provides a compound of formula (I), wherein: $L^1$ is substituted or unsubstituted alkylene, substituted or unsubstituted alkenylene, or substituted or unsubstituted alkynylene, and $R^1$ is substituted or unsubstituted arylene.

In a further embodiment, the present invention provides a compound of formula (I), wherein: $L^1$ is substituted or unsubstituted alkylene, substituted or unsubstituted alkenylene, or substituted or unsubstituted alkynylene, $R^1$ is substituted or unsubstituted arylene; and W is halo.

A further preferred embodiment of the present invention, provides a compound of formula (I), wherein the substituted or unsubstituted arylene, is substituted or unsubstituted phenylene-1,4-diyl, substituted or unsubstituted phenylene-1,3-diyl, or substituted or unsubstituted naphthalene-1,4-diyl.

Yet a further preferred embodiment of the present invention, provides a compound of formula (I), wherein each $R^{3b}$ is H, and m is 0, 1, or 2, if m is 0 then d is 2; if m is 1 then d is independently 3; or if m is 2 then d is 4.

Yet a further preferred embodiment of the present invention, provides a compound of formula (I), wherein $L^1$ is —$CH_2$—; and $R^1$ is substituted or unsubstituted arylene, wherein the substituted or unsubstituted arylene group is substituted or unsubstituted phenylene-1,4-diyl, substituted or unsubstituted phenylene-1,3-diyl, or substituted or unsubstituted naphthalene-1,4-diyl.

In a preferred embodiment, the present invention provides a compound of formula (I), wherein $L^1$ is —$CH_2$—, $R^1$ is substituted or unsubstituted phenylene-1,4-diyl or substituted or unsubstituted phenylene-1,3-diyl, and Rb is H, halo, CN, a substituted or unsubstituted $C_1$-$C_6$ alkyl, or a substituted or unsubstituted alkoxycarbonyl.

In another preferred embodiment, the present invention provides a compound of formula (I), wherein $L^1$ is a single bond, $R^1$ is substituted or unsubstituted arylene.

Yet in another preferred embodiment, the present invention provides a compound of formula (I), wherein W is substituted or unsubstituted heteroarylamino.

Disclosed herein in a preferred embodiment is a compound of formula (I), wherein $L^1$ is a single bond; $R^1$ is substituted or unsubstituted arylene; W is substituted or unsubstituted heteroarylamino, each $R^{3b}$ is H; m is 0, 1, or 2; if m is 0 then d is 2; if m is 1 then d is independently 3; or if m is 2 then d is 4.

Disclosed herein in another preferred embodiment is a compound of formula (I), wherein $R^1$ is substituted or unsubstituted phenylene-1,4-diyl, substituted or unsubstituted phenylene-1,3-diyl, or substituted or unsubstituted naphthalene-1,4-diyl; and $R^{3a}$ is halo, cyano, substituted or unsubstituted alkyl, or substituted or unsubstituted alkoxycarbonyl.

Disclosed herein in yet another preferred embodiment is a compound of formula (I), wherein $R^1$ is substituted or unsubstituted phenylene-1,4-diyl, or substituted or unsubstituted phenylene-1,3-diyl.

In a preferred embodiment, the present invention provides a compound of formula (I), wherein $L^1$ is a single bond; $R^1$ is substituted or unsubstituted heteroarylene; and W is substituted or unsubstituted heteroarylamino.

In another preferred embodiment, the present invention provides a compound of formula (I), wherein $L^1$ is a single bond; $R^1$ is substituted or unsubstituted heteroarylene; W is substituted or unsubstituted heteroarylamino; each $R^{3b}$ is H; m is 0, 1, or 2; if m is 0 then d is 2; if m is 1 then d is independently 3; or if m is 2 then d is 4.

In a further preferred embodiment, the present invention provides a compound of formula (I), wherein $R^1$ is substituted or unsubstituted pyridindiyl, substituted or unsubstituted pyrimidindiyl, substituted or unsubstituted pyrazindiyl, substituted or unsubstituted 1H-pyrazoldiyl, oxazoldiyl, or substituted or unsubstituted isoxazoldiyl; and $R^{3a}$ is halo, cyano, or a substituted or unsubstituted $C_1$-$C_6$ alkyl, a substituted or unsubstituted alkoxycarbonyl.

In yet a further preferred embodiment, the present invention provides a compound of formula (I), wherein $R^1$ is substituted or unsubstituted pyridine-2,4-diyl, substituted or unsubstituted pyridine-2,5-diyl, or substituted or unsubstituted pyridine-2,6-diyl. In yet a further preferred embodiment, the present invention provides a compound of formula (I), wherein W is pyrimidin-2-yl-amino, pyrimidin-4-yl-amino, pyrimidin-5-ylamino, 1H-pyrazol-5-yl-amino, 1H-pyrazol-4-yl-amino, furo[2,3-d]pyrimidin-2-yl-amino, pyridin-2-yl-amino, pyridin-3-yl-amino, or pyridin-4-yl-amino.

Also disclosed herein in a further embodiment, is a compound selected from the group consisting of:

2-(4-chlorobenzylamino)-4-[3-(pyrrolidin-1-yl)azetidin-1-yl]quinoline,
2-(4-chlorobenzylamino)-4-[3-(morpholin-4-yl)azetidin-1-yl]quinoline,
2-(4-chlorobenzylamino)-4-[4-(methylcarbamoyl)piperidin-1-yl]quinoline,
2-(4-chlorobenzylamino)-4-[4-(tert-butylaminocarbonyl)-piperidin-1-yl]-quinoline,
2-(4-chlorobenzylamino)-4-[4-(pyrrolidine-1-carbonyl)piperidin-1-yl]quinoline,
2-(4-chlorobenzylamino)-4-[4-(4-methylpiperazine-1-carbonyl)-piperidin-1-yl]-quinoline,
(2S) 2-(4-chlorobenzylamino)-4-[2-(hydroxymethyl)pyrrolidin-1-yl]quinoline,
(2S) 2-(4-chlorobenzylamino)-4-[2-(methoxymethyl)pyrrolidin-1-yl]quinoline,
(2R)-2-(4-chlorobenzylamino)-4-[2-(hydroxymethyl)-pyrrolidin-1-yl]-quinoline,
2-(4-chlorobenzylamino)-4-(4-hydroxypiperidin-1-yl)quinoline,
2-(4-chlorobenzylamino)-4-[4-(iso-propoxy)-piperidin-1-yl]-quinoline,
2-(4-chlorobenzylamino)-4-(4-phenoxypiperidin-1-yl)-quinoline,
2-(4-chlorobenzylamino)-4-[4-(m-tolyloxy)piperidin-1-yl]quinoline,
2-(4-chlorobenzylamino)-4-[4-(pyridin-4-yloxy)piperidin-1-yl]quinoline,
2-(4-chlorobenzylamino)-4-[4-(pyrazin-2-yloxy)piperidin-1-yl]quinoline,
(3R) 2-(4-chlorobenzylamino)-4-(3-hydroxypyrrolidin-1-yl)quinoline,
(3R) 2-(4-chlorobenzylamino)-4-[3-(phenoxy)pyrrolidin-1-yl]quinoline,
(3R) 2-(4-chlorobenzylamino)-4-[3-(pyridin-2-yloxy)pyrrolidin-1-yl]quinoline,
(3S) 2-(4-chlorobenzylamino)-4-(3-hydroxypyrrolidin-1-yl)-quinoline,
(3S) 2-(4-chlorobenzylamino)-4-[3-(pyridin-2-yloxy)pyrrolidin-1-yl]quinoline,
2-(N-4-chlorobenzyl-N-methylamino)-4-[4-(tert-butylamino)-piperidin-1-yl]-quinoline,
2-(N-4-chlorobenzyl-N-ethylamino)-4-[4-(tert-butylamino)-piperidin-1-yl]-quinoline,
2-(N-4-chlorobenzyl-N-isopropylamino)-4-[4-(tert-butylamino)-piperidin-1-yl]-quinoline,
2-(N-chlorobenzyl-N-isobutylamino)-4-[4-(tert-butylamino)-piperidin-1-yl]-quinoline,
2-(4-chlorobenzylamino)-3-fluoro-4-[4-(tert-butylamino)piperidin-1-yl]quinoline,
2-(4-chlorobenzylamino)-3-methyl-4-[4-(tert-butylamino)piperidin-1-yl]quinoline,
methyl 4-(4-(tert-butylamino) piperidin-1-yl)-2-(4-chlorobenzylamino) quinoline-3-carboxylate,
2-(4-chlorobenzylamino)-4-[4-(tert-butylamino)piperidin-1-yl]-7-methyl-8-fluoroquinoline,
2-(4-chlorobenzylamino)-4-[4-(tert-butylamino)piperidin-1-yl]-6-methyl-8-fluoroquinoline,
2-(4-chlorobenzylamino)-4-[4-(tert-butylamino)piperidin-1-yl]-7-fluoro-8-methylquinoline,
2-(4-chlorobenzylamino)-4-[4-(tert-butylamino)piperidin-1-yl]-6-fluoro-8-methylquinoline,
2-[4-(4-methylpyrimidin-2-ylamino)phenylamino]-3-methyl-4-(4-tert-butylaminopiperidin-1-yl)quinoline,
2-[3-(4-trifluoromethylpyrimidin-2-ylamino)phenylamino]-3-methyl-4-(4-tert-butylaminopiperidin-1-yl)quinoline,
2-(4-chlorobenzylamino)-3-cyano-4-[4-(tert-butylamino)piperidin-1-yl]quinoline,
2-[4-(4-(pyridin-3-yl)pyrimidin-2-ylamino)-3-methylbenzylamino]-3-cyano-4-(4-tert-butylaminopiperidin-1-yl)quinoline,
2-(3-methyl-4-(4-methylpyrimidin-2-ylamino)phenylamino)-3-cyano-4-(4-(tert-butylamino) piperidin-1-yl)-quinoline,
2-[4-(4,6-dimethyl-2-pyrimidinamino)-3-methyl-phenylamino]-3-cyano-4-(4-tert-butylaminopiperidin-1-yl)quinoline,
2-[4-(4-methyl-6-methoxypyrimidin-2-ylamino)-3-methyl-phenylamino]-3-cyano-4-(4-tert-butylaminopiperidin-1-yl)quinoline,
2-[3-methyl-4-(4,6-dimethylfuro[2,3-d]pyrimidin-2-ylamino)phenylamino]-3-cyano-4-(4-tert-butylaminopiperidin-1-yl)quinoline,
2-{3-methyl-4-[2-(pyridin-3-yl)pyrimidin-4-ylamino]phenylamino}-3-cyano-4-(4-tert-butylaminopiperidin-1-yl)quinoline,
2-{3-methyl-4-[2-(pyridin-3-yl)-5-cyanopyrimidin-4-ylamino]phenylamino}-3-cyano-4-(4-tert-butylaminopiperidin-1-yl)quinoline,
2-[4-(4-methylpyrimidin-2-ylamino)phenylamino]-3-cyano-4-(4-tert-butylaminopiperidin-1-yl)quinoline,
2-[3-methyl-4-(4-trifluoromethylpyrimidin-2-ylamino)phenylamino]-3-cyano-4-(4-tert-butylaminopiperidin-1-yl)quinoline,
2-[3-(4-trifluoromethyl-2-pyrmidinamino)-4-methyl-phenylamino]-3-cyano-4-(4-tert-butylaminopiperidin-1-yl)quinoline,
2-[3-(4-trifluoromethylpyrimidin-2-ylamino)phenylamino]-3-cyano-4-(4-tert-butylaminopiperidin-1-yl)quinoline,
2-[4-(4-(pyridin-3-yl)pyrimidin-2-ylamino)-3-methylphenylamino]-3-cyano-4-(4-tert-butylaminopiperidin-1-yl)quinoline,
2-[3-(4-trifluoromethylpyrimidin-2-ylamino)phenylamino]-3-fluoro-4-(4-tert-butylaminopiperidin-1-yl)quinoline,
2-(4-fluorobenzylamino)-3-fluoro-4-[4-(tert-butylamino)piperidin-1-yl]quinoline,
2-(4-fluorobenzylamino)-3-cyano-4-[4-(tert-butylamino)piperidin-1-yl]quinoline,
2-(4-chlorobenzylamino)-3-cyano-4-[4-(tert-butylamino)piperidin-1-yl]-8-methylquinoline,
2-(4-chlorobenzylamino)-3-cyano-4-[4-(tert-butylamino)piperidin-1-yl]-7-methylquinoline,
2-(4-chlorobenzylamino)-3-cyano-4-[4-(tert-butylamino)piperidin-1-yl]-6-methylquinoline,
2-(4-chlorobenzylamino)-3-cyano-4-(3-aminopiperidin-1-yl)quinoline,
2-(4-chlorobenzylamino)-3-cyano-4-[3-(methylamino)piperidin-1-yl]quinoline,
2-(4-chlorobenzylamino)-3-cyano-4-[3-(isopropylamino)piperidin-1-yl]quinoline,
{[(tetrahydro-2H-pyra-4-yl)methyl]amino}-3-fluoro-4-[4-(tert-butylamino)piperidin-1-yl]quinoline,
2-(4-chlorobenzylamino)-3-cyano-4-[3-(cyclopentylamino)piperidin-1-yl]quinoline,
2-(4-chlorobenzylamino)-3-cyano-4-[3-(4-methylpiperazin-1-yl)piperidin-1-yl]quinoline,
2-(4-chlorobenzylamino)-3-cyano-4-{3-[(1-methylpiperidin-4-yl)amino]piperidin-1-yl}quinoline, 2-(4-chlorobenzylamino)-3-cyano-4-[3-(pyrrolidin-1-yl)piperidin-1-yl]quinoline,
2-(4-chlorobenzylamino)-3-cyano-4-[3-(morpholino)piperidin-1-yl]quinoline,
2-(4-chlorobenzylamino)-3-cyano-4-[3-(4-methylpiperazin-1-yl)piperidin-1-yl]quinoline,
2-(4-chlorobenzylamino)-3-cyano-4-[3-(dimethylamino)piperidin-1-yl]quinoline,
2-(4-chlorobenzylamino)-3-cyano-4-[3-(diethylamino)piperidin-1-yl]quinoline,
2-(4-chlorobenzylamino)-3-cyano-4-(4-aminopiperidin-1-yl)quinoline,
2-(4-chlorobenzylamino)-3-cyano-4-[4-(methylamino)piperidin-1-yl]quinoline,
2-(4-chlorobenzylamino)-3-cyano-4-[4-(iso-propylamino)piperidin-1-yl]quinoline,
2-(4-chlorobenzylamino)-3-cyano-4-[4-(tert-butylamino)piperidin-1-yl]quinoline,
2-(4-chloroenzylamino)-3-cyano-4-{4-[(tert-butyloxycarbonyl)amino]piperidin-1-yl}quinoline,
2-(4-chlorobenzylamino)-3-cyano-4-[4-(cyclopentylamino)piperidin-1-yl]quinoline,
2-(4-chlorobenzylamino)-3-cyano-4-{4-[(tetrahydro-2H-pyran-4-yl)amino]piperidin-1-yl}quinoline,
2-(4-chlorobenzylamino)-3-cyano-4-{4-[(1-methylpiperidin-4-yl)amino]piperidin-1-yl}quinoline,
2-(4-chlorobenzylamino)-3-cyano-4-[4-(pyrrolidin-1-yl)piperidin-1-yl]quinoline,
2-(4-chlorobenzylamino)-3-cyano-4-[4-(morpholino)piperidin-1-yl]quinoline,
2-(4-chlorobenzylamino)-3-cyano-4-[4-(4-methylpiperazin-1-yl)piperidin-1-yl]quinoline,
2-(4-chlorobenzylamino)-3-cyano-4-[4-(dimethylamino)piperidin-1-yl]quinoline,
2-(4-chlorobenzylamino)-3-cyano-4-[4-(diethylamino)piperidin-1-yl]quinoline,
2-(4-chlorobenzylamino)-3-cyano-4-[3-aminopyrrolidin-1-yl]quinoline,
2-(4-chlorobenzylamino)-3-cyano-4-[3-(methylamino)pyrrolidin-1-yl]quinoline,
2-(4-chlorobenzylamino)-3-cyano-4-[3-(cyclopentylamino)pyrrolidin-1-yl]quinoline,
2-(4-chlorobenzylamino)-3-cyano-4-{3-[(tetrahydro-2H-pyran-4-yl)amino]pyrrolidin-1-yl}quinoline,
2-(4-chlorobenzylamino)-3-cyano-4-[3-(pyrrolidin-1-yl)pyrrolidin-1-yl]quinoline,
2-(4-chlorobenzylamino)-3-cyano-4-(3-morpholinopyrrolidin-1-yl)quinoline,
2-(4-chlorobenzylamino)-3-cyano-4-[3-(4-methylpiperazin-1-yl)pyrrolidin-1-yl]quinoline,
2-(4-chlorobenzylamino)-3-cyano-4-[3-(dimethylamino)pyrrolidin-1-yl]quinoline,
2-(4-chlorobenzylamino)-3-cyano-4-[3-(diethylamino)pyrrolidin-1-yl]quinoline,
2-(4-chlorobenzylamino)-3-cyano-4-(3-phenoxypiperidin-1-yl)quinoline,
2-(4-chlorobenzylamino)-3-cyano-4-[3-(4-methoxyphenoxy)piperidin-1-yl]quinoline,
2-(4-chlorobenzylamino)-3-cyano-4-[3-(4-methylphenoxy)piperidin-1-yl]quinoline,
2-(4-chlorobenzylamino)-3-cyano-4-[3-(4-fluorophenoxy)piperidin-1-yl]quinoline,
2-(4-chlorobenzylamino)-3-cyano-4-[3-(3-fluorophenoxy)piperidin-1-yl]quinoline,
2-(4-chlorobenzylamino)-3-cyano-4-{3-[(3-methylpyrazin-2-yl)oxy]piperidin-1-yl}quinoline,
2-(4-chlorobenzylamino)-3-cyano-4-(4-phenoxypiperidin-1-yl)quinoline,
2-(4-chlorobenzylamino)-3-cyano-4-[4-(4-methoxyphenoxy)piperidin-1-yl]quinoline,
2-(4-chlorobenzylamino)-3-cyano-4-[4-(p-tolyloxy)piperidin-1-yl]quinoline,
2-(4-chlorobenzylamino)-3-cyano-4-[4-(4-chlorophenoxy)piperidin-1-yl]quinoline,
2-(4-chlorobenzylamino)-3-cyano-4-[4-(4-fluorophenoxy)piperidin-1-yl]quinoline,
2-(4-chlorobenzylamino)-3-cyano-4-[4-(3-fluorophenoxy)piperidin-1-yl]quinoline,
2-(4-chlorobenzylamino)-3-cyano-4-{4-[(pyridin-4-yl)oxy]piperidin-1-yl}quinoline,
2-(4-chlorobenzylamino)-3-cyano-4-{4-[(5-methylisoxazol-3-yl)oxy]piperidin-1-yl}quinoline,
2-(4-chlorobenzylamino)-3-cyano-4-{4-[(3-methylpyrazin-2-yl)oxy]piperidin-1-yl}quinoline,
2-(4-chlorobenzylamino)-3-cyano-4-(3-phenoxypyrrolidin-1-yl)quinoline,
2-(4-chloroenzylamino)-3-cyano-4-[3-(4-methylphenoxy)pyrrolidin-1-yl]quinoline,
2-(4-chlorobenzylamino)-3-cyano-4-[3-(4-methoxyphenoxy)pyrrolidin-1-yl]quinoline,
2-(4-chlorobenzylamino)-3-cyano-4-[3-(4-chlorophenoxy)pyrrolidin-1-yl]quinoline,
2-(4-chlorobenzylamino)-3-cyano-4-[3-(4-fluorophenoxy)pyrrolidin-1-yl]quinoline,
2-(4-chlorobenzylamino)-3-cyano-4-[3-(3-fluorophenoxy)pyrrolidin-1-yl]quinoline,
2-(4-chlorobenzylamino)-3-cyano-4-{3-[(3-methylpyrazin-2-yl)oxy]pyrrolidin-1-yl}quinoline,
2-(4-chlorobenzylamino)-3-cyano-4-{3-[(pyridin-4-yl)oxy]pyrrolidin-1-yl}quinoline,
2-(phenylamino)-3-cyano-4-[4-(tert-butylamino)piperidin-1-yl]quinoline,
2-(4-methylphenylamino)-3-cyano-4-[4-(tert-butylamino)piperidin-1-yl]quinoline,
2-(3-methyl-4-fluorophenylamino)-3-cyano-4-[4-(tert-butylamino)piperidin-1-yl]quinoline,
2-(4-methoxyphenylamino)-3-cyano-4-[4-(tert-butylamino)piperidin-1-yl]quinoline,
2-(2-trifluoromethylphenylamino)-3-cyano-4-[4-(tert-butylamino)piperidin-1-yl]quinoline,
2-(3-trifluoromethylphenylamino)-3-cyano-4-[4-(tert-butylamino)piperidin-1-yl]quinoline,
2-(4-chlorophenylamino)-3-cyano-4-[4-(tert-butylamino)piperidin-1-yl]quinoline,
2-(4-fluorophenylamino)-3-cyano-4-[4-(tert-butylamino)piperidin-1-yl]quinoline,
2-(3-fluorophenylamino)-3-cyano-4-[4-(tert-butylamino)piperidin-1-yl]quinoline,
2-(3,4-difluorophenylamino)-3-cyano-4-[4-(tert-butylamino)piperidin-1-yl]quinoline,
2-[4-(trifluoromethyloxy)phenylamino]-3-cyano-4-[4-(tert-butylamino)piperidin-1-yl]quinoline,
2-[(1-methyl-1H-pyrazol-4-yl)amino]-3-cyano-4-[4-(tert-butylamino)piperidin-1-yl]quinoline,
2-[(1-methyl-1H-1,2,4-triazol-5-yl)amino]-3-cyano-4-[4-(tert-butylamino)piperidin-1-yl]quinoline,
2-[(1,3-dimethyl-1H-1,2,4-triazol-5-yl)amino]-3-cyano-4-[4-(tert-butylamino)piperidin-1-yl]quinoline,
2-{4-[(4,6-dimethylpyrimidin-2-yl)amino]phenylamino}-3-cyano-4-[4-(tert-butylamino)piperidin-1-yl]quinoline,
2-(pyridin-2-ylamino)-3-cyano-4-[4-(tert-butylamino)piperidin-1-yl]quinoline, 2-(pyrimidin-2-ylamino)-3-cyano-4-[4-(tert-butylamino)piperidin-1-yl]quinoline,
2-(pyrimidin-4-ylamino)-3-cyano-4-[4-(tert-butylamino)piperidin-1-yl]quinoline,
2-(pyrazin-2-ylamino)-3-cyano-4-[4-(tert-butylamino)piperidin-1-yl]quinoline,
2-(benzylamino)-3-cyano-4-[4-(tert-butylamino)piperidin-1-yl]quinoline,
2-(4-methylbenzylamino)-3-cyano-4-[4-(tert-butylamino)piperidin-1-yl]quinoline,
2-(4-methoxybenzylamino)-3-cyano-4-[4-(tert-butylamino)piperidin-1-yl]quinoline,
2-[4-(trifluoromethyl)benzylamino]-3-cyano-4-[4-(tert-butylamino)piperidin-1-yl]quinoline,
2-[2-(trifluoromethyl)benzylamino]-3-cyano-4-[4-(tert-butylamino)piperidin-1-yl]quinoline,
2-[(benzo[d][1,3]dioxol-5-ylmethyl)amino]-3-cyano-4-[4-(tert-butylamino)piperidin-1-yl]quinoline,
2-[(furan-2-ylmethyl)amino]-3-cyano-4-[4-(tert-butylamino)piperidin-1-yl]quinoline,
2-[(pyridin-3-ylmethyl)amino]-3-cyano-4-[4-(tert-butylamino)piperidin-1-yl]quinoline,
2-[(pyridin-4-ylmethyl)amino]-3-cyano-4-[4-(tert-butylamino)piperidin-1-yl]quinoline,
2-[(pyridin-2-ylmethyl)amino]-3-cyano-4-[4-(tert-butylamino)piperidin-1-yl]quinoline.

or a pharmaceutically acceptable salt, hydrate, solvate, or prodrug thereof, or an isotopic variant, tautomer, or stereoisomer thereof.

In a preferred embodiment, a compound of formula (II) is provided:

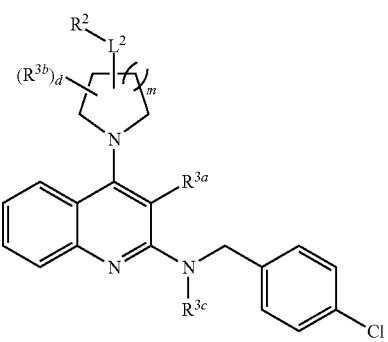

(II)

wherein
$L^2$ is a single bond, carbonyl, substituted or unsubstituted alkylene, substituted or unsubstituted alkenylene, or substituted or unsubstituted alkynylene,
$R^2$ is hydroxyl, substituted or unsubstituted alkoxy, substituted or unsubstituted aryloxy, substituted or unsubstituted heteroaryloxy, substituted or unsubstituted alkoxycarbonylamino, substituted or unsubstituted aryloxycarbonylamino, substituted or unsubstituted heteroaryloxycarbonylamino, substituted or unsubstituted alkylaminocarbonylamino, substituted or unsubstituted arylaminocarbonylamino, substituted or unsubstituted heteroarylaminocarbonylamino, or $NR^5R^6$ wherein each $R^5$ and $R^6$ is independently H, substituted or unsubstituted alkyl, substituted or unsubstituted cycloalkyl, substituted or unsubstituted aryl, substituted or unsubstituted heteroaryl, or substituted or unsubstituted heterocycloalkyl, or $R^5$ and $R^6$ together with the nitrogen atom to which they are attached are combined to form a substituted or unsubstituted heterocyclic ring,
$R^{3a}$ is H, halo, cyano, substituted or unsubstituted alkyl, substituted or unsubstituted aryl, substituted or unsubstituted heteroaryl, substituted or unsubstituted cycloalkyl, substituted or unsubstituted heterocycloalkyl, substituted or unsubstituted alkoxy, substituted or unsubstituted alkoxycarbonyl, substituted or unsubstituted aryloxycarbonyl, substituted or unsubstituted heteroaryloxycarbonyl, or substituted or unsubstituted aminocarbonyl;
each $R^{3b}$ is independently H, hydroxyl, halo, azido, amino, nitro, thiol, cyano, carboxyl, substituted or unsubstituted alkyl, substituted or unsubstituted alkenyl, substituted or unsubstituted alkynyl, substituted or unsubstituted arylalkyl, substituted or unsubstituted aryl, substituted or unsubstituted heteroaryl, substituted or unsubstituted cycloalkyl, substituted or unsubstituted cycloalkenyl, or substituted or unsubstituted heterocycloalkyl;
$R^{3c}$ is H, substituted or unsubstituted alkyl, substituted or unsubstituted alkenyl, substituted or unsubstituted alkynyl, substituted or unsubstituted cycloalkyl, substituted or unsubstituted cycloalkenyl, or substituted or unsubstituted heterocycloalkyl, provided that when $R^{3c}$ is H, $L^2$ is other than a single bond or $R^2$ is other than $NR^5R^6$ or $R^{3a}$ is other than H;
m is 0, 1, 2, 3, or 4;
if m is 0, then d is independently 0, 1 or 2; if m is 1, then d is independently 0, 1, 2 or 3; if m is 2, then d is independently 0, 1, 2, 3 or 4; if m is 3, then d is independently 0, 1, 2, 3, 4 or 5 or if m is 4 then d is independently 0, 1, 2, 3, 4, 5 or 6;
or a pharmaceutically acceptable salt, hydrate, solvate, or prodrug thereof, or an isotopic variant, tautomer, or stereoisomer thereof.

In a preferred embodiment, a compound according to formula (II) is provided, wherein $R^{3c}$ is H, substituted or unsubstituted alkyl, or substituted or unsubstituted cycloalky.

In another preferred embodiment, a compound according to formula (II) is provided, wherein each $R^{3b}$ is independently H.

In a further preferred embodiment, a compound according to formula (II) is provided, wherein $R^{3i}$ is H, halo, cyano, substituted or unsubstituted alkyl or substituted or unsubstituted alkoxycarbonyl. Preferably the halo atom is fluor.

In yet a further preferred embodiment, a compound according to formula (II) is provided, wherein $L^2$ is a single bond, carbonyl, substituted or unsubstituted alkylene.

In yet a further preferred embodiment, a compound according to formula (II) is provided, wherein m is 0, 1, or 2.

The present invention also provides in a preferred embodiment a compound of formula (III) having the structure:

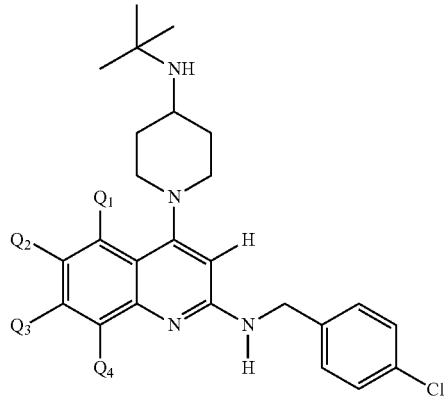

(III)

Wherein:
Q₁, Q₂, Q₃ and Q₄ are each independently H, hydroxyl, halo, amino, nitro, thiol, carboxyl, cyano, azido, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted arylalkyl, substituted or unsubstituted heterocycloalkyl, substituted or unsubstituted aryl, substituted or unsubstituted heteroaryl, substituted or unsubstituted alkoxy, substituted or unsubstituted aryloxy, substituted or unsubstituted heteroaryloxy, substituted or unsubstituted sulfanyl, substituted or unsubstituted alkylamino, substituted or unsubstituted dialkylamino, substituted or unsubstituted arylamino, substituted or unsubstituted heteroarylamino, substituted or unsubstituted acyl, substituted or unsubstituted acylamino, substituted or unsubstituted aminocarbonyl, substituted or unsubstituted alkoxycarbonyl, substituted or unsubstituted aryloxycarbonyl, substituted or unsubstituted heteroaryloxycarbonyl, substituted sulfo, substituted sulfonyl, substituted sulfinyl, substituted or unsubstituted aminosulfonyl, substituted or unsubstituted sulfonylamino, substituted or unsubstituted aminocarbonylamino, substituted or unsubstituted aminocarbonyloxy, substituted or unsubstituted alkoxycarbonylamino, substituted or unsubstituted aryloxycarbonylamino, or substituted or unsubstituted heteroaryloxycarbonylamino; and at least two of Q₁, Q₂, Q₃ and Q₄ are other than H and are distinct.

In a further embodiment, the invention provides a compound according to formula (III), wherein Q₁, Q₂, Q₃ and Q₄ are each independently H, cyano, methyl or halo.

The invention also provides in a preferred embodiment, a compound according to formula (IV) having the structure of:

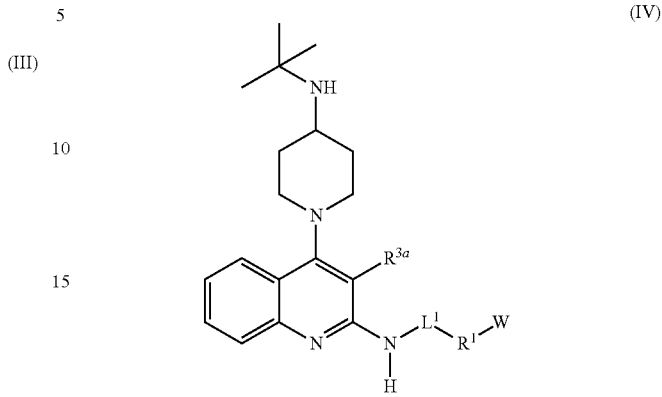

(IV)

wherein
$R^{3a}$ is halo, cyano, substituted or unsubstituted alkyl, substituted or unsubstituted aryl, substituted or unsubstituted heteroaryl, substituted or unsubstituted cycloalkyl, substituted or unsubstituted heterocloalkyl, substituted or unsubstituted alkoxy, substituted or unsubstituted alkoxycarbonyl, substituted or unsubstituted aryloxycarbonyl, substituted or unsubstituted heteroaryloxycarbonyl, or substituted or unsubstituted aminocarbonyl;
$L^1$ is a single bond, or substituted or unsubstituted alkylene, substituted or unsubstituted alkenylene, or substituted or unsubstituted alkynylene;
$R^1$ is substituted or unsubstituted aryl, substituted or unsubstituted heteroaryl, substituted or unsubstituted arylene, or substituted or unsubstituted heteroarylene; and
W is optionally present and if present is H, hydroxyl, halo, azido, amino, nitro, thiol, cyano, carboxyl, substituted or unsubstituted alkyl, substituted or unsubstituted alkenyl, substituted or unsubstituted alkynyl, substituted or unsubstituted arylalkyl, substituted or unsubstituted aryl, substituted or unsubstituted heteroaryl, substituted or unsubstituted cycloalkyl, substituted or unsubstituted cycloalkenyl, substituted or unsubstituted heterocycloalkyl, substituted or unsubstituted alkoxy, substituted or unsubstituted aryloxy, substituted or unsubstituted heteroaryloxy, substituted or unsubstituted sulfanyl, substituted or unsubstituted alkylamino, substituted or unsubstituted dialkylamino, substituted or unsubstituted arylamino, substituted or unsubstituted heteroarylamino, substituted or unsubstituted acyl, substituted or unsubstituted acylamino, substituted or unsubstituted aminocarbonyl, substituted or unsubstituted alkoxycarbonyl, substituted or unsubstituted aryloxycarbonyl, substituted or unsubstituted heteroaryloxycarbonyl, substituted sulfo, substituted sulfonyl, substituted sulfinyl, substituted or unsubstituted aminosulfonyl, substituted or unsubstituted sulfonylamino, substituted or unsubstituted alkylsulfonyl, substituted or unsubstituted arylsulfonyl, substituted or unsubstituted aminocarbonylamino, substituted or unsubstituted aminocarbonyloxy, substituted or unsubstituted alkoxycarbonylamino, substituted or unsubstituted aryloxycarbonylamino, or substituted or unsubstituted heteroaryloxycarbonylamino.

In a further preferred embodiment, the invention provides a compound according to formula (IV), wherein $R^{3a}$ is halo, cyano or substituted or unsubstituted alkoxycarbonyl.

In a another preferred embodiment, the invention provides a compound according to formula (IV), wherein $L^1$ is a single bond, or substituted or unsubstituted alkylene.

In a yet another preferred embodiment, the invention provides a compound according to formula (IV), wherein $R^1$ is substituted or unsubstituted aryl, substituted or unsubstituted heteroaryl.

In a yet another preferred embodiment, the invention provides a compound according to formula (IV), wherein W is substituted or unsubstituted arylamino, or substituted or unsubstituted heteroarylamino.

In another aspect, the present invention also provides a compound according to the invention, or a pharmaceutically acceptable salt, hydrate, solvate, or prodrug thereof, or an isotopic variant, tautomer, or stereoisomer thereof, for use as medicament.

In a further aspect, the present invention also provides a pharmaceutical composition comprising a therapeutically effective amount of a compound according to to the invention, or a pharmaceutically acceptable salt, hydrate, solvate, or prodrug thereof, or an isotopic variant, tautomer, or stereoisomer thereof, and a pharmaceutically acceptable excipient.

In yet a further aspect, the present invention also provides a method of treating a proliferative disease comprising administering to a patient in need a pharmaceutical composition according to the invention.

Provided in another aspect of the present invention is a compound according to the invention, or a pharmaceutically acceptable salt, hydrate, solvate, or prodrug thereof, or an isotopic variant, tautomer, or stereoisomer thereof, for use for the treatment of a proliferative disease. In particular, the proliferative disease is selected from a neoplastic disease and a non-neoplastic disorder. Particularly, the neoplastic disease is cancer. More particularly, the cancer is selected in the group consisting of: malignant tumours, malignant lymphoma, malignant melanoma, malignant astrocytoma, benign tumours, solid tumours, sarcomas, carcinomas, carcinoids, Ewing sarcomas, Kaposi sarcomas, brain tumours, tumours originating from the brain and/or the nervous system and/or the meninges, gliomas, glioblastomas, neuroblastomas, stomach cancer, pancreatic cancer, kidney cancer, kidney cell carcinomas, prostate cancer, prostate carcinomas, connective tissue tumours, soft tissue sarcomas, fibrosarcomas, pancreas tumours, livercancer, head tumours, neck tumours, laryngeal cancer, nasopharyngeal cancer, oesophageal cancer, colon cancer thyroid cancer, osteosarcomas, retinoblastomas, thymoma, testicular cancer, lung cancer, lung adenocarcinoma, small cell lung carcinoma, bronchial carcinomas, breast cancer, mamma carcinomas, intestinal cancer, colorectal tumours, colon carcinomas, prostate cancer, rectum carcinomas, gynaecological tumours, ovary tumours/ovarian tumours, uterine cancer, cervical cancer, cervix carcinomas, cancer of body of uterus, corpus carcinomas, endometrial carcinomas, urinary bladder cancer, urogenital tract cancer, bladder cancer, skin cancer, epithelial tumours, squamous epithelial carcinoma, basal cell carcinoma, basaliomas, spinaliomas, melanomas, intraocular melanomas, leukaemias, monocyte leukaemia, chronic leukaemias, chronic myelotic leukaemia, chronic lymphatic leukaemia, acute leukaemias, acute myelogenous leukemia, acute promyelocytic leukemia (APL), acute lymphatic leukemia, acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia, stem cell leukemia, germ cell cancer, and metastatic growth. Specifically, the cancer is a liver cancer which is selected in the group consisting of: hepatocellular carcinoma, cholangiocarcinoma and hepatoblastoma.

In yet a further aspect, the present invention also provides, a compound according to the invention, or a pharmaceutically acceptable salt, hydrate, solvate, or prodrug thereof, or an isotopic variant, tautomer, or stereoisomer thereof, for use for inhibiting the growth or differentiation of a Cancer Stem Cell (CSC), a tumor initiating cell, a mesenchymal-like cell associated with cancer, a mesenchymal cancerous cell, or a mesenchymal cell.

In a preferred embodiment, the pharmaceutical composition according to present invention, further comprises at least one additional therapeutically active agent. Specifically, the additional therapeutically active agent is for the treatment of cancer.

In yet a further aspect, the present invention also provides the use of a compound according to the invention, or a pharmaceutically acceptable salt, hydrate, solvate, or prodrug thereof, or an isotopic variant, tautomer, or stereoisomer thereof, in the manufacture of a medicament for the treatment of a proliferative disease which is selected from a neoplastic disease and a non-neoplastic disorder.

Prodrugs, stereoisomers, mixtures of stereoisomers, racemates, tautomers, salts, hydrates, solvates, salt hydrates, acid salt hydrates, and isomorphic crystalline forms of the compounds of having the structure of formula I (or II, III, III' or IV) are also contemplated within the scope of the present invention.

DETAILED DESCRIPTION OF THE INVENTION

The present invention is based on the identification that the compounds of formula (I) may be useful for the treatment of cell proliferative diseases, particularly in mammals. The present invention also provides methods for the preparation of the compounds of the invention, the intermediates for their preparation, pharmaceutical compositions comprising a compound of the invention and uses as medicament for the treatment of cell proliferative diseases.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

In the present specification, the term "compounds of the invention", and equivalent expressions, are meant to embrace compounds of general formula (I) as hereinbefore described, which expression includes the pharmaceutically acceptable salts, the hydrates, the solvates, the prodrugs, the isotopic variants, the tautomers, the stereoisomers and the polymorhs thereof, where the context so permits. Similarly, reference to intermediates, whether or not they themselves are claimed, is meant to embrace their salts, solvates, and isotopic variants where the context so permits. For the sake of clarity, particular instances when the context so permits are sometimes indicated in the text, but these instances are purely illustrative and it is not intended to exclude other instances when the context so permits.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

In this specification, the use of the singular includes the plural unless specifically stated otherwise. It must be noted that, as used in the specification and the appended claims, the singular forms "a," "an" and "the" include plural referents unless the context clearly dictates otherwise. In this specification, the use of "or" means "and/or" unless stated otherwise. Furthermore, use of the term "including" as well as other forms, such as "include", "includes," and "included," is not limiting.

Definition of standard chemistry terms may be found in reference works, including Carey and Sundberg "ADVANCED ORGANIC CHEMISTRY 5TH ED." Vols. A (2008) and B (2010), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that theterminology used herein is for the purpose of describing particular embodiments only, and is not intended to limit the scope of the methods and compositions described herein, which will be limited only by the appended claims.

All publications and patents mentioned herein are incorporated herein by reference in their entirety for the purpose of describing and disclosing, for example, the constructs and methodologies that are described in the publications, which might be used in connection with the methods, compositions and compounds described herein. The publications discussed herein are provided solely for their disclosure prior to the filing date of the present application. Nothing herein is to be construed as an admission that the inventors described herein are not entitled to antedate such disclosure by virtue of prior invention or for any other reason.

DEFINITION OF SUBSTITUENTS

The term "independently" is used herein to indicate that a variable is applied in any one instance without regard to the presence or absence of a variable having that same or a different definition within the same compound. Thus, for instance, in a compound in which a substituent Y* appears twice and is defined as "independently group G1 or group G2", both Y* can be G1, both Y* can be G2, or one Y* can be G1 and the other G2.

An "alkyl" group refers to an aliphatic hydrocarbon group. The alkyl moiety may be a "saturated alkyl" group, which means that it does not contain any alkene or alkyne moieties. The alkyl moiety may also be an "unsaturated alkyl" moiety, which means that it contains at least one alkene or alkyne moiety. An "alkene" moiety refers to a group that has at least one carbon-carbon double bond, and an "alkyne" moiety refers to a group that has at least one carbon-carbon triple bond. The alkyl moiety, whether saturated or unsaturated, may be branched, straight chain, or cyclic (in which case, it would also be known as a "cycloalkyl" group). Depending on the structure, an alkyl group can be a monoradical or a diradical (in which case, it would also be known as a "alkylene" group). The alkyl group could also be a "lower alkyl" having 1 to 6 carbon atoms.

As used herein, $C_1$-$C_x$ includes $C_1$-$C_2$, $C_1$-$C_3$ . . . $C_1$-$C_x$. By way of example only, "$C_1$-$C_4$" indicates that there are one to four carbon atoms in the moiety, i.e. groups containing 1 carbon atom, 2 carbon atoms, 3 carbon atoms or 4 carbon atoms, as well as the ranges $C_1$-$C_2$ and $C_1$-$C_3$. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The "alkyl" moiety may have 1 to 10 carbon atoms (whenever it appears herein, a numerical range such as "1 to 10" refers to each integer in the given range; e.g., "1 to 10 carbon atoms" means that the alkyl group may have 1 carbon atom, 2 carbon atoms, 3 carbon atoms, etc., up to and including 10 carbon atoms, although the present definition also covers the occurrence of the term "alkyl" where no numerical range is designated). The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from among methyl, ethyl, propyl, iso-propyl, n-butyl, iso-butyl, sec-butyl, and t-butyl. Thus $C_1$-$C_4$ alkyl includes $C_1$-$C_2$ alkyl and $C_1$-$C_3$ alkyl. Alkyl groups can be substituted or unsubstituted. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like.

The term "alkylene" refers to an alkyl group, where alkyl is diradical as described above. Typically an alkylene group has two points of attachment to the rest of the molecule (e.g. -$L^1$- and or -$L^2$- in the molecule represented by formula I of the present invention). The two points of attachment of the alkylene group can be located on one carbon atom or on two different carbons atoms thereof.

The alkylene group may be branched or straight chain. The alkylene group may also be unsaturated (in which case, it would also be known as a "alkenylene" group or as "alkynylene" group). The alkylene group may also be cyclic (in which case, it would also be known as a "cycloalkylene" group). Alkylene groups can be substituted or unsubstituted.

The alkylene group could have 1 to 10 carbon atoms. Preferred alkylene groups are those having 1 to 8 carbon atoms. Most preferred alkylene groups are those having 1 to 6 carbon atoms.

Typical alkylene groups which are branched or straight chain include, but are in no way limited to, methylene (—CH$_2$—), ethylene (—CH$_2$—CH$_2$—), ethan-1,1-diyl (—CH(CH$_3$)—), propylene (—CH$_2$—CH$_2$—CH$_2$—), 1-methyl-ethylene (—CH(CH$_3$)—CH$_2$—), propan-1,1-diyl (-(—CH)—CH$_2$—CH$_3$), propan-2,2-diyl (—C(CH$_3$)$_2$—), propylen-1,1-diyl (-(—CH)—CH$_2$—CH$_3$), propylen-1,1-3-diyl (-(—CH)—CH$_2$—CH$_2$—), butylene (—CH$_2$—CH$_2$—CH$_2$—CH$_2$—), butan-1,1-diyl (-(—CH)—CH$_2$—CH$_2$—CH$_3$).

Typical alkylene groups which are unsaturated (i.e. alkenylene or alkynylene) include, but are in no way limited to 1-propen-3,3-didyl, 1-propyn-3,3-didyl, 1-buten-4,4-didyl, 1-butyn-4,4-didyl, 2-buten-1,4-didyl, 2-butyn-1,4-didyl, 2-penten-1,5-diyl, 3-penten-1,5-diyl, 2-pentyn-1,5-diyl, 3-pentyn-1,5-diyl, 3-hexen-1,6-diyl, 3-hexyn-1,6-diyl, 4-hexen-1,6-diyl and 4-hexyn-1,6-diyl, Typical alkylene groups which are cyclic (i.e. cycloalkylene), saturated or unsaturated, include, but are in no way limited to cyclopropan-1,1-diyl, cyclopropan-1,2-diyl, cyclobutane-1,1-diyl, cyclobutane-1,3-diyl, cyclopentan-1,1-diyl, cyclopentan-1,3-diyl, cyclohexan-1,1-diyl, cyclohexan-1,2-diyl, cyclohexan-1,3-diyl, cyclohexan-1,4-diyl, 1-cyclo penten-3,5-diyl, 1-cyclohexen-3,4-diyl, 1-cyclohexen-3,5-diyl, or 1-cyclohexen-3,6-diyl, and the like.

As used herein, the term "non-cyclic alkyl" refers to an alkyl that is not cyclic (i.e., a straight or branched chain containing at least one carbon atom). Non-cyclic alkyls can be fully saturated or can contain non-cyclic alkenes and/or alkynes. Non-cyclic alkyls can be optionally substituted.

The term "alkenyl" refers to a type of alkyl group in which the first two atoms of the alkyl group form a double bond that is not part of an aromatic group. That is, an alkenyl group begins with the atoms —C(R)=C(R)—R, wherein R refers to the remaining portions of the alkenyl group, which may be the same or different. The alkenyl moiety may be branched, straight chain, or cyclic (in which case, it would also be known as a "cycloalkenyl" group). Depending on the structure, an alkenyl group can be a monoradical or a diradical (i.e., an alkenylene group). Alkenyl groups can be optionally substituted. Non-limiting examples of an alkenyl group include —CH=CH$_2$, —C(CH$_3$)=CH$_2$, —CH=CHCH$_3$, —C(CH$_3$)=CHCH$_3$. Alkenylene groups include, but are not limited to, —CH=CH—, —C(CH$_3$)=CH—, —CH=CHCH$_2$—, —CH=CHCH$_2$CH$_2$— and —C(CH$_3$)=CHCH$_2$—. Alkenyl groups could have 2 to 10 carbons. The alkenyl group could also be a "lower alkenyl" having 2 to 6 carbon atoms.

The term "alkynyl" refers to a type of alkyl group in which the first two atoms of the alkyl group form a triple bond. That is, an alkynyl group begins with the atoms —C≡C—R, wherein R refers to the remaining portions of the alkynyl group, which may be the same or different. The "R" portion of the alkynyl moiety may be branched, straight chain, or cyclic. Depending on the structure, an alkynyl group can be a monoradical or a diradical (i.e., an alkynylene group). Alkynyl groups can be optionally substituted. Non-limiting examples of an alkynyl group include, but are not limited to, —C≡CH, —C≡CCH$_3$, —C≡CCH$_2$CH$_3$, —C≡C—, and —C≡CCH$_2$—. Alkynyl groups can have 2 to 10 carbons. The alkynyl group could also be a "lower alkynyl" having 2 to 6 carbon atoms.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be monocyclic or polycyclic. Rings can be optionally substituted.

As used herein, the term "ring system" refers to one, or more than one ring.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "fused" refers to structures in which two or more rings share one or more bonds.

The term "carbocyclic" or "carbocycle" refers to a ring wherein each of the atoms forming the ring is a carbon atom. Carbocycle includes aryl and cycloalkyl. The term thus distinguishes carbocycle from heterocycle ("heterocyclic") in which the ring backbone contains at least one atom which is different from carbon (i.e a heteroatom). Heterocycle includes heteroaryl and heterocycloalkyl. Carbocycles and heterocycles can be optionally substituted.

The term "aromatic" refers to a planar ring having a delocalized π-electron system containing 4n+2π electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical in which case it would be known as an arylene group. Examples of arylene groups include, but are not limited to, benzene-1,3-diyl, benzene-1,4-diyl, naphthalene-2,7-diyl, naphthalene-2,6-diyl, naphthalene-1,4-diyl naphthalene-1,5-diyl, acenaphthene-diyl, phenanthren-3,8-diyl, fluoranthene-diyl, and the like.

"Aralkyl" means an alkyl radical, as defined herein, substituted with an aryl group. Non-limiting aralkyl groups include benzyl, phenethyl, and the like.

"Aralkenyl" means an alkenyl radical, as defined herein, substituted with an aryl group, as defined herein.

The term "cycloalkyl" refers to a monocyclic or polycyclic radical that contains only carbon and hydrogen, and may be saturated, partially unsaturated, or fully unsaturated. Cycloalkyl groups include groups having from 3 to 10 ring atoms. Illustrative examples of cycloalkyl groups include the following moieties:

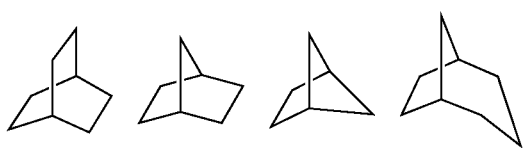

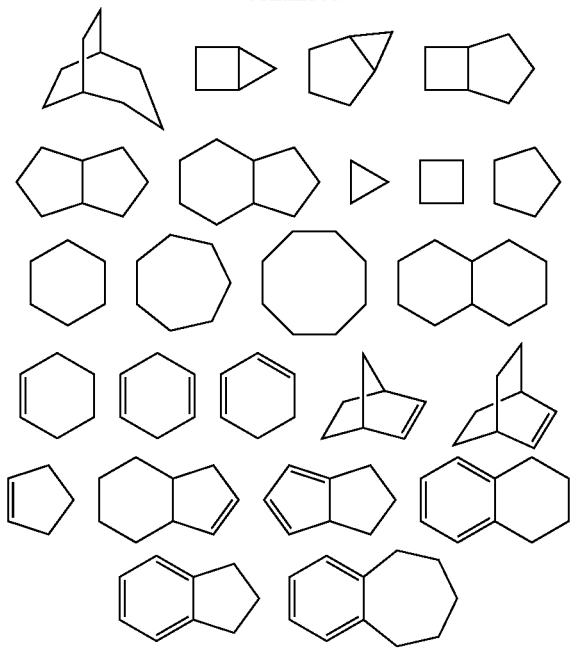

and the like. Depending on the structure, a cycloalkyl group can be a monoradical or a diradical (e.g., a cycloalkylene group). The cycloalkyl group could also be a "lower cycloalkyl" having 3 to 7 carbon atoms.

"Cycloalkylalkyl" means an alkyl radical, as defined herein, substituted with a cycloalkyl group. Non-limiting cycloalkylalkyl groups include cyclopropylmethyl, cyclobutylmethyl, cyclopentylmethyl, cyclohexylmethyl, and the like.

The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocyclic ring can have additional heteroatoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). In heterocycles that have two or more heteroatoms, those two or more heteroatoms can be the same or different from one another. Heterocycles can be optionally substituted. Binding to a heterocycle can be at a heteroatom or via a carbon atom. Non-aromatic heterocyclic groups include groups having only 4 atoms in their ring system, but aromatic heterocyclic groups must have at least 5 atoms in their ring system. The heterocyclic groups include benzo-fused ring systems. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydropyranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (—O) moieties such as pyrrolidin-2-one. Depending on the structure, a heterocycle group can be a monoradical or a diradical (i.e., a heterocyclene group).

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Illustrative examples of heteroaryl groups include the following moieties:

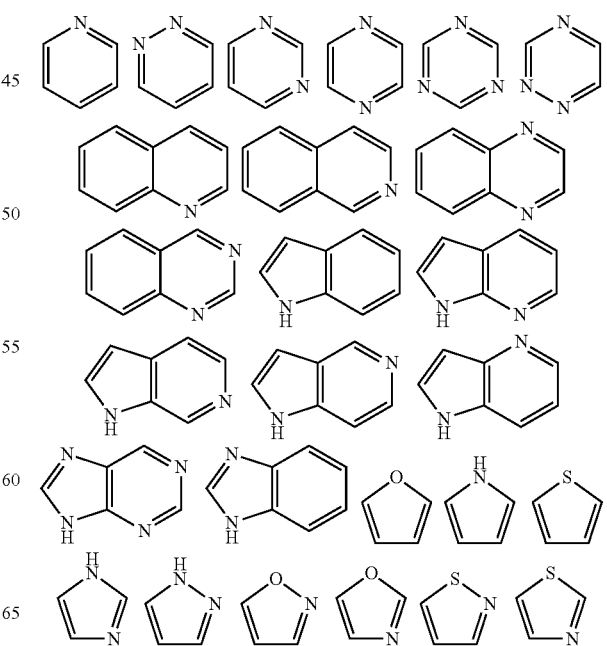

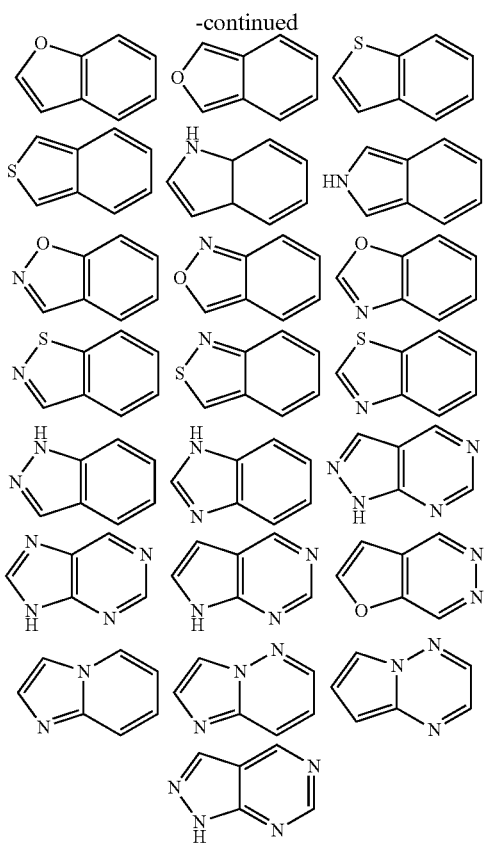

and the like. Depending on the structure, a heteroaryl group can be a monoradical or a diradical (i.e., a heteroarylene group).

Examples of heteroarylene groups include, but not limited to, pyridinediyl, pyrimidinediyl, pyrazinediyl, furanediyl, thiophenediyl, quinolinediyl, isoquinolinediyl, benzofuranediyl, benzothiophenediyl, benzoxazolediyl, benzothiazolediyl and indolediyl. Particular examples of heteroarylene groups include, but not limited to, but are not limited to, furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyrazole-3,4-diyl, pyridine-2,3-diyl, pyridine-2,4-diyl, pyridine-2,5-diyl, 6-methyl-pyridine-2,5-diyl, pyridine-2,6-diyl, pyrimidine-2,4-diyl, pyrimidine-2,5-diyl, quinoline-2,3-diyl, pyridazine-diyl, triazine-diyl, and the like.

As used herein, the term "non-aromatic heterocycle", "heterocycloalkyl" or "heteroalicyclic" refers to a non-aromatic ring wherein one or more atoms forming the ring is a heteroatom. A "non-aromatic heterocycle" or "heterocycloalkyl" group refers to a cycloalkyl group that includes at least one heteroatom selected from nitrogen, oxygen and sulfur. The radicals may be fused with an aryl or heteroaryl. Heterocycloalkyl rings can be formed by three, four, five, six, seven, eight, nine, or more than nine atoms. Heterocycloalkyl rings can be optionally substituted. In certain embodiments, non-aromatic heterocycles contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidinone, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include:

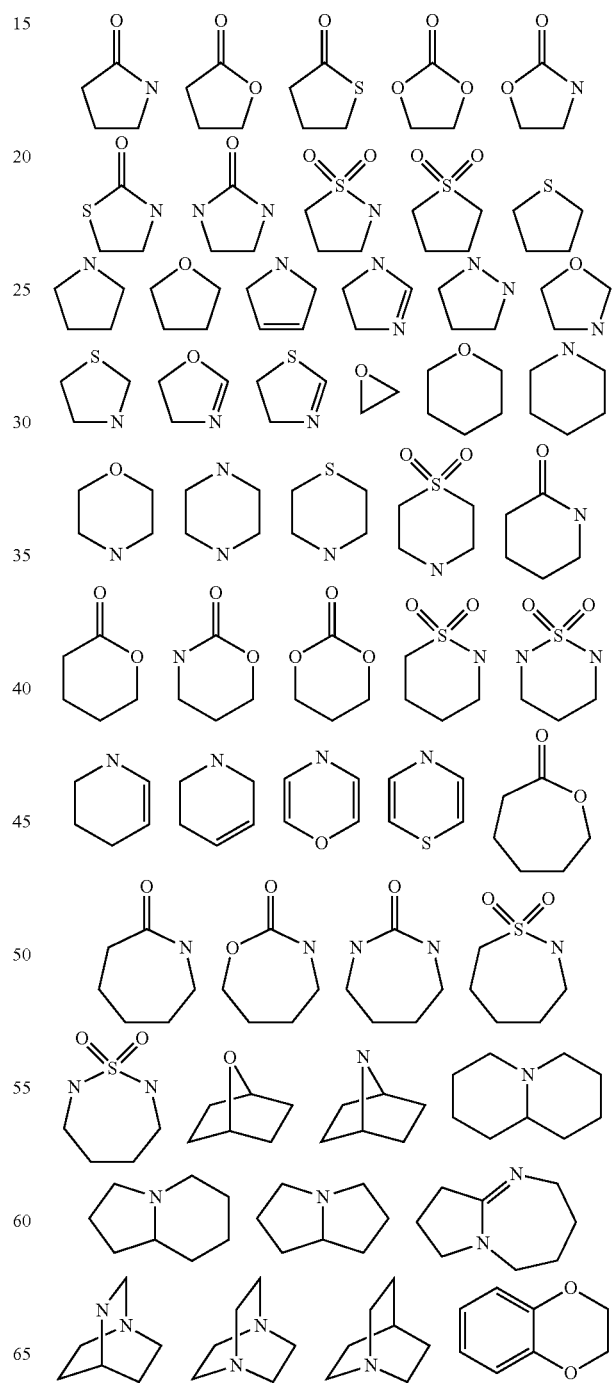

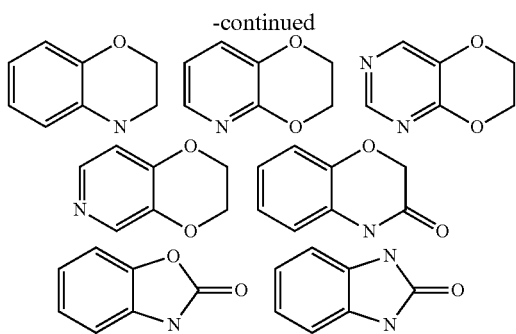

and the like. The term heteroalicyclic also includes all ring forms of the carbohydrates, including but not limited to the monosaccharides, the disaccharides and the oligosaccharides. Depending on the structure, a heterocycloalkyl group can be a monoradical or a diradical (i.e., a heterocycloalkylene group). Non-limiting examples of a heterocycloalkylene group include pyrrolidin-diyl, piperidin-diyl, morpholin-diyl, piperazin-diyl, tetrahydropyran-diyl, 2-oxopiperidin-diyl, or thiomorpholin-diyl, and the like.

The term "halo" or, alternatively, "halogen" or "halide" means fluoro, chloro, bromo and iodo.

The terms "haloalkyl," "haloalkenyl," "haloalkynyl" and "haloalkoxy" include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another.

The term "fluoroalkyl," as used herein, refers to alkyl group in which at least one hydrogen is replaced with a fluorine atom. Examples of fluoroalkyl groups include, but are not limited to, —CF$_3$, —CH$_2$CF$_3$, —CF$_2$CF$_3$, —CH$_2$CH$_2$CF$_3$ and the like.

As used herein, the terms "heteroalkyl" "heteroalkenyl" and "heteroalkynyl" include optionally substituted alkyl, alkenyl and alkynyl radicals in which one or more skeletal chain atoms is a heteroatom, e.g., oxygen, nitrogen, sulfur, silicon, phosphorus or combinations thereof. The heteroatom(s) may be placed at any interior position of the heteroalkyl group or at the position at which the heteroalkyl group is attached to the remainder of the molecule. Examples include, but are not limited to, —CH$_2$—O—CH$_3$, —CH$_2$—CH$_2$—O—CH$_3$, —CH$_2$—NH—CH$_3$, —CH$_2$—CH$_2$—NH—CH$_3$, —CH$_2$—N(CH$_3$)—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —Si(CH$_3$)$_3$, —CH$_2$—CH═N—OCH$_3$, and —CH═CH—N(CH$_3$)—CH$_3$. In addition, up to two heteroatoms may be consecutive, such as, by way of example, —CH$_2$—NH—OCH$_3$ and —CH$_2$—O—Si(CH$_3$)$_3$.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

The term "bond" or "single bond" refers to a chemical bond between two atoms, or two moieties when the atoms joined by the bond are considered to be part of larger substructure.

An "alkoxy" group refers to a —O(alkyl) group, where alkyl is as defined herein. Non-limiting examples of an alkoxy group include, but are not limited to, methoxy, ethoxy, n-propoxy, sec-butoxy, t-butoxy, n-hexyloxy and the like.

"Hydroxyalkyl" refers to an alkyl radical, as defined herein, substituted with at least one hydroxy group. Non-limiting examples of a hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl.

"Alkoxyalkyl" refers to an alkyl radical, as defined herein, substituted with an alkoxy group, as defined herein.

An "alkenyloxy" group refers to a —O(alkenyl) group, where alkenyl is as defined herein.

An "aryloxy" group refers to an —O(aryl) group, where aryl is as defined herein.

The term "amino" refers to the group —NH$_2$.

The term "alkylamino" or "alkylamine" refers to a group —NHR$^{20}$, where R$^{20}$ represents an alkyl group as defined herein. Alkylamino groups can be substituted or unsubstituted. Non-limiting examples of a dialkylamino group include methylamino, ethylamino, propylamino, isopropylamino, butylamino, but-3-enylamino, [(Z)-but-2-enyl]-methyl-amino, hexylamino and the like.

The term "dialkylamino" or "dialkylamine" refers to a group —NR$^{21}$R$^{22}$, where each R$^{21}$ and R$^{22}$ group independently is alkyl, cycloalkyl, aryl, cycloheteroalkyl, or heteroaryl group as defined herein. In certain embodiments, the R$^{21}$ and R$^{22}$ groups, taken together with the N atom to which they are attached, may form a cyclic ring system, particularly a 5 or 6 membered nitrogen containing heterocyclic. Dialkylamino groups can be substituted or unsubstituted. Non-limiting examples of a dialkylamino group include dimethylamino, diethylamino, ethyl(methyl)amino butyl(ethyl)amino, 1-butenyll(ethyl)amino, [(Z)-but-2-enyl]-methyl-amino, dibutylamino, hexyl(methyl)amino, cyclopentyl(methyl)amino, cyclopent-2-en-1-yl(methyl)amino, morpholino, methylpiperazino and the like.

The term "arylamino" or "arylamine" refers to a group —NR$^{23}$R$^{24}$, where the R$^{23}$ is aryl as defined herein and the R$^{24}$ group is hydrogen, alkyl, cycloalkyl, aryl, cycloheteroalkyl, or heteroaryl group as defined herein. Arylamino groups can be substituted or unsubstituted. Non-limiting examples of an arylamino group include phenylamino, tolylamino, 3-methoxyphenylamino, 4-phenylphenylamino, 4-trifluomethylphenylamino, 3-methoxyphenyl(methyl)amino, 2-fluomethylphenylamino, 3-phenylphenylamino, and the like.

The term "heteroarylamino" or "heteroarylamine" refers to a group —NR$^{25}$R$^{26}$, where the R$^{25}$ is heteroaryl as defined herein and the R$^{26}$ group is hydrogen, alkyl, cycloalkyl, aryl, cycloheteroalkyl, or heteroaryl group as defined herein. Heterorylamino groups can be substituted or unsubstituted. Non-limiting examples of an heteroarylamino group include pyrimidin-2-yl-amino, pyrimidin-4-yl-amino, pyrimidin-5-yl-amino, (6-methylpyrimidin-2-yl)amino (4,6-dimethylpyrimidin-2-yl)amino, (4-fluoro-6-methyl-pyrimidin-2-yl)amino, (4-methoxy-6-methyl-pyrimidin-2-yl)amino, (4-cyanopyrimidin-2-yl)amino, [4-(trifluoromethyl)pyrimidin-2-yl]amino, [4-(dimethylamino)-5-fluoro-pyrimidin-2-yl]amino, [4-(3-pyridyl)pyrimidin-2-yl]amino, [4-(3,5-dimethylpyrazol-1-yl)pyrimidin-2-yl]amino, [4-(3,5-dimethylpyrazol-1-yl)-6-methyl-pyrimidin-2-yl]amino, [4-(2,4-dimethylthiazol-5-yl)pyrimidin-2-yl]amino, [4-(2-methyl-1,2,4-triazol-3-yl)pyrimidin-2-yl]amino, 6-(1-methylpyrazol-4-yl)-2-pyridyl]amino, [6-(4-cyclopropyl-1,2,4-triazol-3-yl)-2-pyridyl]amino, [6-(4-isopropyl-1,2,4-triazol-3-yl)-2-pyridyl]amino, [2-(3-pyridyl)pyrimidin-4-yl]amino, [5-cyano-2-(3-pyridyl)pyrimidin-4-yl]amino, (6-fluoro-2-morpholino-pyrimidin-4-yl)amino, (4,6-dimethylfuro[2,3-d]pyrimidin-2-yl)amino, (6-methylfuro[2,3-d]pyrimidin-2-yl)amino, 1H-pyrazol-5-yl-amino, 1H-pyrazol-4-yl-amino, furo[2,3-d]pyrimidin-2-yl-amino, pyridin-2-yl-amino, pyridin-3-yl-amino, or pyridin-4-yl-amino.

"Alkylaminoalkyl" refers to an alkyl radical, as defined herein, substituted with an alkylamine, as defined herein.

The term "acylamino" refers to a radical —N($R^{27}$)—C(=O)$R^{28}$ where $R^{27}$ is hydrogen or alkyl as defined herein, and $R^{28}$ is hydrogen, alkyl, alkenyl, alkynyl, cycloalkyl, heterocycloalkyl, arylalkyl, heteroalkyl, heteroarylalkyl, aryl, or heteroaryl as defined herein. Depending on the structure, the acylamino group would also be known as alkylcarbonylamino, arylcarbonylamino or heteroarylcarbonylamino. Acylamino groups can be substituted or unsubstituted. Non-limiting examples of an acylamino group include formylamino, acetylamino, acetyl(methyl)amino, cyclohexylcarbonylamino, cyclohexylmethyl-carbonylamino, benzylcarbonylamino, methyl(benzylcarbonyl)amino, benzoylamino, benzoyl(methyl)amino, (3-methoxybenzoyl)-methyl-amino, (4-methoxypyridine-2-carbonyl)-amino, pyridine-2-carbonylamino, pyridine-2-carbonyl(methyl)amino, and the like.

The term "aminocarbonyl" refers to a radical —C(=O)N$R^{29}R^{30}$ where $R^{29}$ and $R^{30}$ are each independently hydrogen, alkyl, alkenyl, alkynyl, cycloalkyl, heterocycloalkyl, arylalkyl, heteroalkyl, heteroarylalkyl, aryl, or heteroaryl as defined herein. In certain embodiments, the $R^{29}$ and $R^{30}$ groups, taken together with the N atom to which they are attached, may form a cyclic ring system, particularly a 5 or 6 membered nitrogen containing heterocyclic. Depending on the structure, the aminocarbonyl group would also be known alkylaminocarbonyl, dialkylaminocarbonyl, arylaminocarbonyl, heteroarylaminocarbonyl. Aminocarbonyl groups can be substituted or unsubstituted. The aminocarbonyl group would also be known as carbamoyl. Non-limiting examples of an aminocarbonyl group include aminocarbonyl (—C(=O)NH$_2$), dimethylaminocarbonyl, 2-hydroxyethylaminocarbonyl, 2-methoxyethylaminocarbonyl, 2-dimethylaminoethylaminocarbonyl, benzylaminocarbonyl, phenylaminocarbonyl, phenyl(methyl)aminocarbonyl, tolyl(methyl)aminocarbonyl, piperidine-1-carbonyl, morpholine-4-carbonyl, 4-methylpiperazine-1-carbonyl, pyrimidin-2-yl-aminocarbonyl, 1H-pyrazol-5-yl-aminocarbonyl, and the like.

The "acylamino" group and the "aminocarbonyl" group are, chemically speaking, amide moieties. An amide moiety may form a linkage between an amino acid or a peptide molecule and a compound described herein, thereby forming a prodrug. Any amine, or carboxyl side chain on the compounds described herein can be amidified. The procedures and specific groups to make such amides are known to those of skill in the art and can readily be found in reference sources such as Greene and Wuts, Protective Groups in Organic Synthesis, 3rd Ed., John Wiley & Sons, New York, N.Y., 1999, and Benoiton N. Leo, Chemistry of Peptide synthesis, CRC Press 2005, which are incorporated herein by reference in its entirety.

"Carboxy" means a —C(=O)—OH radical.

The term "acyl" refers to a radical —C(=O)—$R^{31}$ where $R^{31}$ is hydrogen, alkyl, alkenyl, alkynyl, cycloalkyl, heterocycloalkyl, arylalkyl, heteroalkyl, heteroarylalkyl, aryl, or heteroaryl as defined herein. Acyl groups can be substituted or unsubstituted. Non-limiting examples of an acyl group include acetyl, propanoyl, hexanoxyl, octanoyl, decanoyl, benzoyl, pyridine-3-carbonyl, 4-methoxybenzoyl, 2,2,2-trifluoroacetyl, 2-hydroxyacetyl, 9,9,10,10,10-pentafluorodecanoyl, 2-(2-hydroxyethoxy)acetyl or the like.

The term "alkoxycarbonyl" refers to a radical —C(=O)—O$R^{32}$ where $R^{32}$ is alkyl, alkenyl, alkynyl, cycloalkyl, heterocycloalkyl, arylalkyl, heteroalkyl, or heteroarylalkyl, as defined herein. Alcoxycarbonyl groups can be substituted or unsubstituted. Non-limiting examples of an alkoxycarbonyl group include methoxycarbonyl, ethoxycarbonyl, propyloxycarbonyl, allyloxycarbonyl, 2-hyroxyethoxycarbonyl, 2-methoxyethoxycarbonyl, 2-dimethylaminoethoxyarbonyl, 3-(dimethylamino)propoxycarbonyl, benzyloxycarbonyl, 2-(3-methoxyphenyl)ethoxycarbonyl, 2-morpholinoethoxycarbonyl, or the like.

The term "aryloxycarbonyl" refers to a radical —C(=O)—O—$R^{33}$ where $R^{33}$ is aryl as defined herein. Aryloxycarbonyl groups can be substituted or unsubstituted.

The term "heteroaryloxycarbonyl" refers to a radical —C(=O)—O—$R^{34}$ where $R^{34}$ is heteroaryl as defined herein. Heteroaryloxycarbonyl groups can be substituted or unsubstituted.

The term "acyloxy" refers to a radical —O—C(=O)—$R^{31}$ group of wherein $R^{31}$ is as defined above. Acyloxy groups can be substituted or unsubstituted.

The alcoxycarbonyl, the aryloxycarbonyl, the heteroaryloxycarbonyl and the acyloxy groups belong to a family of functional groups known as "ester" groups. The procedures (e.g. esterification reaction) and specific groups to make esters (i.e. alcoxycarbonyl, aryloxycarbonyl, heteroaryloxycarbonyl or acyloxy groups), are known to those of skill in the art and can readily be found in reference sources such as Greene and Wuts, Protective Groups in Organic Synthesis, 3rd Ed., John Wiley & Sons, New York, N.Y., 1999, which is incorporated herein by reference in its entirety. Any hydroxy, or carboxyl side chain on the compounds described herein can be esterified.

The term "aminocarbonylamino" refers to a radical —N($R^{27}$)—C(=O)—N$R^{29}R^{30}$ where $R^{27}$, $R^{29}$ and $R^{30}$ are each independently as described herein. Aminocarbonylamino groups can be substituted or unsubstituted.

The term "aminocarbonyloxy" refers to a radical —O—C(=O)—N$R^{29}R^{30}$ where $R^{29}$ and $R^{30}$ are as defined above. Aminocarbonyloxy groups can be substituted or unsubstituted.

The term "alkoxycarbonylamino" refers to a radical —N($R^{27}$)—C(=O)—O$R^{35}$ where $R^{27}$ is as defined above, and $R^{35}$ is alkyl, alkenyl, alkynyl, cycloalkyl, heterocycloalkyl, arylalkyl, heteroalkyl, or heteroarylalkyl, as defined herein. Alkoxycarbonylamino groups can be substituted or unsubstituted. A representative example of an alkoxycarbonylamino group, but not limited to, is tert-butoxycarbonylamino or 9H-fluoren-9-yloxycarbonylamino.

The term "aryloxycarbonylamino" refers to a radical —N($R^{27}$)—C(=O)—O$R^{36}$ where $R^{27}$ is as defined above, and $R^{36}$ is aryl as defined herein. Aryloxycarbonylamino groups can be substituted or unsubstituted.

The term "heteroaryloxycarbonylamino" refers to a radical —N($R^{27}$)—C(=O)—O$R^{37}$ where $R^{27}$ is as defined above, and $R^{37}$ is heteroaryl as defined herein. Heteroarylalkoxycarbonylamino groups can be substituted or unsubstituted.

The terms "moiety", "chemical moiety", "group" and "chemical group", as used herein refer to a specific segment or functional group of a molecule. Chemical moieties are often recognized chemical entities embedded in or appended to a molecule.

The term "Sulfonyl" refers to the divalent radical —S(=O)$_2$—. "Substituted sulfonyl" group refers to a radical —S(=O)$_2$—$R^{38}$, wherein $R^{38}$ is alkyl, alkenyl, alkynyl, cycloalkyl, heterocycloalkyl, arylalkyl, heteroalkyl, heteroarylalkyl, aryl, or heteroaryl as defined herein.

The term "aminosulfonyl" or "sulfonamide" refers to the group —S(=O)$_2$NH$_2$. "substituted aminosulfonyl" or "substituted sulfonamide" refers to a radical such as —S(=O)$_2$N$R^{29}R^{30}$ wherein $R^{29}$ and $R^{30}$ are each independently as described herein.

The term "sulfonylamino" means and includes a sulfonyl group bonded to an amino group —N($R^{27}$)—S(=O)$_2R^{38}$, wherein $R^{27}$ and $R^{38}$ are each independently as described herein. Sulfonylamino groups can be substituted or unsubstituted.

The term "Sulfo" refers to the —S(=O)$_2$OH. "Substituted sulfonyl" group refers to a radical —S(=O)$_2$O$R^{31}$, wherein $R^{31}$ is as defined above.

The term "sulfinyl" refers to the diradical —S(=O)—. "substituted sulfinyl" refers to a radical such as —S(=O) $R^{38}$, wherein $R^{38}$ is any substituent as defined herein.

The term "sulfanyl" refers to the divalent radical —S—. "Substituted sulfanyl" refers to a radical such as —SR, wherein $R^{38}$ is any substituent as defined herein. Non limiting examples of a substituted sulfanyl group include methylthio, ethylthio, propylthio, isopropylthio, butylthio, isobutylthio, tert-butylthio, but-3-enylsulfanyl, hexylthio, benzylthio, phenylthio, (3-methoxyphenyl)sulfanyl, 2-pyridylsulfanyl or the like.

The term "thiol" as used herein refers to the group —SH.

The term "hydroxyl" as used herein refers to the group —OH.

The term "carbonyl" as used herein refers to the divalent radical —C(=O)—.

An "isocyanato" group refers to a —N=C=O group.

An "isothiocyanato" group refers to a —N=C=S group.

As used herein, the term "trihalomethanesulfonyl" refers to a group of formula —S(=O)$_2$—CX$_3$, wherein X is a halogen.

As used herein, the term "cyano" refers to a group of formula —CN.

"Cyanoalkyl" means an alkyl radical, as defined herein, substituted with at least one cyano group.

As used herein, the term "Azido" refers to the radical —N$_3$.

As used herein, the term "Nitro" refers to the radical —NO$_2$.

As used herein, the term "O-thiocarbamyl" refers to a group of formula —OC(=S)NR$_2$.

As used herein, the term "N-thiocarbamyl" refers to a group of formula —N(H)—C(=S)OR.

The term "substituted" or "optionally substituted" means that the referenced group may be substituted with one or more additional group(s) individually and independently selected from alkyl, alkenyl, alkynyl, cycloalkyl, aryl, heteroaryl, arylalkyl, heteraylalkyl, cycloalkyalkyl, heteroalicyclic, heterocycloalkyalkyl, hydroxy, alkoxy, aryloxy, alkylthio, arylthio, alkylsulfoxide, arylsulfoxide, alkylsulfone, arylsulfone, cyano, halo, acyl, nitro, haloalkyl, fluoroalkyl, amino, including mono- and di-substituted amino groups, and the protected derivatives thereof. By way of example an optional substituents may be L″R″′, wherein each L″ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, -(substituted or unsubstituted C$_1$-C$_6$ alkyl), or -(substituted or unsubstituted C$_2$-C$_6$ alkenyl); and each R″′ is independently selected from H, (substituted or unsubstituted C$_1$-C$_4$ alkyl), (substituted or unsubstituted C$_3$-C$_6$ cycloalkyl), heteroaryl, or heteroalkyl. The protecting groups that may form the protective derivatives of the above substituents are known to those of skill in the art and may be found in references such as Greene and Wuts, above.

I. Other Definitions

Some other terms or phrases used in the present specification are defined below:

The term "acceptable" or "pharmaceutically acceptable", with respect to a material such as a salt, a carrier, an excipient, or diluent, or to a formulation, a composition or an ingredient, as used herein, means having no persistent detrimental effect on the general health of the subject being treated or does not abrogate the biological activity or properties of the compound, and is relatively nontoxic, i.e., the material, formulation, composition or ingredient may be administered to a subject without causing undesirable biological effects or interacting in a deleterious manner with any of the components of the composition in which it is contained.

The term "prodrug" as used herein, refers to a drug precursor that, following administration to an individual and subsequent absorption, is converted to an active, or a more active species via some process, such as conversion by a metabolic pathway. Thus, the term encompasses any derivative of a compound, which, upon administration to a recipient, is capable of providing, either directly or indirectly, a compound of this invention or a pharmaceutically active metabolite or residue thereof. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they may be easier to administer than the parent drug. They may, for instance, be bioavailable by oral administration whereas the parent is not. Particularly favored derivatives or prodrugs are those that increase the bioavailability of the compounds of this invention when such compounds are administered to an individual (e.g. by allowing an orally administered compound to be more readily absorbed into the blood) or which enhance delivery of the parent compound to a biological compartment (e.g. the brain or lymphatic system).

The term "solvate" means a compound of the present invention described herein, that further includes a stoichiometric or non-stoichiometric amount of solvent bound by non-covalent intermolecular forces. In some embodiments solvates may be formed during the process of crystallization with solvents such as water, ethanol, and the like. Non-limitative examples of solvates include hydrates that may be formed when the solvent is water, and alcoholates that may be formed when the solvent is alcohol.

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds of the invention, or by separately reacting a purified compound in its free base form with a suitable organic or inorganic acid, and isolating the salt thus formed.

The terms "treat," "treating" or "treatment," and other grammatical equivalents as used herein, include alleviating, abating or ameliorating a disease or condition or one or more symptoms thereof, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the individual, notwithstanding that the individual is still be afflicted with the underlying disorder. For prophylactic benefit, the compositions are administered to an individual at risk of developing a particular disease, or to an individual reporting one or more of the physiological symptoms of a disease, even though a diagnosis of this disease has not been made.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "inhibiting, inhibition and/or retardation" are intended to refer for the purposes of the present invention to as follows: "partial or complete inhibiting, inhibition and/or retardation". In this case, it is within the specialist knowledge of the average person skilled in the art to measure and determine such inhibiting, inhibition, and/or retardation by means of the usual methods of measurement and determination. Thus, a partial inhibiting, inhibition and/or retardation, for example, can be measured and determined in relation to a complete inhibiting, inhibition and/or retardation.

As used herein, the terms "subject" and "patient" are used interchangeably to refer to an individual being treated for a proliferative disease such as cancer or non-neoplastic condition. In a specific embodiment, the individual is a primate, more specifically a human. In another specific specific, the individual is an animal, including but not limited to, cow, pig, sheep, goat, horse, dog, cat, rabbit, rat, or mouse.

The term "patient", "subject" or "individual" are used interchangeably. As used herein, they refer to individuals suffering from a disease; specifically from a disease associated with abnormal cell proliferation (such as cancer or non-neoplastic disorder, and the like) encompasses mammals and non-mammals. None of the terms require that the individual be under the care and/or supervision of a medical professional. Mammals are any member of the Mammalian class, including but not limited to humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some embodiments of the methods and compositions provided herein, the individual is a mammal. In preferred embodiments, the individual is a human.

The terms "proliferative disorder" and "proliferative disease" refer to disorders associated with abnormal cell proliferation, such as cancer or dysplasia. The proliferative disease may be a benign or malignant proliferative disease, e.g. benign prostatic hyperplasia, or a neoplastic disease, preferably a malignant proliferative disease, e.g. a cancer, e.g. a solid tumor, particularly an advanced solid tumor.

The terms "tumor," "neoplasm," and "neoplastic disorder or disease" are used interchangeably herein and are meant to refer to unwanted cell proliferation of one or more subset of cells in a multicellular organism resulting in harm (i.e., discomfort or decreased life expectancy) to the multicellular organisms. In certain embodiments, a tumor can be benign (noncancerous) or malignant (cancerous) including precancerous lesions.

The term "cancer" is meant to refer to a malignant neoplasm, which is characterized by uncontrolled cell proliferation where cells have lost their normal regulatory controls that would otherwise govern the rate of cell growth. These unregulated, dividing cells can spread throughout the body and invade normal tissues in a process referred to as "metastasis."

The term "neoplastic" refers to those cells having the capacity for autonomous growth, i.e., an abnormal state or condition characterized by rapidly proliferating cell growth. A neoplastic disease state may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness.

The term "inhibit tumor growth" and its grammatical equivalents refer to any mechanism by which abnormal cells proliferation can be inhibited. In certain embodiments, abnormal cells proliferation is inhibited by slowing growth of abnormal cells. In certain embodiments, abnormal cells proliferation is inhibited by halting growth of abnormal cells such as cancer cells. In certain embodiments, tumor cell growth is inhibited by killing abnormal cells such as cancer cells. In certain embodiments, abnormal cells proliferation is inhibited by inducing apoptosis of abnormal cells such as cancer cells. In certain embodiments, abnormal cells proliferation is inhibited by preventing migration of abnormal cells. In certain embodiments, abnormal cells proliferation is inhibited by preventing invasion of abnormal cells such as cancer cells.

The term "cancer stem cells (CSCs)" as used herein refers to cancer cells (found within tumors or hematological cancers) that possess characteristics associated with normal stem cells, specifically the ability to give rise to all cell types found in a particular cancer sample. CSCs may generate tumors through the stem cell processes of self-renewal and differentiation into multiple cell types. In the more recent literature the initial term "cancer stem cells" has been replaced by the terms "tumor stem-like cells" or "tumor initiating cells". Thus, the terms "tumor stem-like cells" or "tumor initiating cells" are essentially synonymous to the term "cancer stem cells".

The term "radiation therapy", "radiotherapeutic treatment" or "radiotherapy" is a term commonly used in the art to refer to multiple types of radiation therapy including internal and external radiation therapy, radioimmunotherapy, and the use of various types of radiation including X-rays, gamma rays, alpha particles, beta particles, photons, electrons, neutrons, radioisotopes, and other forms of ionizing radiation. Preferably, the radiotherapy involves the use of X-rays.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, excipients and the like.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, Remington: The Science and Practice of Pharmacy, 22th ed.; Lippincott Williams & Wilkins: Philadelphia, Pa., 2012; the Handbook of Pharmaceutical Excipients, 6$^{th}$ edition, Rowe et al., Eds., American Pharmaceuticals Association (2011); The Pharmaceutical Press and the American Pharmaceutical Association: 2009; Handbook of Pharmaceutical Additives, 3rd ed.; Ash and Ash Eds.; Gower Publishing Company: 2007; and Pharmaceutical Preformulation and Formulation, 2nd ed.; Gibson Ed.; CRC Press LLC: Boca Raton, Fla., 2009.

The terms "pharmaceutical combination", "administering an additional therapy", "administering an additional therapeutic agent" and the like, as used herein, refer to a pharmaceutical therapy resulting from the mixing or combining of more than one active ingredient and includes both fixed and non-fixed combinations of the active ingredients. The term "fixed combination" means that at least one of the compounds described herein, and at least one co-agent, are both administered to an individual simultaneously in the form of a single entity or dosage. The term "non-fixed combination" means that at least one of the compounds described herein, and at least one co-agent, are administered to an individual as separate entities either simultaneously, concurrently or sequentially with variable intervening time limits, wherein such administration provides effective levels of the two or more compounds in the body of the individual. These also apply to cocktail therapies, e.g. the administration of three or more active ingredients.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In preferred embodiments, the compounds and compositions described herein are administered orally.

The terms "co-administration", "administered in combination with" and their grammatical equivalents or the like, as used herein, are meant to encompass administration of the selected therapeutic agents to a single individual, and are intended to include treatment regimens in which the agents are administered by the same or different route of administration or at the same or different times. In some embodiments the compounds described herein will be co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds of the invention and the other agent(s) are administered in a single composition. In some embodiments, compounds of the invention and the other agent(s) are admixed in the composition.

The terms "active ingredient", "active substance" or "active agent" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount may differ from one individual to another. An appropriate "effective" amount in any individual case may be determined using techniques, such as a dose escalation study.

The term "composition", as in pharmaceutical composition, for the purposes of this invention is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

As used herein, IC50 or EC50 refers to a dosage, concentration or amount of a particular test compound that elicits a dose-dependent response at 50% of maximal expression of a particular response that is induced, provoked or potentiated by the particular test compound.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

It is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

II. Compounds of the Invention

Described herein are compounds of formula (I), pharmaceutically acceptable salts, hydrates, solvates, prodrugs, polymorphs, tautomers, isotopic variants, and stereoisomers thereof.

The compounds of the present invention generally fall within the formula (I) provided below:

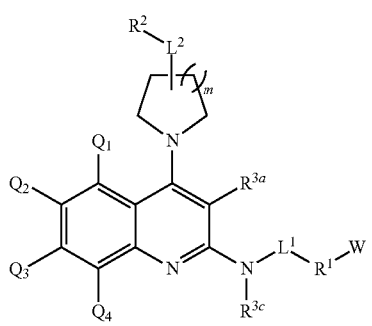

(I)

or a pharmaceutically acceptable salt, hydrate, solvate, or prodrug thereof, or an isotopic variant, tautomer, or stereoisomer thereof.

According to the invention, m is 0, 1, 2, 3, or 4

According to the invention, d is an integer of 0 to 6, with the proviso that if m is 0, then d is independently 0, 1 or 2; if m is 1, then d is independently 0, 1, 2 or 3; if m is 2, then d is independently 0, 1, 2, 3 or 4; if m is 3, then d is independently 0, 1, 2, 3, 4 or 5 or if m is 4 then d is independently 0, 1, 2, 3, 4, 5 or 6.

$L^1$ according to the invention is single bond, alkylene, alkenylene, or alkynylene; the groups alkylene, alkenylene, and alkynylene being optionally substituted. In some embodiments $L^1$ is a single bond. In other embodiments $L^1$ is alkylene, alkenylene or alkynylene. In certain specific embodiments $L^1$ is $C_1$-$C_6$ alkylene, $C_2$-$C_6$ alkenylene, or $C_2$-$C_6$ alkynylene. Particularly, $L^1$ is single bond, or methylene (—CH$_2$)—.

$R^1$ according to the invention is aryl, heteroaryl, arylene, or heteroarylene; the groups aryl, heteroaryl, arylene, or heteroarylene being optionally substituted. According to one embodiment $R^1$ is arylene or heteroarylene, optionally substituted.

Specific examples of arylene for $R^1$ include phenylene-1,4-diyl, 3-methyl-phenylene-1,4-diyl, 2,4-methyl-phenylene-1,4-diyl, 3-methoxy-phenylene-1,4-diyl, 2-fluoro-phenylene-1,4-diyl, 3-fluoro-phenylene-1,4-diyl, phenylene-1,3-diyl, 4-methyl-phenylene-1,3-diyl, 4-methoxy-phenylene-1,3-diyl, 5-methyl-phenylene-1,3-diyl, and naphthalene-1,4-diyl.

Specific examples of heteroarylene for $R^1$ include furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyrazole-3,4-diyl, pyridine-2,3-diyl, pyridine-2,4-diyl, pyridine-2,5-diyl, pyridine-2,5-diyl, 6-methyl-pyridine-2,5-diyl, pyridine-2,6-diyl, pyrimidine-2,4-diyl, pyrimidine-2,5-diyl, quinoline-2,3-diyl, pyridazine-diyl, triazine-diyl, and the like.

According to the invention, $L^2$ is single bond, carbonyl, alkylene, alkenylene, or alkynylene; the groups alkylene, alkenylene, and alkynylene being optionally substituted. In certain specific embodiments, $L^2$ is a single bond. In some embodiments $L^2$ is other than a single bond. In other specific embodiments $L^2$ is carbonyl. In particular embodiments $L^2$ is $C_1$-$C_6$ alkylene, $C_2$-$C_6$ alkenylene, or $C_2$-$C_6$ alkynylene. In some preferred embodiments, $L^2$ is single bond, or carbonyl (—C(=O)—).

$R^2$ according to the invention is hydroxyl, alkoxy, aryloxy, or heteroaryloxy, alkoxycarbonylamino, aryloxycarbonylamino, heteroaryloxycarbonylamino, or alkylaminocarbonylamino, arylaminocarbonylamino, heteroarylaminocarbonylamino, or NR$^5$R$^6$ wherein each R$^5$ and R$^6$ is independently selected from H, alkyl, cycloalkyl, aryl, heteroaryl, or heterocycloalkyl, or R$^5$ and R$^6$ together with the nitrogen atom to which they are attached are combined may form a substituted or unsubstituted heterocyclic ring. For R$^2$, the groups alkoxy, aryloxy, heteroaryloxy, alkyl, cycloalkyl, aryl, heteroaryl, heterocycloalkyl, alkoxycarbonylamino, aryloxycarbonylamino, heteroaryloxycarbonylamino, alkylaminocarbonylamino, arylaminocarbonylamino, and heteroarylaminocarbonylamino are optionally substituted.

According to the invention, $Q_1$, $Q_2$, $Q_3$ and $Q_4$ are each independently selected from the group consisting of: H, hydroxyl, halo, amino, nitro, thiol, carboxyl, cyano, azido, alkyl, alkenyl, alkynyl, cycloalkyl, cycloalkenyl, arylalkyl, heterocycloalkyl, aryl, heteroaryl, alkoxy, aryloxy, heteroaryloxy, sulfanyl, alkylamino, dialkylamino, arylamino, heteroarylamino, acyl, acylamino, aminocarbonyl, alkoxycarbonyl, aryloxycarbonyl, heteroaryloxycarbonyl, substituted sulfo, substituted sulfonyl, substituted sulfinyl, aminosulfonyl, sulfonylamino, aminocarbonylamino, aminocarbonyloxy, alkoxycarbonylamino, aryloxycarbonylamino, and heteroaryloxycarbonylamino. For each of $Q_1$, $Q_2$, $Q_3$ and $Q_4$, the groups, alkyl, alkenyl, alkynyl, cycloalkyl, cycloalkenyl, arylalkyl, heterocycloalkyl, aryl, heteroaryl, alkoxy, aryloxy, heteroaryloxy, sulfanyl, alkylamino, dialkylamino, arylamino, heteroarylamino, acyl, acylamino, aminocarbonyl, alkoxycarbonyl, aryloxycarbonyl, heteroaryloxycarbonyl, aminosulfonyl, sulfonylamino, aminocarbonylamino, aminocarbonyloxy, alkoxycarbonylamino, aryloxycarbonylamino, and heteroaryloxycarbonylamino are optionally substituted. In some embodiments, $Q_1$, $Q_2$, $Q_3$ and $Q_4$ are each independently selected from the group consisting of: H, hydroxyl, halo, amino, nitro, thiol, carboxyl, cyano, azido, $C_1$-$C_6$ alkyl, $C_2$-$C_6$ alkenyl, $C_2$-$C_6$ alkynyl, $C_3$-$C_7$ cycloalkyl, $C_3$-$C_7$ cycloalkyl, $C_3$-$C_7$ cycloalkenyl, aryl-$C_1$-$C_6$ alkyl, $C_1$-$C_6$ alkoxy, $C_1$-$C_6$ alkylamino and $C_1$-$C_6$ dialkylamino. In specific embodiments, at least two of $Q_1$, $Q_2$, $Q_3$ and $Q_4$ are other than H and are distinct.

$R^{3a}$ according to the invention is selected from the group consisting of H, halo, cyano, alkyl, aryl, heteroaryl, cycloalkyl, heterocycloalkyl, alkoxy, alkoxycarbonyl, aryloxycarbonyl, heteroaryloxycarbonyl, and aminocarbonyl; the groups alkyl, aryl, heteroaryl, cycloalkyl, heterocycloalkyl, alkoxy, alkoxycarbonyl, aryloxycarbonyl, heteroaryloxycarbonyl, and aminocarbonyl being optionally substituted. In some embodiments $R^{3a}$ is H. In other embodiments $R^{3a}$ is halo, cyano, $C_1$-$C_6$ alkyl or $C_1$-$C_6$ alkoxycarbonyl.

According to the invention, each $R^{3b}$ is independently selected from the group consisting of H, hydroxyl, halo, azido, amino, nitro, thiol, cyano, carboxyl, alkyl, alkenyl, alkynyl, arylalkyl, aryl, heteroaryl, cycloalkyl, cycloalkenyl, heterocycloalkyl. For each of $R^{3b}$, the groups, alkyl, alkenyl, alkynyl, cycloalkyl, cycloalkenyl, arylalkyl, heterocycloalkyl, aryl, heteroaryl, are optionally substituted. In some embodiments, each $R^{3b}$ is H. In some specific embodiments, at least one of $R^{3b}$ is other than H. In other embodiments at least one of $R^{3b}$ is $C_1$-$C_6$ alkyl.

$R^{3c}$ according to the invention is H, alkyl, alkenyl, alkynyl, cycloalkyl, cycloalkenyl, or heterocycloalkyl, provided that when $R^{3c}$ is H, $L^2$ is other than a single bond or $R^2$ is other than $NR^5R^6$ or $R^{3a}$ is other than H or at least two of $Q_1$, $Q_2$, $Q_3$ and $Q_4$ are other than H and are distinct. For $R^{3c}$ the groups alkyl, alkenyl, alkynyl, cycloalkyl, cycloalkenyl, heterocycloalkyl are optionally substituted. In some embodiments, $R^{3C}$ is H. In other embodiments $R^{3a}$ is $C_1$-$C_6$ alkyl, $C_2$-$C_6$ alkenyl, $C_2$-$C_6$ alkynyl, $C_3$-$C_7$ cycloalkyl or $C_3$-$C_7$ cycloalkenyl.

According to the invention, W is optionally present and if present is selected in the group consisting of H, hydroxyl, halo, azido, amino, nitro, thiol, cyano, carboxyl, alkyl, alkenyl, alkynyl, arylalkyl, aryl, heteroaryl, cycloalkyl, cycloalkenyl, heterocycloalkyl, alkoxy, aryloxy, heteroaryloxy, sulfanyl, alkylamino, dialkylamino, arylamino, heteroarylamino, acyl, acylamino, aminocarbonyl, alkoxycarbonyl, aryloxycarbonyl, heteroaryloxycarbonyl, a substituted sulfo, a substituted sulfonyl, a substituted sulfinyl, aminosulfonyl, sulfonylamino, alkylsulfonyl, arylsulfonyl, aminocarbonylamino, aminocarbonyloxy, alkoxycarbonylamino, aryloxycarbonylamino, and heteroaryloxycarbonylamino. For W, the groups, alkyl, alkenyl, alkynyl, cycloalkyl, cycloalkenyl, arylalkyl, heterocycloalkyl, aryl, heteroaryl, alkoxy, aryloxy, heteroaryloxy, sulfanyl, alkylamino, dialkylamino, arylamino, heteroarylamino, acyl, acylamino, aminocarbonyl, alkoxycarbonyl, aryloxycarbonyl, heteroaryloxycarbonyl, aminosulfonyl, sulfonylamino, aminocarbonylamino, aminocarbonyloxy, alkoxycarbonylamino, aryloxycarbonylamino, and heteroaryloxycarbonylamino, are optionally substituted. In some specific embodiments, W is halo, preferably chlore. In other specific embodiments W is substituted or unsubstituted heteroarylamino.

Pharmaceutically acceptable salts, hydrates, solvates, prodrugs, isotopic variants, tautomers, and stereoisomers of the compounds according to formula (I) are also contemplated by the present invention.

Any combination of two or more of the embodiments described herein is considered within the scope of the present invention.

The present invention provides a compound of Formula (I), wherein $L^1$ is a single bond, or substituted or unsubstituted alkylene.

The present invention provides a compound of Formula (I), wherein $L^2$ is a single bond, carbonyl, substituted or unsubstituted alkylene.

The present invention provides also a compound of formula (I), wherein $R^2$ is hydroxyl, substituted or unsubstituted alkoxy, substituted or unsubstituted aryloxy, substituted or unsubstituted heteroaryloxy, or $NR^5R^6$ wherein each $R^5$ and $R^6$ is independently H, substituted or unsubstituted alkyl, substituted or unsubstituted cycloalkyl, substituted or unsubstituted aryl, substituted or unsubstituted heteroaryl, or substituted or unsubstituted heterocycloalkyl, or $R^5$ and $R^6$ together with the nitrogen atom to which they are attached are combined to form a substituted or unsubstituted heterocyclic ring. In another preferred embodiment, the present invention provides a compound of formula (I), wherein m is 0, 1, or 2.

The present invention also provides a compound of formula (I), wherein: $R^{3a}$ is H, halo, cyano, substituted or unsubstituted alkyl or substituted or unsubstituted alkoxycarbonyl; and each $R^{3b}$ is independently H.

The present invention also provides a compound of formula (I), wherein: $R^{3c}$ is H, substituted or unsubstituted alkyl or substituted or unsubstituted cycloalkyl.

The present invention also provides a compound of formula (I), wherein: $Q_1$, $Q_2$, $Q_3$ and $Q_4$ are each independently H, halo, cyano, or substituted or unsubstituted alkyl.

Further, the present invention provides a compound of formula (I), wherein: $L^2$ is a single bond and $R^2$ is $NR^5R^6$.

The present invention also provides a compound of formula (I), wherein: $L^1$ is substituted or unsubstituted alkylene, substituted or unsubstituted alkenylene, or substituted or unsubstituted alkynylene, and $R^1$ is substituted or unsubstituted arylene.

The present invention also provides a compound of formula (I), wherein: $L^1$ is substituted or unsubstituted alkylene, substituted or unsubstituted alkenylene, or substituted or unsubstituted alkynylene, $R^1$ is substituted or unsubstituted arylene; and W is halo.

The present invention also provides a compound of formula (I), wherein the substituted or unsubstituted arylene, is substituted or unsubstituted phenylene-1,4-diyl, substituted or unsubstituted phenylene-1,3-diyl, or substituted or unsubstituted naphthalene-1,4-diyl.

Further the present invention, provides a compound of formula (I), wherein each $R^{3b}$ is H, and m is 0, 1, or 2, if m is 0 then d is 2; if m is 1 then d is independently 3; or if m is 2 then d is 4.

The present invention also provides a compound of formula (I), wherein $L^1$ is —$CH_2$—; and $R^1$ is substituted or unsubstituted arylene, wherein the substituted or unsubstituted arylene group is substituted or unsubstituted phenylene-1,4-diyl, substituted or unsubstituted phenylene-1,3-diyl, or substituted or unsubstituted naphthalene-1,4-diyl.

The present invention further provides a compound of formula (I), wherein $L^1$ is —$CH_2$—, $R^1$ is substituted or unsubstituted phenylene-1,4-diyl or substituted or unsubstituted phenylene-1,3-diyl, and $R^{3a}$ is H, halo, CN, a substituted or unsubstituted $C_1$-$C_6$ alkyl, or a substituted or unsubstituted alkoxycarbonyl.

The present invention also provides a compound of formula (I), wherein $L^1$ is a single bond, $R^1$ is substituted or unsubstituted arylene.

The present invention also provides a compound of formula (I), wherein W is substituted or unsubstituted heteroarylamino.

The present invention further provides a compound of formula (I), wherein $L^1$ is a single bond; $R^1$ is substituted or unsubstituted arylene; W is substituted or unsubstituted heteroarylamino, each $R^{3b}$ is H; m is 0, 1, or 2; if m is 0 then d is 2; if m is 1 then d is independently 3; or if m is 2 then d is 4.

The present invention also provides a compound of formula (I), wherein $R^1$ is substituted or unsubstituted phenylene-1,4-diyl, substituted or unsubstituted phenylene-1,3-diyl, or substituted or unsubstituted naphthalene-1,4-diyl; and $R^{3a}$ is halo, cyano, substituted or unsubstituted alkyl, or substituted or unsubstituted alkoxycarbonyl.

The present invention further provides a compound of formula (I), wherein $R^1$ is substituted or unsubstituted phenylene-1,4-diyl, or substituted or unsubstituted phenylene-1,3-diyl.

The present invention also provides a compound of formula (I), wherein $L^1$ is a single bond; $R^1$ is substituted or unsubstituted heteroarylene; and W is substituted or unsubstituted heteroarylamino.

Further, the present invention provides a compound of formula (I), wherein $L^1$ is a single bond; $R^1$ is substituted or unsubstituted heteroarylene; W is substituted or unsubstituted heteroarylamino; each $R^{3b}$ is H; m is 0, 1, or 2; if m is 0 then d is 2; if m is 1 then d is independently 3; or if m is 2 then d is 4.

The present invention also provides a compound of formula (I), wherein $R^1$ is substituted or unsubstituted pyridindiyl, substituted or unsubstituted pyrimidindiyl, substituted or unsubstituted pyrazindiyl, substituted or unsubstituted 1H-pyrazoldiyl, oxazoldiyl, or substituted or unsubstituted isoxazoldiyl; and $R^{3a}$ is halo, cyano, or a substituted or unsubstituted $C_1$-$C_6$ alkyl, a substituted or unsubstituted alkoxycarbonyl.

The present invention further provides a compound of formula (I), wherein $R^1$ is substituted or unsubstituted pyridine-2,4-diyl, substituted or unsubstituted pyridine-2,5-diyl, or substituted or unsubstituted pyridine-2,6-diyl. In yet a further preferred embodiment, the present invention provides a compound of formula (I), wherein W is pyrimidin-2-yl-amino, pyrimidin-4-yl-amino, pyrimidin-5-yl-amino, 1H-pyrazol-5-yl-amino, 1H-pyrazol-4-yl-amino, furo[2,3-d]pyrimidin-2-yl-amino, pyridin-2-yl-amino, pyridin-3-yl-amino, or pyridin-4-yl-amino.

A preferred compound according to the present invention is selected from the group consisting of:

2-(4-chlorobenzylamino)-4-[3-(pyrrolidin-1-yl)azetidin-1-yl]quinoline,
2-(4-chlorobenzylamino)-4-[3-(morpholin-4-yl)azetidin-1-yl]quinoline,
2-(4-chlorobenzylamino)-4-[4-(methylcarbamoyl)piperidin-1-yl]quinoline,
2-(4-chlorobenzylamino)-4-[4-(tert-butylaminocarbonyl)-piperidin-1-yl]-quinoline,
2-(4-chlorobenzylamino)-4-[4-(pyrrolidine-1-carbonyl)piperidin-1-yl]-quinoline,
2-(4-chlorobenzylamino)-4-[4-(4-methylpiperazine-1-carbonyl)-piperidin-1-yl]-quinoline,
(2S) 2-(4-chlorobenzylamino)-4-[2-(hydroxymethyl)pyrrolidin-1-yl]quinoline,
(2S) 2-(4-chlorobenzylamino)-4-[2-(methoxymethyl)pyrrolidin-1-yl]quinoline,
(2R)-2-(4-chlorobenzylamino)-4-[2-(hydroxymethyl)-pyrrolidin-1-yl]-quinoline,
2-(4-chlorobenzylamino)-4-(4-hydroxypiperidin-1-yl)quinoline,
2-(4-chlorobenzylamino)-4-[4-(iso-propoxy)-piperidin-1-yl]-quinoline,
2-(4-chlorobenzylamino)-4-(4-phenoxypiperidin-1-yl)-quinoline,
2-(4-chlorobenzylamino)-4-[4-(m-tolyloxy)piperidin-1-yl]quinoline,
2-(4-chlorobenzylamino)-4-[4-(pyridin-4-yloxy)piperidin-1-yl]quinoline,
2-(4-chlorobenzylamino)-4-[4-(pyrazin-2-yloxy)piperidin-1-yl]quinoline,
(3R) 2-(4-chlorobenzylamino)-4-(3-hydroxypyrrolidin-1-yl)quinoline,
(3R) 2-(4-chlorobenzylamino)-4-[3-(phenoxy)pyrrolidin-1-yl]quinoline,
(3R) 2-(4-chlorobenzylamino)-4-[3-(pyridin-2-yloxy)pyrrolidin-1-yl]quinoline,
(3S) 2-(4-chlorobenzylamino)-4-(3-hydroxypyrrolidin-1-yl)-quinoline,
(3S) 2-(4-chlorobenzylamino)-4-[3-(pyridin-2-yloxy)pyrrolidin-1-yl]quinoline,
2-(N-4-chlorobenzyl-N-methylamino)-4-[4-(tert-butylamino)-piperidin-1-yl]-quinoline,
2-(N-chlorobenzyl-N-ethylamino)-4-[4-(tert-butylamino)-piperidin-1-yl]-quinoline,
2-(N-4-chlorobenzyl-N-isopropylamino)-4-[4-(tert-butylamino)-piperidin-1-yl]-quinoline,
2-(N-4-chlorobenzyl-N-isobutylamino)-4-[4-(tert-butylamino)-piperidin-1-yl]-quinoline,
2-(4-chloroenzylamino)-3-fluoro-4-[4-(tert-butylamino)piperidin-1-yl]quinoline,
2-(4-chlorobenzylamino)-3-methyl-4-[4-(tert-butylamino)piperidin-1-yl]quinoline,
methyl 4-(4-(tert-butylamino) piperidin-1-yl)-2-(4-chlorobenzylamino) quinoline-3-carboxylate,
2-(4-chlorobenzylamino)-4-[4-(tert-butylamino)piperidin-1-yl]-7-methyl-8-fluoroquinoline,
2-(4-chlorobenzylamino)-4-[4-(tert-butylamino)piperidin-1-yl]-6-methyl-8-fluoroquinoline,
2-(4-chlorobenzylamino)-4-[4-(tert-butylamino)piperidin-1-yl]-7-fluoro-8-methylquinoline,
2-(4-chlorobenzylamino)-4-[4-(tert-butylamino)piperidin-1-yl]-6-fluoro-8-methylquinoline,
2-[4-(4-methylpyrimidin-2-ylamino)phenylamino]-3-methyl-4-(4-tert-butylaminopiperidin-1-yl)quinoline,
2-[3-(4-trifluoromethylpyrimidin-2-ylamino)phenylamino]-3-methyl-4-(4-tert-butylaminopiperidin-1-yl)quinoline,
2-(4-chlorobenzylamino)-3-cyano-4-[4-(tert-butylamino)piperidin-1-yl]quinoline,
2-[4-(4-(pyridin-3-yl)pyrimidin-2-ylamino)-3-methylbenzylamino]-3-cyano-4-(4-tert-butylaminopiperidin-1-yl)quinoline,
2-(3-methyl-4-(4-methylpyrimidin-2-ylamino)phenylamino)-3-cyano-4-(4-(tert-butylamino) piperidin-1-yl)-quinoline,
2-[4-(4,6-dimethyl-2-pyrimidinamino)-3-methyl-phenylamino]-3-cyano-4-(4-tert-butylaminopiperidin-1-yl)quinoline,
2-[4-(4-methyl-6-methoxypyrimidin-2-ylamino)-3-methylphenylamino]-3-cyano-4-(4-tert-butylaminopiperidin-1-yl)quinoline, 2-[3-methyl-4-(4,6-dimethylfuro[2,3-d]pyrimidin-2-ylamino)phenylamino]-3-cyano-4-(4-tert-butylaminopiperidin-1-yl)quinoline,
2-{3-methyl-4-[2-(pyridin-3-yl)pyrimidin-4-ylamino]phenylamino)-3-cyano-4-(4-tert-butylaminopiperidin-1-yl}quinoline,
2-{3-methyl-4-[2-(pyridin-3-yl)-5-cyanopyrimidin-4-ylamino]phenylamino}-3-cyano-4-(4-tert-butylaminopiperidin-1-yl)quinoline,
2-[4-(4-methylpyrimidin-2-ylamino)phenylamino]-3-cyano-4-(4-tert-butylaminopiperidin-1-yl)quinoline,
2-[3-methyl-4-(4-trifluoromethylpyrimidin-2-ylamino)phenylamino]-3-cyano-4-(4-tert-butylaminopiperidin-1-yl)quinoline,
2-[3-(4-trifluoromethyl-2-pyrimidinamino)-4-methyl-phenylamino]-3-cyano-4-(4-tert-butylaminopiperidin-1-yl)quinoline,
2-[3-(4-trifluoromethylpyrimidin-2-ylamino)phenylamino]-3-cyano-4-(4-tert-butylaminopiperidin-1-yl)quinoline,
2-[4-(4-(pyridin-3-yl)pyrimidin-2-ylamino)-3-methylphenylamino]-3-cyano-4-(4-tert-butylaminopiperidin-1-yl)quinoline,
2-[3-(4-trifluoromethylpyrimidin-2-ylamino)phenylamino]-3-fluoro-4-(4-tert-butylaminopiperidin-1-yl)quinoline,
2-(4-fluorobenzylamino)-3-fluoro-4-[4-(tert-butylamino)piperidin-1-yl]quinoline,
2-(4-fluorobenzylamino)-3-cyano-4-[4-(tert-butylamino)piperidin-1-yl]quinoline,
2-(4-chlorobenzylamino)-3-cyano-4-[4-(tert-butylamino)piperidin-1-yl]-8-methylquinoline,
2-(4-chlorobenzylamino)-3-cyano-4-[4-(tert-butylamino)piperidin-1-yl]-7-methylquinoline,
2-(4-chlorobenzylamino)-3-cyano-4-[4-(tert-butylamino)piperidin-1-yl]-6-methylquinoline,
2-(4-chlorobenzylamino)-3-cyano-4-(3-aminopiperidin-1-yl)quinoline,
2-(4-chlorobenzylamino)-3-cyano-4-[3-(methylamino)piperidin-1-yl]quinoline,
2-(4-chlorobenzylamino)-3-cyano-4-[3-(isopropylamino)piperidin-1-yl]quinoline,
{[(tetrahydro-2H-pyra-4-yl)methyl]amino}-3-fluoro-4-[4-(tert-butylamino)piperidin-1-yl]quinoline,
2-(4-chlorobenzylamino)-3-cyano-4-[3-(cyclopentylamino)piperidin-1-yl]quinoline,
2-(4-chlorobenzylamino)-3-cyano-4-[3-(4-methylpiperazin-1-yl)piperidin-1-yl]quinoline,
2-(4-chlorobenzylamino)-3-cyano-4-{3-[(1-methylpiperidin-4-yl)amino]piperidin-1-yl}quinoline,
2-(4-chlorobenzylamino)-3-cyano-4-[3-(pyrrolidin-1-yl)piperidin-1-yl]quinoline,
2-(4-chlorobenzylamino)-3-cyano-4-[3-(morpholino)piperidin-1-yl]quinoline,
2-(4-chlorobenzylamino)-3-cyano-4-[3-(4-methylpiperazin-1-yl)piperidin-1-yl]quinoline,
2-(4-chlorobenzylamino)-3-cyano-4-[3-(dimethylamino)piperidin-1-yl]quinoline,
2-(4-chlorobenzylamino)-3-cyano-4-[3-(diethylamino)piperidin-1-yl]quinoline,
2-(4-chlorobenzylamino)-3-cyano-4-(4-aminopiperidin-1-yl)quinoline,
2-(4-chlorobenzylamino)-3-cyano-4-[4-(methylamino)piperidin-1-yl]quinoline,
2-(4-chlorobenzylamino)-3-cyano-4-[4-(iso-propylamino)piperidin-1-yl]quinoline,
2-(4-chlorobenzylamino)-3-cyano-4-[4-(tert-butylamino)piperidin-1-yl]quinoline,
2-(4-chlorobenzylamino)-3-cyano-4-{4-[(tert-butyloxycarbonyl)amino]piperidin-1-yl}quinoline,
2-(4-chlorobenzylamino)-3-cyano-4-[4-(cyclopentylamino)piperidin-1-yl]quinoline,
2-(4-chlorobenzylamino)-3-cyano-4-{4-[(tetrahydro-2H-pyran-4-yl)amino]piperidin-1-yl}quinoline,
2-(4-chlorobenzylamino)-3-cyano-4-{4-[(1-methylpiperidin-4-yl)amino]piperidin-1-yl}quinoline,
2-(4-chloroenzylamino)-3-cyano-4-[4-(pyrrolidin-1-yl)piperidin-1-yl]quinoline,
2-(4-chlorobenzylamino)-3-cyano-4-[4-(morpholino)piperidin-1-yl]quinoline,
2-(4-chlorobenzylamino)-3-cyano-4-[4-(4-methylpiperazin-1-yl)piperidin-1-yl]quinoline,
2-(4-chlorobenzylamino)-3-cyano-4-[4-(dimethylamino)piperidin-1-yl]quinoline,
2-(4-chlorobenzylamino)-3-cyano-4-[4-(diethylamino)piperidin-1-yl]quinoline,
2-(4-chlorobenzylamino)-3-cyano-4-[3-aminopyrrolidin-1-yl]quinoline,
2-(4-chloroenzylamino)-3-cyano-4-[3-(methylamino)pyrrolidin-1-yl]quinoline,
2-(4-chlorobenzylamino)-3-cyano-4-[3-(cyclopentylamino)pyrrolidin-1-yl]quinoline,
2-(4-chloroenzylamino)-3-cyano-4-{3-[(tetrahydro-2H-pyran-4-yl)amino]pyrrolidin-1-yl}quinoline,
2-(4-chlorobenzylamino)-3-cyano-4-[3-(pyrrolidin-1-yl)pyrrolidin-1-yl]quinoline,
2-(4-chlorobenzylamino)-3-cyano-4-(3-morpholinopyrrolidin-1-yl)quinoline,
2-(4-chlorobenzylamino)-3-cyano-4-[3-(4-methylpiperazin-1-yl)pyrrolidin-1-yl]quinoline,
2-(4-chlorobenzylamino)-3-cyano-4-[3-(dimethylamino)pyrrolidin-1-yl]quinoline,
2-(4-chloroenzylamino)-3-cyano-4-[3-(diethylamino)pyrrolidin-1-yl]quinoline,
2-(4-chlorobenzylamino)-3-cyano-4-(3-phenoxypiperidin-1-yl)quinoline,
2-(4-chlorobenzylamino)-3-cyano-4-[3-(4-methoxyphenoxy)piperidin-1-yl]quinoline,
2-(4-chlorobenzylamino)-3-cyano-4-[3-(4-methylphenoxy)piperidin-1-yl]quinoline,
2-(4-chlorobenzylamino)-3-cyano-4-[3-(4-fluorophenoxy)piperidin-1-yl]quinoline,
2-(4-chlorobenzylamino)-3-cyano-4-[3-(3-fluorophenoxy)piperidin-1-yl]quinoline,
2-(4-chlorobenzylamino)-3-cyano-4-{3-[(3-methylpyrazin-2-yl)oxy]piperidin-1-yl}quinoline,
2-(4-chlorobenzylamino)-3-cyano-4-(4-phenoxypiperidin-1-yl)quinoline,
2-(4-chlorobenzylamino)-3-cyano-4-[4-(4-methoxyphenoxy)piperidin-1-yl]quinoline,
2-(4-chlorobenzylamino)-3-cyano-4-[4-(p-tolyloxy)piperidin-1-yl]quinoline,
2-(4-chlorobenzylamino)-3-cyano-4-[4-(4-chlorophenoxy)piperidin-1-yl]quinoline,
2-(4-chlorobenzylamino)-3-cyano-4-[4-(4-fluorophenoxy)piperidin-1-yl]quinoline,
2-(4-chlorobenzylamino)-3-cyano-4-[4-(3-fluorophenoxy)piperidin-1-yl]quinoline,
2-(4-chlorobenzylamino)-3-cyano-4-{4-[(pyridin-4-yl)oxy]piperidin-1-yl}quinoline,
2-(4-chlorobenzylamino)-3-cyano-4-{4-[(5-methylisoxazol-3-yl)oxy]piperidin-1-yl}quinoline,
2-(4-chlorobenzylamino)-3-cyano-4-{4-[(3-methylpyrazin-2-yl)oxy]piperidin-1-yl}quinoline, 2-(4-chlorobenzylamino)-3-cyano-4-(3-phenoxypyrrolidin-1-yl)quinoline,
2-(4-chloroenzylamino)-3-cyano-4-[3-(4-methylphenoxy)pyrrolidin-1-yl]quinoline,
2-(4-chlorobenzylamino)-3-cyano-4-[3-(4-methoxyphenoxy)pyrrolidin-1-yl]quinoline,
2-(4-chlorobenzylamino)-3-cyano-4-[3-(4-chlorophenoxy)pyrrolidin-1-yl]quinoline,
2-(4-chlorobenzylamino)-3-cyano-4-[3-(4-fluorophenoxy)pyrrolidin-1-yl]quinoline,
2-(4-chlorobenzylamino)-3-cyano-4-[3-(3-fluorophenoxy)pyrrolidin-1-yl]quinoline,
2-(4-chlorobenzylamino)-3-cyano-4-{3-[(3-methylpyrazin-2-yl)oxy]pyrrolidin-1-yl}quinoline,
2-(4-chlorobenzylamino)-3-cyano-4-{3-[(pyridin-4-yl)oxy]pyrrolidin-1-yl}quinoline,
2-(phenylamino)-3-cyano-4-[4-(tert-butylamino)piperidin-1-yl]quinoline,
2-(4-methylphenylamino)-3-cyano-4-[4-(tert-butylamino)piperidin-1-yl]quinoline,
2-(3-methyl-4-fluorophenylamino)-3-cyano-4-[4-(tert-butylamino)piperidin-1-yl]quinoline,
2-(4-methoxyphenylamino)-3-cyano-4-[4-(tert-butylamino)piperidin-1-yl]quinoline,
2-(2-trifluoromethylphenylamino)-3-cyano-4-[4-(tert-butylamino)piperidin-1-yl]quinoline,
2-(3-trifluoromethylphenylamino)-3-cyano-4-[4-(tert-butylamino)piperidin-1-yl]quinoline,
2-(4-chlorophenylamino)-3-cyano-4-[4-(tert-butylamino)piperidin-1-yl]quinoline,
2-(4-fluorophenylamino)-3-cyano-4-[4-(tert-butylamino)piperidin-1-yl]quinoline,
2-(3-fluorophenylamino)-3-cyano-4-[4-(tert-butylamino)piperidin-1-yl]quinoline,
2-(3,4-difluorophenylamino)-3-cyano-4-[4-(tert-butylamino)piperidin-1-yl]quinoline,
2-[4-(trifluoromethyloxy)phenylamino]-3-cyano-4-[4-(tert-butylamino)piperidin-1-yl]quinoline,
2-[(1-methyl-1H-pyrazol-4-yl)amino]-3-cyano-4-[4-(tert-butylamino)piperidin-1-yl]quinoline,
2-[(1-methyl-1H-1,2,4-triazol-5-yl)amino]-3-cyano-4-[4-(tert-butylamino)piperidin-1-yl]quinoline,
2-[(1,3-dimethyl-1H-1,2,4-triazol-5-yl)amino]-3-cyano-4-[4-(tert-butylamino)piperidin-1-yl]quinoline,
2-{4-[(4,6-dimethylpyrimidin-2-yl)amino]phenylamino}-3-cyano-4-[4-(tert-butylamino)piperidin-1-yl]quinoline,
2-(pyridin-2-ylamino)-3-cyano-4-[4-(tert-butylamino)piperidin-1-yl]quinoline,
2-(pyrimidin-2-ylamino)-3-cyano-4-[4-(tert-butylamino)piperidin-1-yl]quinoline,
2-(pyrimidin-4-ylamino)-3-cyano-4-[4-(tert-butylamino)piperidin-1-yl]quinoline,
2-(pyrazin-2-ylamino)-3-cyano-4-[4-(tert-butylamino)piperidin-1-yl]quinoline,
2-(benzylamino)-3-cyano-4-[4-(tert-butylamino)piperidin-1-yl]quinoline,
2-(4-methylbenzylamino)-3-cyano-4-[4-(tert-butylamino)piperidin-1-yl]quinoline,
2-(4-methoxybenzylamino)-3-cyano-4-[4-(tert-butylamino)piperidin-1-yl]quinoline,
2-[4-(trifluoromethyl)benzylamino]-3-cyano-4-[4-(tert-butylamino)piperidin-1-yl]quinoline,
2-[2-(trifluoromethyl)benzylamino]-3-cyano-4-[4-(tert-butylamino)piperidin-1-yl]quinoline,
2-[(benzo[d][1,3]dioxol-5-ylmethyl)amino]-3-cyano-4-[4-(tert-butylamino)piperidin-1-yl]quinoline,
2-[(furan-2-ylmethyl)amino]-3-cyano-4-[4-(tert-butylamino)piperidin-1-yl]quinoline,
2-[(pyridin-3-ylmethyl)amino]-3-cyano-4-[4-(tert-butylamino)piperidin-1-yl]quinoline,
2-[(pyridin-4-ylmethyl)amino]-3-cyano-4-[4-(tert-butylamino)piperidin-1-yl]quinoline,
2-[(pyridin-2-ylmethyl)amino]-3-cyano-4-[4-(tert-butylamino)piperidin-1-yl]quinoline.

or a pharmaceutically acceptable salt, hydrate, solvate, or prodrug thereof, or an isotopic variant, tautomer, or stereoisomer thereof.

A preferred compound of present invention has the formula (II) below:

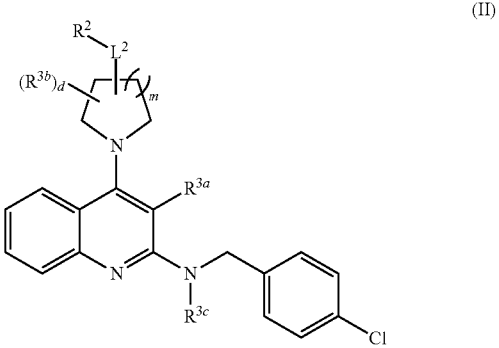

(II)

wherein
  $L^2$ is a single bond, carbonyl, substituted or unsubstituted alkylene, substituted or unsubstituted alkenylene, or substituted or unsubstituted alkynylene,
  $R^2$ is hydroxyl, substituted or unsubstituted alkoxy, substituted or unsubstituted aryloxy, substituted or unsubstituted heteroaryloxy, substituted or unsubstituted alkoxycarbonylamino, substituted or unsubstituted aryloxycarbonylamino, substituted or unsubstituted heteroaryloxycarbonylamino, substituted or unsubstituted alkylaminocarbonylamino, substituted or unsubstituted arylaminocarbonylamino, substituted or unsubstituted heteroarylaminocarbonylamino, or $NR^5R^6$ wherein each $R^5$ and $R^6$ is independently H, substituted or unsubstituted alkyl, substituted or unsubstituted cycloalkyl, substituted or unsubstituted aryl, substituted or unsubstituted heteroaryl, or substituted or unsubstituted heterocycloalkyl, or $R^5$ and $R^6$ together with the nitrogen atom to which they are attached are combined to form a substituted or unsubstituted heterocyclic ring,
  $R^{3a}$ is H, halo, cyano, substituted or unsubstituted alkyl, substituted or unsubstituted aryl, substituted or unsubstituted heteroaryl, substituted or unsubstituted cycloalkyl, substituted or unsubstituted heterocycloalkyl, substituted or unsubstituted alkoxy, substituted or unsubstituted alkoxycarbonyl, substituted or unsubstituted aryloxycarbonyl, substituted or unsubstituted heteroaryloxycarbonyl, or substituted or unsubstituted aminocarbonyl;
  each $R^{3b}$ is independently H, hydroxyl, halo, azido, amino, nitro, thiol, cyano, carboxyl, substituted or unsubstituted alkyl, substituted or unsubstituted alkenyl, substituted or unsubstituted alkynyl, substituted or unsubstituted arylalkyl, substituted or unsubstituted aryl, substituted or unsubstituted heteroaryl, substituted or unsubstituted cycloalkyl, substituted or unsubstituted cycloalkenyl, or substituted or unsubstituted heterocycloalkyl;

R$^{3c}$ is H, substituted or unsubstituted alkyl, substituted or unsubstituted alkenyl, substituted or unsubstituted alkynyl, substituted or unsubstituted cycloalkyl, substituted or unsubstituted cycloalkenyl, or substituted or unsubstituted heterocycloalkyl, provided that when R$^{3c}$ is H, L$^2$ is other than a single bond or R$^2$ is other than NR$^5$R$^6$ or R$^{3a}$ is other than H;

m is 0, 1, 2, 3, or 4;

if m is 0, then d is independently 0, 1 or 2; if m is 1, then d is independently 0, 1, 2 or 3; if m is 2, then d is independently 0, 1, 2, 3 or 4; if m is 3, then d is independently 0, 1, 2, 3, 4 or 5 or if m is 4 then d is independently 0, 1, 2, 3, 4, 5 or 6;

or a pharmaceutically acceptable salt, hydrate, solvate, or prodrug thereof, or an isotopic variant, tautomer, or stereoisomer thereof.

The present invention provides a specific compound according to formula (II), wherein R$^{3c}$ is H, substituted or unsubstituted alkyl, or substituted or unsubstituted cycloalky.

The present invention provides another specific compound according to formula (II), wherein each R$^{3b}$ is independently H.

The present invention also provides another specific compound according to formula (II), wherein R$^{3a}$ is H, halo, cyano, substituted or unsubstituted alkyl or substituted or unsubstituted alkoxycarbonyl.

The present invention also provides a further specific compound according to formula (II), wherein L$^2$ is a single bond, carbonyl, substituted or unsubstituted alkylene.

Further, the present invention also provides a specific compound according to formula (II), wherein m is 0, 1, or 2.

Representative compounds of formula (I) according to the present invention include, but are not limited to, the compounds of Formula (II) which are shown in Table 1 below:

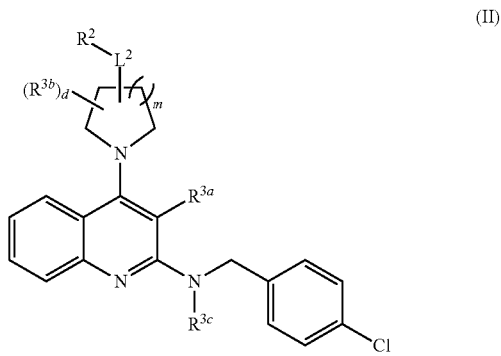

(II)

TABLE 1

Representative compounds according to the general formula (II)

| Example | R$^{3c}$ | R$^{3a}$ | |
|---|---|---|---|
| 100 | H | H | HN(Boc)—azetidine—N— |
| 102 | H | H | HN(Et)—azetidine—N— |
| 116 | H | H | pyrrolidine—N—azetidine—N— |
| 118 | H | H | morpholine—N—azetidine—N— |
| 212 | H$_3$C— | H | tBu-HN—piperidine—N— |

TABLE 1-continued

Representative compounds according to the general formula (II)

| Example | R³ᶜ | R³ᵃ | (structure) |
|---|---|---|---|
| 214 | ethyl | H | 4-(tert-butylamino)piperidin-1-yl |
| 216 | isopropyl | H | 4-(tert-butylamino)piperidin-1-yl |
| 218 | cyclopropyl | H | 4-(tert-butylamino)piperidin-1-yl |
| 220 | isobutyl | H | 4-(tert-butylamino)piperidin-1-yl |
| 1598 | H | H | 4-(methylcarbamoyl)piperidin-1-yl |
| 1604 | H | H | 4-(tert-butylcarbamoyl)piperidin-1-yl |
| 1648 | H | H | 4-(pyrrolidine-1-carbonyl)piperidin-1-yl |
| 1652 | H | H | 4-(morpholine-4-carbonyl)piperidin-1-yl |

TABLE 1-continued
Representative compounds according to the general formula (II)
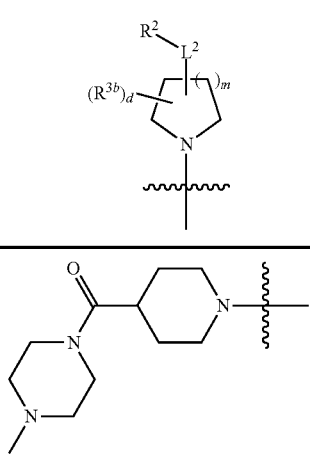
| Example | R³ᶜ | R³ᵃ | |
|---------|-----|-----|---|
| 1656 | H | H | 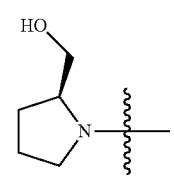 [SMILES: *N1CCC[C@H]1CO] |
| 2308 | H | H | 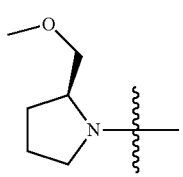 [SMILES: *N1CCC[C@H]1COC] |
| 2310 | H | H | 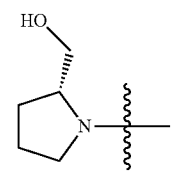 [SMILES: *N1CCC[C@@H]1CO] |
| 2380 | H | H | 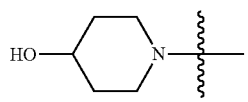 |
| 2916 | H | H | 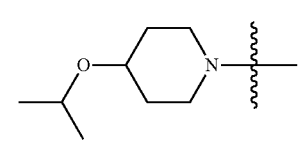 |
| 2918 | H | H | 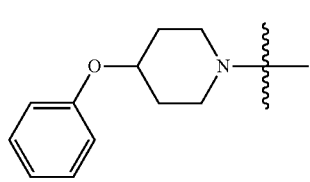 [SMILES: *N1CCC(Oc2ccccc2)CC1] |
| 2940 | H | H | 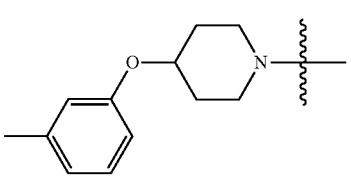 [SMILES: *N1CCC(Oc2cccc(C)c2)CC1] |
| 2946 | H | H | |

TABLE 1-continued

Representative compounds according to the general formula (II)

| Example | R³ᶜ | R³ᵃ | |
|---------|-----|-----|---|
| 2950 | H | H | 4-(pyridin-4-yloxy)piperidin-1-yl |
| 2958 | H | H | 4-(pyrazin-2-yloxy)piperidin-1-yl |
| 2988 | H | H | (3S)-3-hydroxypyrrolidin-1-yl |
| 3012 | H | H | (3S)-3-phenoxypyrrolidin-1-yl |
| 3026 | H | H | (3S)-3-(pyridin-2-yloxy)pyrrolidin-1-yl |
| 3060 | H | H | (3R)-3-hydroxypyrrolidin-1-yl |
| 3098 | H | H | (3S)-3-(pyridin-2-ylmethyl)pyrrolidin-1-yl |
| 348 | H | F (tert) | 4-(tert-butylamino)piperidin-1-yl |
| 350 | H | CH₃ (tert) | 4-(tert-butylamino)piperidin-1-yl |
| 352 | H | CN (tert) | 4-(tert-butylamino)piperidin-1-yl |

TABLE 1-continued
Representative compounds according to the general formula (II)
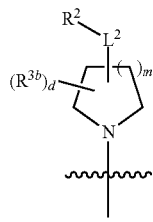
| Example | R³ᶜ | R³ᵃ | |
|---|---|---|---|
| 354 | H | -C(=O)-O-CH₃ | t-Bu-NH-(4-piperidinyl)- |
| 3156-F | H | -CHF- | H₂N-(3-piperidinyl)- |
| 3170-F | H | -CHF- | H₂N-(4-piperidinyl)- |
| 3158-F | H | -CHF- | H₃C-NH-(3-piperidinyl)- |
| 3172-F | H | -CHF- | H₃C-NH-(4-piperidinyl)- |
| 3160-F | H | -CHF- | iPr-NH-(3-piperidinyl)- |
| 3174-F | H | -CHF- | iPr-NH-(4-piperidinyl)- |
| 156-F | H | -CHF- | t-Bu-NH-(3-piperidinyl)- |
| 348-F | H | -CHF- | t-Bu-NH-(4-piperidinyl)- |

TABLE 1-continued

Representative compounds according to the general formula (II)

| Example | R³ᶜ | R³ᵃ | |
|---|---|---|---|
| 154-F | H | ⋯/F | BOC—NH-[piperidin-3-yl]-N- |
| 182-F | H | ⋯/F | BOC-NH-[piperidin-4-yl]-N- |
| 162-F | H | ⋯/F | cyclopentyl-NH-[piperidin-3-yl]-N- |
| 3178-F | H | ⋯/F | cyclopentyl-NH-[piperidin-4-yl]-N- |
| 168-F | H | ⋯/F | tetrahydropyran-4-yl-NH-[piperidin-3-yl]-N- |
| 3180-F | H | ⋯/F | tetrahydropyran-4-yl-NH-[piperidin-4-yl]-N- |
| 3162-F | H | ⋯/F | (1-methylpiperidin-4-yl)-NH-[piperidin-3-yl]-N- |
| 3182-F | H | ⋯/F | (1-methylpiperidin-4-yl)-NH-[piperidin-4-yl]-N- |

TABLE 1-continued
Representative compounds according to the general formula (II)
| Example | R³ᶜ | R³ᵃ | |
|---|---|---|---|
| 176-F | H | 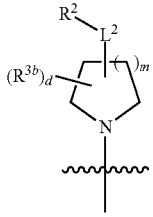 |  |
| 200-F | H | 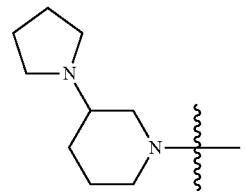 [SMILES: *N1CCCC(N2CCCC2)C1] |  |
| 178-F | H | 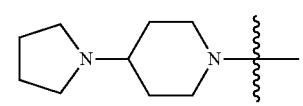 |  |
| 202-F | H | 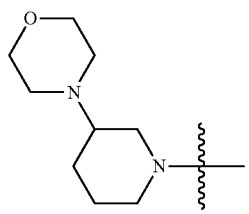 [SMILES: *N1CCCC(N2CCOCC2)C1] |  |
| 3168-F | H | 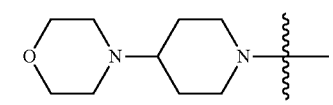 |  |
| 3188-F | H | 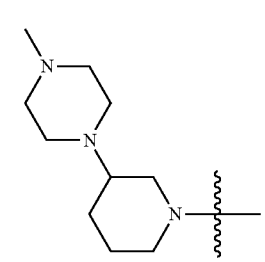 [SMILES: *N1CCCC(N2CCN(C)CC2)C1] |  |
| 3164-F | H | 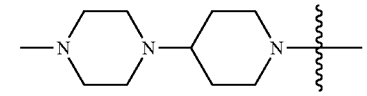 |  |
| 3184-F | H | 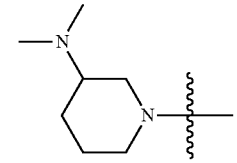 [SMILES: *N1CCCC(N(C)C)C1] |  |

TABLE 1-continued

Representative compounds according to the general formula (II)

| Example | R³ᶜ | R³ᵃ | (substituent) |
|---------|-----|-----|---------------|
| 160-F | H | -CH(F)- | 3-(diethylamino)piperidin-1-yl |
| 184-F | H | -CH(F)- | 4-(diethylamino)piperidin-1-yl |
| 3166-F | H | -CH(F)- | 3-(N-tert-butyl-N-ethylamino)piperidin-1-yl |
| 3186-F | H | -CH(F)- | 4-(N-tert-butyl-N-ethylamino)piperidin-1-yl |
| 3190-F | H | -CH(F)- | 3-aminopyrrolidin-1-yl |
| 3192-F | H | -CH(F)- | 3-(methylamino)pyrrolidin-1-yl |
| 3194-F | H | -CH(F)- | 3-(isopropylamino)pyrrolidin-1-yl |
| 124-F | H | -CH(F)- | 3-(tert-butylamino)pyrrolidin-1-yl |
| 3196-F | H | -CH(F)- | 3-(BOC-amino)pyrrolidin-1-yl |
| 134-F | H | -CH(F)- | 3-(cyclopentylamino)pyrrolidin-1-yl |

TABLE 1-continued
Representative compounds according to the general formula (II)
| Example | R³ᶜ | R³ᵃ | |
|---|---|---|---|
| 136-F | H | 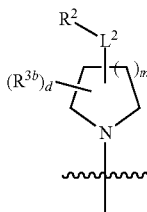 |  |
| 3198-F | H | 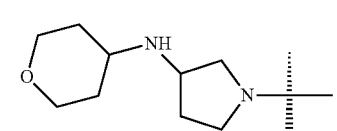 |  |
| 148-F | H | 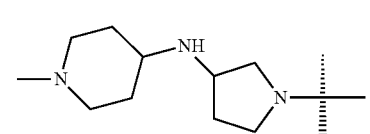 |  |
| 150-F | H | 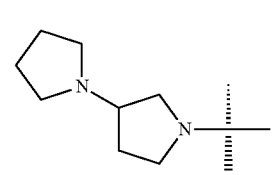 |  |
| 3200-F | H | 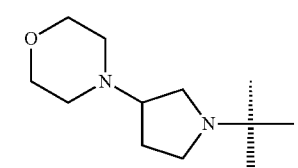 |  |
| 3202-F | H | 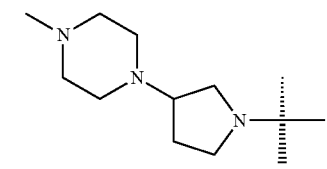 |  |
| 126-F | H | 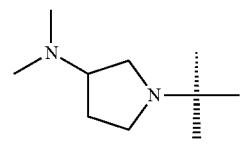 |  |
| 3204-F | H | 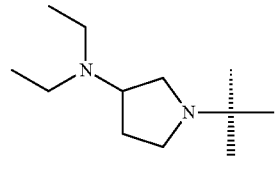 |  |

TABLE 1-continued
Representative compounds according to the general formula (II)
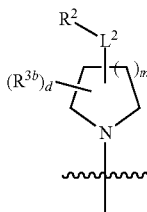
| Example | R³ᶜ | R³ᵃ | |
|---|---|---|---|
| 3206-CN | H | 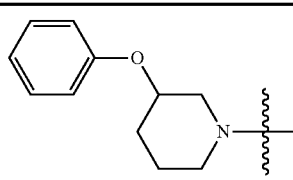 |  |
| 2940-CN | H | 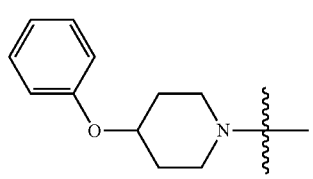 [SMILES: *N1CCC(Oc2ccccc2)CC1] |  |
| 3232-CN | H | 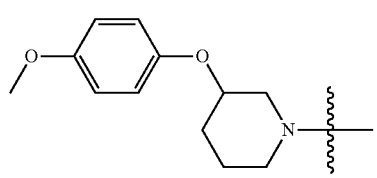 [SMILES: *N1CCCC(Oc2ccc(OC)cc2)C1] |  |
| 3224-CN | H | 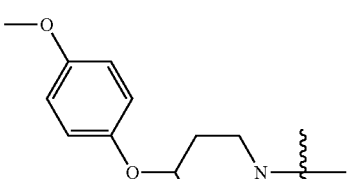 |  |
| 3234-CN | H | 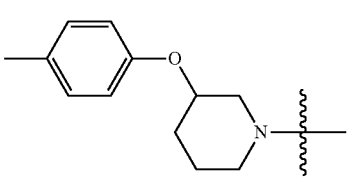 [SMILES: *N1CCCC(Oc2ccc(C)cc2)C1] |  |
| 2944-CN | H | 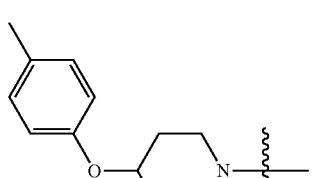 |  |
| 3236-CN | H | 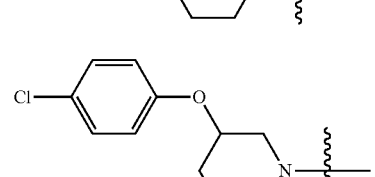 |  |

TABLE 1-continued

Representative compounds according to the general formula (II)

| Example | R³ᶜ | R³ᵃ | |
|---------|-----|-----|---|
| 3226-CN | H | —C≡N | 4-Cl-phenyl-O-(piperidin-4-yl)-N- |
| 3238-CN | H | —C≡N | 4-F-phenyl-O-(piperidin-3-yl)-N- |
| 2942-CN | H | —C≡N | 4-F-phenyl-O-(piperidin-4-yl)-N- |
| 3240-CN | H | —C≡N | 3-F-phenyl-O-(piperidin-3-yl)-N- |
| 3228-CN | H | —C≡N | 3-F-phenyl-O-(piperidin-4-yl)-N- |
| 3242-CN | H | —C≡N | 4-CF₃-phenyl-O-(piperidin-3-yl)-N- |
| 3230-CN | H | —C≡N | 4-CF₃-phenyl-O-(piperidin-4-yl)-N- |

TABLE 1-continued
Representative compounds according to the general formula (II)
| Example | R³ᶜ | R³ᵃ | |
|---|---|---|---|
| 3244-CN | H | 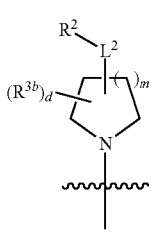 | 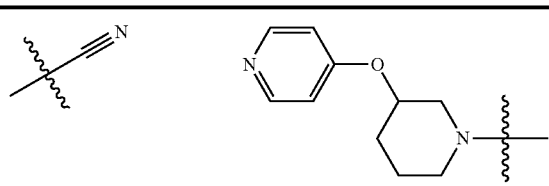 |
| 2950-CN | H | 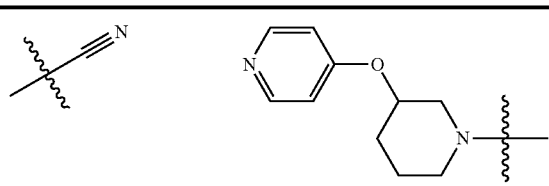 | 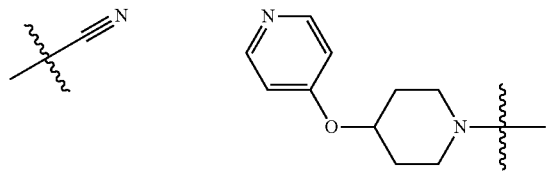 |
| 3312-CN | H | 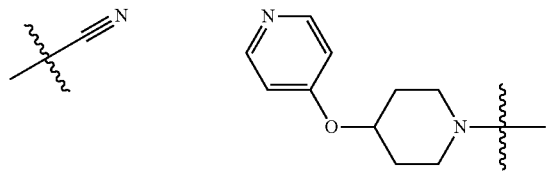 | 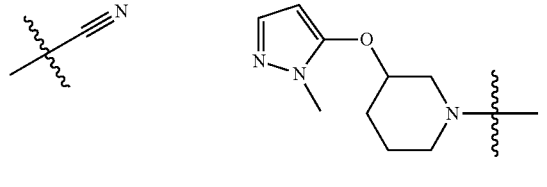 |
| 2974-CN | H | 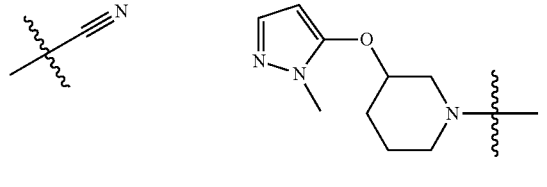 | 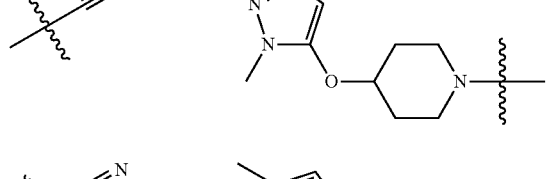 |
| 3314-CN | H | 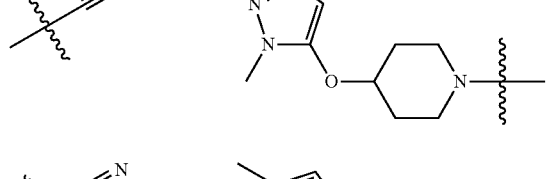 | 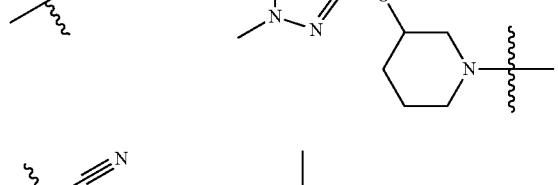 |
| 2972-CN | H | 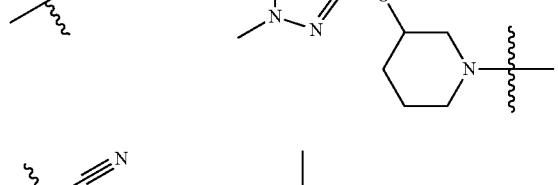 | 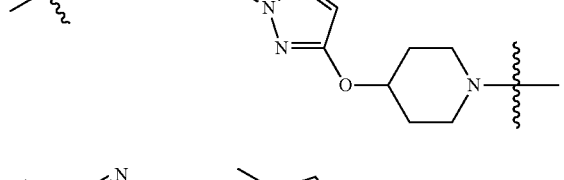 |
| 3316-CN | H | 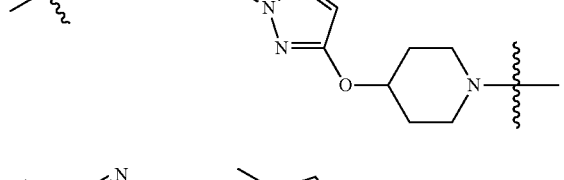 | 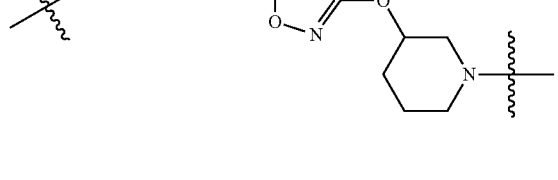 |

TABLE 1-continued
Representative compounds according to the general formula (II)
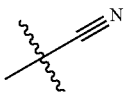
| Example | R³ᶜ | R³ᵃ | |
|---|---|---|---|
| 2978-CN | H | 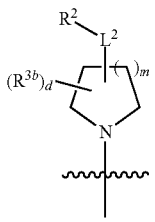 | 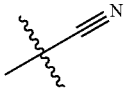 [SMILES: *C#N] |
| 3318-CN | H | 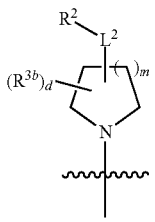 | 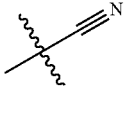 [SMILES: *C#N] |
| 2976-CN | H | 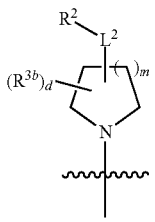 | 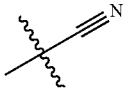 |
| 3320-CN | H | 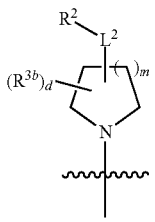 | 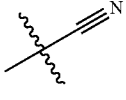 [SMILES: *C#N] |
| 2980-CN | H | 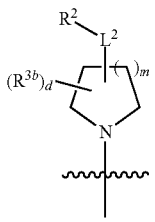 | 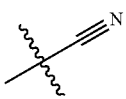 [SMILES: *C#N] |
| 3322-CN | H | 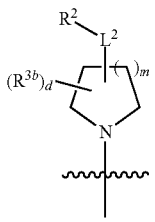 | 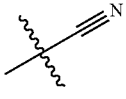 |
| 2982-CN | H | 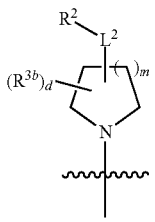 | |

TABLE 1-continued
Representative compounds according to the general formula (II)
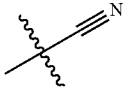
| Example | R³ᶜ | R³ᵃ | |
|---|---|---|---|
| 3324-CN | H | 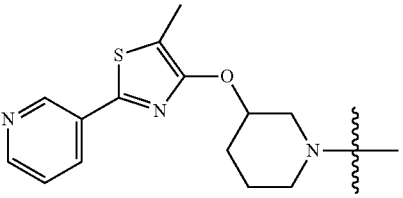 [SMILES: *N1CCCC(Oc2nc(-c3cccnc3)sc2C)C1] | 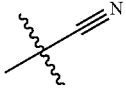 [SMILES: *C#N] |
| 2986-CN | H | 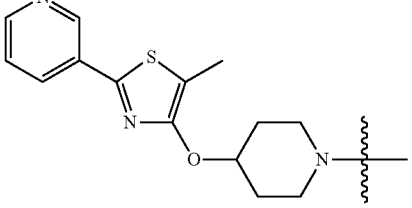 | 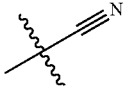 |
| 3326-CN | H | 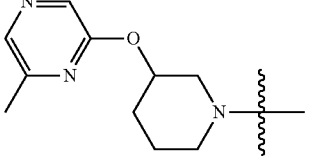 | 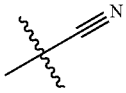 [SMILES: *C#N] |
| 3310-CN | H | 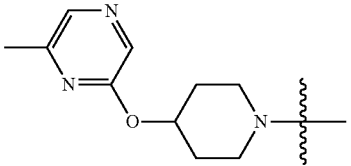 [SMILES: *N1CCC(Oc2cncc(C)n2)CC1] | 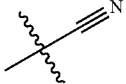 [SMILES: *C#N] |
| 3328-CN | H | 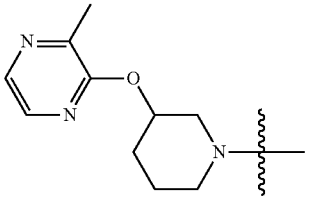 [SMILES: *N1CCCC(Oc2nccnc2C)C1] | 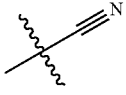 [SMILES: *C#N] |
| 2970-CN | H | 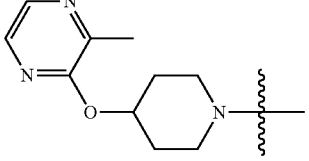 | 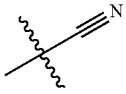 [SMILES: *C#N] |
| 3330-CN | H | 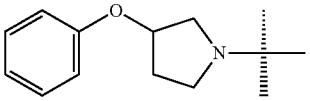 | |

TABLE 1-continued

Representative compounds according to the general formula (II)

| Example | R³ᶜ | R³ᵃ | |
|---|---|---|---|
| 3332-CN | H | CN | 4-methoxyphenoxy-pyrrolidinyl |
| 3334-CN | H | CN | 4-methylphenoxy-pyrrolidinyl |
| 3336-CN | H | CN | 4-chlorophenoxy-pyrrolidinyl |
| 3338-CN | H | CN | 4-fluorophenoxy-pyrrolidinyl |
| 3340-CN | H | CN | 3-fluorophenoxy-pyrrolidinyl |
| 3342-CN | H | CN | 4-(trifluoromethyl)phenoxy-pyrrolidinyl |
| 3344-CN | H | CN | pyridin-4-yloxy-pyrrolidinyl |
| 3346-CN | H | CN | (1-methyl-1H-pyrazol-5-yl)oxy-pyrrolidinyl |
| 3348-CN | H | CN | (1,5-dimethyl-1H-pyrazol-3-yl)oxy-pyrrolidinyl |
| 3350-CN | H | CN | (5-methylisoxazol-3-yl)oxy-pyrrolidinyl |
| 3352-CN | H | CN | (1-methyl-3-(trifluoromethyl)-1H-pyrazol-5-yl)oxy-pyrrolidinyl |

TABLE 1-continued

Representative compounds according to the general formula (II)

| Example | R³ᶜ | R³ᵃ | (structure) |
|---|---|---|---|
| 3354-CN | H | −CN | 5-fluorobenzoxazol-2-yloxy-pyrrolidinyl-N-tBu |
| 3356-CN | H | −CN | 2-(4-fluorophenyl)oxazol-4-yloxy-pyrrolidinyl-N-tBu |
| 3358-CN | H | −CN | 2-(pyridin-3-yl)-4-methylthiazol-5-yloxy-pyrrolidinyl-N-tBu |
| 3360-CN | H | −CN | 6-methylpyrazin-2-yloxy-pyrrolidinyl-N-tBu |
| 3362-CN | H | −CN | 3-methylpyrazin-2-yloxy-pyrrolidinyl-N-tBu |

The present invention also provides in a preferred embodiment a compound of formula (III) having the structure:

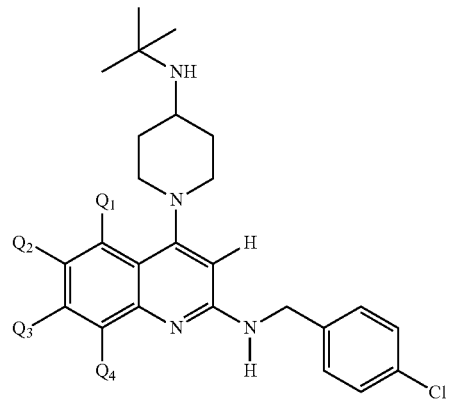

(III)

wherein
Q₁, Q₂, Q₃ and Q₄ are each independently H, hydroxyl, halo, amino, nitro, thiol, carboxyl, cyano, azido, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted arylalkyl, substituted or unsubstituted heterocycloalkyl, substituted or unsubstituted aryl, substituted or unsubstituted heteroaryl, substituted or unsubstituted alkoxy, substituted or unsubstituted aryloxy, substituted or unsubstituted heteroaryloxy, substituted or unsubstituted sulfanyl, substituted or unsubstituted alkylamino, substituted or unsubstituted dialkylamino, substituted or unsubstituted arylamino, substituted or unsubstituted heteroarylamino, substituted or unsubstituted acyl, substituted or unsubstituted acylamino, substituted or unsubstituted aminocarbonyl, substituted or unsubstituted alkoxycarbonyl, substituted or unsubstituted aryloxycarbonyl, substituted or unsubstituted heteroaryloxycarbonyl, substituted sulfo, substituted sulfonyl, substituted sulfinyl, substituted or unsubstituted aminosulfonyl, substituted or unsubstituted sulfonylamino, substituted or unsubstituted aminocarbonylamino, substituted or unsubstituted aminocarbonyloxy, substituted or unsubstituted alkoxycarbonylamino, substituted or unsubstituted aryloxycarbonylamino, or substituted or unsubstituted heteroaryloxycarbonylamino; and at least two of Q₁, Q₂, Q₃ and Q₄ are other than H and are distinct.

Preferably, $Q_1$, $Q_2$, $Q_3$ and $Q_4$ are each independently H, cyano, methyl or halo.

Representative compounds of the invention include, but are not limited to the compounds shown in Table 2 below and according to the following Formula (III):

TABLE 2

Representative compounds according to the general formula (III)

| Example | $Q_1$ | $Q_2$ | $Q_3$ | $Q_4$ |
|---|---|---|---|---|
| 564 | H | H | H$_3$C— | F— |
| 566 | H | H | N≡— | F— |
| 568 | H | H$_3$C— | H | F— |
| 570 | H | N≡— | H | F— |
| 572 | H | H | F— | H$_3$C— |
| 580 | H | F— | H | H$_3$C— |

The present invention also provides in a preferred embodiment a compound of formula (III') having the structure:

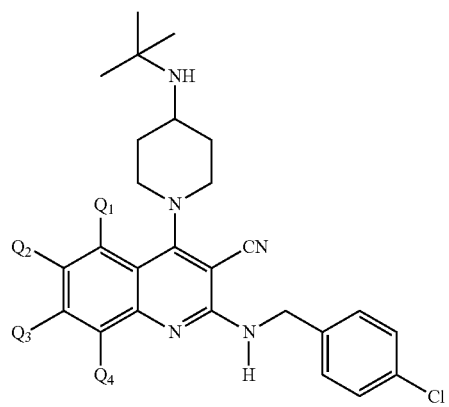

(III')

wherein $Q_1$, $Q_2$, $Q_3$ and $Q_4$ are as defined under formula I. Preferably, $Q_1$, $Q_2$, $Q_3$ and $Q_4$ are each independently H, halo, substituted or unsubstituted alkyl, substituted or unsubstituted alkoxy, Representative compounds of the invention include, but are not limited to the compounds shown in Table 2' below and according to the following Formula (III'):

TABLE 2'

Representative compounds according to the general formula (III')

| Example | $Q_1$ | $Q_2$ | $Q_3$ | $Q_4$ |
|---|---|---|---|---|
| 414-CN | H | H | H | H$_3$C— |
| 416-CN | H | H | H$_3$C— | H |
| 418-CN | H | H$_3$C— | H | H |
| 3210-CN | H | F$_3$C— | H | H |
| 3212-CN | H | H | F$_3$C— | H |
| 3214-CN | H | H | H | F$_3$C— |
| 3218-CN | H | F$_3$C—O— | H | H |
| 3220-CN | H | H | F$_3$C—O— | H |
| 3222-CN | H | H | H | F$_3$C—O— |

The present invention also provides a specific compound according to formula (IV) having the following structure:

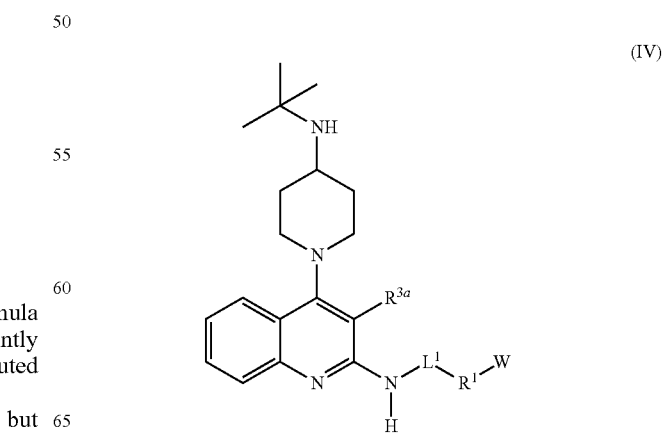

(IV)

wherein
- R³ᵃ is halo, cyano, substituted or unsubstituted alkyl, substituted or unsubstituted aryl, substituted or unsubstituted heteroaryl, substituted or unsubstituted cycloalkyl, substituted or unsubstituted heterocycloalkyl, substituted or unsubstituted alkoxy, substituted or unsubstituted alkoxycarbonyl, substituted or unsubstituted aryloxycarbonyl, substituted or unsubstituted heteroaryloxycarbonyl, or substituted or unsubstituted aminocarbonyl;
- L¹ is a single bond, or substituted or unsubstituted alkylene, substituted or unsubstituted alkenylene, or substituted or unsubstituted alkynylene;
- R¹ is substituted or unsubstituted aryl, substituted or unsubstituted heteroaryl, substituted or unsubstituted arylene, or substituted or unsubstituted heteroarylene; and
- W is optionally present and if present is H, hydroxyl, halo, azido, amino, nitro, thiol, cyano, carboxyl, substituted or unsubstituted alkyl, substituted or unsubstituted alkenyl, substituted or unsubstituted alkynyl, substituted or unsubstituted arylalkyl, substituted or unsubstituted aryl, substituted or unsubstituted heteroaryl, substituted or unsubstituted cycloalkyl, substituted or unsubstituted cycloalkenyl, substituted or unsubstituted heterocycloalkyl, substituted or unsubstituted alkoxy, substituted or unsubstituted aryloxy, substituted or unsubstituted heteroaryloxy, substituted or unsubstituted sulfanyl, substituted or unsubstituted alkylamino, substituted or unsubstituted dialkylamino, substituted or unsubstituted arylamino, substituted or unsubstituted heteroarylamino, substituted or unsubstituted acyl, substituted or unsubstituted acylamino, substituted or unsubstituted aminocarbonyl, substituted or unsubstituted alkoxycarbonyl, substituted or unsubstituted aryloxycarbonyl, substituted or unsubstituted heteroaryloxycarbonyl, substituted sulfo, substituted sulfonyl, substituted sulfinyl, substituted or unsubstituted aminosulfonyl, substituted or unsubstituted sulfonylamino, substituted or unsubstituted alkylsulfonyl, substituted or unsubstituted arylsulfonyl, substituted or unsubstituted aminocarbonylamino, substituted or unsubstituted aminocarbonyloxy, substituted or unsubstituted alkoxycarbonylamino, substituted or unsubstituted aryloxycarbonylamino, or substituted or unsubstituted heteroaryloxycarbonylamino.

Further the present invention provides a specific compound according to formula (IV), wherein R³ᵃ is halo, cyano or substituted or unsubstituted alkoxycarbonyl.

The present invention also provides a specific compound according to formula (IV), wherein L¹ is a single bond, or substituted or unsubstituted alkylene.

The present invention provides a further specific compound according to formula (IV), wherein R¹ is substituted or unsubstituted aryl, substituted or unsubstituted heteroaryl.

The present invention also provides another specific compound according to formula (IV), wherein W is substituted or unsubstituted arylamino, or substituted or unsubstituted heteroarylamino.

Representative compounds according to formula (IV) include without limitation, the compounds shown in Table 3 below:

TABLE 3

Representative compounds according to the general formula (IV)

| Example | R³ᵃ | ⸺L¹⸺E⸺W |
|---------|-----|---------|
| 498CN | —C≡N | 2-methyl-4-(pyridin-3-yl)pyrimidin-2-ylaminophenyl-CH₂— |
| 500F | —F | 2-methyl-4-methylpyrimidin-2-ylaminophenyl— |
| 500CH3 | —CH₃ | 2-methyl-4-methylpyrimidin-2-ylaminophenyl— |

TABLE 3-continued
Representative compounds according to the general formula (IV)
| Example | R³ᵃ | ⸺L¹−E−W |
|---|---|---|
| 500CN | 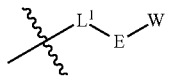 | 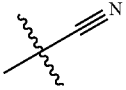 [SMILES: *C#N] |
| 502CN | 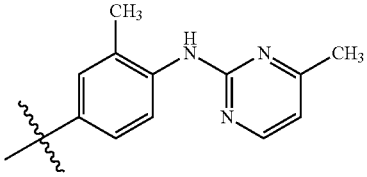 [SMILES: *c1ccc(Nc2nccc(C)n2)c(C)c1] | 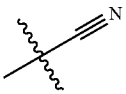 [SMILES: *C#N] |
| 510CN | 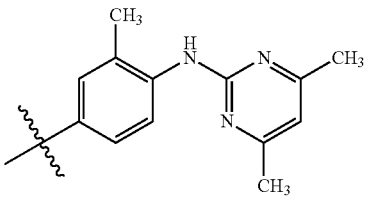 | 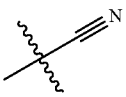 [SMILES: *C#N] |
| 512CN | 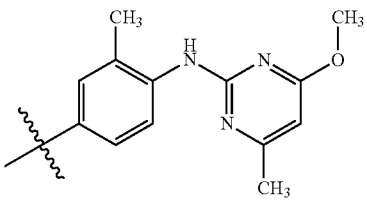 | 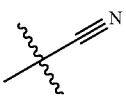 |
| 522CN | 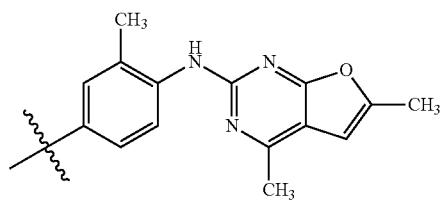 [SMILES: *c1ccc(Nc2nc(C)c3cc(C)oc3n2)c(C)c1] | 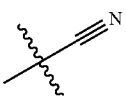 [SMILES: *C#N] |
| 532F | 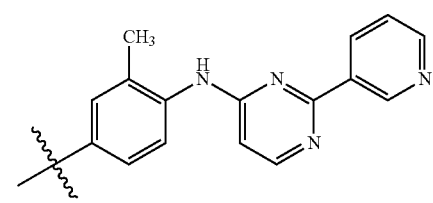 [SMILES: *c1ccc(Nc2ccnc(-c3cccnc3)n2)c(C)c1] |  |
| 532CH3 | 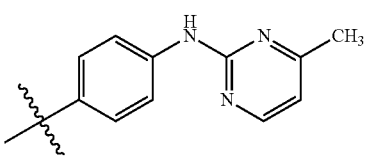 [SMILES: *c1ccc(Nc2nccc(C)n2)cc1] |  |

TABLE 3-continued

Representative compounds according to the general formula (IV)

| Example | R³ᵃ | ⸺L¹–E–W |
|---|---|---|
| 532CN | –C≡N | 4-[(4-methylpyrimidin-2-yl)amino]phenyl |
| 534F | –F | 4-[(4-(trifluoromethyl)pyrimidin-2-yl)amino]-3-methylphenyl |
| 534CH3 | –CH₃ | 4-[(4-(trifluoromethyl)pyrimidin-2-yl)amino]-3-methylphenyl |
| 534CN | –C≡N | 4-[(4-CF₃-pyrimidin-2-yl)amino]-3-methylphenyl |
| 538CN | –C≡N | 4-Me-3-[(4-CF₃-pyrimidin-2-yl)amino]phenyl |
| 540F | –F | 3-[(4-CF₃-pyrimidin-2-yl)amino]phenyl |
| 540CH3 | –CH₃ | 3-[(4-CF₃-pyrimidin-2-yl)amino]phenyl |
| 540CN | –C≡N | 3-[(4-CF₃-pyrimidin-2-yl)amino]phenyl |

TABLE 3-continued
Representative compounds according to the general formula (IV)
| Example | R³ᵃ | L¹–E–W |
|---|---|---|
| 546CN | 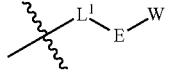 | 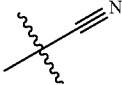 |
| 556CN | 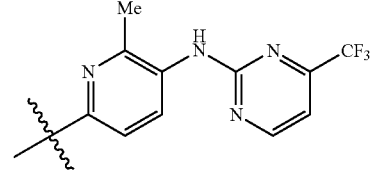 [SMILES: *c1ccc(Nc2nccc(C(F)(F)F)n2)c(C)n1] | 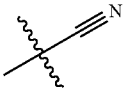 [SMILES: *C#N] |
| 3131F | 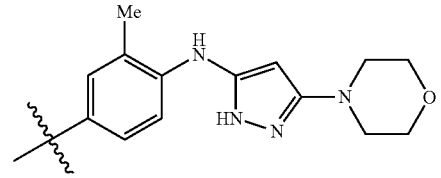 [SMILES: *c1ccc(Nc2cc(N3CCOCC3)n[nH]2)c(C)c1] |  |
| 3131CH3 | 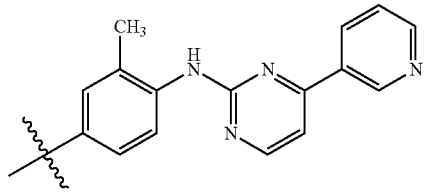 [SMILES: *c1ccc(Nc2nccc(-c3cccnc3)n2)c(C)c1] | 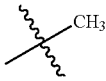 |
| 3131CN | 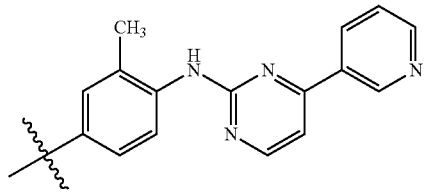 [SMILES: *c1ccc(Nc2nccc(-c3cccnc3)n2)c(C)c1] | 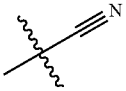 [SMILES: *C#N] |
| 3246-CN | 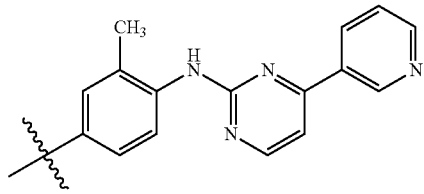 [SMILES: *c1ccc(Nc2nccc(-c3cccnc3)n2)c(C)c1] | 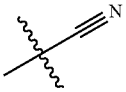 |
| 3248-CN | 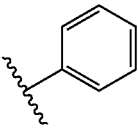 [SMILES: *c1ccccc1] |  |
| 3250-CN | 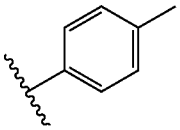 [SMILES: *c1ccc(C)cc1] |  |

TABLE 3-continued
Representative compounds according to the general formula (IV)
| Example | R³ᵃ | 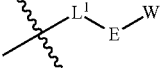 |
|---|---|---|
| 3252-CN | 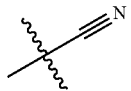 [SMILES: *C#N] | 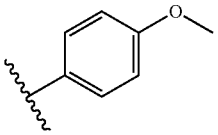 [SMILES: *c1ccc(OC)cc1] |
| 3254-CN | 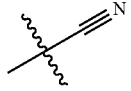 [SMILES: *C#N] | 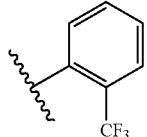 |
| 3256-CN | 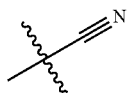 | 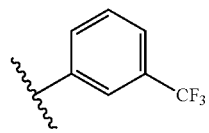 [SMILES: *c1cccc(C(F)(F)F)c1] |
| 3258-CN | 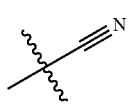 [SMILES: *C#N] | 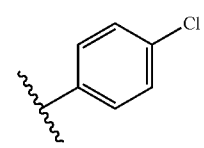 [SMILES: *c1ccc(Cl)cc1] |
| 3260-CN | 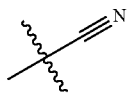 [SMILES: *C#N] | 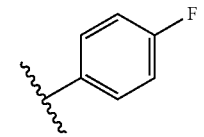 [SMILES: *c1ccc(F)cc1] |
| 3262-CN | 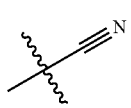 [SMILES: *C#N] | 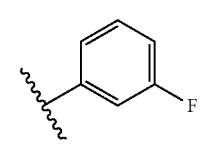 [SMILES: *c1cccc(F)c1] |
| 3264-CN | 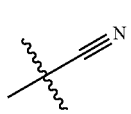 | 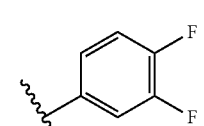 |
| 3266-CN | 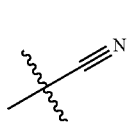 | 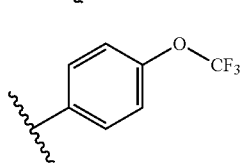 |
| 3268-CN | 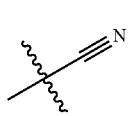 [SMILES: *C#N] | 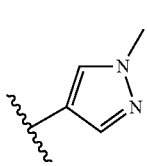 [SMILES: *c1cnn(C)c1] |
| 3270-CN | 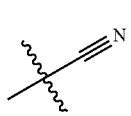 | 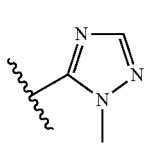 [SMILES: *c1ncnn1C] |

TABLE 3-continued
Representative compounds according to the general formula (IV)
| Example | R³ᵃ | 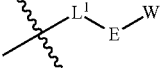 |
|---|---|---|
| 3272-CN | 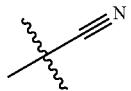 [SMILES: *C#N] | 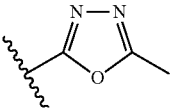 [SMILES: *c1nnc(C)o1] |
| 3274-CN | 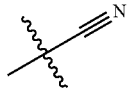 [SMILES: *C#N] | 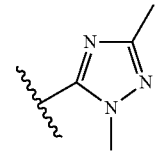 [SMILES: *c1nc(C)nn1C] |
| 3276-CN | 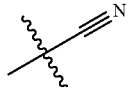 [SMILES: *C#N] | 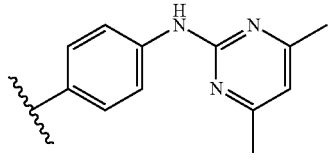 [SMILES: *c1ccc(Nc2nc(C)cc(C)n2)cc1] |
| 3278-CN | 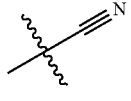 [SMILES: *C#N] | 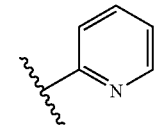 [SMILES: *c1ccccn1] |
| 3280-CN | 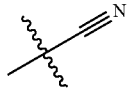 [SMILES: *C#N] | 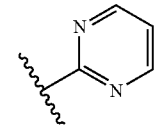 [SMILES: *c1ncccn1] |
| 3282-CN | 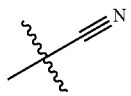 [SMILES: *C#N] | 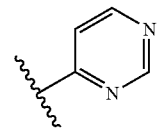 [SMILES: *c1ccncn1] |
| 3284-CN | 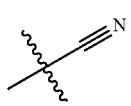 [SMILES: *C#N] | 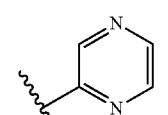 |
| 3364-CN | 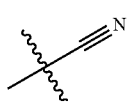 [SMILES: *C#N] | 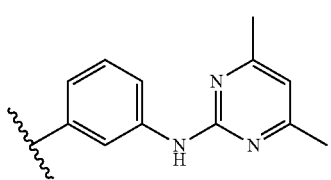 [SMILES: *c1cccc(Nc2nc(C)cc(C)n2)c1] |
| 3286-CN | 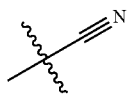 [SMILES: *C#N] | 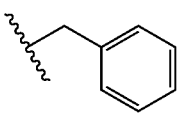 [SMILES: *Cc1ccccc1] |
| 3288-CN | 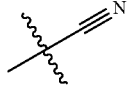 [SMILES: *C#N] | 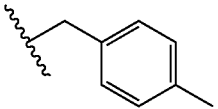 [SMILES: *Cc1ccc(C)cc1] |

TABLE 3-continued

Representative compounds according to the general formula (IV)

| Example | R³ᵃ | L¹–E–W |
|---|---|---|
| 3290-CN | –C≡N | –CH₂–C₆H₄–OMe (4-methoxybenzyl) |
| 3292-CN | –C≡N | –CH₂–C₆H₄–CF₃ (4-trifluoromethylbenzyl) |
| 3294-CN | –C≡N | –CH₂–(2,6-difluorophenyl) |
| 3296-CN | –C≡N | –CH₂–(2-cyanophenyl) |
| 3298-CN | –C≡N | –CH₂–(2-trifluoromethylphenyl) |
| 3300-CN | –C≡N | –CH₂–(3,4-methylenedioxyphenyl) |
| 3302-CN | –C≡N | –CH₂–(2-furyl) |
| 3304-CN | –C≡N | –CH₂–(3-pyridyl) |
| 3306-CN | –C≡N | –CH₂–(4-pyridyl) |
| 3308-CN | –C≡N | –CH₂–(2-pyridyl) |

All stereoisomers of the compounds of formula (I) (for example, those which may exist due to asymmetric carbons on various substituents), enantiomeric forms and diastereomeric forms, are contemplated within the scope of this invention, either in a mixture, or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers. Thus, for example, the compounds of the invention which have one or more centers of chirality and which occur as racemates or as diastereomer mixtures can be fractionated by methods known per se into their optical pure isomers, i.e. enantiomers or diastereomers. The chiral centers of the present invention may have the S or R configuration as defined by the IUPAC 1974 Recommendations. The separation of the compounds of the invention that may be present in racemate or diastereomer mixtures can take place by column separation on chiral or nonchiral phases, by fractional crystallization, or by recrystallization from an optionally optically active solvent or with use of an optically active acid or base or by derivatization with an optically active reagent such as, for example, an optically active alcohol, and subsequent elimination of the radical. In some instances, the compounds of the invention may possess one or more double bonds wherein each double bond exists in the E (trans) or Z (cis) configuration, or combinations thereof.

Techniques for inverting or leaving unchanged a particular stereocenter, and those for resolving mixtures of stereoisomers are found, for example, Furniss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; and Heller, Acc. Chem. Res. 1990, 23, 128.

Where possible, the compounds of the invention may be in the form of the tautomers, such as keto-enol tautomers.

The Compounds of formula (I) (or (II), (III), (III') or (IV)) may be provided in any form suitable for the intended use in therapy. Suitable forms include pharmaceutically acceptable salt, hydrates, solvates, polymorphs, prodrugs and isotopic variants which are also within the scope of this invention.

The term "salt(s)", as employed herein, denotes acidic and/or basic salts formed with inorganic and/or organic acids and bases. In addition, when a compound of formula (I) contains both a basic moiety, such as but not limited to a pyridinyl, imidazolyl, or amine and an acidic moiety such as but not limited to a carboxylic acid, zwitterions may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula (I) may be formed, for example, by reacting a compound of formula (I) with an amount of acid or base, such as an equivalent amount, in a medium such as one in which the salt precipitates or in an aqueous medium followed by lyophilization.

Lists of suitable salts can be found, e.g., in "Remington's Pharmaceutical Sciences", 22th ed., Allen Loyd V. Jr., (2012); and in "Handbook of Pharmaceutical Salts: Properties, Selection, and Use" $2^{nd}$ ed. by Stahl and Wermuth (Wiley-VCH, Weinheim, Germany, 2011).

The compounds of formula (I) that contain a basic moiety, such as but not limited to an amine, or a pyridyl or pyrimidinyl ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula (I) that contain an acidic moiety, such as but not limited to a carboxylic acid, may form salts with a variety of organic and inorganic bases. Exemplary basic salts include ammonium salts; alkali metal salts such as sodium, lithium, and potassium salts; alkaline earth metal salts such as calcium and magnesium salts; salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines; and salts with amino acids such as arginine, lysine, and the like. Basic nitrogen-containing groups may be quaternized with agents such as lower alkyl halides (e.g. methyl, ethyl, propyl, and butyl chlorides, bromides, and iodides), dialkyl sulfates (e.g. dimethyl, diethyl, dibutyl, and diamyl sulfates), long chain halides (e.g. decyl, lauryl, myristyl, and stearyl chlorides, bromides, and iodides), aralkyl halides (e.g. benzyl and phenethyl bromides), and others.

The term "hydrate" means a compound of the present invention described herein, that further includes a stoichiometric or non-stoichiometric amount of water bound by non-covalent intermolecular forces. The hydrates include but are not limited to hemihydrate, monohydrate, dihydrate, trihydrate and the like. Hydrates of the compounds of the present invention and of pharmaceutically acceptable salts thereof may be prepared by contacting these compounds or their pharmaceutically acceptable salts with water under suitable conditions to produce the hydrate of choice.

The term "solvate" means a compound of the present invention described herein, that further includes a stoichiometric or non-stoichiometric amount of solvent bound by non-covalent intermolecular forces. In some embodiments solvates may be formed during the process of crystallization with solvents such as water, ethanol, and the like. Non-limitative examples of solvates include hydrates that may be formed when the solvent is water, and alcoholates that may be formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and uses thereof provided herein.

The term "prodrug" means a derivative of a compound that can hydrolyze, oxidize, or otherwise react under biological conditions (in vitro or in vivo) to provide a compound of the present invention. Prodrugs may become active upon such reaction under biological conditions, or they may have activity in their unreacted forms. Additionally, prodrugs can be converted to the compounds of the present application by chemical or biochemical methods in an ex vivo environment. For example, prodrugs can be slowly converted to the compounds of the present application when placed in a transdermal patch reservoir with a suitable enzyme or chemical reagent. Prodrug may be formed using means generally known in the art, and therefore may take essentially any form that would be recognized to one of ordinary skill in the art. Moieties to be modified for forming a prodrug include reactive functional groups such as hydroxyl, carboxyl, amino, and thiol. Specific examples of the modifying group for hydroxyl include an acetyl, propionyl, isobutyryl, pivaloyl, benzoyl, 4-methylbenzoyl, dimethylcarbamoyl, alkoxycarbonyl (such as ethoxycarbonyl), monoesters formed with dicarboxylic acids (such as succinyl), phosphate, sulfate, sulfonate, sulfonyl, sulfinyl and the like. Specific examples of the modifying group for carboxyl include ethyl, pivaloyloxymethyl, 1-(acetyloxy)ethyl, 1-(ethoxycarbonyloxy)ethyl, 1-(cyclohexyloxycarbonyloxy)ethyl, carboxylmethyl, methyl(5-methyl-2-oxo-1,3-dioxol-4-yl), phenyl, o-tolyl, and the like. Specific examples of the modifying group for amino include a hexylcarbamoyl, 3-methylthio-1-(acetylamino)propylcarbonyl, 1-sulfo-1-(3-ethoxy-4-hydroxyphenyl)-methyl, methyl(5-methyl-2-oxo-1,3-dioxol-4-yl), and the like. Various forms of prodrugs are well known in the art and are described for instance in: (i) Wermuth C G et al., Chapter 31: 671-696, The Practice of Medicinal Chemistry, Academic Press 1996; (ii) Bundgaard H, Design of Prodrugs, Elsevier 1985; and (iii) Bundgaard H, Chapter 5: 131-191, A Textbook of Drug Design and Development, Harwood Academic Publishers 1991. Said references are incorporated herein by reference.

Prodrugs are often useful because, in some situations, they may be easier to administer than the parent drug. They may, for instance, be bioavailable by oral administration whereas the parent is not. Particularly favored derivatives or prodrugs are those that increase the bioavailability of the compounds of the present invention when such compounds are administered to an individual (e.g. by allowing an orally administered compound to be more readily absorbed into the blood) or which enhance delivery of the parent compound to a biological compartment (e.g. the brain or lymphatic system).

As used herein, an "Isotopic variant" refers to a presently disclosed compound including pharmaceutical salts, hydrates, solvates and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{8}F$, and $^{36}Cl$, respectively. Isotopic variants of the presently disclosed compounds may be useful in drug and/or substrate tissue distribution assays. Tritiated ($^{3}H$) and carbon-14 ($^{14}C$) labeled compounds are particularly preferred for their ease of preparation and detectability. Further, substitution with heavier isotopes such as deuterium ($^{2}H$) can afford certain therapeutic advantages resulting from greater metabolic stability, for example increased in vivo half-life or reduced dosage requirements and, hence, may be preferred in some circumstances. Isotopic variants of the compounds of the present invention, including pharmaceutical salts, esters, solvates, hydrates, and prodrugs thereof, can be prepared by any means known in the art. Further, substitution of normally abundant hydrogen ($^{1}H$) with heavier isotopes such as deuterium can afford certain therapeutic advantages, e.g., resulting from improved absorption, distribution, metabolism and/or excretion (ADME) properties, creating drugs with improved efficacy, safety, and/or tolerability. Benefits may also be obtained from replacement of normally abundant $^{12}C$ with $^{13}C$. See, WO 2007/005643, WO 2007/005644, WO 2007/016361, and WO 2007/016431.

In some instances, the compounds of the invention or pharmaceutically acceptable salts or prodrugs thereof may be present in various polymorphic forms and certain modifications may moreover be metastable. All these polymorphic forms of the compounds are to be regarded as belonging to the invention. All these polymorphic forms of the compounds are to be regarded as belonging to the invention. As used herein, the term "polymorph" means solid crystalline forms of a compound of the present invention described herein. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

It is further known that chemical substances are converted in the body into metabolites which may where appropriate likewise elicit the desired biological effect in some circumstances even in more pronounced form. Any biologically active compound that was converted in vivo by metabolism from any of the compounds of the invention is a metabolite within the scope and spirit of the invention. As used herein, the term "metabolite", refers to a derivative of a compound which is formed when the compound is metabolized. The term "active metabolite," as used herein, refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from The Pharmacological Basis of Therapeutics, 9th Edition, McGraw-Hill (1996).

III. General Synthesis Process for Preparing the Compounds of the Invention

The invention further provides a general process for preparing the compounds of formula (I) as defined above.

The compounds of formula (I) according to the invention can be prepared using various organic chemistry methods, including those known to those skilled in the art.

In some embodiments, synthesis of the compounds of formula (I) according to the invention can be performed following the general synthesis procedure which comprises the following steps (see also scheme I):

Step (1):

reacting a compound of formula (I-a) having the following structure:

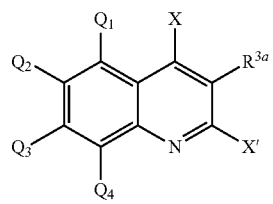

(I-a)

wherein X, X' are independently halo and $R^3$, $Q_1$, $Q_2$, $Q_3$, and $Q_4$ are as defined under the general formula (I), with an amine compound of formula (I-b) having the following structure:

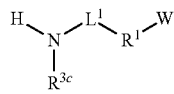

(I-b)

wherein $L^1$, $R^1$, $R^3$, and W are as are as defined under the general formula (I), to form an intermediate compound of formula (I-c)

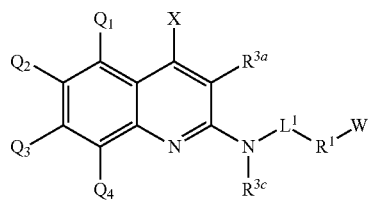

(I-c)

wherein X is halo, and $L^1$, $R^1$, $Q_1$, $Q_2$, $Q_3$, $Q_4$, $R^{3a}R^{3c}$, and W are as defined under the general formula (I), Step (2):

reacting the intermediate compound of formula (I-c) with a cyclic amino compound of formula (I-d) having the following structure:

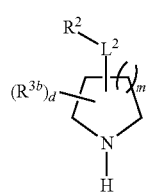

(I-d)

Wherein d, m, $L^2$, $R^2$, and $R^{3b}$ are as defined under the general formula (I).

Scheme I:

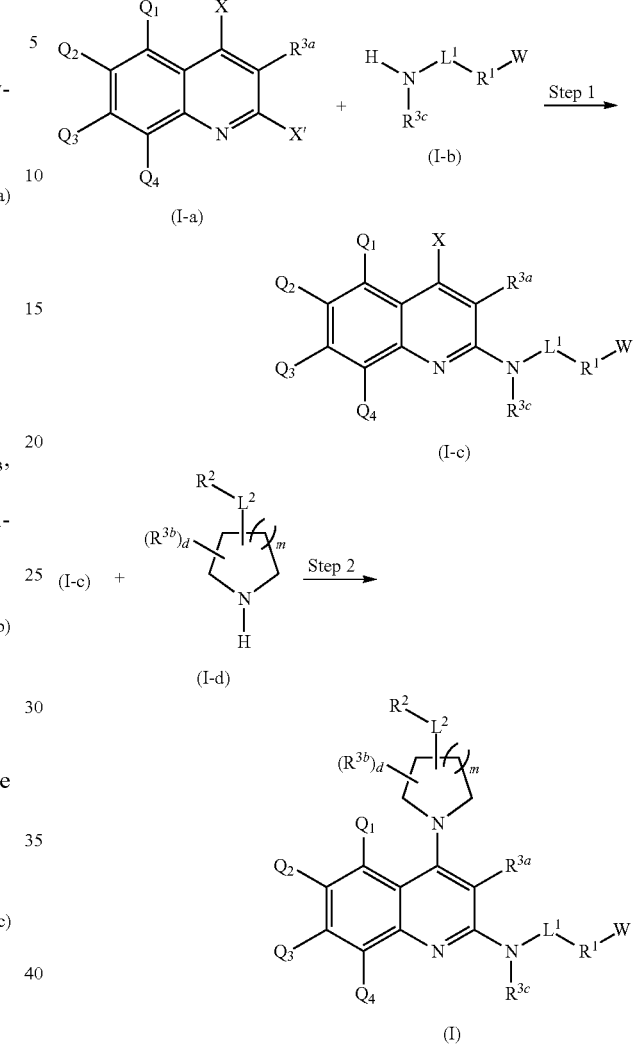

Step 1) of this general synthesis procedure may be carried under standard Buchwald (or Buchwald-Hartwig) amination conditions (Buchwald, S L et al.; J. Org. Chem. 2001, 66 (8), 2560-2565; or Buchwald, S L, et al.; J. Am. Chem. Soc. 2014, 136, 1617-1627; Surry D. S et al. Chemical Science 2011, 2, 27-50), in particular in the presence of a palladium catalyst, such as palladium acetate (Pd(OAc)$_2$), of a ligand, preferably of a bidentate organophosphorus ligand such as xantphos (CAS Number: 161265-03-8), and of a base, such as sodium tert-butyloxide, in a solvent such as toluene, tetrahydrofurane (THF), dimethoxyethane (DME), dimethyl-formamide (DMF), dimethyl sulfoxide (DMSO), N-methyl-2-pyrrolidone (NMP) or 1,4-dioxane and any mixtures thereof. Step 1) can be carried out at from room temperature up to a temperature of 150° C., preferably from 70° C. to 120° C.

Note:

compound of formula (I-a) (2,4-dihalo-quinoline, eventually bearing the group $R^{3a}$ and/or one or more of the groups $Q_1$, $Q_2$, $Q_3$ and $Q_4$) can be either commercially available or prepared according to methods known to those skilled in the art.

Step 2) of the general synthetic method can be carried out under various conditions well-known to those skilled in the art. In particular, the resulting compound (1-b) which bears a halo (e.g. chloro or bromo) substituent at posstion-4, can be subjected to a nucleophilic aromatic substitution reaction (SNAr) with the compound (1-d) (a cyclic secondary amine) in the presence of a base such as N,N-Diisopropylethylamine (DiPEA), in a polar solvent such as N-methyl-2-pyrrolidone (NMP), under microwaves irradiation and at a temperature ranging from 80° C. to 250° C., in particular from 120° C. to 200°. The coupling of the compound (1-d) (cyclic secondary amine) with the halo-compound (1-b) can also be accomplished under palladium (0) catalysis in the presence of a suitable phosphine based ligand which promotes efficient cross-coupling between the 2 organic substrates. Many variations on the conditions for efficiently coupling heteroaromatic halides and amines are known in the chemical literature (see e.g. Surry D S, Buchwald S L., Chem. Sci., 2011, 2(1), 27-51).

Scheme II:

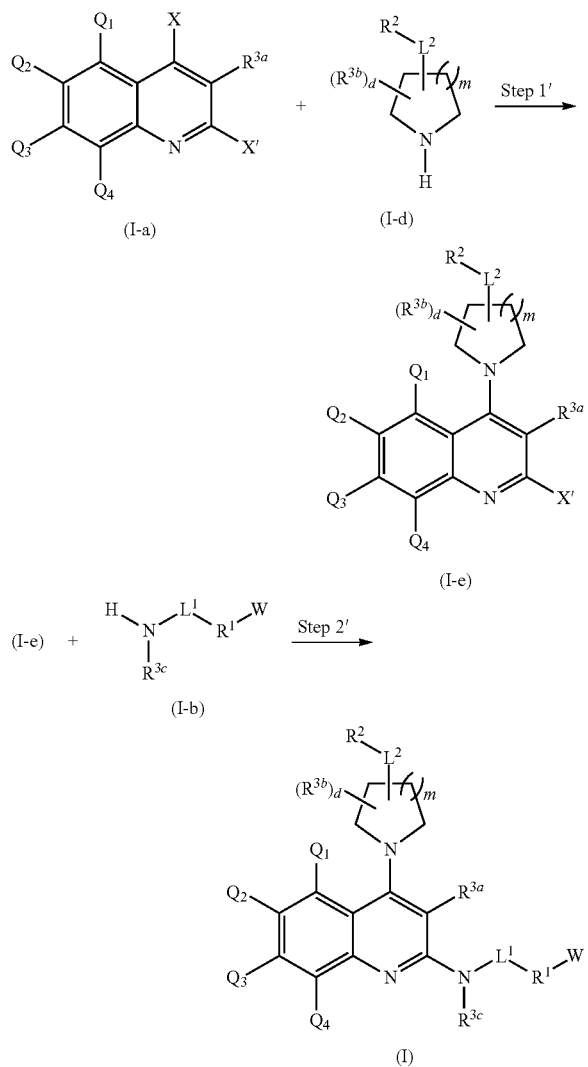

The compounds of formula (I) according to the invention, can also be prepared as shown in reaction scheme II, wherein steps 1') and 2') can be carried out as indicated above, respectively for step 2) and 1).

Scheme III:

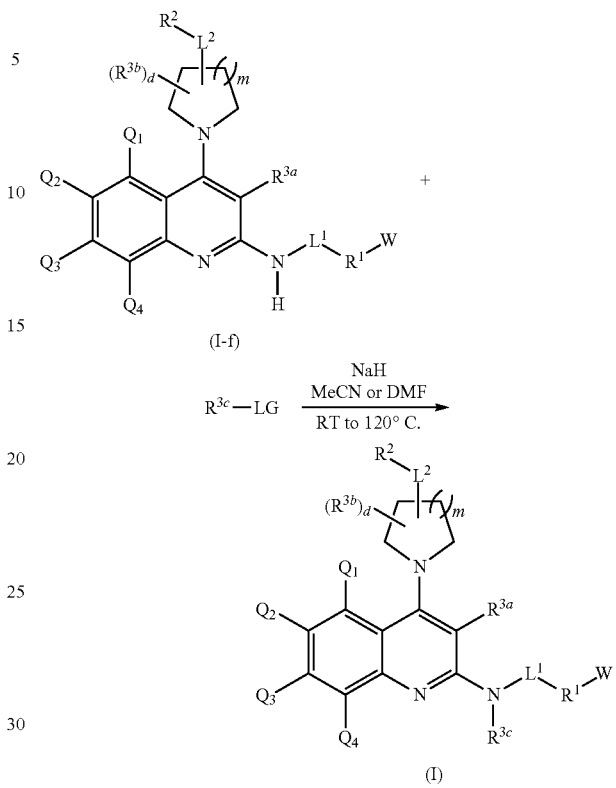

In some embodiments, compounds of formula (I) (or I-f) in which $R^{3c}$ is H may be subjected to a N-alkylation reaction (see scheme II) in the presence of the following alklating agent: $R^{3c}$-LG (I-g), wherein LG is a suitable leaving group such as halo (e.g. chloro, iodo, bromo) or sulfonate ester (e.g. trifluoromethanesulfonate (triflate), methanesulfonate (mesylate), or p-toluenesulfonate (tosylate)), and $R^{3c}$ is substituted or unsubstituted alkyl, substituted or unsubstituted alkenyl, substituted or unsubstituted alkynyl, substituted or unsubstituted cycloalkyl, substituted or unsubstituted cycloalkenyl, or substituted or unsubstituted heterocycloalkyl. According to these embodiments, the N-alkylation reaction may be carried out in a reaction-inert organic solvent, such as acetonitrile (MeCN) or dimethylformamide (DMF), by stirring at an temperature below 150° C., preferably from 25° C. to 120. In particular, said N-alkylation reaction carried out in the presence of a base, such as sodium hydride (NaH), and optionally in the presence of an alkali metal iodide, such as KI or NaI.

Notes:

In some instances, compounds of formula (I-a) to (1-f) and/or the alklating agent (I-g) may independently bear one or more particular chemically reactive functional groups (e.g. amine, hydroxy, thiol, carboxy, aldehyde, etc.) that could compete with the desired reaction and lead to undesired side-reaction products. In order to prevent the formation of undesired bonds and side reaction products, the functional group protection strategy may be used. This group protection strategy is well-known to those skilled in the art. Thus protecting groups may be used to temporarily mask the particular chemically reactive functional group to allow the formation of the desired intermediate or the final compound.

As used in the specification, the terms "protected," "protecting group" and "protective group" refer to the presence of a moiety (i.e., the protecting group) that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule, if any. Protecting groups known in the art can be found in Greene, T. W., et al., PROTECTIVE GROUPS IN ORGANIC SYNTHESIS, 3rd ed., John Wiley & Sons, Inc., New York, N.Y. (1999).

In the schemes (I), (II) and (III) above, the starting compounds (e.g. compounds (I-a), (I-b) and (I-d)), the reactants (e.g. alkylating agent (I-f)) and the intermediates, when their method of preparation is not described, are commercially available, or described in the literature or else can be prepared according to methods which are described therein or which are known to those skilled in the art.

IV. Pharmacology and Utility

Advantageously, the compounds of the present invention exhibit a strong growth inhibitory effect against different cancer cell lines. This strong growth inhibitory effect is easily demonstrated by in vitro assays on cancer cells samples, for example as described herein on the following cancer cell lines: Hepatocellular carcinoma cells (HepG2 and Huh7), colorectal carcinoma cells (HCT-116), acute myeloid leukemia cells (MOLM-14), Malignant melanoma cells (A375), prancreatic carcinoma cells (PANC-1) and renal adenocarcinoma (786-O) cells. The compounds of the invention generally have an inhibition value EC50 of less than about 10 µM, and preferably less than about 5 µM.

Due to their surprisingly strong anticancer effects the compounds of the invention can be advantageously administered at lower doses compared to other less potent anticancer drugs of the prior art while still achieving equivalent or even superior desired biological effects. In addition, such a dose reduction may advantageously lead to less or even no medicinal adverse effects. Further, the high inhibitory effects of the compounds of the invention may translate into a decrease of undesired side effects on its own regardless of the dose applied.

The compounds of the present invention are thus believed to be effective against cell proliferative diseases which may be caused by neoplastic or non-neoplastic disorders in an individual.

The compounds of the present invention are also believed to be effective against drug-resistant cancer or radiation-resistant cancer.

It is also believed that the compounds of the present invention can effect a regression of cancer and increase the survivability of a patient with cancer.

Furthermore, the compounds of the present invention can also be used to sensitize a subject to other therapies, such as radiation therapy, or can be used as maintenance therapy of cancer patients.

Therefore, the present invention also provides a compound according to formula I or to formula II, or to formula III, or to formula III' or to formula IV, or respectively a pharmaceutically acceptable salt, hydrate, solvate, or prodrug thereof, or an isotopic variant, tautomer, or stereoisomer thereof, for use as medicament. Such a medicament can in particular be intended for the treatment or prevention of a disease in a mammal.

The present invention also relates to the use of a compound of formula (I) as defined above, for preparing a medicament intended for the treatment of a proliferative disease which can be selected from a neoplastic disease and a non-neoplastic disorder.

The proliferative disease to be treated according to the invention is preferably a neoplastic disease or a non-neoplastic disorder. In particular, the neoplastic disease is a cancer which may be selected in the group consisting of cancer, tumour, malignant tumours, malignant lymphoma, malignant melanoma, malignant astrocytoma, benign tumours, solid tumours, sarcomas, carcinomas, hyperproliferative disorders, myeloproliferative diseases, carcinoids, Ewing sarcomas, Kaposi sarcomas, brain tumours, tumours originating from the brain and/or the nervous system and/or the meninges, gliomas, glioblastomas, neuroblastomas, stomach cancer, pancreatic cancer, kidney cancer, kidney cell carcinomas, prostate cancer, prostate carcinomas, connective tissue tumours, soft tissue sarcomas, fibrosarcomas, pancreas tumours, liver tumours, head tumours, neck tumours, laryngeal cancer, nasopharyngeal cancer, oesophageal cancer, colon cancer thyroid cancer, osteosarcomas, retinoblastomas, thymoma, testicular cancer, lung cancer, lung adenocarcinoma, small cell lung carcinoma, bronchial carcinomas, breast cancer, mamma carcinomas, intestinal cancer, colorectal tumours, colon carcinomas, prostate cancer, rectum carcinomas, gynaecological tumours, ovary tumours/ovarian tumours, uterine cancer, cervical cancer, cervix carcinomas, cancer of body of uterus, corpus carcinomas, endometrial carcinomas, urinary bladder cancer, urogenital tract cancer, bladder cancer, skin cancer, epithelial tumours, squamous epithelial carcinoma, basal cell carcinoma, basaliomas, spinaliomas, melanomas, intraocular melanomas, leukaemias, monocyte leukaemia, chronic leukaemias, chronic myelotic leukaemia, chronic lymphatic leukemia, acute leukaemias, acute myelogenous leukemia, acute promyelocytic leukemia (APL), acute lymphatic leukemia, acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia, stem cell leukemia, germ cell cancer, metastatic growth, as well as other neoplastic diseases known to those skilled in the art.

In general, metastasis of any cancer can be prevented or treated with the compounds of the present invention.

Representative examples of non-neoplastic disorders include, without limitation, benign tumors psoriasis, benign proliferative skin diseases, ichthyosis, papilloma, restinosis, scleroderma and hemangioma, and leukoplakia rheumatoid arthritis, ischemic-reperfusion related brain edema and injury, cortical ischemia, ovarian hyperplasia and hypervascularity, (polycystic ovary syndrome), endometriosis, diabetic retinopaphy, and other ocular angiogenic diseases such as retinopathy of prematurity (retrolental fibroplastic), macular degeneration, corneal graft rejection, neuroscular glaucoma and Oster Webber syndrome, opthalmic diseases, choroidal neovascularization, diabetic retinopathy, inflammatory diseases, arthritis, neurodegeneration, transplant rejection, fibrosis, restenosis, atherosclerosis, inflammation, disorders of wound healing, and angiogenesis, as well as other non-neoplastic disorders known to those skilled in the art.

The neoplastic disease can in particular be selected in the group consisting of liver cancer, pancreatic cancer, lung cancer, bladder cancer, colorectal cancer, acute myeloid leukemia, malignant melanoma, renal adenocarcinoma and gastrointestinal cancer, including esophageal, gastric, small bowel, large bowel, rectal and colon cancer. Particularly, the neoplastic disease is a liver cancer selected in the group consisting of hepatocellular carcinoma, cholangiocarcinoma and hepatoblastoma.

The compounds have demonstrated a high inhibitory effect against different liver cancer cell lines (e.g. HepG2 or Huh7). Thus, an object of the present invention is quite particularly, the use of a compound of formula (I) as defined above, for preparing a medicament intended for the treatment of a neoplastic disease wherein the neoplastic disease is a liver cancer selected from hepatocellular carcinoma, cholangiocarcinoma and hepatoblastoma.

Further, the compounds of the present invention may also be suitable for targeting and killing cancer stem cells (CSC). Therefore, the present invention also provides, a compound a compound according to formula I or to formula II, or to formula III, or to formula III' or to formula IV, or respectively a pharmaceutically acceptable salt, hydrate, solvate, or prodrug thereof, or an isotopic variant, tautomer, or stereoisomer thereof, for use for inhibiting the growth or differentiation of a Cancer Stem Cell (CSC), a tumor initiating cell, a mesenchymal-like cell associated with cancer, a mesenchymal cancerous cell, or a mesenchymal cell.

The compounds of the present invention may also be useful for inhibiting cancer recurrence, in particular in liver and pancreas.

V. Pharmaceutical
Compositions—Formulations—Kits

The compounds of the present invention can be formulated in compositions (see section "pharmaceutical compositions" below). Optionally, the compositions can comprise one or more additional active substances (see section "Pharmaceutical combinations" below). The pharmaceutical compositions as well as the pharmaceutical combinations can be in any suitable form (depending upon the desired path of administration to an individual).
Pharmaceutical Compositions:

Accordingly, in another aspect, the present invention also provides pharmaceutical compositions which comprise as active ingredient one or more of the compounds of the invention. Typically, the compounds of the invention used as active ingredients are formulated together with one or more pharmaceutically acceptable carriers (e.g. excipient, diluent or adjuvant). Generally, the compounds of the invention, as active ingredients, are present in a therapeutically-effective amount in the pharmaceutical compositions according to the invention.

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) pulmonary; or (10) intrathecally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

Representative examples of materials which can serve as pharmaceutically-acceptable carriers include, without limitation: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or poly anhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and poly anhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or nonaqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, touches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to a subject in need thereof (e.g. humans or animals), they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to a subject in need (e.g. humans or animals), for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art. Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will firstly be dependent on the subject (human or animal) being treated and on the activity of the particular compound of the present invention being employed, or the pharmaceutically acceptable salt, hydrate, solvate, prodrug, isotopic variant, tautomer or stereoisomer thereof. In the instances where pharmaceutical compositions are administered to a human individual, the daily dosage will normally be determined by the prescribing physician with the dosage generally varying according to the age, sex, diet, weight, general health and response of the individual, the severity of the individual's symptoms, the precise indication or condition being treated, the severity of the indication or condition being treated, time of administration, route of administration, the disposition of the composition, rate of excretion, drug combination, and the discretion of the prescribing physician. Also, the route of administration may vary depending on the condition and its severity. Preferably, the pharmaceutical composition is in unit dosage form. In such form, the preparation is subdivided into unit doses containing appropriate quantities of the active component, e.g., an effective amount to achieve the desired purpose. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. The amount and frequency of administration of the compounds described herein, and if applicable other therapeutic agents and/or therapies, will be regulated according to the judgment of the attending clinician (physician) considering such factors as described above. Thus the amount of pharmaceutical composition to be administered may vary widely. Administration may occur in an amount of between about 0.001 mg/kg of body weight to about 100 mg/kg of body weight per day (administered in single or divided doses), more preferably at least about 0.1 mg/kg of body weight per day. A particular therapeutic dosage can include, e.g., from about 0.01 mg to about 7000 mg of compound, and preferably includes, e.g., from about 0.05 mg to about 2500 mg. More particularly, in the case of oral or parenteral administration to adult humans weighing approximately 70 kg, a daily dosage of 0.1 mg to 5 g, preferably from about 0.1 mg to 1 g, more preferably from 0.5 mg to 500 mg, and most preferably from about 1 mg to 300 mg, should be appropriate, although the upper limit can be exceeded when indicated. The quantity of active compound in a unit dose of preparation may be varied or adjusted from about 0.1 mg to 1000 mg, preferably from about 1 mg to 300 mg, more preferably 10 mg to 200 mg, according to the particular application. In some instances, dosage levels below the lower limit of the aforesaid range may be more than adequate, while in other cases still larger doses may be employed without causing any harmful side effect, e.g. by dividing such larger doses into several small doses for administration throughout the day. The amount administered will vary depending on the particular $IC_{50}$ or $EC_{50}$ value of the compound used. In combinational applications in which the compound is not the sole therapy, it may be possible to administer lesser amounts of compound and still have therapeutic or prophylactic effect. If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition). The compounds according to the invention may be formulated for administration in any convenient way for use in human or veterinary medicine, by analogy with other pharmaceuticals.

In another aspect, the present invention provides pharmaceutical compositions which comprise a therapeutically-effective amount of one or more of the subject compounds of the invention, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered. Microemulsification technology can improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C, et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation. While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastrointestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols. Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide). Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG-750). Polymers may also be defined by the number of monomers therein; a preferred embodiment of the present invention utilizes polymers of at least about three monomers, such PEG polymers consisting of three monomers (approximately 150 daltons). Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins are cyclic oligosaccharides, consisting of 6, 7 or 8 glucose units, designated by the Greek letter alpha, beta or gamma, respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17.beta-estradiol (see, e.g., van Uden et al. Plant Cell Tiss. Org. Cult. 38: 1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 µm in diameter; large unilamellar vesicles (LUVS) are typically larger than 0.05 µm. Oligolamellar large vesicles and multilamellar vesicles have multiple, usually concentric, membrane layers and are typically larger than 0.1µmη. Liposomes with several non-concentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively, or in addition, the compound of the present invention may be contained within, or adsorbed onto, the liposome bilayer of the liposome. The compound of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment. Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about $C_{14}$ to about $C_{20}$). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic D D, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art. In particular, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988). The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Pharmaceutical Combinations

In addition, the compounds of the invention may be used in combination with one or more other active agent (ingredients, drugs) in the treatment, prevention, suppression or amelioration of diseases or conditions for which compounds of the invention or the other active agent have utility.

Typically the combination of the drugs is safer or more effective than either drug alone, or the combination is safer or more effective than would it be expected based on the additive properties of the individual drugs. Such other drug(s) may be administered, by a route and in an amount commonly used contemporaneously or sequentially with a compound of the invention. When a compound of the invention is used contemporaneously with one or more other drugs, a combination product containing such other drug(s) and the compound of the invention is preferred. However, combination therapy also includes therapies in which the compound of the invention and one or more other drugs are administered on different overlapping schedules. It is contemplated that when used in combination with other active ingredients, the compound of the present invention or the other active ingredient or both may be used effectively in lower doses than when each is used alone. Accordingly, the pharmaceutical compositions of the present invention may include those that contain one or more other active agents, in addition to a compound of the invention.

In a particular embodiment, the additional active agent(s) that could be included in the pharmaceutical compositions of the invention is for the treatment of cancer. Preferably, the additional active agent is selected from the following classes of anticancer drugs: BCPv-ABL inhibitors, ALK inhibitors, BRAF inhibitors, FLT3 inhibitors, MEK Inhibitors, Vascular Endothelial Growth Factor (VEGF) receptor inhibitors, HER2 receptor inhibitors, CD20 antibodies, Tyrosine kinase inhibitors, DNA Synthesis inhibitors, Antineoplastic agents, Epidermal growth factor receptor (EGFR) inhibitors, HER dimerization inhibitors, Human Granulocyte colony-stimulating factor (G-CSF) modulators, Immunomodulators, CD40 inhibitors, Pro-apoptotic receptor agonists (PARAs), Hedgehog antagonists, PI3K inhibitors, Phospholipase A2 inhibitors, BCL-2 inhibitors, Mitogen-activated protein kinase kinase (MEK) inhibitors, Aromatase inhibitors, Topoisomerase I inhibitors, Topoisomerase II inhibitors, mTOR inhibitors, Osteoclastic bone resorption inhibitors, CD33 Antibody Drug Conjugates, CD22 Antibody Drug Conjugates, CD20 Antibody Drug Conjugates, Somatostain analogs, Synthetic Interleukin-11 (IL-11), Synthetic erythropoietin, Receptor Activator for Nuclear Factor is B (RANK) inhibitors, Thrombopoietin mimetic peptibodies, Cell growth stimulators, Anti-Insulin-like Growth Factor-1 receptor (IGF-1R) antibodies, Anti-CSI antibodies, CD52 antibodies, CTLA-4 inhibitors, Histone deacetylase inhibitors (HDI), Alkylating agents, Biologic response modifiers, Anti-tumor antibiotics, Anti-microtubule agents, Cathepsin K inhibitors, Epothilone B analogs, Heat Shock Protein (HSP) inhibitors, TpoR agonists, Anti-mitotic agents, Adrenal steroid inhibitors, Anti-androgens, Androgens, Proteasome inhibitors, CDK1 inhibitors, Gonadotropin-releasing hormone (GnRH) receptor agonists, Taxane anti-neoplastic agents, 5HTIa receptor agonists, HPC vaccines, Iron Chelating agents, Anti-metabolites, Bisphosphonates, Demethylating agents, Plant Alkaloids, Glucocorticosteroids, Cytokines, Estrogen receptor downregulators, Anti-estrogens, Selective estrogen receptor modulators (SERMs), Leutinizing hormone releasing hormone (LHRH) agonists, Progesterones, Miscellaneous cytotoxic agents.

Specific examples of each of theses classes of anticancer drugs are shown in table 4 below:

TABLE 4

Classes of anticancer drugs and some specific examples of anticancer drugs

| Classe of anticancer drugs | Specific examples |
| --- | --- |
| BCPv-ABL inhibitors | Imatinib (Gleevec ®); Inilotinib hydrochloride; Nilotinib (Tasigna ®); Dasatinib (BMS-345825); Bosutinib (SKI-606); Ponatinib (AP24534); Bafetinib (INNO406); Danusertib (PHA-739358), AT9283 (CAS 1133385-83-7); Saracatinib (AZD0530); and N-[2-[(1S,4R)-6-[[4-(Cyclobutylamino)-5-(trifluoromethyl)-2-pyrimidinyl]-amino]-1,2,3,4-tetrahydronaphthalen-1,4-imin-9-yl]-2-oxoethyl]-acetamide (PF-03814735, CAS 942487-16-3); and LGX818. |
| ALK inhibitors | PF-2341066 (XALKORI ®; crizotinib); 5-chloro-N4-(2-(isopropylsulfonyl)phenyl)-N2-(2-methoxy-4-(4-(4-methyl-piperazin-1-yl)piperidin-1-yl)phenyl)pyrimidine-2,4-diamine; GSK1838705A; and CH5424802. |
| BRAF inhibitors | Vemurafanib (PLX4032); and Dabrafenib. |
| FLT3 inhibitors | sunitinib malate (sold under the tradename Sutent ® by Pfizer); and PKC412 (midostaurin). |
| MEK Inhibitors | trametinib |
| Vascular Endothelial | Bevacizumab (sold under the trademark Avastin ® by |

TABLE 4-continued

Classes of anticancer drugs and some specific examples of anticancer drugs

| Classe of anticancer drugs | Specific examples |
|---|---|
| Growth Factor (VEGF) receptor inhibitors | Genentech/Roche), axitinib, (N-methyl-2-[[3-[(E)-2-pyridin-2-ylethenyl]-1H-indazol-6-yl]sulfanyl]benzamide, also known as AGO 13736, and described in PCT Publication No. WO 01/002369), Brivanib Alaninate ((S)-((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indol-6-yl)-2-[(4-pyridinylmethyl)amino]-3-pyridine-carboxamide, and described in PCT Publication No. WO 02/066470), pasireotide (also known as SOM230, and described in PCT Publication No. WO 02/010192), sorafenib (sold under the tradename Nexavar ®); |
| HER2 receptor inhibitors | Trastuzumab (sold under the trademark Herceptin ® by Genentech/Roche), neratinib (also known as HKI-272, (2E)-N-[4-[[3-chloro-4-[(pyridin-2-yl)methoxy]phenyl]amino]-3-cyano-7-ethoxyquinolin-6-yl]-4-dimethylamino)-but-2-enamide, and described PCT Publication No. WO 05/028443), lapatinib or lapatinib ditosylate (sold under the trademark Tykerb ® by Glaxo SmithKline); |
| CD20 antibodies | Rituximab (sold under the trademarks Riuxan ® and MabThera ® by Genentech/Roche), tositumomab sold under the trademarks Bexxar ® by GlaxoSmithKline), ofatumumab (sold under the trademark Arzerra ® by GlaxoSmithKline); |
| Tyrosine kinase inhibitors | Erlotinib hydrochloride (sold under the trademark Tarceva ® by Genentech/Roche), Linifanib (N-[4-(3-amino-1H-indazol-4-yl)phenyl]-N'-(2-fluoro-5-methyl-phenyl)-urea, also known as ABT 869, available from Genentech), sunitinib malate (sold under the tradename Sutent ® by Pfizer), bosutinib (4-[(2,4-dichloro-5-methoxyphenyl)amino]-6-methoxy-7-[3-(4-methyl-piperazin-1-yl)propoxy]quinoline-3-carbonitrile, also known as SKI-606, and described in U.S. Pat. No. 6,780,996), dasatinib (sold under the tradename Sprycel ® by Bristol-Myers Squibb), armala (also known as pazopanib, sold under the tradename Votrient ® by GlaxoSmithKline), imatinib and imatinib mesylate (sold under the tradenames Gilvec ® and Gleevec ® by Novartis); |
| DNA Synthesis inhibitors | Capecitabine (sold under the trademark Xeloda ® by Roche), gemcitabine hydrochloride (sold under the trademark Gemzar ® by Eli Lilly and Company), nelarabine ((2R,3S,4R,5R)-2-(2-amino-6-methoxy-purin-9-yl)-5-(hydroxymethyl)oxolane-3,4-diol, sold under the tradenames Arranon ® and Atriance ® by GlaxoSmithKline); |
| Antineoplastic agents | oxaliplatin (sold under the tradename Eloxatin ® ay Sanofi-Aventis and described in U.S. Pat. No. 4,169,846); |
| Epidermal growth factor receptor (EGFR) inhibitors | Gefitnib (sold under the tradename Iressa ®), N-[4-[(3-Chloro-4-fluorophenyl)amino]-7-[[(3"S")-tetrahydro-3-furanyl]oxy]-6-quinazolinyl]-4(dimethylamino)-2-buten-amide, sold under the tradename Tovok ® by Boehringer Ingelheim), cetuximab (sold under the tradename Erbitux ® by Bristol-Myers Squibb), panitumumab (sold under the tradename Vectibix ® by Amgen); |
| HER dimerization inhibitors | Pertuzumab (sold under the trademark Omnitarg ®, by Genentech); |
| Human Granulocyte colony-stimulating factor (G-CSF) modulators | Filgrastim (sold under the tradename Neupogen ® by Amgen); |
| Immunomodulators | Afutuzumab (available from Roche ®), pegfilgrastim (sold under the tradename Neulasta ® by Amgen), lenalidomide (also known as CC-5013, sold under the tradename Revlimid ®), thalidomide (sold under the tradename Thalomid ®); |
| CD40 inhibitors | Dacetuzumab (also known as SGN-40 or huS2C6, available from Seattle Genetics, Inc); |
| Pro-apoptotic receptor agonists (PARAs) | Dulanermin (also known as AMG-951, available from Amgen/Genentech); |
| Hedgehog antagonists | 2-chloro-N-[4-chloro-3-(2-pyridinyl)phenyl]-4-(methyl-sulfonyl)-benzamide (also known as GDC-0449, and described in PCT Publication No. WO 06/028958); |
| PI3K inhibitors | 4-[2-(1H-Indazol-4-yl)-6-[[4-(methylsulfonyl)piperazin-1-yl]-methyl]thieno[3,2-d]pyrimidin-4-yl]mo holine (also known as GDC 0941 and described in PCT Publication Nos. WO 09/036082 and WO 09/055730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806); |

TABLE 4-continued

Classes of anticancer drugs and some specific examples of anticancer drugs

| Classe of anticancer drugs | Specific examples |
|---|---|
| Phospholipase A2 inhibitors | Anagrelide (sold under the tradename Agrylin ®); |
| BCL-2 inhibitors | 4-[4-[[2-(4-chlorophenyl)-5,5-dimethyl-1-cyclohexen-1-yl] methyl]-1-piperazinyl]-N-[[4-[[(1R)-3-(4-morpholinyl)-1-[(phenylthio)methyl]propyl]amino]-3-[trifluoromethyl)-sulfonyl]-phenyl]sulfonyl]benzamide (also known as ABT-263 and described in PCT Publication No. WO 09/155386); |
| Mitogen-activated protein kinase kinase (MEK) inhibitors | XL-518 (Cas No. 1029872-29-4, available from ACC Corp.); |
| Aromatase inhibitors | Exemestane (sold under the trademark Aromasin ® by Pfizer), letrozole (sold under the tradename Femara ® by Novartis), anastrozole (sold under the tradename Arimidex ®); |
| Topoisomerase I inhibitors | Irinotecan (sold under the trademark Camptosar ® by Pfizer), topotecan hydrochloride (sold under the tradename Hycamtin ® by Glaxo SmithKline); |
| Topoisomerase II inhibitors | etoposide (also known as VP-16 and Etoposide phosphate, sold under the tradenames Toposar ®, VePesid ® and Etopophos ®), teniposide (also known as VM-26, sold under the tradename Vumon ®); |
| mTOR inhibitors | Temsirolimus (sold under the tradename Torisel ® by Pfizer), ridaforolimus (formally known as deferolimus, (1R,2R,4S)-4-[(2R)-2[(1R,9S,12S,15R,16E,18R,19R,21R, 23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0] hexatriaconta-16,24,26,28-tetraen-12-yl]propyl]-2-methoxycyclohexyl dimethylphosphinate, also known as AP23573 and MK8669, and described in PCT Publication No. WO 03/064383), everolimus (sold under the tradename Afinitor ® by Novartis); |
| Osteoclastic bone resorption inhibitors | 1-Hydroxy-2-imidazol-1-yl-phosphonoethyl) phosphonic acid monohydrate (sold under the tradename Zometa ® by Novartis); |
| CD33 Antibody Drug Conjugates | Gemtuzumab ozogamicin (sold under the tradename Mylotarg ® by Pfizer/Wyeth); |
| CD22 Antibody Drug Conjugates | Inotuzumab ozogamicin (also referred to as CMC-544 and WAY-207294, available from Hangzhou Sage Chemical Co., Ltd.); |
| CD20 Antibody Drug Conjugates | Ibritumomab tiuxetan (sold under the tradename Zevalin ®); |
| Somatostain analogs: | octreotide (also known as octreotide acetate, sold under the tradenames Sandostatin ® and Sandostatin LAR ®); |
| Synthetic Interleukin-11 (IL-11) | oprelvekin (sold under the tradename Neumega ® by Pfizer/Wyeth); |
| Synthetic erythropoietin | Darbepoetin alfa (sold under the tradename Aranesp ® by Amgen); |
| Receptor Activator for Nuclear Factor κ B (RANK) inhibitors | Denosumab (sold under the tradename Prolia ® by Amgen); |
| Thrombopoietin mimetic peptibodies | Romiplostim (sold under the tradename Nplate ® by Amgen; |
| Cell growth stimulators | Palifermin (sold under the tradename Kepivance ® by Amgen); |
| Anti-Insulin-like Growth Factor-1 receptor (IGF-1R) antibodies | Figitumumab (also known as CP-751,871, available from ACC Corp), robatumumab (CAS No. 934235-44-6); |
| Anti-CS1 antibodies | Elotuzumab (HuLuc63, CAS No. 915296-00-3); |
| CD52 antibodies | Alemtuzumab (sold under the tradename Campath ®); |
| CTLA-4 inhibitors | Tremelimumab (IgG2 monoclonal antibody available from Pfizer, formerly known as ticilimumab, CP-675,206), ipilimumab (CTLA-4 antibody, also known as MDX-010, CAS No. 477202-00-9); |
| Histone deacetylase inhibitors (HDI) | Voninostat (sold under the tradename Zolinza ® by Merck); |
| Alkylating agents | Temozolomide (sold under the tradenames Temodar ® and Temodal ® by Schering-Plough Merck), dactinomycin (also known as actinomycin-D and sold under the tradename Cosmegen ®), melphalan (also known as L-PAM, L-sarcolysin, and phenylalanine mustard, sold under the tradename Alkeran ®), altretamine (also known as hexamethylmelamine (HMM), sold under the tradename Hexalen ®), carmustine (sold under the tradename BiCNU ®), bendamustine (sold under the |

TABLE 4-continued

Classes of anticancer drugs and some specific examples of anticancer drugs

| Classe of anticancer drugs | Specific examples |
|---|---|
| | tradename Treanda ®), busulfan (sold under the tradenames Busulfex ® and Myleran ®), carboplatin (sold under the tradename Paraplatin ®), lomustine (also known as CCNU, sold under the tradename CeeNU ®), cisplatin (also known as CDDP, sold under the tradenames Platinol ® and Platinol ®-AQ), chlorambucil (sold under the tradename Leukeran ®), cyclophosphamide (sold under the tradenames Cytoxan ® and Neosar ®), dacarbazine (also known as DTIC, DIC and imidazole carboxamide, sold under the tradename DTIC-Dome ®), altretamine (also known as hexamethylmelamine (HMM) sold under the tradename Hexalen ®), ifosfamide (sold under the tradename Hex ®), procarbazine (sold under the tradename Matulane ®), mechlorethamine (also known as nitrogen mustard, mustine and mechloroethamine hydrochloride, sold under the tradename Mustargen ®), streptozocin (sold under the tradename Zanosar ®), thiotepa (also known as thiophosphoamide, TESPA and TSPA, sold under the tradename Thioplex ®; |
| Biologic response modifiers | bacillus calmette-guerin (sold under the tradenames theraCys ® and TICE ® BCG), denileukin diftitox (sold under the tradename Ontak ®); |
| Anti-tumor antibiotics | doxorubicin (sold under the tradenames Adriamycin ® and Rubex ®), bleomycin (sold under the tradename lenoxane ®), daunorubicin (also known as dauorubicin hydrochloride, daunomycin, and rubidomycin hydrochloride, sold under the tradename Cerubidine ®), daunorubicin liposomal (daunorubicin citrate liposome, sold under the tradename DaunoXome ®), mitoxantrone (also known as DHAD, sold under the tradename Novantrone ®), epirubicin (sold under the tradename Ellence ™), idarubicin (sold under the tradenames Idamycin ®, Idamycin PFS ®), mitomycin C (sold under the tradename Mutamycin ®); |
| Anti-microtubule agents | Estramustine (sold under the tradename Emcyl ®); |
| Cathepsin K inhibitors | Odanacatib (also know as MK-0822, N-(1-cyanocyclopropyl)-4-fluoro-N2-{(1S)-2,2,2-trifluoro-1-[4'-(methylsulfonyl)biphenyl-4-yl]ethyl}-L-leucinamide, available from Lanzhou Chon Chemicals, ACC Corp., and ChemieTek, and described in PCT Publication no. WO 03/075836); |
| Epothilone B analogs | lxabepilone (sold under the tradename Lxempra ® by Bristol-Myers Squibb); |
| Heat Shock Protein (HSP) inhibitors | Tanespimycin (17-allylamino-17-demethoxygeldanamycin, also known as KOS-953 and 17-AAG, available from SIGMA, and described in U.S Pat. No. 4,261,989); |
| TpoR agonists | Eltrombopag (sold under the tradenames Promacta ® and Revolade ® by Glaxo SmithKline); |
| Anti-mitotic agents | Docetaxel (sold under the tradename Taxotere ® by Sanofi-Aventis); |
| Adrenal steroid inhibitors | aminoglutethimide (sold under the tradename Cytadren ®); |
| Anti-androgens | Nilutamide (sold under the tradenames Nilandron ® and Anandron ®), bicalutamide (sold under tradename Casodex ®), flutamide (sold under the tradename Fulexin ™); |
| Androgens | Fluoxymesterone (sold under the tradename Halotestin ®); |
| Proteasome inhibitors | Bortezomib (sold under the tradename Velcade ®); |
| CDK1 inhibitors | Alvocidib (also known as flovopirdol or HMR-1275, 2-(2-chlorophenyl)-5,7-dihydroxy-8-[(3S,4R)-3-hydroxy-1-methyl-4-piperidinyl]-4-chromenone, and described in U.S. Pat. No. 5,621,002); |
| Gonadotropin-releasing hormone (GnRH) receptor agonists | Leuprolide or leuprolide acetate (sold under the tradenames Viadure ® by Bayer AG, Eligard ® by Sanofi-Aventis and Lupron ® by Abbott Lab); |
| Taxane anti-neoplastic agents | Cabazitaxel (1-hydroxy,7β,10β-dimethoxy-9-oxo-5β,20-epoxy-tax-11-ene-2α,4,13α-triyl-4-acetate-2-benzoate-13-[(2R,3S)-3-{[(tert-butoxy)carbonyl]amino}-2-hydroxy-3-phenyl-propanoate), larotaxel ((2α,3ξ,4α,5β,7α,10β,13α)-4,10-bis(acetyloxy)-13-({(2R,3S)-3-[(tert-butoxycarbonyl) amino]-2-hydroxy-3-phenylpropanoyl}oxy)-1-hydroxy-9-oxo-5,20-epoxy-7,19-cyclotax-11-en-2-yl benzoate); |
| 5HTIa receptor agonists | Xaliproden (also known as SR57746, 1-[2-(2-naphthypethyl]-4-[3-(trifluoromethyl)phenyl]-1,2,3,6 tetrahydropyridine, and described in U.S. Pat. No. 5,266,573); |

TABLE 4-continued

Classes of anticancer drugs and some specific examples of anticancer drugs

| Classe of anticancer drugs | Specific examples |
| --- | --- |
| HPC vaccines | Cervarix ® sold by Glaxo SmithKline, Gardasil ® sold by Merck; |
| Iron Chelating agents | Deferasinox (sold under the tradename Exjade ® by Novartis); |
| Anti-metabolites | Claribine (2-chlorodeoxyadenosine, sold under the tradename leustatin ®), 5-fluorouracil (sold under the tradename Adrucil ®), 6-thioguanine (sold under the tradename Purinethol ®), pemetrexed (sold under the tradename Alimta ®), cytarabine (also known as arabinosylcytosine (Ara-C), sold under the tradename Cytosar-U ®), cytarabine liposomal (also known as Liposomal Ara-C, sold under the tradename DepoCyt ™), decitabine (sold under the tradename Dacogen ®), hydroxyurea (sold under the tradenames Hydrea ®, Droxia ™ and Mylocel ™), fludarabine (sold under the tradename Fludara ®), floxuridine (sold under the tradename FUDR ®), cladribine (also known as 2-chlorodeoxyadenosine (2-CdA) sold under the tradename Leustatin ™), methotrexate (also known as amethopterin, methotrexate sodim (MTX), sold under the tradenames Rheumatrex ® and Trexall ™), pentostatin (sold under the tradename Nipent ®); |
| Bisphosphonates | Pamidronate (sold under the tradename Aredia ®), zoledronic acid (sold under the tradename Zometa ®); |
| Demethylating agents | 5-azacitidine (sold under the tradename Vidaza ®), decitabine (sold under the tradename Dacogen ®); |
| Plant Alkaloids | Paclitaxel protein-bound (sold under the tradename Abraxane ®), vinblastine (also known as vinblastine sulfate, vincaleukoblastine and VLB, sold under the tradenames Alkaban-AQ ® and Velban ®), vincristine (also known as vincristine sulfate, LCR, and VCR, sold under the tradenames Oncovin ® and Vincasar Pfs ®), vinorelbine (sold under the tradename Navelbine ®), paclitaxel (sold under the tradenames Taxol and Onxal ™); Retinoids: Alitretinoin (sold under the tradename Panretin ®), tretinoin (all-trans retinoic acid, also known as ATRA, sold under the tradename Vesanoid ®), Isotretinoin (13-cis-retinoic acid, sold under the tradenames Accutane ®, Amnesteem ®, Claravis ®, Claras ®, Decutan ®, Isotan ®, Izotech ®, Oratane ®, Isotret ®, and Sotret ®), bexarotene (sold under the tradename Targretin ®); |
| Glucocorticosteroids | Hydrocortisone (also known as cortisone, hydrocortisone sodium succinate, hydrocortisone sodium phosphate, and sold under the tradenames Ala-Cort ®, Hydrocortisone Phosphate, Solu-Cortef ®, Hydrocort Acetate ® and Lanacort ®), dexamethazone ((8S,9R,10S,11S,13S,14S,16R,17R)-9-fluoro-11, 17-dihydroxy-17-(2-hydroxy acetyl)-10,13,16-trimethyl-6,7,8,9,10,11,12,13,14,15,16,17-dodecahydro-3H-cyclopenta[a]phenanthren-3-one), prednisolone (sold under the tradenames Delta-Cortel ®, Orapred ®, Pediapred ® and Prelone ®), prednisone (sold under the tradenames Deltasone ®, Liquid Red ®, Meticorten ® and Orasone ®), methylprednisolone (also known as 6-Methylprednisolone, Methylprednisolone Acetate, Methylprednisolone Sodium Succinate, sold under the tradenames Duralone ®, Medralone ®, Medrol ®, M-Prednisol ® and Solu-Medrol ®); |
| Cytokines | interleukin-2 (also known as aldesleukin and IL-2, sold under the tradename Proleukin ®), interleukin-11 (also known as oprevelkin, sold under the tradename Neumega ®), alpha interferon alfa (also known as IFN-alpha, sold under the tradenames Intron ®A, and Roferon-A ®); |
| Estrogen receptor downregulators | Fulvestran (sold under the tradename Faslodex ®); |
| Anti-estrogens | tamoxifen (sold under the tradename Novaldex ®); Toremifene (sold under the tradename Fareston ®); |
| Selective estrogen receptor modulators (SERMs) | Raloxifene (sold under the tradename Evista ®); |
| Leutinizing hormone releasing hormone (LHRH) agonists | Goserelin (sold under the tradename Zoladex ®); |
| Progesterone | megetrol (also known as megestrol acetate, sold under the tradename Megace ®); |
| Miscellaneous cytotoxic agents | Arsenic trioxide (sold under the tradename Trisenox ®), asparaginase (also known as L-asparaginase, Erwinia L-asparaginase, sold under the tradenames Elspar ® and Kidrolase ®); |

A compound of formula (I) according to the invention can also be used in combination with the following adjunct therapies:

A compound of formula (I) according to the invention can also be used in combination with the following adjunct therapies:

Anti-nausea: NK-1 receptor antagonists: Casopitant (sold under the tradenames Rezonic® and Zunrisa® by GlaxoSmithKline); and Cytoprotective agents: Amifostine (sold under the tradename Ethyol®), leucovorin (also known as calcium leucovorin, citrovorum factor and folinic acid).

None of the quotations of references made within the present disclosure is to be understood as an admission that the references cited are prior art that would negatively affect the patentability of the present invention.

Kits

In another aspect, the present invention relates to a kit comprising (a) a compound of formula according to the present invention; and (b) an additional active substance (e.g. anti-cancer drug) as a pharmaceutical combination for simultaneous, separate or sequential use, for treating cancer.

Methods of Treatment

In another aspect, the present invention also provides a method for treating a proliferative disease comprising administering to a patient in need thereof a therapeutically effective amount of the compound of Formula I, of Formula II, of Formula III, or of Formula IV.

The present invention also provides a method for treating a neoplastic disease such as cancer, comprising administering to a patient in need thereof a therapeutically effective amount of a compound according to present invention or a pharmaceutical composition according to the present invention.

The present invention also provides a method for treating a non-neoplastic disease, comprising administering to a patient in need thereof a therapeutically effective amount of a compound according to present invention or a pharmaceutical composition according to the present invention.

In order that this invention may be better understood, the following examples are set forth. These examples are for the purpose of illustration only, and are not to be construed as limiting the scope of the invention in any manner. All publications mentioned herein are incorporated by reference in their entirety.

V. Examples

I. Chemical Syntheses
Materials & Methods Chemistry
Abbreviations and Acronyms

A comprehensive list of the abbreviations used by organic chemists of ordinary skill in the art appears in The ACS Style Guide (third edition) or the Guidelines for Authors for the Journal of Organic Chemistry. The abbreviations contained in said lists, and all abbreviations utilized by organic chemists of ordinary skill in the art are hereby incorporated by reference. For purposes of this invention, the chemical elements are identified in accordance with the Periodic Table of the Elements, CAS version, Handbook of Chemistry and Physics, 67th Ed., 1986-87.

More specifically, when the following abbreviations are used throughout this disclosure, they have the following meanings:

AcOEt: Ethyl acetate;
Ar: argon
Boc or BOC: tert-butyloxycarbonyl
DCM: Dichloromethane
DIAD: diisopropyl azodicarboxylate
DiPEA: N,N-Diisopropylethylaminhe
DMF: N,N-Dimethylformamide
$Et_2O$: Diethylether
ES+: Electrospray Ionisation
HCl: Hydrochloric acid
HMBC: Heteronuclear Multiple Bond Correlation, nuclear magnetic resonance
HPLC: High Performance Liquid Chromatography
MeCN: acetonitrile
MS: Mass spectrum, Mass spectrometry
MTBE: Methyl tert-Butyl ether
NMP: N-Methyl-2-Pyrrolidinone
NMR: Nuclear Magnetic Resonance experiment
RT: Room Temperature
UPLC: Ultra Performance Liquid Chromatography
THF: Tetrahydrofuran
TLC: Thin Layer Chromatography
$^1$H NMR: Proton Nuclear Magnetic Resonance
$^{13}$C NMR: Carbon Nuclear Magnetic Resonance
Δ: Reflux
g gram
h hour, hours
M mol L−1 (molar)
m multiplet
MHz megahertz
min minute, minutes
ml milliliter
μM micromolar
mol mole
mmol milimole
MW microwave
m/z mass-to-charge ratio
q quartet
RT retention time (HPLC)
rt room temperature
s singlet
t triplet Since compounds of the present invention, may contain more than one basic amine function, the salt form of the compounds of this invention can contain more than one acid addition (e.g. HCl). For example for HCl as acid addition, the stoichiometry of the hydrochloride salts can be variable and dependent of the compound's pKa and HCl's equivalent used for salification. Therefore, the hydrochloride salt form is presented as x.HCl, wherein x is ≥1.

Reagents and solvents were obtained from commercial suppliers and were used without further purification.

Flash chromatography purifications were performed on Merck silica gel (40-63 μM) as the stationary phase.

Analytical Methods

Reagents and solvents were obtained from commercial suppliers and were used without further purification.

Flash chromatography purifications were performed on Merck silica gel (40-63 μM) as the stationary phase.

The structures of compounds of this invention were confirmed using one or more of the following analytical methods.

NMR Methods:

Method 1: $^1$H and $^{13}$C NMR were performed using a BRUKER spectrometer Avance III nanobay—300 MHz.

Method 2: $^1$H and $^{13}$C NMR were performed using a BRUKER spectrometer Avance III nanobay—300 MHz Infrared Method: Infrared Spectra were recorded using IRAFFINITY-1 Fourier Transform infrared Spectrophotometer (SHIMADZU)

HPLC/MS/UV Methods

Method 1 HPLC/MS/UV/MS was performed using an AGILENT 1260 Infinity series and Mass quadrupole Agilent 6120 apparatus mainly with the gradient method described below:

Flow: 2 ml/min
Temperature: 35° C.
Column: Poroshell 120 SB-C18 2.7 µm 4.6×75 mm
Mobile Phase A: Formic acid 0.1% aq. (v/v)
Mobile Phase B: Methanol
Gradient elution:

| Time | A | B |
|------|-----|----|
| 0.5  | 95  | 5  |
| 4    | 10  | 90 |

Analysis run time: 8 min

Method 2 HPLC/UV/MS was performed using an AGILENT 1290 series and Mass 6130 quadrupole apparatus mainly with the gradient method described below:

Flow: 0.8 ml/min
Temperature: 60° C.
Column: Acquity UPLC BEH C18 1.7 µm 2.1×50 mm
Mobile Phase A: Formic acid 0.1% aq. (v/v)
Mobile Phase B: Formic acid 0.1% Acetonitrile
Gradient elution:

| Time | A  | B  |
|------|----|----|
| 0    | 97 | 3  |
| 0.2  | 97 | 3  |
| 1.5  | 5  | 95 |
| 2.5  | 5  | 95 |
| 2.6  | 97 | 3  |

Analysis run time: 2.6 min

Method 3 HPLC/UV was performed using Waters Alliance 2695 series apparatus mainly with the gradient method described below:

Flow: 1 ml/min
Temperature: Room temperature
Column: X-bridge C18 3.5 µm 4.6×150 mm
Mobile Phase A: 10 mM Ammonium acetate in water
Mobile Phase B: Acetonitrile
Gradient elution:

| Time | A  | B   |
|------|----|-----|
| 0    | 95 | 5   |
| 1.2  | 95 | 5   |
| 3    | 45 | 55  |
| 5    | 30 | 70  |
| 7    | 5  | 95  |
| 10   | 5  | 95  |
| 12   | 0  | 100 |
| 14   | 95 | 5   |
| 16   | 95 | 5   |

Analysis run time: 16 min

Method 4 HPLC/UV/MS was performed using an AGILENT 1290 series and Mass Agilent 6130 quadrupole apparatus mainly with the gradient method described below:

Flow: 0.5 ml/min
Temperature: 45° C.
Column: Acquity UPLC BEH C18 1.7 µm 2.1×50 mm
Mobile Phase A: Formic acid 0.1% aq. (v/v)
Mobile Phase B: Formic acid 0.1% Acetonitrile
Gradient elution:

| Time | A  | B  |
|------|----|----|
| 0    | 98 | 2  |
| 0.2  | 98 | 2  |
| 1.5  | 2  | 98 |
| 2.6  | 2  | 98 |
| 2.61 | 2  | 98 |
| 3.2  | 98 | 2  |

Analysis run time: 3.2 min

Method 5 HPLC/UV/MS was performed using Waters Alliance 2695 series and Mass Agilent 6130 quadrupole apparatus mainly with the gradient method described below:

Flow: 2 ml/min
Temperature: Room temperature
Column: X-bridge C18 3.5 µm 4.6×75 mm
Mobile Phase A: 10 mM Ammonium acetate in water
Mobile Phase B: Acetonitrile
Gradient elution:

| Time | A  | B   |
|------|----|-----|
| 0    | 90 | 10  |
| 0.2  | 90 | 10  |
| 2.5  | 75 | 25  |
| 3    | 0  | 100 |
| 4.8  | 0  | 100 |
| 5    | 90 | 10  |

Analysis run time: 5 min

Method 6 HPLC/UV/MS was performed using Waters Alliance 2695 series and Mass Agilent 6130 quadrupole apparatus mainly with the gradient method described below:

Flow: 0.8 ml/min
Temperature: 60° C.
Column: Acquity UPLC BEH C18 1.7 µm 2.1×50 mm
Mobile Phase A: Formic acid 0.1% aq. (v/v)
Mobile Phase B: Formic acid 0.1% Acetonitrile
Gradient elution:

| Time | A | B  |
|------|---|----|
| 0    |   | 2  |
| 0.4  |   | 3  |
| 2.2  |   | 98 |
| 2.6  |   | 98 |
| 2.61 |   | 3  |
| 3.0  |   | 3  |

Analysis run time: 3 min

Method 7 HPLC/UV/MS was performed using an AGILENT 1200 series and Mass Agilent 6130 quadrupole apparatus mainly with the gradient method described below:

Flow: 0.8 ml/min
Temperature: 60° C.
Column: Acquity UPLC BEH C18 1.7 µm 2.1×50 mm Mobile Phase A: Formic acid 0.1% aq. (v/v)
Mobile Phase B: Formic acid 0.1% Acetonitrile
Gradient elution:

| Time | A | B |
|------|-----|----|
| 0    | 97  | 3  |
| 0.2  | 97  | 3  |
| 1.5  | 5   | 95 |
| 2.5  | 5   | 95 |
| 2.6  | 97  | 3  |

Analysis run time: 2.6 min

Method 8 HPLC/UV/MS was performed using an AGILENT 1290 series and Mass Agilent 6130 quadrupole apparatus mainly with the gradient method described below:

Flow: 0.6 ml/min
Temperature: 35° C.
Column: Acquity UPLC BEH C18 1.7 μm 2.1×50 mm
Mobile Phase A: Formic acid 0.05% aq. (v/v)
Mobile Phase B: Formic acid 0.05% Acetonitrile
Gradient elution:

| Time | A  | B  |
|------|----|----|
| 0    | 97 | 3  |
| 0.4  | 97 | 3  |
| 3.2  | 2  | 98 |
| 3.8  | 2  | 98 |
| 4.2  | 97 | 3  |
| 4.5  | 97 | 3  |

Analysis run time: 4.5 min

Compounds of Formula I, II, III, IV, as well of starting materials, the reactants (e.g. alkylating agent (I-g)), and the intermediates, may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9): 1910-16, (1985); Helvetica Chimica Acta, 41: 1052-60, (1958); Arzneimittel-Forschung, 40(12): 1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-23, Wiley, N.Y. (1967-2006 ed.), or Beilsteins Handbuch der organischen Chemie, 4, Aufl. ed. Springer-Verlag, Berlin, including supplements (also available via the Beilstein online database).

Synthetic chemistry transformations and protecting group methodologies (protection and deprotection) useful in synthesizing Formula I (or II, III, IV) compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, 3r Ed., John Wiley and Sons (1999); and L. Paquette, ed., Encyclopedia of Reagents for Organic Synthesis, John Wiley and Sons (1995) and subsequent editions thereof.

The Examples provide exemplary methods for preparing Formula I (and II, III, IV) compounds. Those skilled in the art will appreciate that other synthetic routes may be used to synthesize the Formula I and II compounds. Although specific starting materials and reagents are depicted and discussed in the Figures and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

General Procedure for Palladium Coupling Assisted of Amine to 2,4-dichloroquinoline Substituted or Substituted for Synthesis of of 2-(Substituted-amino)-4-chloroquinoline Derivatives

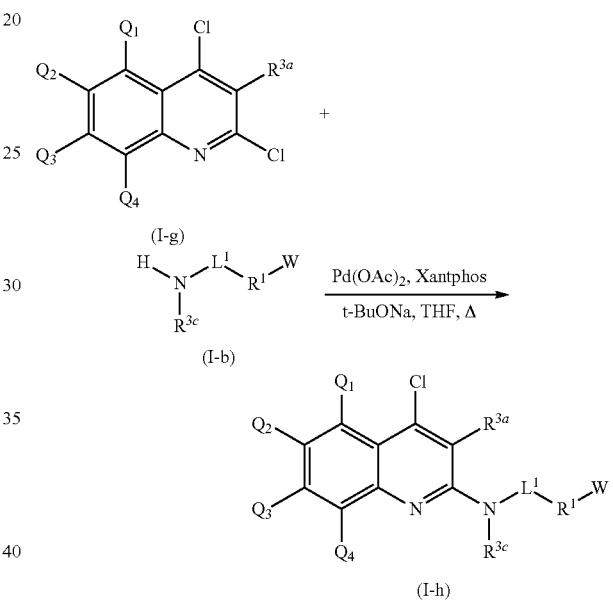

To a solution under nitrogen gas of 2,4-dichloroquinoline (10 mmol) in dry THF (20 ml) (Toluene and Dioxane can equally be used in such reactions) was added amine derivative (20 mmol, 2 eq.) and t-BuONa (28 mmol, 2.8 eq.). The resulting mixture was degassed 10 min with Argon, then Xantphos or other bidentate phosphine ligand usually used in amino aryl-halogen or amino heteroaryl-halogen Pd assisted coupling reaction (10 mmol, 0.1 eq.) and Pd(OAc)$_2$ (5.0 mmol, 0.05 eq.) (0.5 eq. of "Pd" is used regarding bidentate phosphine ligand used, other Pd$^{(II)}$ sources can be used, but preferentially Pd(OAc)$_2$) were added and the reaction mixture was heated under reflux until completion of the reaction. The reaction mixture was then cooled to room temperature and concentrated under reduced pressure. The residue was partitioned between brine and AcOEt and the aqueous layer was extracted with AcOEt. The combined organic layers were dried over MgSO4, filtered and concentrated under reduced pressure to give a crude mixture. The crude product was purified by flash chromatography to give the 2-(substituted amino)-4-chloroquinoline.

The amino substituent can be equally assembled, particularly R$^1$—W sub-structure using palladium assisted Aryl/Aryl coupling or palladium assisted Aryl/amino-aryl coupling.

Synthesis of Scaffold
2-(4-chlorobenzylamino)-4-chloroquinoline

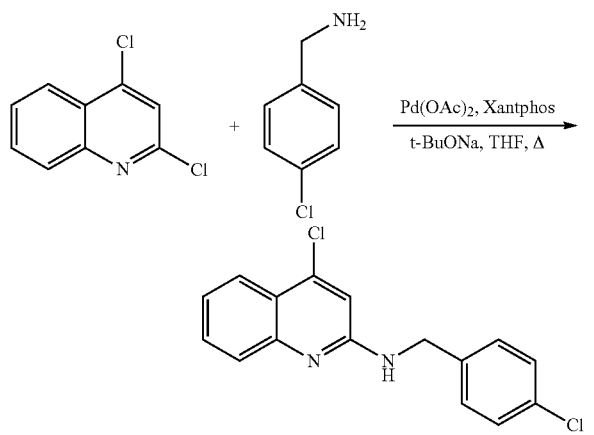

To a solution under nitrogen gas of 2,4-dichloroquinoline (20.0 g, 101 mmol) in dry THF (200 ml) was added 4-chlorobenzylamine (24.7 ml, 202 mmol, 2 eq.) and t-BuONa (27.2 g, 283 mmol, 2.8 eq.). The resulting mixture was degassed 10 min with nitrogen, then Xantphos (5.8 g, 10.1 mmol, 0.1 eq.) and Pd(OAc)$_2$ (1.1 g, 5.0 mmol, 0.05 eq.) were added and the reaction mixture was heated under reflux for 3 h. The reaction mixture was then cooled to room temperature and concentrated under reduced pressure. The residue was partitioned between brine and AcOEt and the aqueous layer was extracted with AcOEt. The combined organic layers were dried over MgSO$_4$, filtered and concentrated under reduced pressure to give a brown oil. The crude product was purified by flash chromatography (gradient Petroleum ether/DCM from 5/5 to 0/10) to give 13.5 g (yield 44%) of a brown solid corresponding to 2-(4-chlorobenzylamino)-4-chloroquinoline.

Mass: (ES+) C$_{18}$H$_{12}$Cl$_2$N$_2$, required 303; found 303-305 [M+H], HPLC/MS method 1.

Synthesis A: General Synthesis of 4-(Substituted Secondary cycloamine)-2-(4-chlorobenzylamino)-quinoline, Hydrochloride Salt Compound of Formula (I) with R$^{3a}$ and R$^{3c}$ Equals to H (See Table 5 Below)

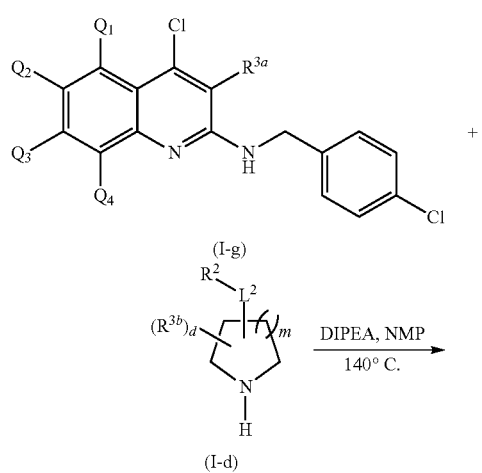

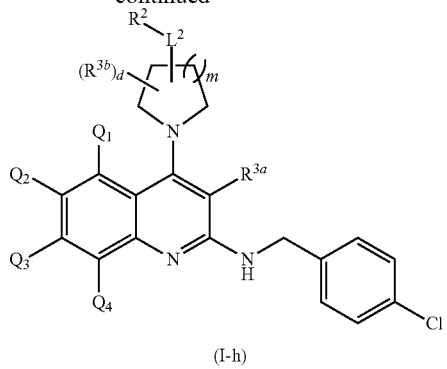

To a solution of 2-(4-chlorobenzylamino)-4-chloroquinoline (300 mg, 0.99 mmol) and corresponding substituted secondary cycloamine (1.25 eq.) in 2 ml of NMP was added N,N-Diisopropylethylamine (DiPEA) and the resulting mixture was heated for 24 h at 140° C. Then, the reaction mixture was cooled, diluted with a 1N NaOH aqueous solution (25 ml) and the resulting mixture was extracted with AcOEt. The combined organic layers were dried over MgSO$_4$, filtered and concentrated under reduced pressure to give a brown oil. The crude product was purified by flash chromatography.

Then, the compound was converted into a hydrochloride salt by dilution in DCM and addition of a solution of HCl 2N in Et$_2$O (4 eq.). The resulting solution was stirred for 15 min at room temperature, and then concentrated under reduced pressure. The obtained hydrochloride salt was dissolved in H$_2$O and freeze dried.

TABLE 5

Compounds synthetized according to procedure described above

| Example | Amine | Eq. of DiPEA | Gradient of flash chromatography | yield |
|---|---|---|---|---|
| 116 | 1-(Azetidin-3-yl) pyrrolidine HCl | 3 | DCM/AcOEt (10/0 > 0/10) | 35% |
| 118 | 4-(azetidin-3-yl) morpholine HCl | 3 | DCM/AcOEt (10/0 > 0/10) | 50% |
| 1598 | Piperidine-4-carboxylic acid methylamide | 1.6 | DCM/AcOEt (10/0 > 0/10) | 80% |
| 1604 | N-t-butylpiperidine-4-carboxamide | 1.6 | DCM/AcOEt (10/0 > 0/10) | 80% |

TABLE 5-continued

Compounds synthetized according to procedure described above

| Example | Amine | Eq. of DiPEA | Gradient of flash chromatography | yield |
|---|---|---|---|---|
| 1648 | 4-(1-pyrrolidinylcarbonyl)piperidine nitrate | 1.6 | DCM/MeOH (10/0 > 7/3) | 65% |
| 1656 | (4-Methylpiperazin-1-yl)piperidin-4-yl-methanone diHCl | 4 | DCM/MeOH (10/0 > 8/2) | 40% |
| 2308 | L-Prolinol | 1.6 | DCM/MeOH (10/0 > 7/3) | 70% |
| 2310 | (S)-(+)-2-Methoxymethyl-pyrrolidine | 1.6 | DCM/AcOEt (10/0 > 0/10) | 70% |
| 2380 | D-Prolinol | 1.6 | DCM/MeOH (10/0 > 8/2) | 60% |
| 2916 | 4-Hydroxypiperidine | 1.6 | DCM/MeOH (10/0 > 7/3) | 85% |
| 2918 | 4-Isopropoxypiperidine | 1.6 | DCM/AcOEt (10/0 > 0/10) | 70% |
| 2940 | 4-Phenoxypiperidine | 1.6 | DCM/AcOEt (10/0 > 0/10) | 60% |
| 2946 | 4-(3-methylphenoxy)piperidine HCl | 3 | DCM/AcOEt (10/0 > 0/10) | 85% |
| 2950 | 4-(Piperidin-4-yloxy)pyridine 2HCl | 4 | DCM/AcOEt (10/0 > 0/10) | 80% |
| 2958 | 2-(Piperidin-4-yloxy)pyrazine HCl | 3 | DCM/MeOH (10/0 > 8/2) | 65% |
| 2988 | (R)-3-Pyrrolidinol | 1.6 | DCM/MeOH (10/0 > 7/3) | 80% |
| 3012 | (R)-3-Phenoxy-pyrrolidine·HCl | 3 | DCM/AcOEt (10/0 > 0/10) | 75% |
| 3026 | (R)-2-(Pyrrolidin-3-yloxy)-pyridine, 2HCl | 4 | DCM/AcOEt (10/0 > 0/10) | 80% |
| 3060 | (S)-3-Pyrrolidinol | 1.6 | DCM/MeOH (10/0 > 7/3) | 80% |

TABLE 5-continued

Compounds synthetized according to procedure described above

| Example | Amine | Eq. of DiPEA | Gradient of flash chromatography | yield |
|---|---|---|---|---|
| 3098 | 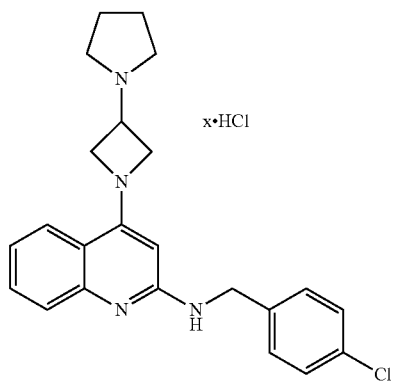<br>(S)-2-(Pyrrolidin-3-yloxy)-pyridine 2HCl | 4 | DCM/AcOEt (10/0 > 0/10) | 80% |

Chemical Structure of Compounds Prepared According to the General Procedure A Described Above:

2-(4-chlorobenzylamino)-4-[3-(pyrrolidin-1-yl)azetidin-1-yl]quinoline hydrochloride (116), 2-(4-chlorobenzylamino)-4-[3-(morpholin-4-yl)azetidin-1-yl]quinoline hydrochloride (118), 2-(4-chlorobenzylamino)-4-[4-(methylcarbamoyl)piperidin-1-yl]quinoline hydrochloride (1598), 2-(4-chlorobenzylamino)-4-[4-(tert-butylaminocarbonyl)-piperidin-1-yl]-quinoline hydrochloride (1604), 2-(4-chlorobenzylamino)-4-[4-(pyrrolidine-1-carbonyl)piperidin-1-yl]quinoline, hydrochloride (1648), 2-(4-chloro-benzylamino)-4-[4-(4-methylpiperazine-1-carbonyl)-piperidin-1-yl]-quinoline hydrochloride (1656), (2S) 2-(4-chlorobenzylamino)-4-[2-(hydroxymethyl)pyrrolidin-1-yl]quinoline, hydrochloride (2308), (2S) 2-(4-chlorobenzylamino)-4-[2-(methoxymethyl)pyrrolidin-1-yl]quinoline, hydrochloride (2310), (2R)-2-(4-chlorobenzylamino)-4-[2-(hydroxymethyl)-pyrrolidin-1-yl]-quinoline hydrochloride (2380), 2-(4-chlorobenzylamino)-4-(4-hydroxypiperidin-1-yl)quinoline, hydrochloride (2916), 2-(4-chlorobenzylamino)-4-[4-(isopropoxy)-piperidin-1-yl]-quinoline hydrochloride (2918), 2-(4-chlorobenzylamino)-4-(4-phenoxypiperidin-1-yl)-quinoline hydrochloride (2940):

116

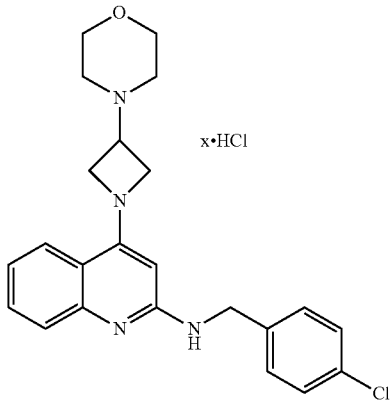

118

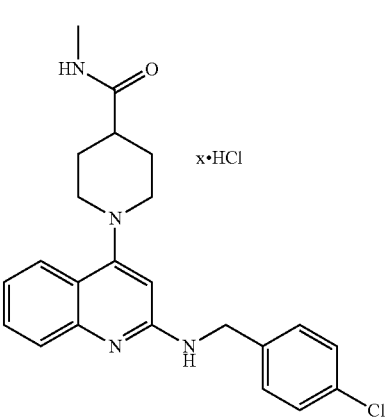

1598

1604

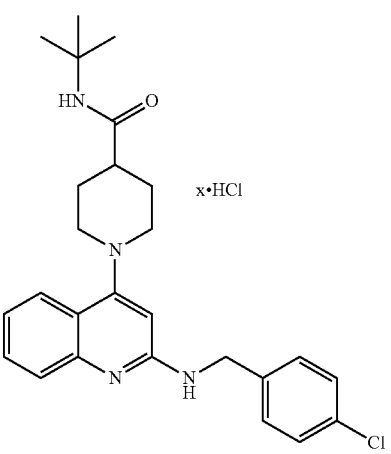

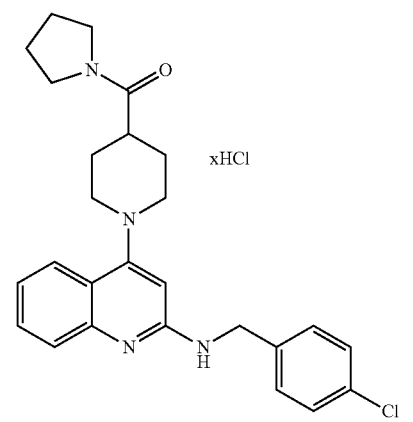

1648

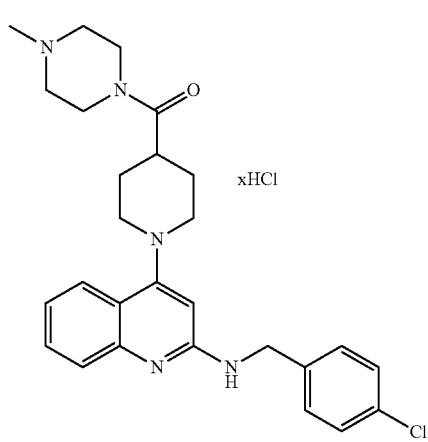

1598

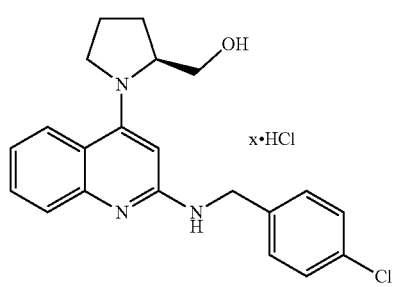

2308

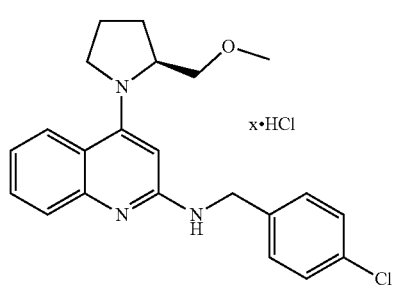

2310

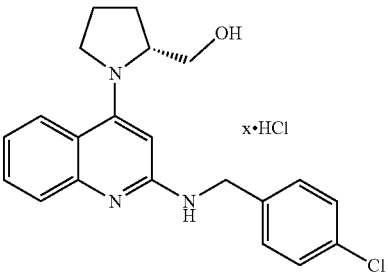

2380

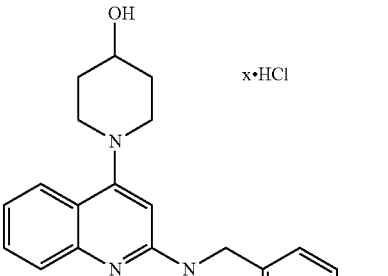

2916

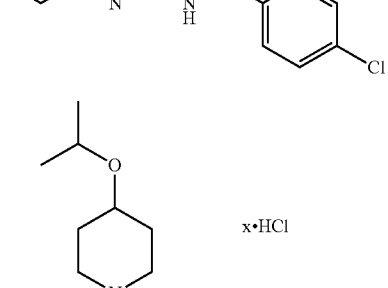

2918

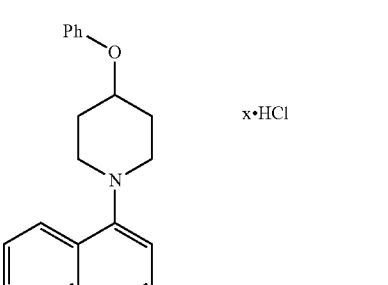

2940

Chemical Structure of Compounds Prepared According to the General Procedure A Described Above:

2-(4-chlorobenzylamino)-4-[4-(m-tolyloxy)piperidin-1-yl]quinoline hydrochloride (2946), 2-(4-chlorobenzylamino)-4-[4-(pyridin-4-yloxy)piperidin-1-yl]quinoline hydrochloride (2950), 2-(4-chlorobenzylamino)-4-[4-(pyrazin-2-yloxy)piperidin-1-yl]quinoline hydrochloride (2958), (3R) 2-(4-chlorobenzylamino)-4-(3-hydroxypyrrolidin-1-yl)quinoline hydrochloride (2988), (3R) 2-(4-chlorobenzylamino)-4-[3-(phenoxy)pyrrolidin-1-yl]quinoline hydrochloride (3012), (3R) 2-(4-chlorobenzylamino)-4-[3-(pyridin-2-yloxy)pyrrolidin-1-yl]quinoline hydrochloride (3026), (3S) 2-(4-chlorobenzylamino)-4-(3-hydroxypyrrolidin-1-yl)-quinoline hydrochloride (3060), (3S) 2-(4-chlorobenzylamino)-4-[3-(pyridin-2-yloxy)pyrrolidin-1-yl]quinoline hydrochloride (3098):
2946
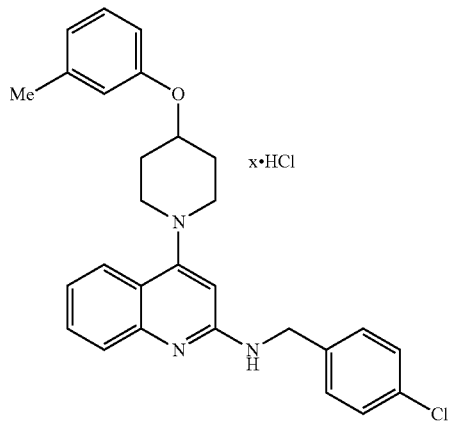
2950
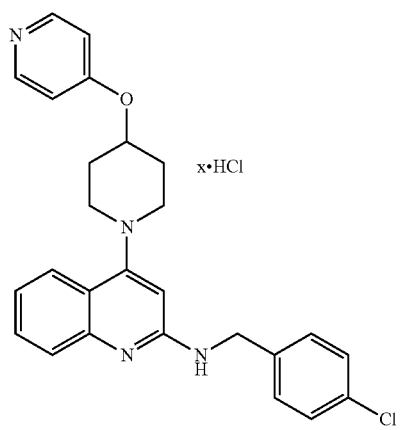
2958
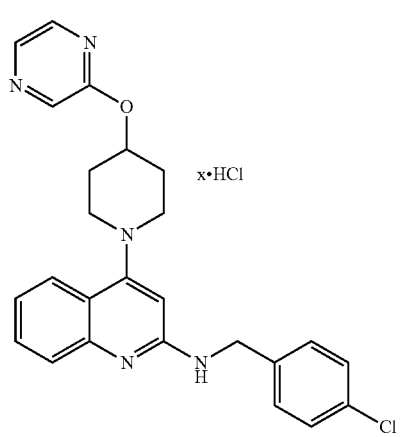
-continued
2988
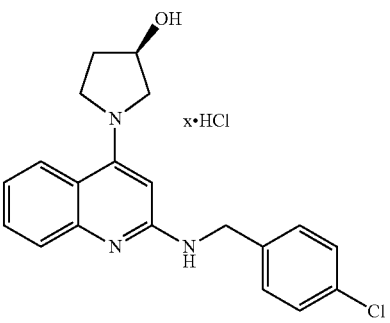
3012
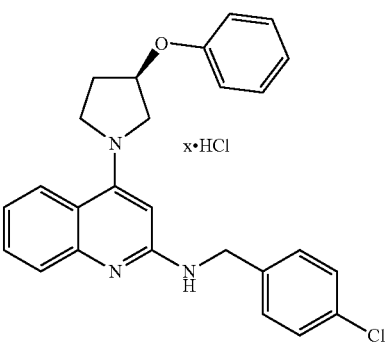
3026
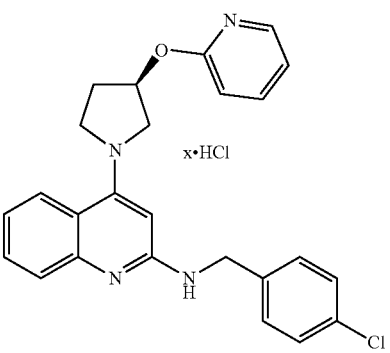
3060
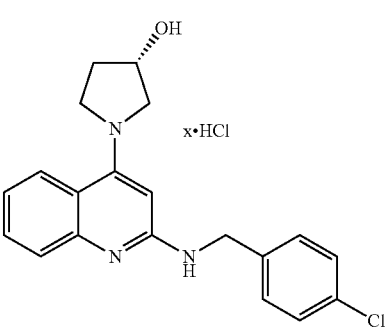

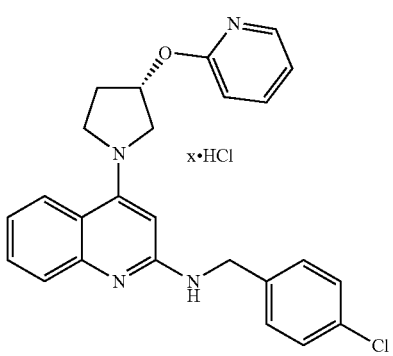

3098

General Procedure for Synthesis of 4-(Substituted Secondary cycloamine)-2-(Substituted, Unsubstituted aryl-heteroaryl amine)-quinoline, Hydrochloride Salt Compound of Formula (I) with

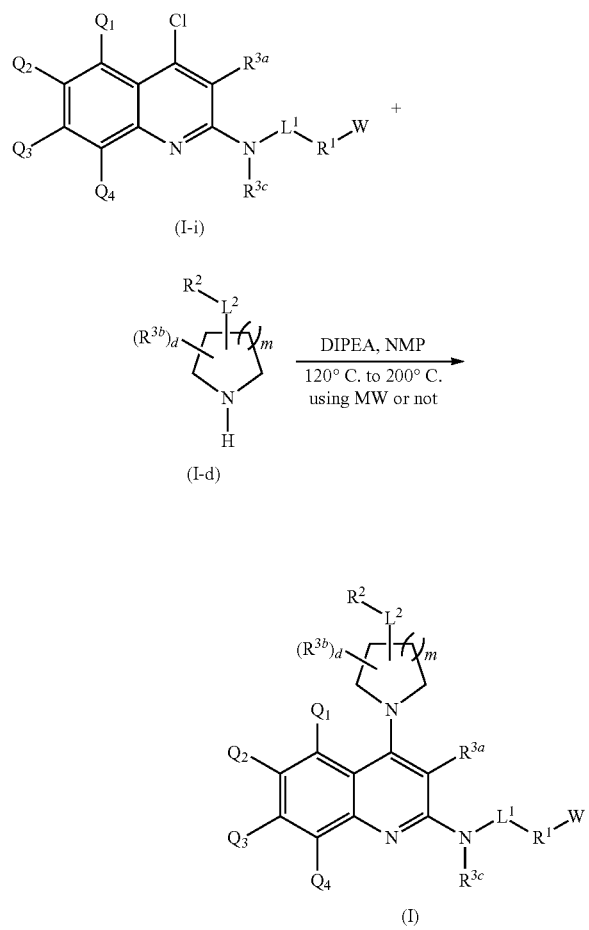

To a solution of 2-(substituted, unsubstituted aryl-heteroaryl amine)-4-chloroquinoline (1 mmol, 1.0 eq.) and the corresponding substituted secondary cycloamine (1.25 mmol, 1.25 eq.) in 2 ml of NMP was added N,N-Diisopropylethylamine (DIPEA, 2 to 6 eq.) and the resulting mixture was heated at 140° C. until completion of the reaction (Dependent of the substrate reactivity, the reaction temperature can be adjusted between 120° C. to 200° C. with or without a microwave oven). Then, the reaction mixture was cooled, diluted with a 1N NaOH aqueous solution (25 ml) and the resulting mixture was extracted with AcOEt. The combined organic layers were dried over $MgSO_4$, filtered and concentrated under reduced pressure to give a brown oil. The crude product was purified by flash chromatography.

Then, the compound was converted into a hydrochloride salt by dilution in DCM and addition of a solution of HCl 2N in $Et_2O$ (4 eq.). The resulting solution was stirred for 15 min at room temperature, and then concentrated under reduced pressure. The obtained hydrochloride salt was dissolved in $H_2O$ and finally freeze dried.

Preparation of Compound 212: 2-(N-4-chlorobenzyl-N-methylamino)-4-[4-(tert-butylamino)-piperidin-1-yl]-quinoline, Hydrochloride Salt Synthesis of 2-(4-chloro-N-methylbenzylamino)-4-chloroquinoline, Intermediate 212-I-1

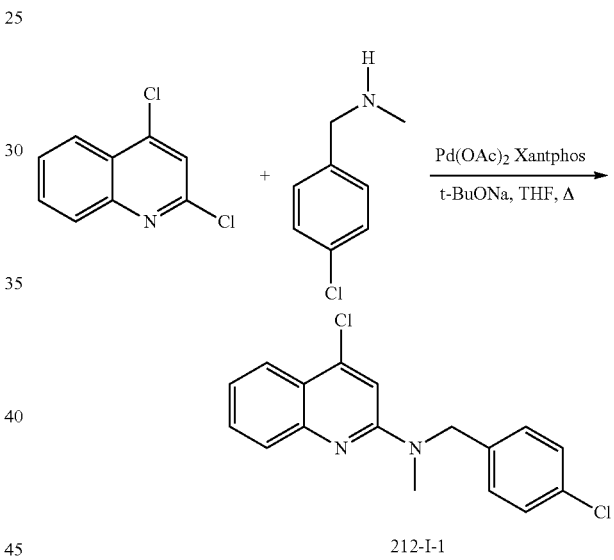

To a solution under nitrogen gas of 2,4-dichloroquinoline (1.00 g, 5.0 mmol) in dry THF (10 ml) was added 4-chloro-N-methylbenzylamine (1.57 g, 10.1 mmol, 2 eq.) and t-BuONa (1.36 g, 14.1 mmol, 2.8 eq.). The resulting mixture was degassed 5 min with nitrogen, then Xantphos (292 mg, 0.51 mmol, 0.1 eq.) and $Pd(OAc)_2$ (57 mg, 0.25 mmol) were added and the reaction mixture was heated under reflux for 3 h. The reaction mixture was then cooled to room temperature and concentrated under reduced pressure. The residue was partitioned between brine and AcOEt and the aqueous layer was extracted with AcOEt. The combined organic layers were dried over $MgSO_4$, filtered and concentrated under reduced pressure to give a brown oil. The crude product was purified by flash chromatography (gradient Petroleum ether/DCM from 5/5 to 0/10) to give 800 mg (yield 50%) of a brown solid corresponding to 2-(4-chloro-N-methylbenzylamino)-4-chloroquinoline.

Mass: (ES+) $C_{17}H_{14}Cl_2N_2$, required 317; found 317-319 [M+H], HPLC/MS method 1.

Synthesis of Compound 212: 2-(N-4-chlorobenzyl-N-methylamino)-4-[4-(tert-butylamino)-piperidin-1-yl]-quinoline, Hydrochloride Salt

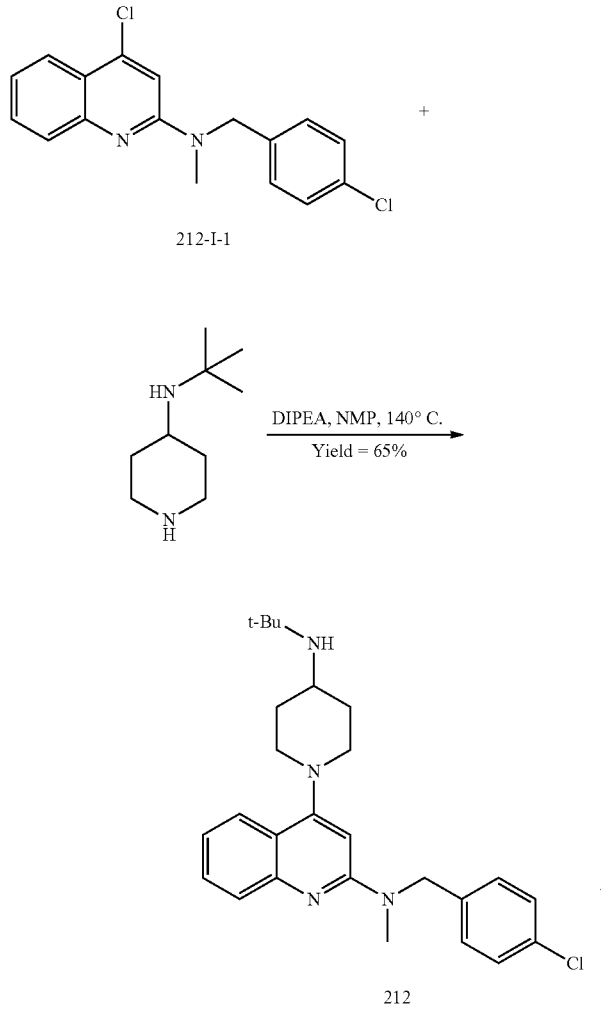

To a solution of 2-(4-chloro-N-methylbenzylamino)-4-chloroquinoline (200 mg, 0.63 mmol) and 4-(tert-butylamino)-piperidine (123 mg, 0.79 mmol, 1.25 eq.) in 2 ml of NMP was added N,N-Diisopropylethylamine (175 μl, 1.0 mmol) and the resulting mixture was heated for 42 h at 140° C. Then, the reaction mixture was cooled, diluted with a 1N NaOH aqueous solution (25 ml) and the resulting mixture was extracted with AcOEt. The combined organic layers were dried over MgSO4, filtered and concentrated under reduced pressure to give a yellow oil. The crude product was purified by flash chromatography (gradient DCM/MeOH from 10/0 to 8/2). The compound was converted into a hydrochloride salt by dilution in DCM and addition of a solution of HCl 2N in Et2O (4 eq.). The solution was stirred for 15 min at room temperature and then concentrated under reduced pressure. The obtained hydrochloride salt was dissolved in H2O and then freeze-dried to give 194 mg (yield 65%) of a white solid corresponding to 2-(N-4-chlorobenzyl-N-methylamino)-4-[4-(tert-butylamino)-piperidin-1-yl]-quinoline, hydrochloride salt.

Synthesis B: General Synthesis of 2-(N-4-chlorobenzyl-N-alkylamino)-4-[4-(tert-butylamino)-piperidin-1-yl]-quinoline Derivatives (214, 216, 220)

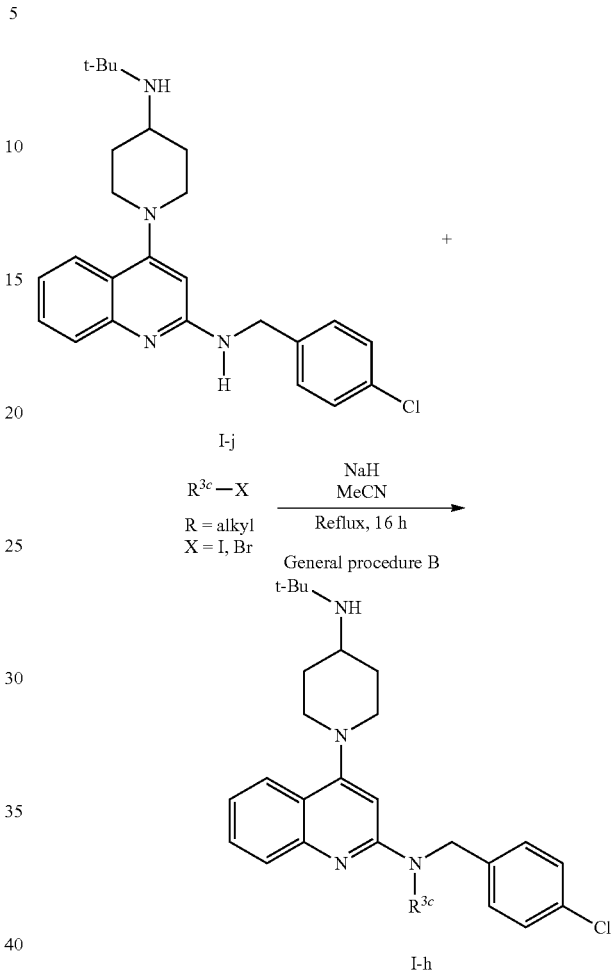

To a solution of 2-(4-chlorobenzylamino)-4-(4-tert-butylaminopiperidin-1-yl)-quinoline (100 mg, 0.24 mmol) in acetonitrile (3 ml) were added Alkyl halide (4 eq.) and NaH (60% in oil, 4 eq.). The resulting mixture was heated under reflux for 24 h. Then, the reaction mixture was cooled to room temperature, diluted with cold water (10 ml) and the resulting mixture was extracted with AcOEt. The combined organic layers were dried over MgSO4, filtered and concentrated under reduced pressure. The crude product was purified by flash chromatography.

TABLE 6

Compounds prepared by N-alkylation of 2-(4-benzylamino)quinoline derivatives

| Compound | Alkyl halide | Equivalent of NaH | Gradient Flash chromatography | Yield |
|---|---|---|---|---|
| 214 | Iodoethane | 4 | DCM/MeOH (10/0 > 8/2) | 25% |
| 216 | 2-Bromopropane | 4 | DCM/MeOH (10/0 > 8/2)) | 10% |
| 220 | 1-Bromo-2-methylpropane | 4 | DCM/MeOH (10/0 > 8/2) | 10% |

The compound was converted into a hydrochloride salt by dilution in DCM and addition of a solution of HCl 2N in Et$_2$O (4 eq.). The solution was stirred for 15 min at room temperature and then concentrated under reduced pressure. Then, the obtained hydrochloride salt was dissolved in H$_2$O and freeze dried.

Chemical Structure of Compounds Prepared According to the General Procedure B Described Above:

2-(N-4-chlorobenzyl-N-ethylamino)-4-[4-(tert-butylamino)-piperidin-1-yl]-quinoline hydrochloride (214), 2-(N-4-chlorobenzyl-N-isopropylamino)-4-[4-(tert-butylamino)-piperidin-1-yl]-quinoline hydrochloride (216), 2-(N-4-chlorobenzyl-N-isobutylamino)-4-[4-(tert-butylamino)-piperidin-1-yl]-quinoline (220).

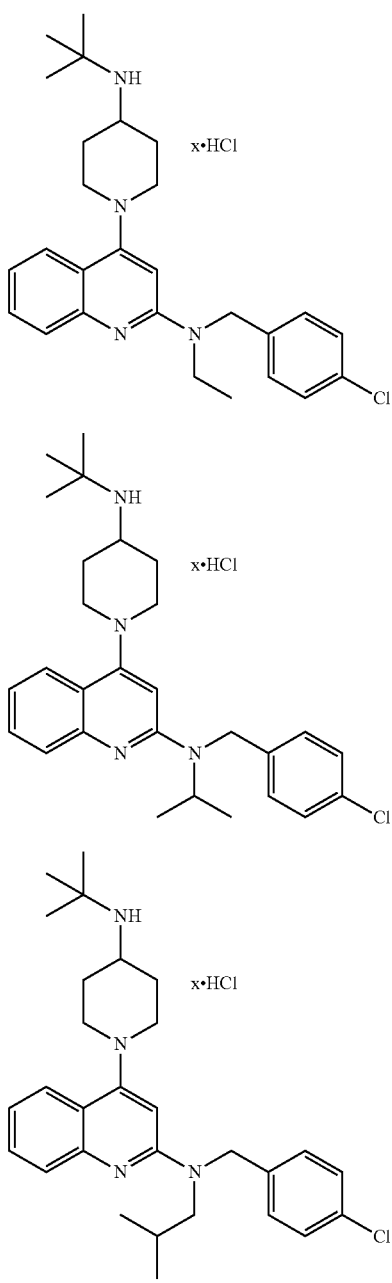

General Procedure for Synthesis of 2-(N,N-Disubstituted-amino)-4-[Substituted Secondary cycloamine)-quinoline Derivatives Obtained by N-alkylation

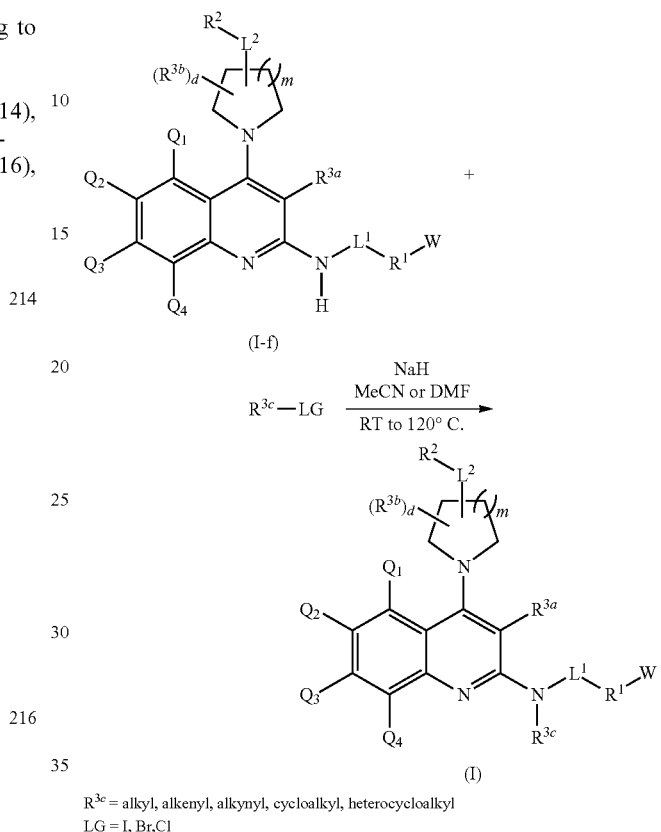

$R^{3c}$ = alkyl, alkenyl, alkynyl, cycloalkyl, heterocycloalkyl
LG = I, Br, Cl

To a solution at 0° C. of mono substituted 2-aminoquinoline derivative A-1 (1 mmol) in acetonitrile (3 to 10 ml) were added alkylation halide agent (4 eq.) and NaH (60% in oil, 4 eq.). The resulting mixture was heated to room temperature or dependent of the substrate reactivity the reaction mixture can be heated from room temperature to 120° C. (using MeCN, THF, MTHF or DMF as solvent) under until reaction completion. Catalytic amount of quaternary ammonium halide can be used during the reaction such as tetrabutylammonium bromide, tetrabutylammonium iodide, benzyltriethylammonium bromide, benzyltriethylammonium chloride, and dependent of the reactivity of the mono-substituted 2-amino-quinoline derivative (I-f), sodium hydride might be replaced by K$_2$CO$_3$, K$_2$CO$_3$ or Cs$_2$CO$_3$ (2 to 6 eq.). When carbonate base is used, MeCN, THF, MTHF, DMF, NMP or toluene can be used as solvent. Then, the reaction mixture was cooled to room temperature, diluted with cold water (10-50 ml) and the resulting mixture was extracted with AcOEt. The combined organic layers were dried over MgSO$_4$, filtered and concentrated under reduced pressure. The crude product was purified by flash chromatography to give the R$^{3c}$ substituted 2-amino-quinoline derivative for formula (I).

Preparation of Compound 348, 2-(4-chlorobenzylamino)-3-fluoro-4-[4-(tert-butylamino)piperidin-1-yl]quinoline Hydrochloride Salt

Synthesis 2-fluoromalonic acid, Intermediate 348-I-1

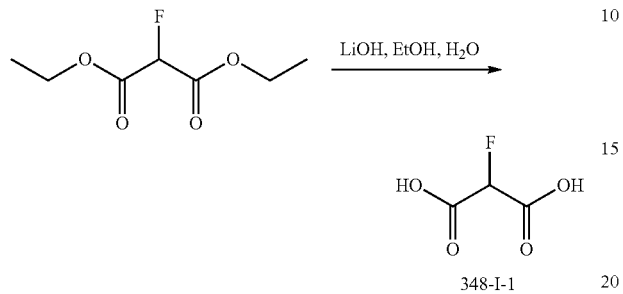

348-I-1

To diethyl 2 fluoromalonate ester (1.0 g, 5.617 mmol) was added ethanol (10 ml), water (10 ml), and lithium hydroxide monohydrate (0.943 g, 22.47 mmol), then the reaction was stirred well for 16 h at 50° C. Then the reaction mixture was cooled to room temperature and concentrated under reduced pressure. The residue was diluted in MTBE and water, then mixture was acidify with 6N HCl and then extracted with MTBE (5×50 ml). The combined organic layer were dried over Na₂SO₄, filtered and concentrated under reduced pressure to give 400 mg (yield 58%) of a white solid corresponding to 2-fluoromalonic acid. The crude product used in the next step without further purification.

Synthesis of 2,4-dichloro-3-fluoroquinoline, Intermediate 348-I-2

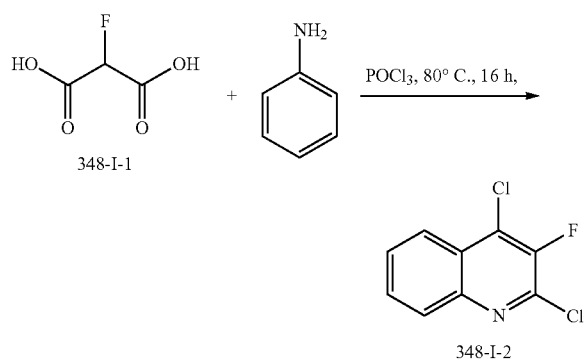

348-I-1

348-I-2

To compound 348-I-1 (1.0 g, 8.196 mmol) was added Phosphoryl chloride (20 ml), then the reaction was stirred well for 30 min at 80° C., then the reaction mixture was cooled to 50° C. To the crude mixture was added the aniline (0.609 g, 6.557 mmol) portion wise and the resulting mixture was stirred at 80° C. for 16 h. The reaction mixture was allowed to room temperature and poured into ice water, then quenched with aqueous ammonia solution, and then the aqueous layer was extracted with AcOEt (2×50 ml). The combined organic layer were dried over Na₂SO₄, filtered and concentrated under reduced pressure to give a crude compound which upon purification by flash chromatography using (silica-gel: 100-200 mesh, AcOEt-petroleum ether; 2:98→5:95) gave 400 mg (yield 23%) of a white solid corresponding to 2,4-dichloro-3-fluoroquinoline.

Mass: (ES+) $C_9H_4Cl_2FN$ required 214.97; found 215.9 [M+H], HPLC/MS method 7

Synthesis of 2-(4-chlorobenzylamino)-3-fluoro-4-chloroquinoline, Intermediate 348-I-3

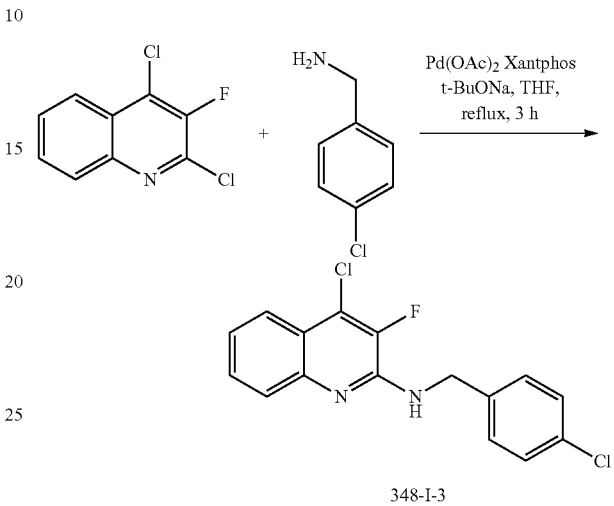

348-I-3

To a solution under nitrogen gas of compound 348-I-2 (0.4 g, 1.860 mmol) in THF (20 ml) was added 4-chlorobenzylamine (0.395 g, 2.791 mmol) and t-BuONa (0.541 g, 5.582 mmol). The resulting mixture was degassed 30 min with Ar gas, then Xantphos (108 mg, 0.1860 mmol) and palladium acetate (42 mg, 0.1860 mmol) were added and the reaction mixture was stirred at 80° C. for 3 h. The reaction mixture was then cooled to room temperature, filtered and concentrated under reduced pressure. The residue was partitioned between brine and AcOEt and the aqueous layer was extracted with AcOEt. The combined organic layers were dried over Na₂SO₄, filtered and concentrated under reduced pressure to give brown oil. The crude compound which upon purification by flash chromatography using (silica-gel: 100-200 mesh, AcOEt-petroleum ether; 10:90→50:50) gave 300 mg (yield 50%) of a white solid corresponding 2-(4-chlorobenzylamino)-3-fluoro-4-chloroquinoline. (Compound 348-I-3 has been confirmed by HMBC NMR experiment).

Mass: (ES+) $C_{16}H_{11}Cl_2FN_2$ required 320.03; found 321.22 [M+H], HPLC/MS method 4.

Synthesis of Compound 348 Free Base, 2-(4-chlorobenzylamino)-3-fluoro-4-[4-(tert-butylamino)piperidin-1-yl]quinoline

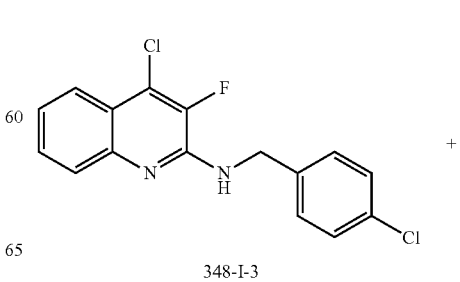

348-I-3

-continued

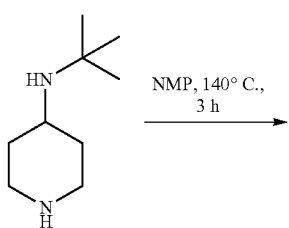

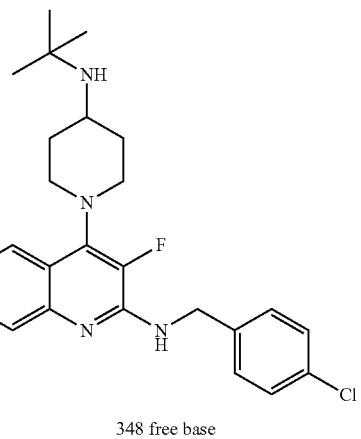

348 free base

To a solution of compound 348-I-3 (300 mg, 0.936 mmol) in 6 ml of NMP was added 4-(tert-butylamino)-piperidine (580 mg, 3.75 mmol) and the mixture was heated in a microwave oven for 3 h at 140° C. Then, the reaction mixture was cooled, diluted with ice water and filtered, collected solid was purified by flash chromatography using (silica-gel: 100-200 mesh, AcOEt-petroleum ether; 10:90→50:50) to give 100 mg (yield 24%) of a white solid corresponding 2-(4-chlorobenzylamino)-3-fluoro-4-[4-(tert-butylamino)piperidin-1-yl]quinoline.

Mass: (ES+) $C_{25}H_{30}ClFN_4$ required 440.21; found 441.22 [M+H], HPLC/MS method 2.

Synthesis of Compound 348, 2-(4-chlorobenzy-lamino)-3-fluoro-4-[4-(tert-butylamino)piperidin-1-yl]quinoline Hydrochloride Salt

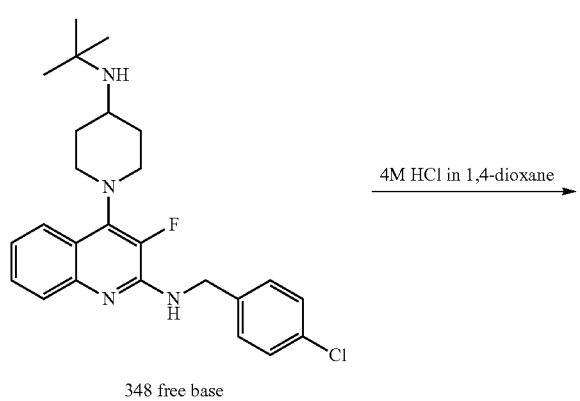

348 free base

4M HCl in 1,4-dioxane
→

-continued

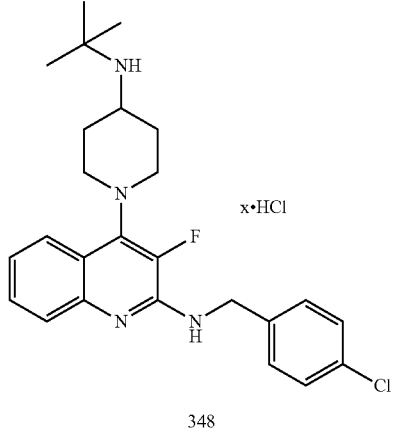

348

To a solution of compound 348 free base (0.1 g, 0.227 mmol) in 2 ml of 1,4-Dioxane was added 4M HCl in 1,4-Dioxane (2.0 ml) and the mixture was stirred for 1 h at room temperature. The reaction mixture was concentrated under reduced pressure and washed with diethyl ether to give 95 mg (yield 88%) of an off-white solid corresponding to 2-(4-chlorobenzylamino)-3-fluoro-4-[4-(tert-butylamino) piperidin-1-yl]quinoline hydrochloride salt.

Mass: (ES+) $C_{25}H_{31}Cl_2FN_4$ required 476.19; found 441 [M−HCl+H], HPLC/MS method 2.

Preparation of Compound 240-F, 2-(4-fluorobenzy-lamino)-3-fluoro-4-[4-(tert-butylamino)piperidin-1-yl]quinoline Synthesis of 2-(4-fluorobenzylamino)-3-fluoro-4-chloroquinoline (348-I-4)

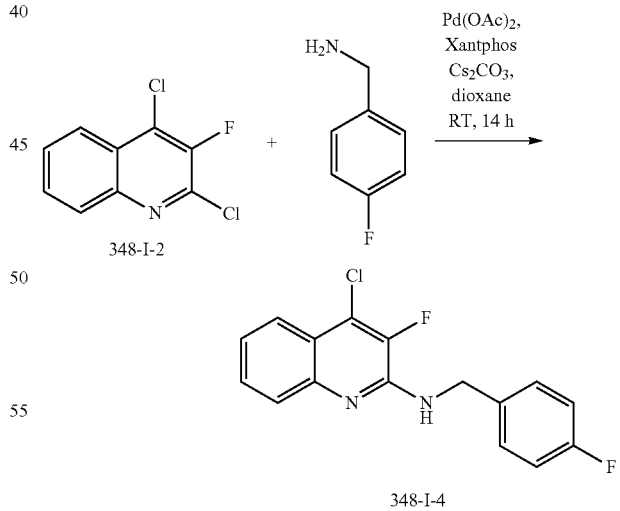

348-I-4

To a solution under nitrogen gas of 2,4-dichloro-3-fluo-roquinoline (1.0 mmol) in THF (10 ml) was added 4-flurobenzylamine (1.1 mmol) and $Cs_2CO_3$ (3.0 mmol). The resulting mixture was degassed 30 min with Ar gas, then Xantphos (0.05 mmol) and $Pd_2(dba)_3$ (0.05 mmol) were added and the reaction mixture was stirred at RT for 14 h. The reaction mixture was then filtered and concentrated under reduced pressure. The residue was partitioned between brine and EtOAc and the aqueous layer was extracted with EtOAc. The combined organic layers were dried over Na₂SO₄, filtered and concentrated under reduced pressure to give a brown solid. The crude compound was purified by flash chromatography using (silica-gel: 100-200 mesh, EtOAc-petroleum ether) to give a white solid corresponding to 2-(4-fluorobenzylamino)-3-fluoro-4-chloroquinoline in 50% yield.

Synthesis of 2-(4-fluorobenzylamino)-3-fluoro-4-[4-(tert-butylamino)piperidin-1-yl]quinoline (240-F)

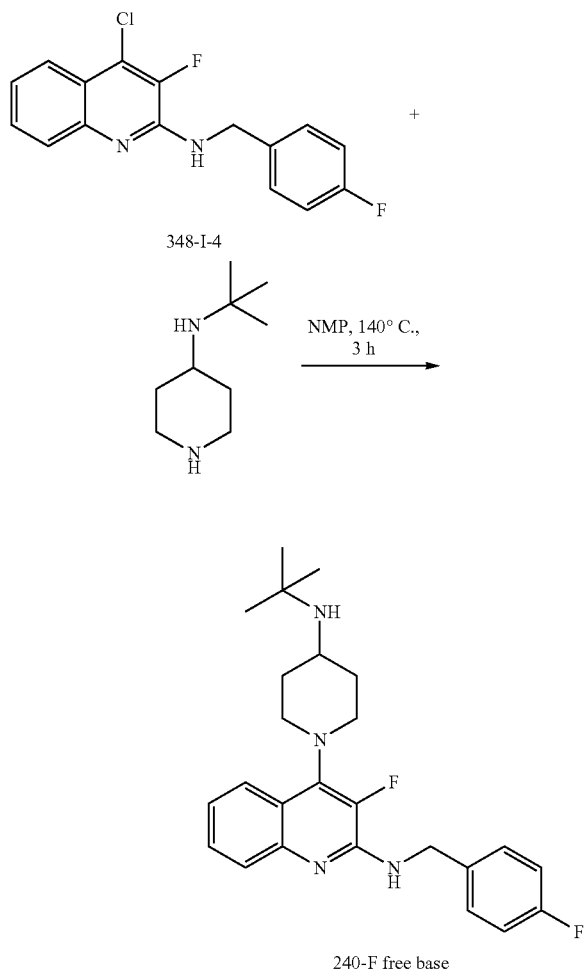

240-F free base

The 2-(4-fluorobenzylamino)-3-fluoro-4-chloro-quinoline (1.0 mmol) and N-tert-butylpiperidin-4-amine (2.0 mmol) was taken in a sealed tube and the reaction mixture was stirred at 180° C. for 24 h. The reaction mixture was then cooled to RT and the residue was dissolved in methanol and concentrated under reduced pressure to give a brown solid. The crude compound was purified by flash chromatography using (silica-gel: 100-200 mesh, DCM-MeOH; 1% to 3%) to give 100 mg of a white solid with some little impurities. The material was purified by Prep HPLC to give 2-(4-fluorobenzylamino)-3-fluoro-4-[4-(tert-butylamino)piperidin-1-yl]quinoline as an off-white solid in 13% yield.

Preparation of Compound 350, 2-(4-chlorobenzylamino)-3-methyl-4-[4-(tert-butylamino)piperidin-1-yl]quinoline Hydrochloride Salt Synthesis of 2-(4-chlorobenzylamino)-3-methyl-4-chloroquinoline, Intermediate 350-I-1

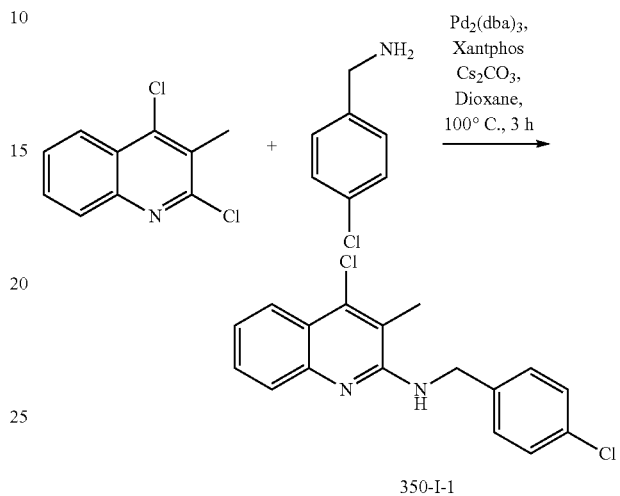

350-I-1

To a solution under nitrogen gas of 2,4-dichloro-3-methylquinoline (0.05 g, 0.236 mmol) in 1,4-dioxane (2 ml) was added 4-chlorobenzylamine (0.049 g, 0.35 mmol) and cesium carbonate (0.192 g, 0.59 mmol). The resulting mixture was degassed 30 min with Ar gas, then Xantphos (13 mg, 0.023 mmol) and Pd₂(dba)₃ (22 mg, 0.023 mmol) were added and the reaction mixture was stirred at 100° C. for 3 h. The reaction mixture was then cooled to room temperature, filtered and concentrated under reduced pressure. The residue was partitioned between brine and AcOEt and the aqueous layer was extracted with AcOEt. The combined organic layers were dried over Na₂SO₄, filtered and concentrated under reduced pressure to give brown oil. The crude compound was purified by flash chromatography using (silica-gel: 100-200 mesh, AcOEt-petroleum ether; 10:90→15:85) to give 35 mg (yield 47%) of a white solid corresponding to 4-chloro-N-(4-chlorobenzyl)-3-methylquinolin-2-amine.

Mass: (ES+) $C_{17}H_{14}Cl_2N_2$ required 316; found 317 [M+H], HPLC/MS method 2.

Synthesis of 2-(4-chlorobenzylamino)-3-methyl-4-[4-(tert-butylamino)piperidin-1-yl]quinoline, Compound of Example 350 Free Base

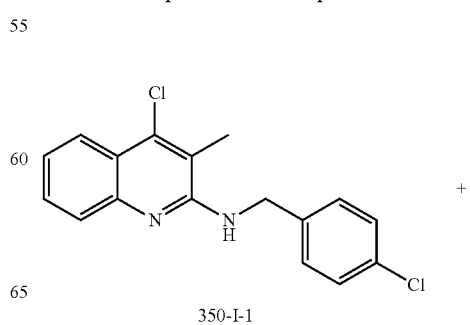

350-I-1

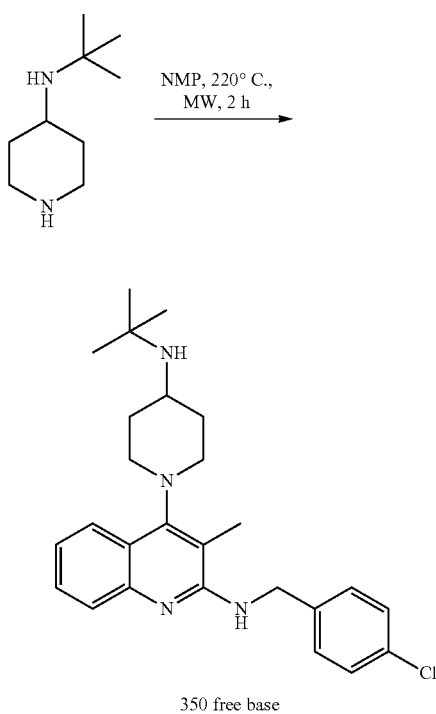

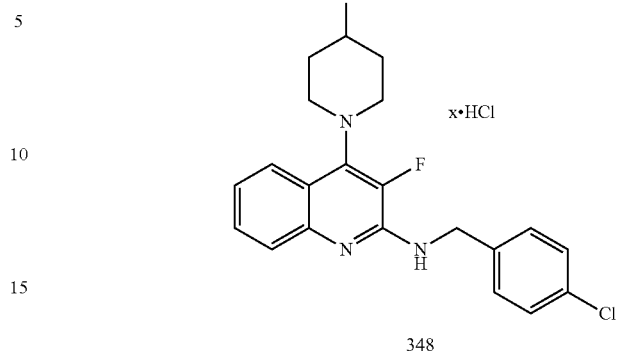

348

To a solution of 2-(4-chlorobenzylamino)-3-methyl-4-[4-(tert-butylamino)piperidin-1-yl]quinoline (45 mg, 103 mmol) in 1 ml of DCM was added 2 M HCl in diethyl ether (1.0 ml) and the mixture was stirred at room temperature for 30 min. The reaction mixture was concentrated under reduced pressure and washed with diethyl ether to give 41 mg (yield 78%) of an off-white solid corresponding to 2-(4-chlorobenzylamino)-3-methyl-4-[4-(tert-butylamino) piperidin-1-yl]quinoline hydrochloride.

Mass: (ES+) $C_{26}H_{34}Cl_2N_4$ required 436 [M−HCl]; found 437 [M−HCl+H], HPLC/MS method 2.

To a solution of 2-(4-chlorobenzylamino)-3-methyl-4-chloroquinoline 350-I-1 (0.33 g, 1.04 mmol) in 2 ml of NMP was added 4-(tert-butylamino)-piperidine (0.49 g, 3.13 mmol) and the mixture was heated in microwave for 2 h at 220° C. Then, the reaction mixture was cooled, diluted with ice water and filtered, collected solid was purified by the preparative HPLC to give 45 mg (yield 11%) of a white solid corresponding to 2-(4-chlorobenzylamino)-3-methyl-4-[4-(tert-butylamino)piperidin-1-yl]quinoline.

Mass: (ES+) $C_{26}H_{33}ClN_4$, required 436; found 437 [M+H], HPLC/MS method 2

Synthesis of Compound of Example 350, 2-(4-chlorobenzylamino)-3-methyl-4-[4-(tert-butylamino) piperidin-1-yl]quinoline Hydrochloride Salt Preparation of Compound 354, methyl 4-(4-(tert-butylamino) piperidin-1-yl)-2-(4-chlorobenzylamino) quinoline-3-carboxylate Hydrochloride Salt Synthesis of methyl 4-hydroxy-2-oxo-1,2-dihydroquinoline-3-carboxylate, Intermediate 354-I-1

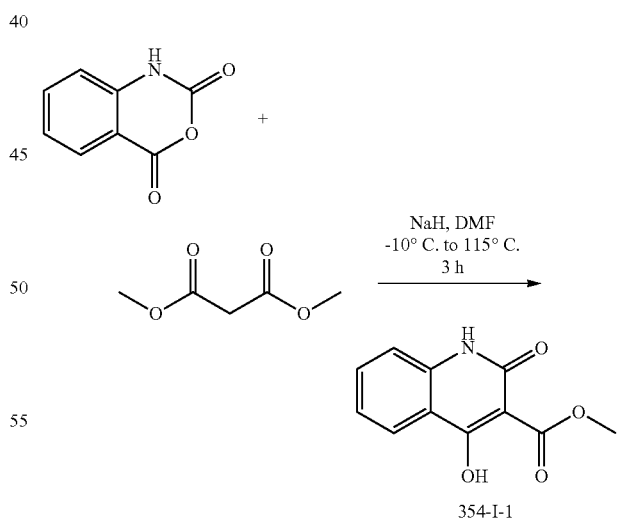

354-I-1

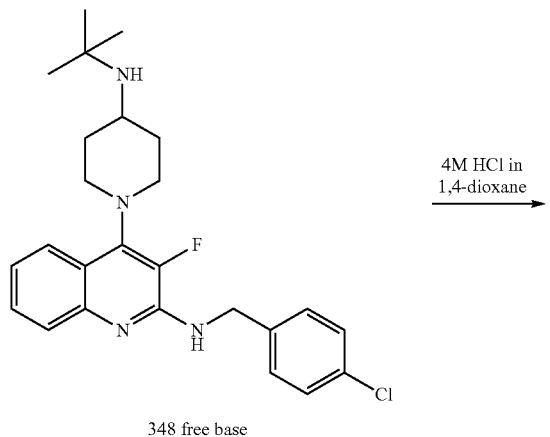

Dimethyl malonate (2.9 ml, 22 mmol) was added slowly under nitrogen to a suspension of 60% sodium hydride in mineral oil (0.883 g 36.8 mmol) in anhydrous DMF (50 ml) at −10° C. After stirring at room temperature for 30 min, isatoic anhydride (3.0 g 18.4 mmol) was added and reaction mixture was heated to 115° C. for 3 h. Then, the reaction mixture was cooled to room temperature then poured into ice water and acidified with 2M HCl. The resultant precipitate was collected by filtration to give crude methyl 4-hydroxy-2-oxo-1,2-dihydroquinoline-3-carboxylate which was used for the next step without further purification (Yield 2.89 g≈60%).

Synthesis of methyl 2,4-dichloroquinoline-3-carboxylate, Intermediate 354-I-2

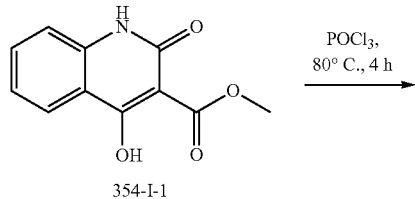

To methyl 4-hydroxy-2-oxo-1,2-dihydroquinoline-3-carboxylate (1.5 g, 6.84 mmol) was added Phosphoryl chloride (25 ml). The resulting mixture was stirred at 80° C. for 4 h. Reaction was monitored by TLC (30% Ethyl acetate/Pet ether), After completion of the reaction, the reaction mixture was allowed to room temperature and poured into ice water and extracted with AcOEt (2×50 ml). The combined organic layers were dried over Na$_2$SO$_4$, filtered and concentrated under reduced pressure to give a crude compound which upon purification by flash chromatography using (silica-gel: 100-200 mesh, AcOEt-petroleum ether; 1:99→10:90) gave 1.0 g (yield 47%) of an off-white solid corresponding to methyl 2,4-dichloroquinoline-3-carboxylate.

Synthesis of methyl 4-(4-(tert-butylamino) piperidin-1-yl)-2-chloroquinoline-3-carboxylate, Intermediate 354-I-3

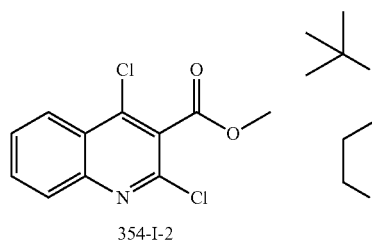

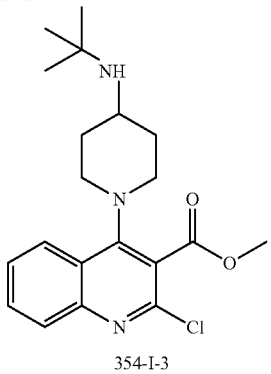

To a stirred solution of methyl 2,4-dichloroquinoline-3-carboxylate (0.89 g, 3.50 mmol) in MeCN (25 ml) was added 4-tert-butylaminopiperidine (0.67 g, 4.64 mmol) in a flask at room temperature and stirred for 16 h at 100° C. Reaction was monitored by TLC (30% Ethyl acetate/Petroleum ether). After completion of the reaction, the reaction mixture was allowed to room temperature and poured into ice water and extracted with AcOEt (2×25 ml). The combined organic layers were dried over Na$_2$SO$_4$, filtered and concentrated under reduced pressure to give a crude compound, which was purified by flash chromatography using (silica-gel: 100-200 mesh, AcOEt-pet éther; 5:95→20:80) to give 0.5 g (yield 38%) of an off-white solid corresponding to methyl 4-(4-(tert-butylamino)piperidin-1-yl)-2-chloro-quinoline-3-carboxylate. Compound was confirmed by NOE $^1$H NMR experiment.

Mass: (ES+) C$_{20}$H$_{26}$ClN$_3$O$_2$ required 375 found 376 [M+H], HPLC/MS method 2.

Synthesis of methyl 4-(4-(tert-butylamino) piperidin-1-yl)-2-(4-chlorobenzylamino) quinoline-3-carboxylate, Compound of Example 354 Free Base

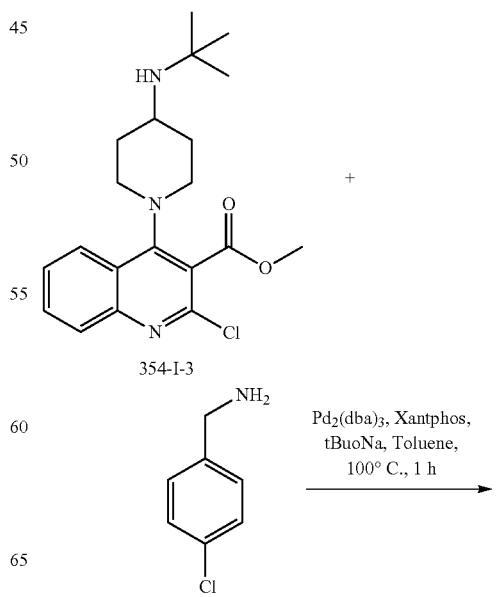

155
-continued

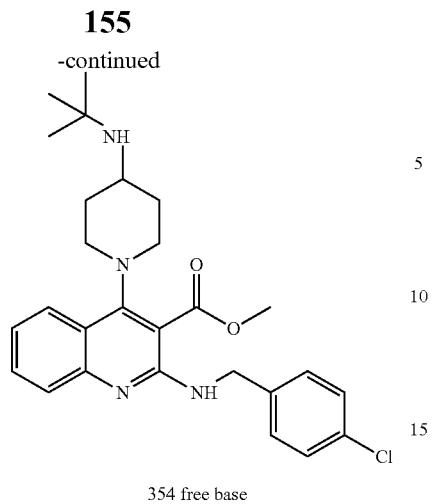

354 free base

To a solution under nitrogen gas of methyl 4-(4-(tert-butylamino)piperidin-1-yl)-2-chloroquinoline-3-carboxylate (0.2 g, 0.53 mmol) in toluene (20 ml) was added 4-chlorobenzylamine (0.113 g, 0.799 mmol) and sodium tert-butoxide (0.127 g, 1.32 mmol). The resulting mixture was degassed 30 min with Argon gas, then Xantphos (0.028 mg, 0.05 mmol) and $Pd_2(dba)_3$ (0.048 mg, 0.05 mmol) were added and the reaction mixture was stirred at 100° C. for 1 h. The reaction mixture was then cooled to room temperature, filtered and concentrated under reduced pressure. The residue was partitioned between brine and AcOEt and the aqueous layer was extracted with AcOEt. The combined organic layers were dried over $Na_2SO_4$, filtered and concentrated under reduced pressure to give a brown oil. The crude compound which upon purification by flash chromatography using (silica-gel: 100-200 mesh MeOH-DCM 0-10) gave 0.04 g (yield 28%) of a white solid corresponding to methyl 4-(4-(tert-butylamino) piperidin-1-yl)-2-(4-chlorobenzylamino) quinoline-3-carboxylate.

Synthesis of Compound 354, methyl 4-(4-(tert-butylamino) piperidin-1-yl)-2-(4-chlorobenzylamino) quinoline-3-carboxylate Hydrochloride Salt

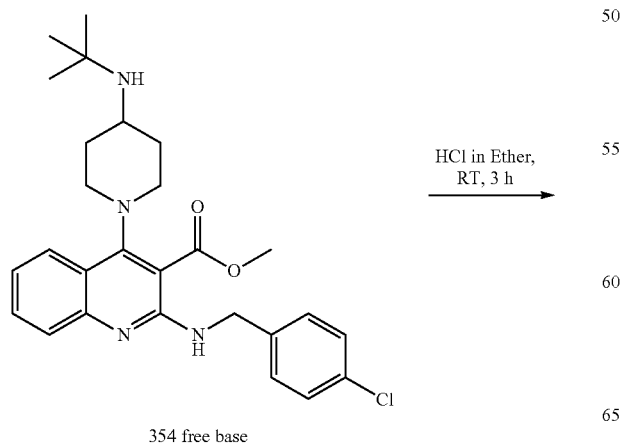

354 free base

HCl in Ether, RT, 3 h

156
-continued

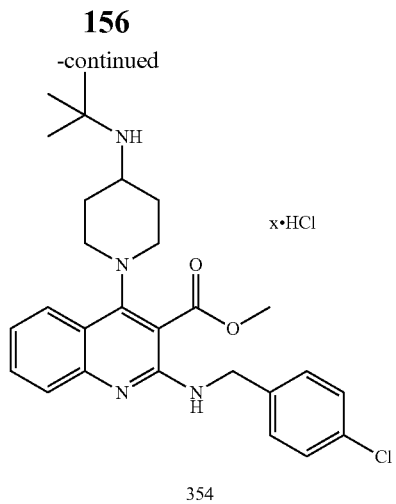

354

To a solution methyl 4-(4-(tert-butylamino)piperidin-1-yl)-2-(4-chlorobenzylamino)quinoline-3-carboxylate (0.04 g, 0.072 mmol) in 2 ml of diethyl ether was added 2 M HCl in diethyl ether (2.0 ml) and the mixture was stirred at room temperature for 3 h. The reaction mixture was concentrated under reduced pressure and washed with diethyl ether to give 43 mg (yield 93%) of an off-white solid corresponding to methyl 4-(4-(tert-butylamino)piperidin-1-yl)-2-(4-chlorobenzylamino)quinoline-3-carboxylate hydrochloride.

Mass: (ES+) $C_{27}H_{34}Cl_2N_4O_2$ required 480 (M−HCl) found 481 [M+H], HPLC/MS method 4.

Preparation of Compound 564: 2-(4-chlorobenzylamino)-4-[4-(tert-butylamino)piperidin-1-yl]-7-methyl-8-fluoroquinoline Hydrochloride Salt Synthesis of 2,4-dichloro-7-methyl-8-fluoro-quinoline, Intermediate 564-I-1

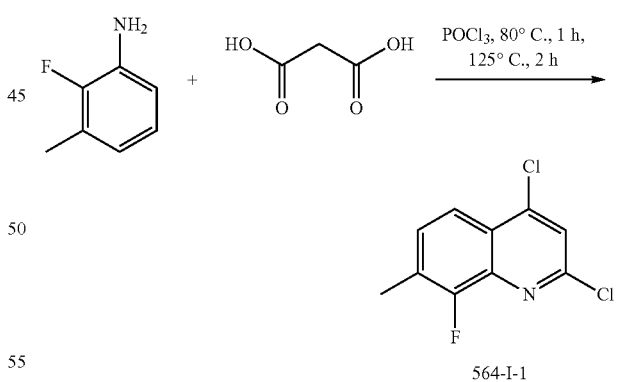

564-I-1

To 2-fluoro-3-methylaniline (5.0 g, 40 mmol) was added Phosphoryl chloride (100 ml), and then was added portion wise the malonic acid (12.4 g, 120 mmol). The resulting mixture was stirred at 80° C. for 1 h. Then, the mixture was stirred at 125° C. for 2 h. the reaction mixture was allowed to room temperature and poured in to ice water and extracted with AcOEt (2×100 ml). The combined organic layers were dried over $Na_2SO_4$, filtered and concentrated under reduced pressure to give crude compound which upon purification by flash chromatography using (silica-gel: 100-200 mesh, AcOEt-petroleum ether; 8:92→10:90) gave 2.5 g (yield 27%) of a white solid corresponding to 2,4-dichloro-8-fluoro-7-methylquinoline.

Mass: (ES+) $C_{10}H_6Cl_2FN$, required 229; found 230 [M+H], HPLC/MS method 2.

Synthesis of 2-(4-chlorobenzylamino)-4-chloro-7-methyl-8-fluoroquinoline, Intermediate 564-I-2

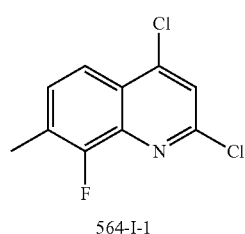

564-I-1

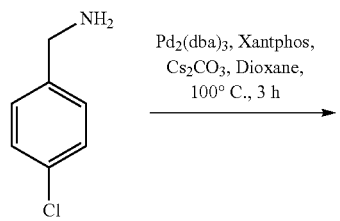

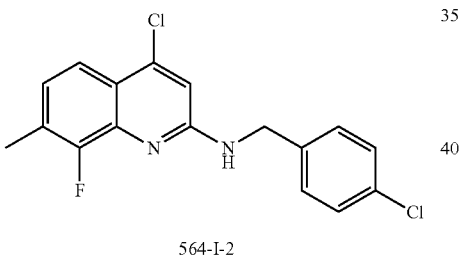

564-I-2

To a solution under nitrogen gas of 2,4-dichloro-7-methyl-8-fluoro-quinoline (2.5 g, 10.9 mmol) in 1,4-dioxane (25 ml) was added 4-chlorobenzylamine (2.3 g, 16.3 mmol) and cesium carbonate (8.8 g, 27.2 mmol). The resulting mixture was degassed 30 min with Argon gas, then Xantphos (630 mg, 1.09 mmol) and $Pd_2(dba)_3$ (990 mg, 1.09 mmol) were added and the reaction mixture was stirred at 100° C. for 3 h. The reaction mixture was then cooled to room temperature, filtered and concentrated under reduced pressure. The residue was partitioned between brine and AcOEt and the aqueous layer was extracted with AcOEt. The combined organic layers were dried over $Na_2SO_4$, filtered and concentrated under reduced pressure to give a brown oil. The crude compound which upon purification by flash chromatography using (silica-gel: 100-200 mesh, AcOEt-petroleum ether; 12:88→15:85) gave 1.1 g (yield 31%) of a white solid corresponding to 2-(4-chlorobenzylamino)-4-chloro-7-methyl-8-fluoroquinoline.

Mass: (ES+) $C_{17}H_{13}Cl_2FN_2$ required 334; found 335 [M+H], HPLC/MS method 4.

Synthesis of 2-(4-chlorobenzylamino)-4-[4-(tert-butylamino)piperidin-1-yl]-7-methyl-8-fluoroquinoline, Compound of Example 564 Free Base

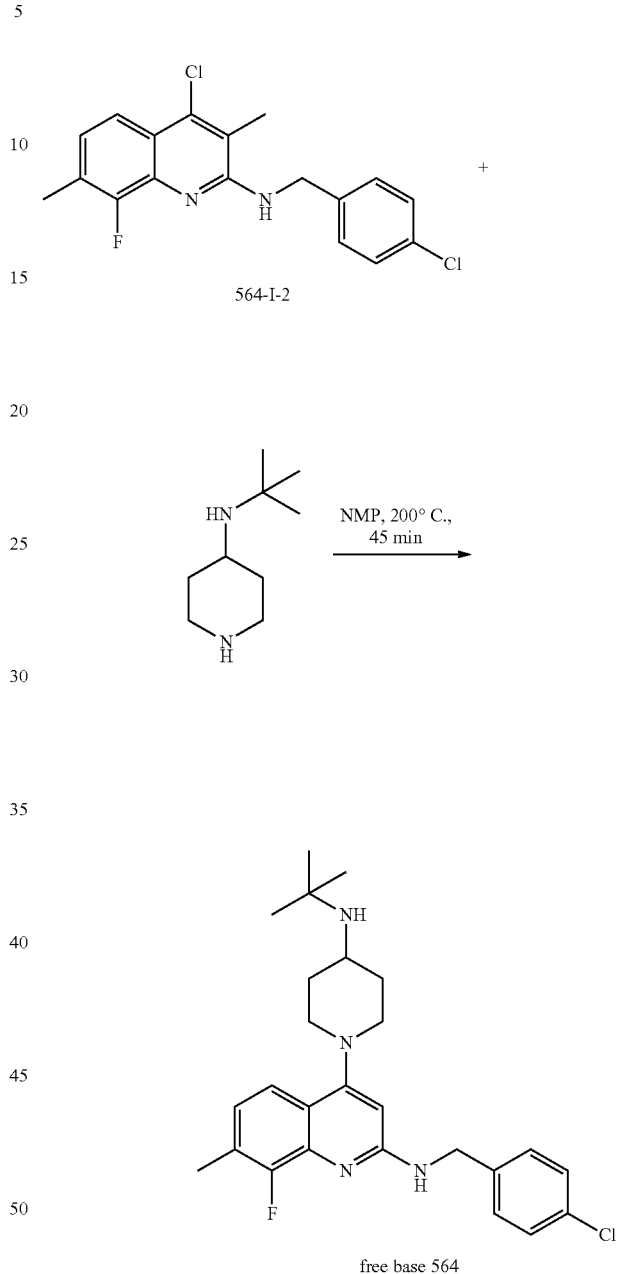

To a solution of 2-(4-chlorobenzylamino)-4-chloro-7-methyl-8-fluoroquinoline (0.2 g, 0.598 mmol) in 2 ml of NMP was added 4-(tert-butylamino)-piperidine (0.32 g, 2.05 mmol) and the mixture was heated in microwave oven for 45 min at 200° C. Then, the reaction mixture was cooled, diluted with ice water and filtered, collected solid was purified by the preparative HPLC to give 60 mg (yield 25%) of a white solid corresponding to 2-(4-chlorobenzylamino)-4-[4-(tert-butylamino)piperidin-1-yl]-7-methyl-8-fluoroquinoline.

Mass: (ES+) $C_{26}H_{32}ClFN_4$, required 454; found 455 [M+H], HPLC/MS method 2

Synthesis of Compound of 564, 2-(4-chlorobenzylamino)-4-[4-(tert-butylamino)piperidin-1-yl]-7-methyl-8-fluoroquinoline Hydrochloride Salt

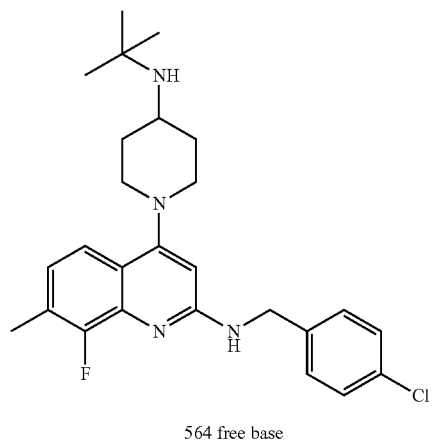

564 free base

HCl in Ether, RT, 3 h

564

To a solution of 2-(4-chlorobenzylamino)-4-[4-(tert-butylamino)piperidin-1-yl]-7-methyl-8-fluoroquinoline. (0.06 g) in 4 ml of diethyl ether was added 2 M HCl in diethyl ether (1.0 ml) and the mixture was stirred at room temperature for 3 h. The reaction mixture was concentrated under reduced pressure and washed with diethyl ether to give 50 mg (yield 72%) of an off-white solid corresponding to 2-(4-chlorobenzylamino)-4-[4-(tert-butylamino)piperidin-1-yl]-7-methyl-8-fluoroquinoline hydrochloride salt.

Mass: (ES+) $C_{26}H_{32}ClFN_4$ required 454 (M−HCl); found 455 [M+H], HPLC/MS method 2

Preparation of Compound 568: 2-(4-chlorobenzylamino)-4-[4-(tert-butylamino)piperidin-1-yl]-6-methyl-8-fluoroquinoline, Hydrochloride Salt

Synthesis of 2,4-dichloro-6-methyl-8-fluoro-quinoline Intermediate 568-I-1

568-I-1

To a 2-fluoro-3-methylaniline (2.0 g, 16 mmol) was added phosphoryl chloride (40 ml), and then was added portion wise the malonic acid (2.4 g, 24 mmol). The resulting mixture was stirred at 80° C. for 16 h. The reaction mixture was allowed to room temperature and poured into ice water mixture. The aqueous layer was extracted with AcOEt (2×50 ml). The combined organic layer were dried over $Na_2SO_4$, filtered and concentrated under reduced pressure to give a crude compound which upon purification by flash chromatography using (silica-gel: 100-200 mesh, AcOEt-petroleum ether; 2:98→5:95) gave 700 mg (yield 19%) of a white solid corresponding to 2,4-dichloro-6-methyl-8-fluoroquinoline.

Mass: (ES+) $C_{10}H_6Cl_2FN$ required 229; found 230 [M+H], HPLC/MS method 2

Synthesis of 2-(4-chlorobenzylamino)-4-[4-(tert-butylamino)piperidin-1-yl]-6-methyl-8-fluoroquinoline, Intermediate 568-I-2

568-I-1

Pd₂(dba)₃, Xantphos, Cs₂CO₃, Dioxane, 100° C., 3 h
Sealed tube

568-I-2

To a solution under nitrogen gas of 2, 4-dichloro-6-methyl-8-fluoroquinoline (300 mg, 1.31 mmol) in 1, 4-dioxane (10 ml) was added 4-chlorobenzylamine (221 mg, 1.57 mmol) and cesium carbonate (859 mg, 2.62 mmol). The resulting reaction mixture was degassed 10 min with Argon gas, then Xantphos (75 mg, 0.131 mmol) and $Pd_2(dba)_3$ (119 mg, 0.131 mmol) were added and the reaction mixture was stirred at 100° C. for 3 h. The reaction mixture was then cooled to room temperature, filtered and concentrated under reduced pressure. The residue was partitioned between brine and AcOEt and the aqueous layer was extracted with AcOEt. The combined organic layers were dried over $Na_2SO_4$, filtered and concentrated under reduced pressure to give brown oil. The crude compound which upon purification by flash chromatography using (silica-gel: 100-200 mesh, AcOEt-petroleum ether; 12:88→15:85) gave 100 mg (yield 22%) of an off white solid corresponding to 2-(4-chlorobenzylamino)-4-chloro-6-methyl-8-fluoroquinoline.

Mass: (ES+) $C_{17}H_{13}Cl_2FN_2$ required 334; found 335 [M+H], HPLC/MS method 2.

Synthesis of Compound 568 Free Base, 2-(4-chlorobenzylamino)-4-[4-(tert-butylamino)piperidin-1-yl]-6-methyl-8-fluoroquinoline

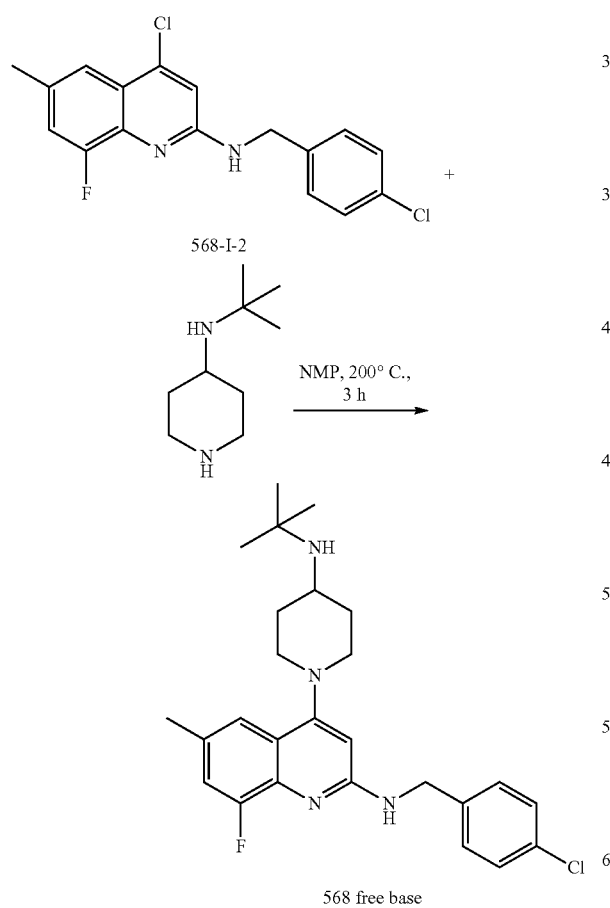

To a solution of 2-(4-chlorobenzylamino)-4-chloro-6-methyl-8-fluoroquinoline (100 mg, 0.299 mmol) in 2 ml of NMP was added 4-(tert-butylamino)-piperidine (0.163 mg, 1.04 mmol) and the mixture was heated in a microwave oven for 3 h at 200° C. Then, the reaction mixture was cooled, diluted with ice water and filtered. The collected solid was purified by the preparative HPLC to give 40 mg (yield 29%) of an off white solid corresponding to 2-(4-chlorobenzylamino)-4-[4-(tert-butylamino)piperidin-1-yl]-6-methyl-8-fluoroquinoline.

Mass: (ES+) $C_{26}H_{32}ClFN_4$ required 454; found 455 [M+H], HPLC/MS method 2.

Synthesis of Compound 568: 2-(4-chlorobenzylamino)-4-[4-(tert butylamino)piperidin-1-yl]-6-methyl-8-fluoroquinoline Hydrochloride Salt

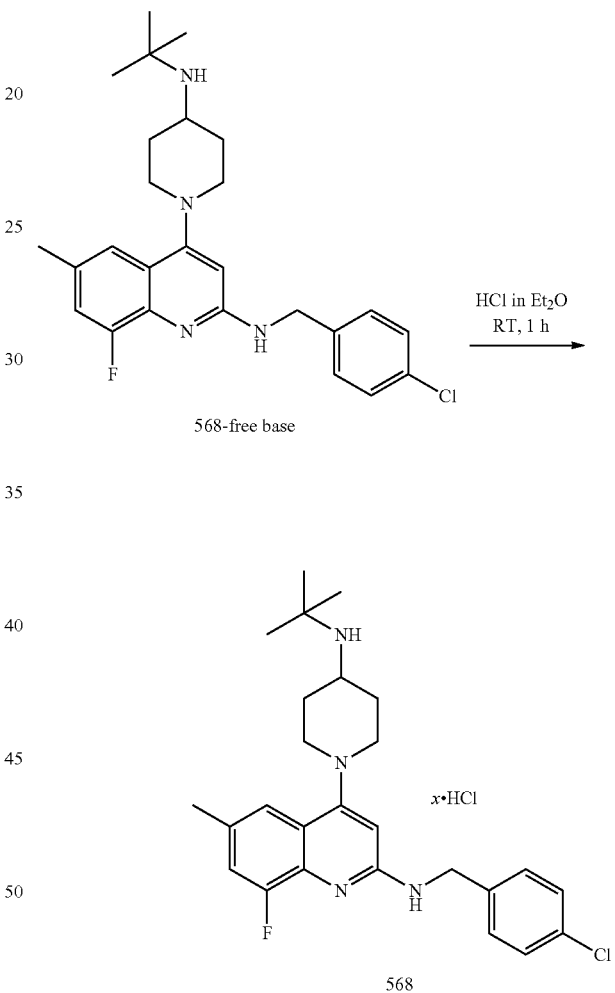

To a solution of 2-(4-chlorobenzylamino)-4-[4-(tert-butylamino)piperidin-1-yl]-6-methyl-8-fluoroquinoline (0.04 g, 0.088 mmol) in 5 ml of DCM was added 1 M HCl in diethyl ether (2.0 ml) and the mixture was stirred for 1 h at room temperature. The reaction mixture was concentrated under reduced pressure and washed with diethyl ether to give 35 mg (yield 81%) of an off-white solid corresponding to 2-(4-chlorobenzylamino)-4-[4-(tert-butylamino)piperidin-1-yl]-6-methyl-8-fluoroquinoline hydrochloride salt.

Mass: (ES+) $C_{26}H_{32}ClFN_4$ required 454 (M−HCl); found 455[M+H], HPLC/MS method 2

Preparation of Compound 572: 2-(4-chlorobenzy-lamino)-4-[4-(tert-butylamino)piperidin-1-yl]-7-fluoro-8-methylquinoline, Hydrochloride Salt Synthesis of 2,4-dichloro-7-fluoro-8-methylquinoline Intermediate 572-I-1

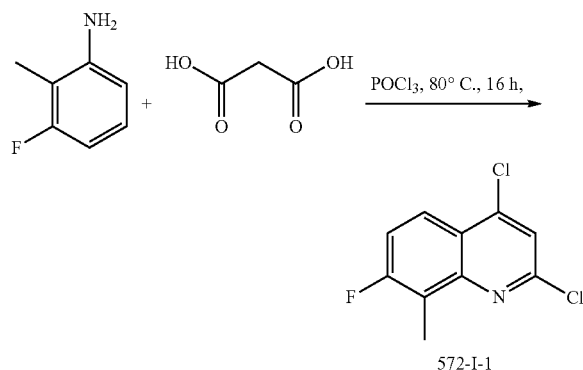

To a 2-fluoro-3-methylaniline (2.0 g, 16 mmol) was added Phosphoryl chloride (40 ml), and then malonic acid (2.4 g, 24 mmol) was added portion wise. The resulting mixture was stirred at 80° C. for 16 h. The reaction mixture was allowed to room temperature and poured into ice water mixture. The aqueous layer was extracted with AcOEt (2×50 ml). The combined organic layer were dried over $Na_2SO_4$, filtered and concentrated under reduced pressure to give a crude compound which upon purification by flash chromatography using (silica-gel: 100-200 mesh, AcOEt-petroleum ether; 2:98→5:95) gave 1.2 g (yield 33%) of a white solid corresponding to 2,4-dichloro-7-fluoro-8-methylquinoline.

Mass: ((ES+) $C_{26}H_{32}ClFN_4$ required 229; found 230 [M+H], HPLC/MS method 4.

Synthesis of 2-(4-chlorobenzylamino)-4-chloro-7-fluoro-8-methylquinoline, Intermediate 572-I-2

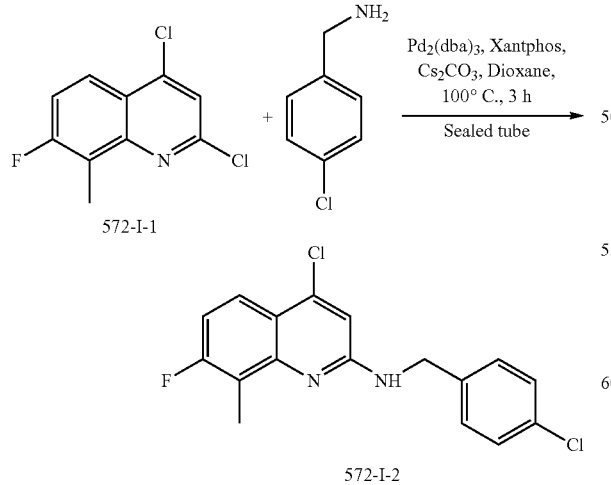

To a solution under nitrogen gas of 2,4-dichloro-7-fluoro-8-methylquinoline (650 mg, 2.82 mmol) in 1,4-dioxane (10 ml) was added 4-chlorobenzylamine (478 mg, 3.39 mmol) and cesium carbonate (1.84 mg, 5.64 mmol). The resulting mixture was degassed 10 min with Argon gas, then Xantphos (162 mg, 0.282 mmol) and $Pd_2(dba)_3$ (258 mg, 0.282 mmol) were added and the reaction mixture was stirred at 100° C. for 3 h. The reaction mixture was then cooled to room temperature, filtered and concentrated under reduced pressure. The residue was partitioned between brine and AcOEt and the aqueous layer was extracted with AcOEt. The combined organic layers were dried over $Na_2SO_4$, filtered and concentrated under reduced pressure to give a brown oil. The crude compound which upon purification by flash chromatography using (silica-gel: 100-200 mesh, AcOEt-petroleum ether; 10:90→15:85) gave 350 mg (yield 35%) of an off white solid corresponding to 2-(4-chlorobenzylamino)-4-chloro-7-fluoro-8-methylquinoline.

Mass: (ES+) $C_{26}H_{32}ClFN_4$ required 334; found 335 [M+H], HPLC/MS method 4.

Synthesis of Compound 572 Free Base, 2-(4-chlorobenzylamino)-4-[4-(tert-butylamino)piperidin-1-yl]-7-fluoro-8-methylquinoline

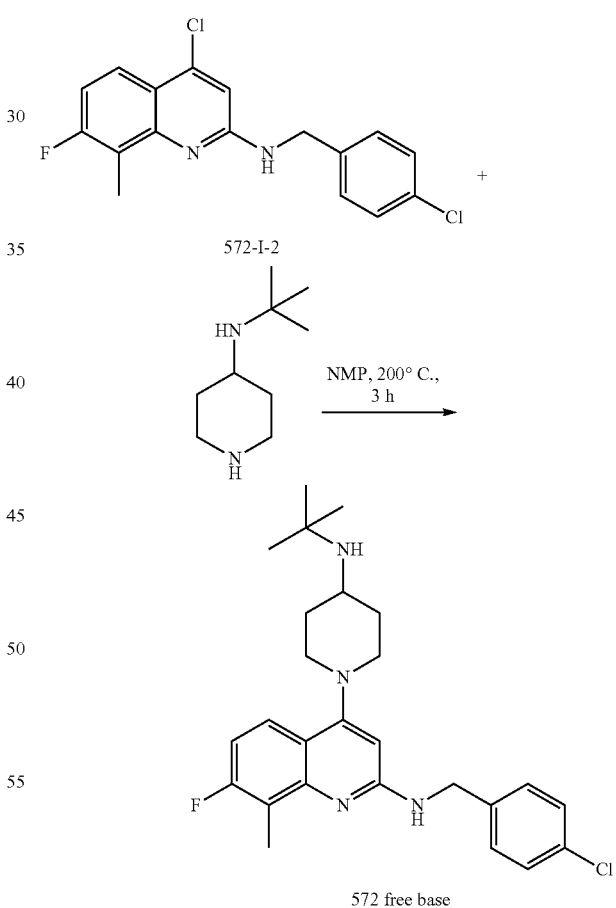

To a solution of 2-(4-chlorobenzylamino)-4-chloro-7-fluoro-8-methylquinoline (200 mg, 0.599 mmol) in 2 ml of NMP was added 4-(tert-butylamino)piperidine (0.299 mg, 1.94 mmol) and the mixture was then heated in a microwave oven for 3 hours at 200° C. Then, the reaction mixture was cooled, diluted with ice water and filtered. The collected solid was purified by preparative HPLC to give 80 mg (yield 30%) of an off white solid corresponding to 2-(4-chlorobenzylamino)-4-[4-(tert-butylamino)piperidin-1-yl]-7-fluoro-8-methylquinoline.

Mass: (ES+) $C_{26}H_{32}ClFN_4$ required 454; found 455 [M+H], HPLC/MS method 4.

Synthesis of Compound 572, 2-(4-chlorobenzylamino)-4-[4-(tert-butylamino)piperidin-1-yl]-7-fluoro-8-methylquinoline Hydrochloride Salt

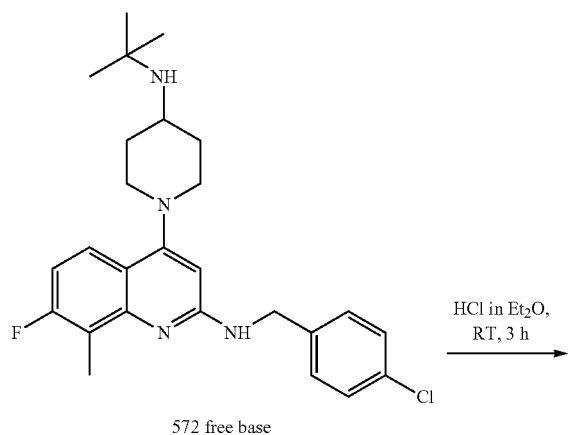

572 free base

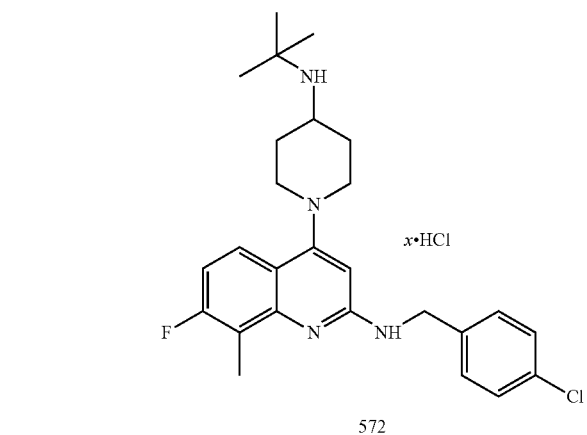

572

To a solution of 2-(4-chlorobenzylamino)-4-[4-(tert-butylamino)piperidin-1-yl]-7-fluoro-8-methylquinoline (80 mg, 0.175 mmol) in 4 ml of ether was added 4 M HCl in Et₂O (2.0 ml) and the mixture was stirred for 3 h at room temperature. Then, the reaction mixture was concentrated under reduced pressure and washed with diethyl ether to give 70 mg (yield 82%) of an off-white solid corresponding to 2-(4-chlorobenzylamino)-4-[4-(tert-butylamino)piperidin-1-yl]-7-fluoro-8-methylquinoline hydrochloride salt.

Mass: (ES+) $C_{26}H_{32}ClFN_4$ required 454 (M–HCl); found 455 [M+H], HPLC/MS method 2.

Preparation of Compound 580, 2-(4-chlorobenzylamino)-4-[4-(tert-butylamino)piperidin-1-yl]-6-fluoro-8-methylquinoline, Hydrochloride Salt Synthesis of 2,4-dichloro-6-fluoro-8-methylquinoline, Intermediate 580-I-1

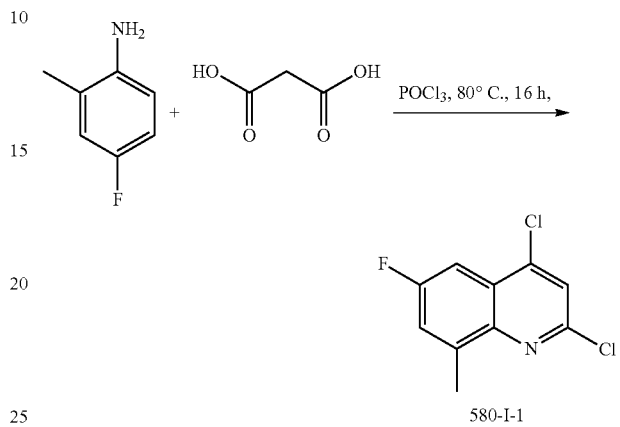

580-I-1

To 2-fluoro-3-methylaniline (2.5 g, 20 mmol) was added phosphoryl chloride (40 ml), and then was added portion wise the malonic acid (4.2 g, 40 mmol). The resulting reaction mixture was stirred at 80° C. for 16 h. Then, the reaction mixture was allowed to room temperature and poured into ice water. The aqueous layer was extracted with AcOEt (2×50 ml). The combined organic layer were dried over Na₂SO₄, filtered and concentrated under reduced pressure to give a crude compound which upon purification by flash chromatography using (silica-gel: 100-200 mesh, AcOEt-petroleum ether; 2:98→5:95) gave 0.75 g (yield 20%) of a white solid corresponding to 2,4-dichloro-6-fluoro-8-methylquinoline.

Mass: (ES+) $C_{26}H_{32}ClFN_4$ required 229; found 230 [M+H], HPLC/MS method 4

Synthesis of 2-(4-chlorobenzylamino)-4-chloro-6-fluoro-8-methylquinoline, Intermediate 580-I-2

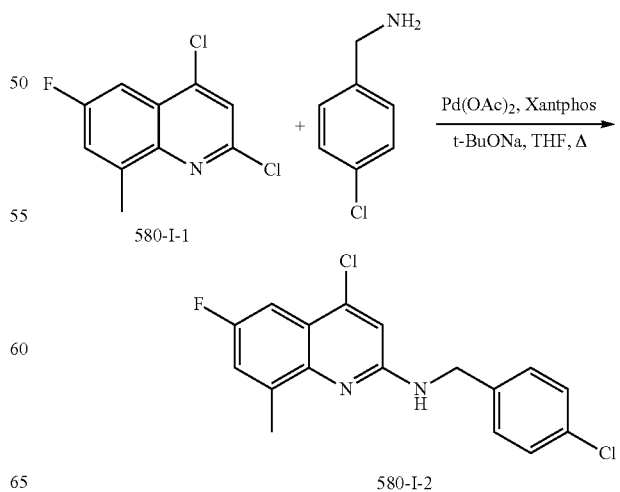

580-I-1

580-I-2

To a solution under nitrogen gas of 2, 4-dichloro-6-fluoro-8-methylquinoline (750 mg, 3.26 mmol) in 1,4-dioxane (10 ml) was added 4-chlorobenzylamine (550 mg, 3.91 mmol) and t-BuONa (0.78 g, 8.15 mmol). The resulting mixture was degassed 5 min with nitrogen, then Xantphos (188 mg, 0.32 mmol) and Pd(OAc)$_2$ (36 mg, 0.16 mmol) were added and the reaction mixture was heated under reflux for 2 hours. The reaction mixture was then cooled to room temperature and concentrated under reduced pressure. The residue was partitioned between brine and AcOEt and the aqueous layer was extracted with AcOEt. The combined organic layers were dried over Na$_2$SO$_4$, filtered and concentrated under reduced pressure to give a brown oil. The crude compound which upon purification by flash chromatography using (silica-gel: 100-200 mesh, AcOEt-petroleum ether; 10:90→15:85) gave 550 mg (yield 55%) of an off white solid corresponding to 2-(4-chlorobenzylamino)-4-chloro-6-fluoro-8-methylquinoline.

Mass: (ES+) C$_{26}$H$_{32}$ClFN$_4$ required 334; found 335 [M+H], HPLC/MS method 4.

Synthesis of Compound 580 Free Base, 2-(4-chlorobenzylamino)-4-[4-(tert-butylamino)piperidin-1-yl]-6-fluoro-8-methylquinoline

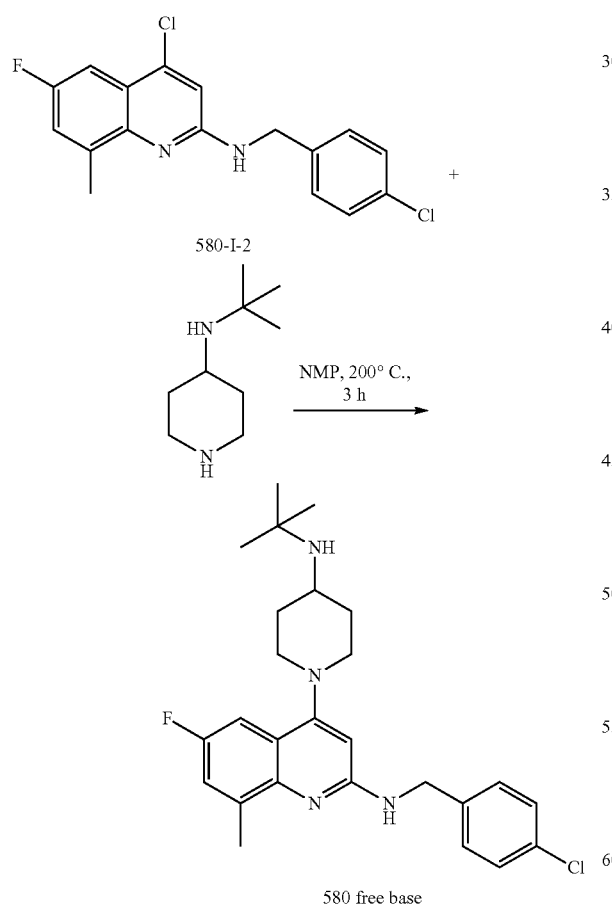

To a solution of 2-(4-chlorobenzylamino)-4-chloro-6-fluoro-8-methylquinoline (150 mg, 0.44 mmol) in 2 ml of NMP was added 4-(tert-butylamino)piperidine (0.209 mg, 1.34 mmol) and the resulting mixture was heated in a microwave oven for 3 hours at 200° C. Then, the reaction mixture was cooled, diluted with ice water and filtered. The collected solid was purified by preparative HPLC to give 100 mg (yield 50%) of an off white solid corresponding to 2-(4-chlorobenzylamino)-4-[4-(tert-butylamino)piperidin-1-yl]-6-fluoro-8-methylquinoline.

Mass: ((ES+) C$_{26}$H$_{32}$ClFN$_4$ required 454; found 455 [M+H], HPLC/MS method 5

Synthesis of Compound 580, 2-(4-chlorobenzylamino)-4-[4-(tert-butylamino)piperidin-1-yl]-6-fluoro-8-methylquinoline Hydrochloride Salt

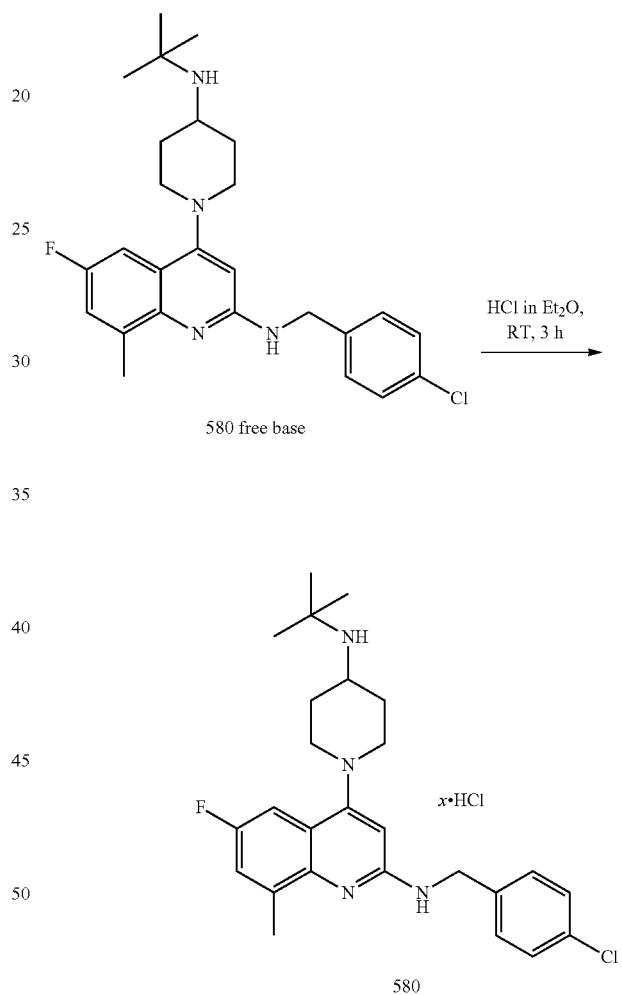

To a solution of 2-(4-chlorobenzylamino)-4-[4-(tert-butylamino)piperidin-1-yl]-6-fluoro-8-methylquinoline (0.1 g, 0.22 mmol) in 4 ml of ether was added 4 M HCl in Et$_2$O (2.0 ml) and the resulting mixture was stirred for 3 h at room temperature. Then, the reaction mixture was concentrated under reduced pressure and washed with diethyl ether to give 90 mg (yield 82%) of an off-white solid corresponding to 2-(4-chlorobenzylamino)-4-[4-(tert-butylamino)piperidin-1-yl]-6-fluoro-8-methylquinoline hydrochloride salt.

Mass: (ES+) C$_{26}$H$_{32}$ClFN$_4$ required 454 (M−HCl); found 455 [M+H], HPLC/MS method 2

Preparation of Compound of 532-Me, 2-[4-(4-methylpyrimidin-2-ylamino)phenylamino]-3-methyl-4-(4-tert-butylaminopiperidin-1-yl)quinoline Hydrochloride Salt

Synthesis of N-(4-methylpyrimidin-2-yl)benzene-1,4-diamine, Intermediate 532-Me-I-1

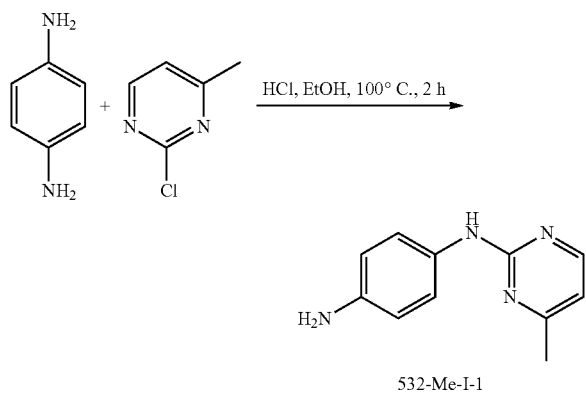

532-Me-I-1

To a stirred solution of benzene-1,4-diamine (5.0 g, 46.29 mmol) and 2-chloro-4-methylpyrimidine (5.9 g, 46.29 mmol) in 10% aqueous ethanol (100 ml) at 0° C. was added dropwise aqueous concentrated HCl (3.4 ml, 92.58 mmol). The resulting reaction mixture was stirred at 100° C. for 2 h. The solvent was evaporated and the resulting residue was diluted with cold water, neutralized with aqueous 10% NaHCO₃ and extracted with AcOEt (2×100 ml). The combined organic layers were washed with brine (50 ml), dried over Na₂SO₄, filtered and concentrated under reduced pressure to yield crude compound which upon purification by flash chromatography using (REVELERIS-Grace 40 g, silica-gel: 230-400 mesh, AcOEt-petroleum ether; 1:4→3:7) gave 3 g (yield 32%) of a pale brown solid corresponding to N¹-(4-methylpyrimidin-2-yl)benzene-1,4-diamine.

Mass: (ES+) $C_{11}H_{12}N_4$, required 200; found 201.1 [M+H], HPLC/MS method 5.

Synthesis of 2-[4-(4-methylpyrimidin-2-ylamino)phenylamino]-3-methyl-4-chloroquinoline, Intermediate 532-Me-I-2

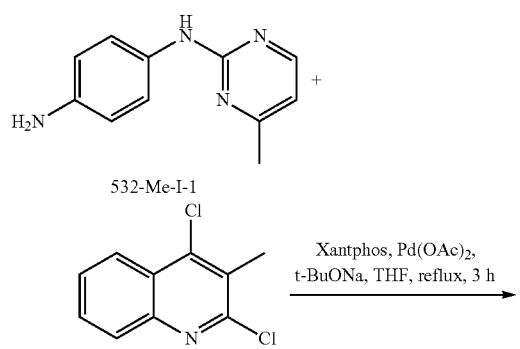

-continued

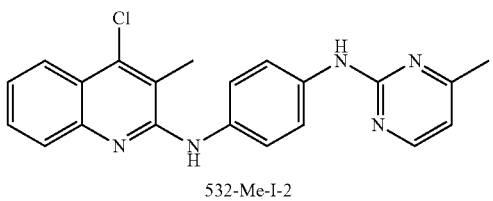

532-Me-I-2

To a solution under argon gas of 2,4-dichloro-3-methylquinoline (0.5 g, 2.35 mmol) in THF (20 ml) was added N¹-(4-methylpyrimidin-2-yl)benzene-1,4-diamine (0.57 g, 2.83 mmol) and t-BuONa (0.63 g, 6.58 mmol). The resulting mixture was degassed 10 min with argon gas, then Xantphos (0.14 g, 0.23 mmol) and Pd(OAc)₂ (27 mg, 0.12 mmol) were added and the reaction mixture was then stirred at 80° C. for 3 hours. The reaction mixture was then cooled to room temperature, diluted with cold water (30 ml), extracted with AcOEt (2×50 ml). The combined organic layers were washed with brine (30 ml), dried over Na₂SO₄, filtered and concentrated under reduced pressure to give brown oil which upon purification by flash chromatography using (REVELERIS-Grace, 40 g, silica-gel: 230-400 mesh, AcOEt-petroleum ether; 1:4→3:7) gave 0.18 g (yield 20%) of a pale brown solid corresponding to 2-[4-(4-methylpyrimidin-2-ylamino)phenylamino]-3-methyl-4-chloroquinoline.

Mass: (ES+) $C_{21}H_{18}ClN_5$ required 375.13; found 376.1 [M+H], method HPLC/MS method 6.

Synthesis of Compound 532-Me Free Base, 2-[4-(4-methylpyrimidin-2-ylamino)phenylamino]-3-methyl-4-(4-tert-butylaminopiperidin-1-yl)quinoline

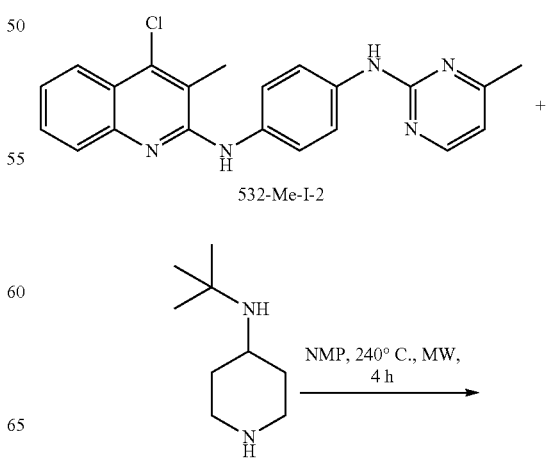

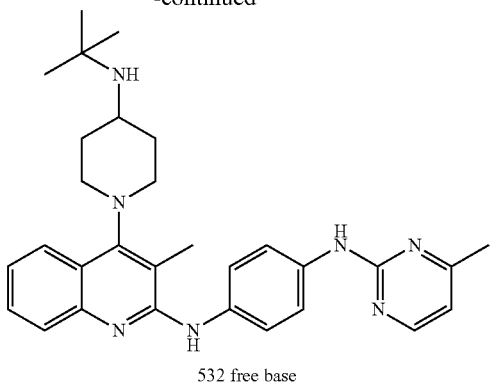

532 free base

To a solution of 2-[4-(4-methylpyrimidin-2-ylamino)phenylamino]-3-methyl-4-chloroquinoline (0.4 g, 1.06 mmol) in 3 ml of NMP was added 4-(tert-butylamino)-piperidine (0.83 g, 5.30 mmol) and the mixture was then heated in a microwave oven for 4 h at 240° C. Then, the reaction mixture was cooled, diluted with ice water and filtered. The collected solid was purified by SFC preparative chromatography to give 70 mg (yield 13%) of a pale yellow solid corresponding to 2-[4-(4-methylpyrimidin-2-ylamino)phenylamino]-3-methyl-4-(4-tert-butylaminopiperidin-1-yl)quinoline.

Mass: (ES+) $C_{30}H_{37}N_7$, required 495.31; found 496.3 [M+H], HPLC/MS method 5

Synthesis of Compound 532-Me, 2-[4-(4-methylpyrimidin-2-ylamino)phenylamino]-3-methyl-4-(4-tert-butylaminopiperidin-1-yl)quinoline Hydrochloride Salt

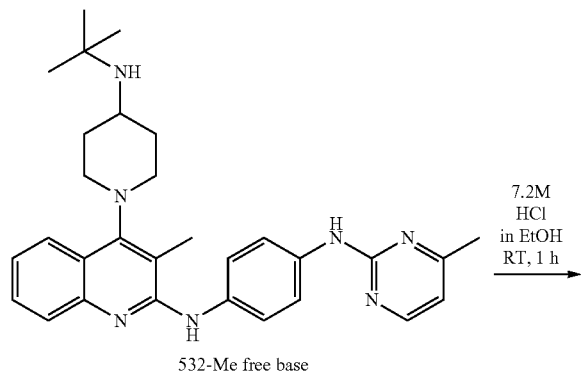

532-Me free base 7.2M HCl in EtOH RT, 1 h

532-Me

To a solution of 2-[4-(4-methylpyrimidin-2-ylamino)phenylamino]-3-methyl-4-(4-tert-butylaminopiperidin-1-yl)quinoline (0.07 g, 0.091 mmol) in 2 ml of ethanol at 0° C. was added 7.2 M HCl in ethanol (2 ml) and the mixture was stirred at room temperature for 1 h. The reaction mixture was concentrated under reduced pressure and washed with diethyl ether to give 60 mg (yield 80%) of a pale yellow solid corresponding to 2-[4-(4-methylpyrimidin-2-ylamino)phenylamino]-3-methyl-4-(4-tert-butylaminopiperidin-1-yl)quinoline hydrochloride salt.

Mass: (ES+) $C_{30}H_{38}ClN_7$ required 531.29; found 496.3 [(M−HCl+H)]+, HPLC method 6

Preparation of Compound 540-Me: 2-[3-(4-trifluoromethylpyrimidin-2-ylamino)phenylamino]-3-methyl-4-(4-tert-butylaminopiperidin-1-yl)quinoline Hydrochloride Salt Synthesis of $N^1$-(4-(trifluoromethyl)pyrimidin-2-yl)benzene-1,3-diamine, Intermediate 540-Me-I-1

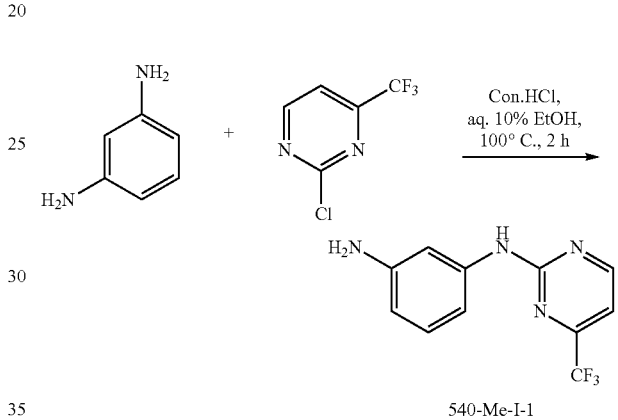

540-Me-I-1

To a stirred solution of benzene-1,3-diamine (2.0 g, 18.51 mmol) and 2-chloro-4-(trifluoromethyl) pyrimidine (3.4 g, 18.51 mmol) in 10% aqueous ethanol at 0° C. was added dropwise aqueous concentrated HCl (1.1 ml). Then, the resulting mixture was stirred at 100° C. for 2 h. The solvent was then evaporated and the resulting residue was diluted with cold water, basified with 10% NaHCO$_3$, extracted with AcOEt (2×50 ml). The combined organic layers were washed with brine (20 ml), dried over Na$_2$SO$_4$, filtered and concentrated under reduced pressure to give a crude compound which upon purification by flash chromatography using (REVELERIS-Grace 40 g, silica-gel: 230-400 mesh, AcOEt-petroleum ether; 1:9→1.5:8.5) gave 1 g (yield 21%) of a pale brown solid corresponding to $N^1$-(4-(trifluoromethyl)pyrimidin-2-yl)benzene-1,3-diamine Mass: (ES+) $C_{11}H_9F_3N_4$, required 254; found 255 [M+H], HPLC/MS method 4.

Synthesis of 2-[3-(4-trifluoromethylpyrimidin-2-ylamino)phenylamino]-3-methyl-4-chloroquinoline, Intermediate 540-Me-1-2

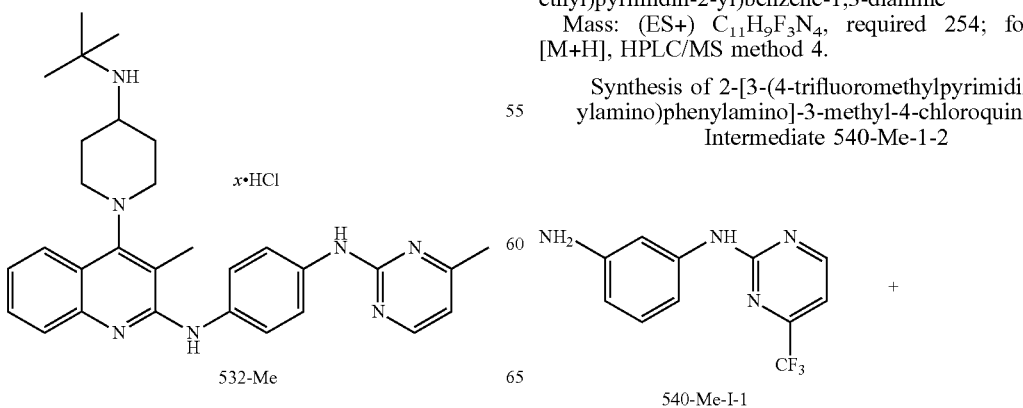

540-Me-I-1

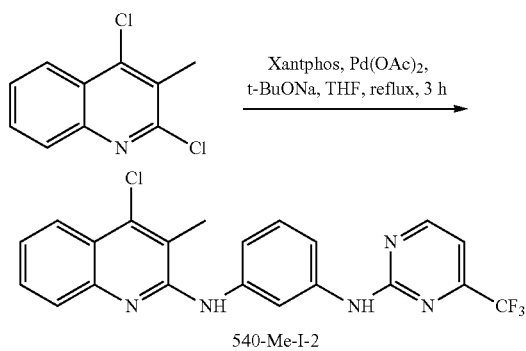

To a solution under argon gas of 2,4-dichloro-3-methylquinoline (0.1 g, 0.47 mmol) in THF (10 ml) was added N$^1$-(4-(trifluoromethyl)pyrimidin-2-yl)benzene-1,3-diamine (0.18 g, 0.70 mmol) and t-BuONa (0.13 g, 96.1 mmol). The resulting reaction mixture was degassed 10 min with argon gas, then Xantphos (27 mg, 0.047 mmol) and Pd(OAc)$_2$ (6 mg, 0.023 mmol) were added and the reaction mixture was stirred at 80° C. for 3 h. The reaction mixture was then cooled to room temperature, diluted with cold water (10 ml), extracted with AcOEt (2×20 ml). The combined organic layers were washed with brine (10 ml), dried over Na$_2$SO$_4$, filtered and concentrated under reduced pressure to give brown oil which upon purification by flash chromatography using (REVELERIS Grace, 40 g, silica-gel: 230-400 mesh, AcOEt-Petroleum ether; 1:9→2:8) gave 1 g (yield 20%) of a pale brown solid corresponding to 2-[3-(4-trifluoromethylpyrimidin-2-ylamino)phenylamino]-3-methyl-4-chloroquinoline.

Mass: (ES+) C$_{21}$H$_{15}$ClF$_3$N$_5$ required 429.10; found 430 [M+H], HPLC/MS method 4.

Synthesis of Compound 540-Me Free Base, 2-[3-(4-trifluoromethylpyrimidin-2-ylamino)phenylamino]-3-methyl-4-(4-tert-butylaminopiperidin-1-yl)quinoline

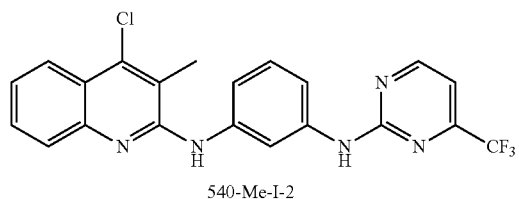

+

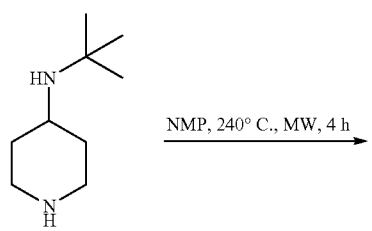

NMP, 240° C., MW, 4 h →

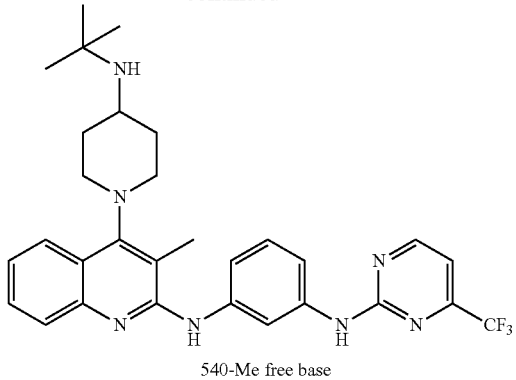

To a solution of 2-[3-(4-trifluoromethpyrimidin-2-amino)phenylamino]-3-meth-4-chloroquinoline (0.3 g, 0.598 mmol) in 3 ml of NMP was added 4-(tert-butylamino)-piperidine (0.55 g, 3.49 mmol) and the mixture was heated in a microwave oven for 4 hours at 240° C. Then, the reaction mixture was cooled, diluted with ice water and filtered. The collected solid was purified by the preparative HPLC to give 60 mg (yield 15%) of a pale yellow solid corresponding to 2-[3-(4-trifluoromethylpyrimidin-2-ylamino)phenylamino]-3-methyl-4-(4-tert-butylaminopiperidin-1-yl)quinoline.

Mass: (ES+) C$_{30}$H$_{34}$F$_3$N$_7$, required 549.28; found 550 [M+H], HPLC/MS method 5

Synthesis of Compound 540-Me: 2-[3-(4-trifluoromethylpyrimidin-2-ylamino)phenylamino]-3-methyl-4-(4-tert-butylaminopiperidin-1-yl)quinoline Hydrochloride Salt

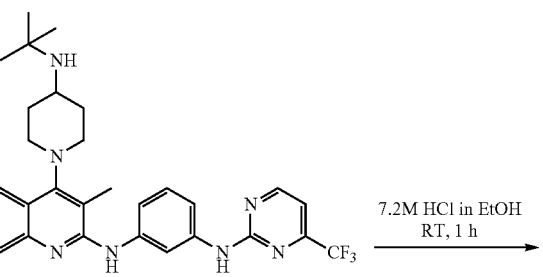

To a solution of 2-[3-(4-trifluoromethylpyrimidin-2-ylamino)phenylamino]-3-methyl-4-(4-tert-butylaminopiperidin-1-yl)quinoline (0.05 g, 0.091 mmol) in 2 ml of ethanol at 0° C. was added 7.2 M HCl in ethanol (2 ml) and the resulting mixture was stirred at room temperature for 1 h. The reaction mixture was concentrated under reduced pressure and washed with diethyl ether to give 40 mg (yield 75%) of a pale yellow solid corresponding to 2-[3-(4-trifluoromethylpyrimidin-2-ylamino)phenylamino]-3-methyl-4-(4-tert-butylaminopiperidin-1-yl)quinoline hydrochloride salt.

Mass: (ES+) $C_{30}H_{35}ClF_3N_7$ required 549 (M–HCl); found 550 [(M–HCl+H)]+, HPLC/MS method 4

Preparation of Compound 352-CN, 2-(4-chlorobenzylamino)-3-cyano-4-[4-(tert-butylamino)piperidin-1-yl]quinoline Hydrochloride Salt Preparation of Intermediate 2-chloro-3-cyano-4-[4-(tert-butylamino)piperidin-1-yl]quinoline, Intermediate 352-CN-I-1

Synthesis of Compound 352-CN Free Base, 2-(4-chlorobenzylamino)-3-cyano-4-[4-(tert-butylamino) piperidin-1-yl]quinoline

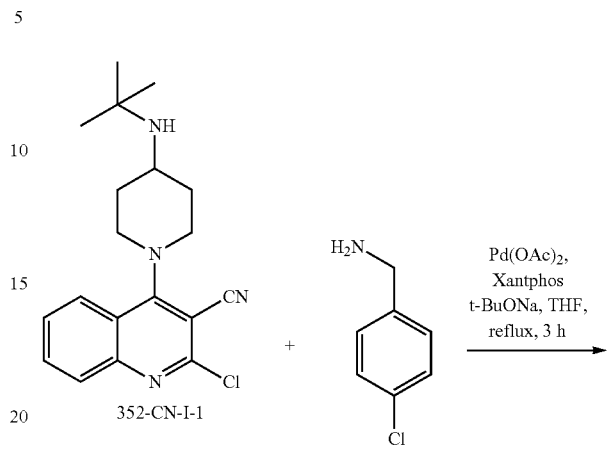

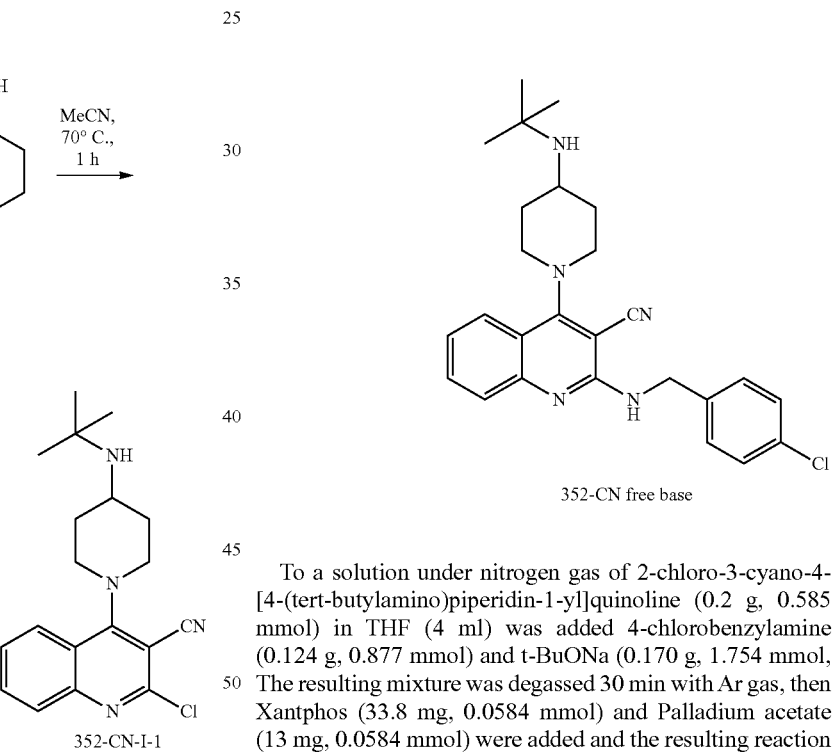

To a stirred solution of 2,4-dichloroquinoline-3-carbonitrile (0.6 g, 2.702 mmol) in acetonitrile (70 ml) was added 4-(tert-butylamino)piperidine (0.42 g, 2.702 mmol) and the reaction was stirred 1 hour at 70° C. The reaction mixture was then cooled to room temperature. The reaction mixture was concentrated under reduced pressure and washed with diethyl ether to give 600 mg (yield 65%) of an off-white solid corresponding to 2-chloro-3-cyano-4-[4-(tert-butylamino)piperidin-1-yl]quinoline. This compound was confirmed by NOE $^1$H NMR experiment and LCMS.

Mass: (ES+) $C_{19}H_{23}ClN_4$ required 342.16; found 343 [M+H], HPLC/MS method 4.

To a solution under nitrogen gas of 2-chloro-3-cyano-4-[4-(tert-butylamino)piperidin-1-yl]quinoline (0.2 g, 0.585 mmol) in THF (4 ml) was added 4-chlorobenzylamine (0.124 g, 0.877 mmol) and t-BuONa (0.170 g, 1.754 mmol, The resulting mixture was degassed 30 min with Ar gas, then Xantphos (33.8 mg, 0.0584 mmol) and Palladium acetate (13 mg, 0.0584 mmol) were added and the resulting reaction mixture was stirred at 100° C. for 3 h. The reaction mixture was then cooled to room temperature, filtered and concentrated under reduced pressure. The residue was partitioned between brine and AcOEt and the aqueous layer was extracted with AcOEt. The combined organic layers were dried over $Na_2SO_4$, filtered and concentrated under reduced pressure to give a brown oil. The crude compound which upon purification by flash chromatography using (silica-gel: 100-200 mesh, AcOEt-petroleum ether; 10:90→15:85) gave 60 mg (yield 22%) of a white solid corresponding to 2-(4-chlorobenzylamino)-3-cyano-4-[4-(tert-butylamino)piperidin-1-yl]quinoline.

Mass: (ES+) $C_{26}H_{30}ClN_5$ required 447.2; found 448.22 [M+H], HPLC method 4.

177

Synthesis of Compound 352-CN, 2-(4-chlorobenzylamino)-3-cyano-4-[4-(tert-butylamino)piperidin-1-yl]quinoline Hydrochloride Salt

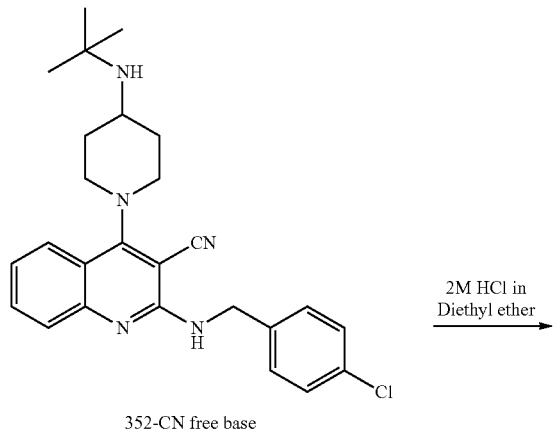

352-CN free base

2M HCl in Diethyl ether →

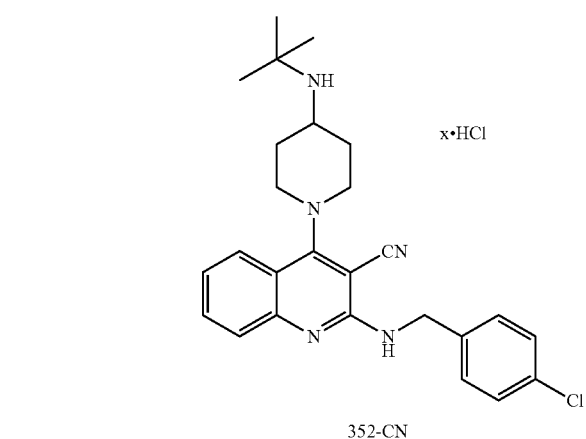

352-CN

To a solution of 2-(4-chlorobenzylamino)-3-cyano-4-[4-(tert-butylamino)piperidin-1-yl]quinoline (60 mg, 103 mmol) in 2 ml of dichloromethane was added 2 M HCl in diethyl ether (2.0 ml) and the mixture was stirred at room temperature for 30 min. The reaction mixture was concentrated under reduced pressure and washed with diethyl ether to give 55 mg (yield 78%) of an off-white solid corresponding to 2-(4-chlorobenzylamino)-3-cyano-4-[4-(tert-butylamino)piperidin-1-yl]quinoline hydrochloride.

Mass: (ES+) $C_{26}H_{31}Cl_2N_5$ required 483; found 446 [M−HCl-H], HPLC method 4.

178

Preparation of Compound 498-CN, 2-[4-(4-(pyridin-3-yl)pyrimidin-2-ylamino)-3-methylbenzylamino]-3-cyano-4-(4-tert-butylaminopiperidin-1-yl)quinoline Hydrochloride Salt Synthesis of 2-(3-methyl-4-bromobenzylamino)-3-cyano-4-(4-tert butylaminopiperidin-1-yl)quinoline, Intermediate 498-CN-I-1

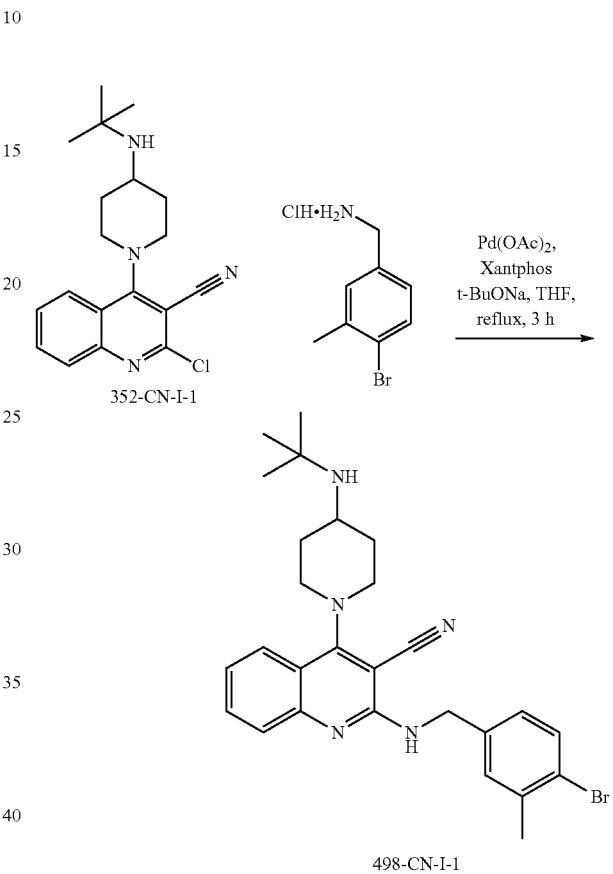

To a solution under nitrogen gas of 2-chloro-3-cyano-4-(4-tert-butylaminopiperidin-1-yl)quinoline, Intermediate 352-CN-I-1 (500 mg, 1.46 mmol) in THF (10 ml) was added -3-methyl-4-bromobenzylamine hydrochloride (377 mg, 1.608 mmol) and t-BuONa (280 mg, 2.922 mmol). The resulting mixture was degassed 10 min with Argon gas, then Xantphos (84 mg, 0.1461 mmol) and Pd(OAc)$_2$ (16 mg, 0.073 mmol) were added and the reaction mixture was stirred at reflux for 3 h. The reaction mixture was then cooled to room temperature, filtered and concentrated under reduced pressure. Then, the residue was partitioned between brine and EtOAc and the aqueous layer was extracted with EtOAc. The combined organic layers were dried over Na$_2$SO$_4$, filtered and concentrated under reduced pressure to give a brown oil. The crude compound which upon purification by flash chromatography using (silica-gel: 100-200 mesh, EtOAc-petroleum ether; 40:60→100:0) gave 200 mg (yield 27%) of an off white solid corresponding to 2-(3-methyl-4-bromobenzylamino)-3-cyano-4-(4-tert-butylaminopiperidin-1-yl)quinoline.

Mass: (ES+) $C_{27}H_{32}BrN_5$ required 505; found 506 [M+H], HPLC/MS method 2

Synthesis of Compound 498-CN Free Base, 2-[4-(4-(pyridin-3-yl)pyrimidin-2-ylamino)-3-methylbenzylamino]-3-cyano-4-(4-tert-butylaminopiperidin-1-yl)quinoline

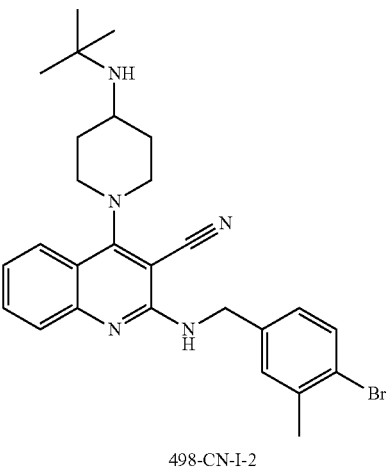

498-CN-I-2

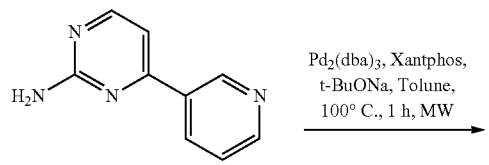

Pd$_2$(dba)$_3$, Xantphos, t-BuONa, Tolune, 100° C., 1 h, MW

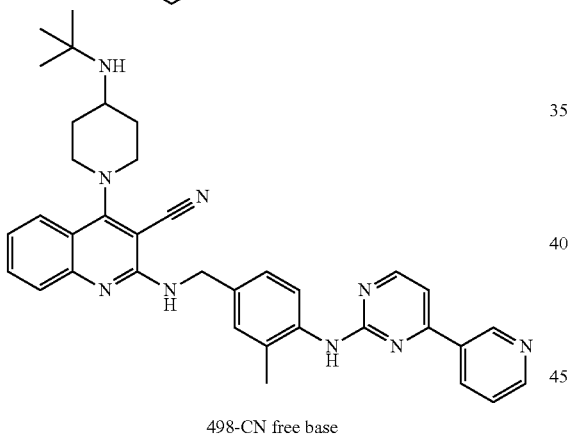

498-CN free base

To a solution under nitrogen gas of 2-(3-methyl-4-bromobenzylamino)-3-cyano-4-(4-tert-butylaminopiperidin-1-yl)quinoline (190 mg, 0.376 mmol) in toluene (10 ml) was added 4-(pyridin-3-yl)pyrimidin-2-amine (71 mg, 0.413 mmol) and t-BuONa (72 mg, 0.752 mmol). The resulting mixture was degassed 10 min with Argon gas, then Xantphos (21 mg, 0.0376 mmol) and Pd$_2$(dba)$_3$ (34 mg, 0.0376 mmol) were added and the reaction mixture was stirred at 100° C. for 1 h. The reaction mixture was then cooled to room temperature, filtered and concentrated under reduced pressure. The residue was partitioned between brine and EtOAc and the aqueous layer was extracted with EtOAc. The combined organic layers were dried over Na$_2$SO$_4$, filtered and concentrated under reduced pressure to give yellow oil. The crude compound which upon purification by flash chromatography using (silica-gel: 100-200 mesh, MeOH—CHCl$_3$; 0:100→20:80) gave 60 mg (yield 26%) of an pale-yellow solid corresponding to 2-[4-(4-(pyridin-3-yl)pyrimidin-2-ylamino)-3-methylbenzylamino]-3-cyano-4-(4-tert-butylaminopiperidin-1-yl)quinoline.

Mass: (ES+) C$_{36}$H$_{39}$N$_9$ required 597; found 598 [M+H], HPLC/MS method 6

Synthesis of Compound 498-CN, 2-[4-(4-(pyridin-3-yl)pyrimidin-2-ylamino)-3-methylbenzylamino]-3-cyano-4-(4-tert-butylaminopiperidin-1-yl)quinoline Hydrochloride Salt

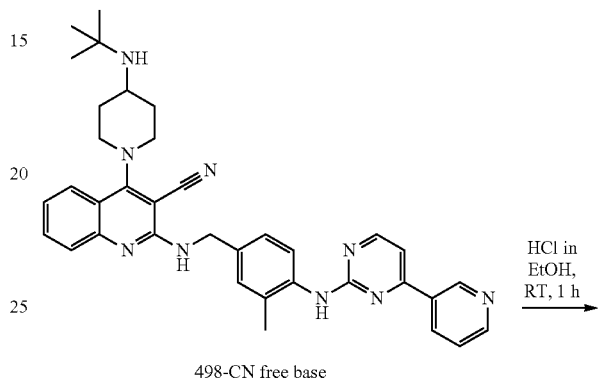

498-CN free base

HCl in EtOH, RT, 1 h

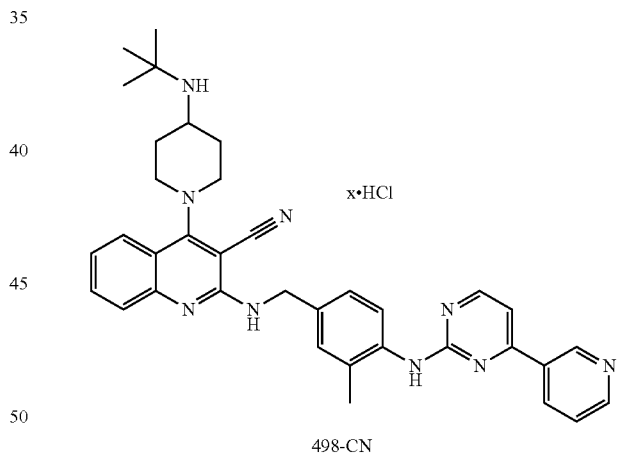

498-CN

To a solution of 2-[4-(4-(pyridin-3-yl)pyrimidin-2-ylamino)-3-methylbenzylamino]-3-cyano-4-(4-tert-butylaminopiperidin-1-yl)quinoline (0.06 g, 0.100 mmol) in 0.5 ml of EtOH was added 7.2M HCl in EtOH (0.5 ml) and the mixture was stirred for 1 hour at room temperature. The reaction mixture was concentrated under reduced pressure and washed with diethyl ether to give 55 mg (yield 87%) of a pale-yellow solid corresponding to 2-[4-(4-(pyridin-3-yl)pyrimidin-2-ylamino)-3-methylbenzylamino]-3-cyano-4-(4-tert-butylaminopiperidin-1-yl)quinoline hydrochloride salt.

Mass: (ES+) C$_{36}$H$_{40}$N$_9$Cl required 597 (M−HCl); found 598[M+H], method 4.

Preparation of Compound of Example 500-CN, 4-(4-(tert-butylamino) piperidin-1-yl)-2-(3-methyl-3-cyano-4-(4-methylpyrimidin-2-ylamino)phenylamino)quinoline Hydrochloride Salt Synthesis of 4-methyl-N-(2-methyl-4-nitrophenyl) pyrimidin-2-amine, Intermediate 500-CN-I-1

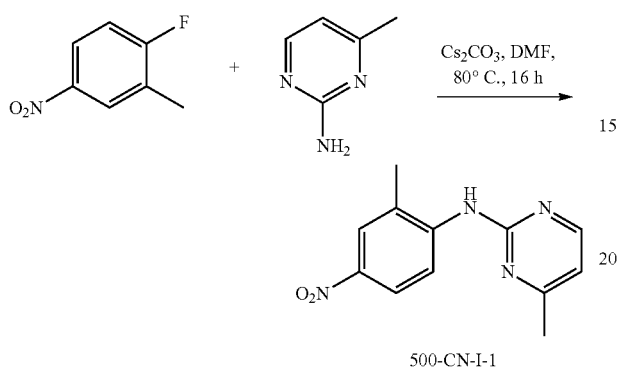

To a stirred solution of 2-fluoro-5-nitrotoluene (1.0 g, 6.451 mmol) in DMF (15 ml) was added 2-amino-4-methylpyrimidine (0.77 g, 6.451 mmol) and $Cs_2CO_3$ (2.41 g, 9.677 mmol) in a round bottom Flask at room temperature and stirred for 16 hours at 80° C. Reaction was monitored by TLC (30% Ethyl acetate/Pet ether). After completion of the reaction, the reaction material was allowed to room temperature and poured into ice water and extracted with AcOEt (2×25 ml). The combined organic layers were dried over $Na_2SO_4$, filtered and concentrated under reduced pressure to give crude 4-methyl-N-(2-methyl-4-nitrophenyl) pyrimidin-2-amine (2.3 g). We have proceeded for next step directly without purification.

Mass: (ES+) $C_{12}H_{12}N_4O_2$ required 244; found 245.1 [M+H], HPLC/MS method 7.

Synthesis of 2-methyl-$N^1$-(4-methylpyrimidin-2-yl) benzene-1,4-diamine, Intermediate 500-CN-I-2

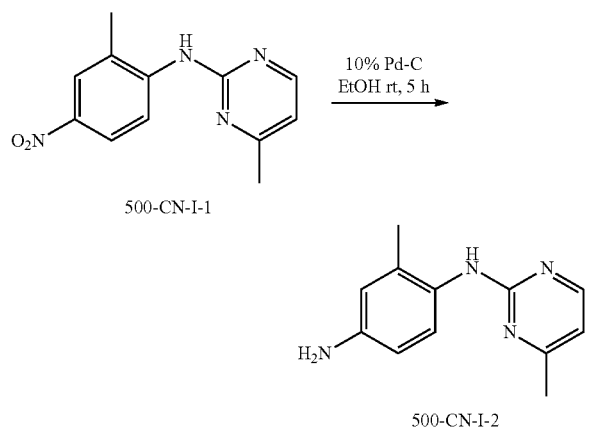

10% Pd—C (100 mg) was added to a stirred solution of compound 500-CN-I-1 (2.3 g, 9.387 mmol) in ethanol at room temperature. The reaction mixture was stirred under Hydrogen (50 Psi) at room temperature for 5 h. The reaction mixture was filtered and concentrated under reduced pressure to give brown oil. The crude compound was washed with ether to give 500 mg (yield 23% over two steps) of a brown solid corresponding to 2-methyl-$N^1$-(4-methylpyrimidin-2-yl) benzene-1, 4-diamine.

Mass: (ES+) $C_{12}H_{14}N_4$ required 214.12; found 215.2 [M+H], HPLC/MS method 4.

Synthesis of Compound 500-CN Free Base, 2-[4-(4-methyl-2-pyrimidinamino)-3-methyl-phenylamino]-3-cyano-4-(4-tert-butylaminopiperidin-1-yl)-quinoline

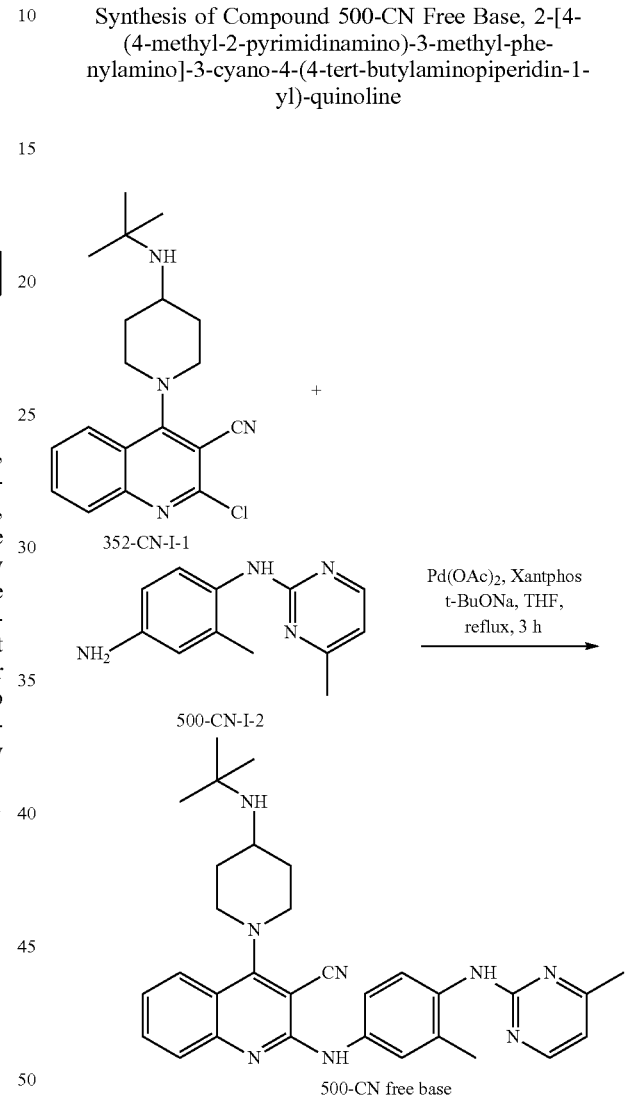

To a solution under nitrogen gas of compound 500-CN-I-2 (0.220 g, 0.964 mmol) in THF (20 ml) was added 2-chloro-3-cyano-4-(4-tert-butylaminopiperidin-1-yl)quinoline 352-CN-I-1 (0.3 g, 0.877 mmol) and t-BuONa (0.168 g, 1.754 mmol, The resulting mixture was degassed 30 min with Argon gas, then Xantphos (50 mg, 0.087 mmol) and Pd(OAc)$_2$ (10 mg, 0.043 mmol) were added and the reaction mixture was stirred at 80° C. for 3 h. The reaction mixture was then cooled to room temperature, filtered and concentrated under reduced pressure. The residue was partitioned between brine and AcOEt and the aqueous layer was extracted with AcOEt. The combined organic layers were dried over $Na_2SO_4$, filtered and concentrated under reduced pressure to give a brown oil. The crude compound which upon purification by flash chromatography using (silica-gel:

100-200 mesh, (10% MeOH: DCM) gave 50 mg (yield 10.9%) of a white solid corresponding to 2-[4-(4-methyl-2-pyrimidinamino)-3-methyl-phenylamino]-3-cyano-4-(4-tert-butylaminopiperidin-1-yl)-quinoline.

Mass: (ES+) $C_{31}H_{36}N_8$ required 520.31; found 521.3 [M+H], method 4.

Synthesis of Compound 500-CN, 2-[4-(4-methyl-2-pyrimidinamino)-3-methyl-phenylamino]-3-cyano-4-(4-tert-butylaminopiperidin-1-yl)-quinoline Hydrochloride Salt

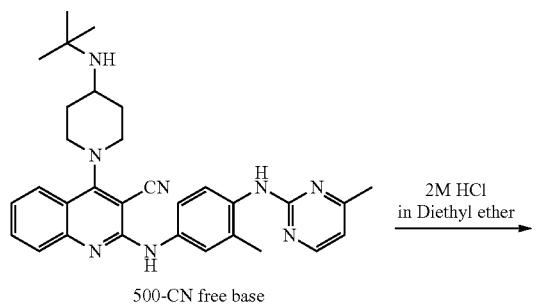

500-CN free base

2M HCl in Diethyl ether

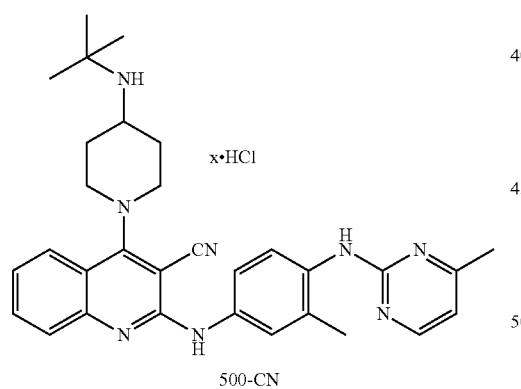

500-CN

To a solution of 2-[4-(4-methyl-2-pyrimidinamino)-3-methyl-phenylamino]-3-cyano-4-(4-tert-butylaminopiperidin-1-yl)-quinoline (50 mg, 0.059 mmol) in 1 ml of dichloromethane was added 2 M HCl in diethyl ether (1.0 ml) and the mixture was stirred at room temperature for 30 min. The reaction mixture was concentrated under reduced pressure and washed with diethyl ether to give 41 mg (yield 75%) of an off-white solid corresponding to 2-[4-(4-methyl-2-pyrimidinamino)-3-methyl-phenylamino]-3-cyano-4-(4-tert-butylaminopiperidin-1-yl)-quinoline hydrochloride salt.

Mass: (ES+) $C_{31}H_{37}ClN_8$ required 555.1; found 521.1 [M−HCl+H], HPLC/MS method 2

Preparation of Compound of Example 502-CN, 2-[4-(4,6-dimethyl-2-pyrimidinamino)-3-methyl-phenylamino]-3-cyano-4-(4-tert-butylaminopiperidin-1-yl)-quinoline Hydrochloride Salt Synthesis of 4,6-dimethyl-N-(2-methyl-4-nitrophenyl)pyrimidin-2-amine, Intermediate 502-CN-I-1

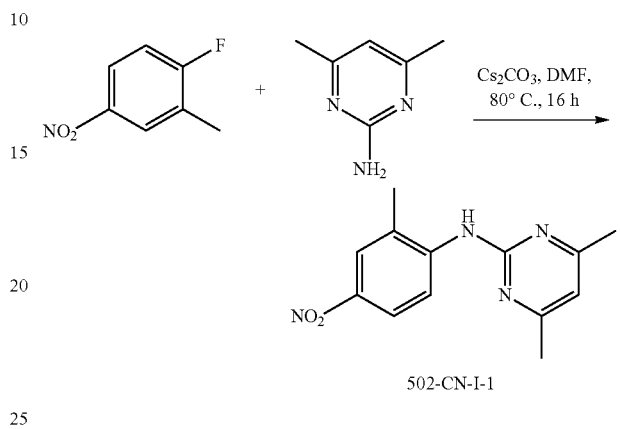

502-CN-I-1

To a stirred solution of 2-fluoro-5-nitrotoluene (2 g, 12.903 mmol) in DMF (15 ml) was added 2-amino-3,5-dimethylpyrimidine (1.58 g, 12.90 mmol) and $Cs_2CO_3$ (6.2 g, 25.806 mmol) in a flask at room temperature and stirred for 16 h at 80° C. Reaction mixture was monitored by TLC (50% Ethyl acetate/Pet ether). After completion of the reaction, the reaction was allowed to room temperature and poured into ice water mixture and extracted with AcOEt (2×100 ml). The combined organic layers were dried over $Na_2SO_4$, filtered and concentrated under reduced pressure to give crude 4-methyl-N-(2-methyl-4-nitrophenyl) pyrimidin-2-amine (2.2 g). The crude product was used for next step without purification.

Mass: (ES+) $C_{13}H_{14}N_4O_2$ required 258.1; found 259.1 [M+H], HPLC/MS method 2.

Synthesis of $N^1$-(4,6-dimethylpyrimidin-2-yl)-2-methylbenzene-1,4-diamine, Intermediate 502-CN-I-2

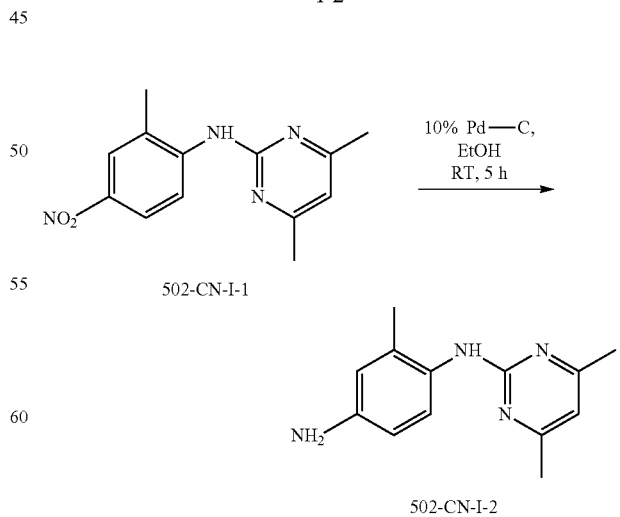

502-CN-I-2

10% Pd—C (100 mg) was added to a stirred solution of compound 502-CN-I-1 (2.2 g 8.523 mmol) in ethanol at room temperature. The reaction mixture was stirred under hydrogen (50 Psi) at room temperature for 5 hours. Then, the reaction mixture was filtered and concentrated under reduced pressure to give a brown oil. The crude compound which upon purification by flash chromatography using (silica-gel: 100-200 mesh, 2% MeOH:DCM) gave 500 mg (yield 16% over two steps) of a brown solid corresponding to 2-methyl-$N^1$-(4-methylpyrimidin-2-yl) benzene-1,4-diamine.

Mass: (ES+) $C_{13}H_6N_4$ required 228.14; found 229.2 [M+H], HPLC/MS method 7.

Synthesis of Compound 502-CN Free Base, 2-[4-(4,6-dimethyl-2-pyrimidinamino)-3-methyl-phenylamino]-3-cyano-4-(4-tert-butylaminopiperidin-1-yl)-quinoline

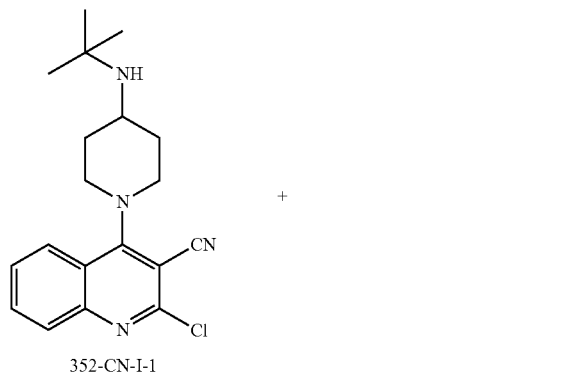

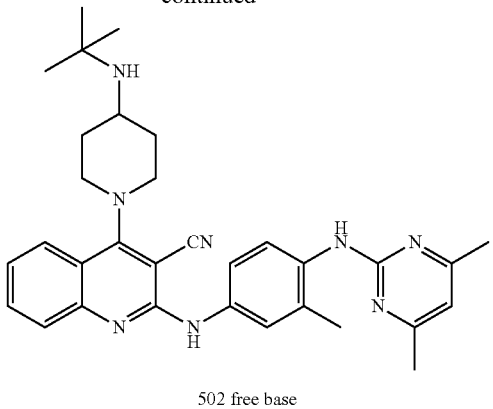

502 free base

To a solution under nitrogen gas of compound 502-CN-I-2 (0.199 g, 0.877 mmol) in THF (20 ml) was added 2-chloro-3-cyano-4-(4-tert-butylaminopiperidin-1-yl)-quinoline, intermediate 352-CN-I-1 (0.3 g, 0.877 mmol) and t-BuONa (0.168 g, 1.754 mmol) The resulting mixture was degassed 30 min with Argon gas, then Xantphos (50 mg, 0.087 mmol) and Pd(OAc)$_2$ (10 mg, 0.043 mmol) were added and the reaction mixture was stirred at 80° C. for 3 h. The reaction mixture was then cooled to room temperature, filtered and concentrated under reduced pressure. The residue was partitioned between brine and AcOEt and the aqueous layer was extracted with AcOEt. The combined organic layers were dried over Na$_2$SO$_4$, filtered and concentrated under reduced pressure to give brown oil. The crude compound which upon purification by flash chromatography using (silica-gel: 100-200 mesh, (10% MeOH:DCM) gave 70 mg (yield 14.5%) of a white solid corresponding to 2-[4-(4,6-dimethyl-2-pyrimidinamino)-3-methyl-phenylamino]-3-cyano-4-(4-tert-butylaminopiperidin-1-yl)-quinoline.

Mass: (ES+) $C_{32}H_{38}N_8$ required 534.32; found 535.3 [M+H], HPLC/MS method 6.

Synthesis of Compound 502-CN, 2-[4-(4,6-dimethyl-2-pyrimidinamino)-3-methyl-phenylamino]-3-cyano-4-(4-tert-butylaminopiperidin-1-yl)-quinoline Hydrochloride Salt

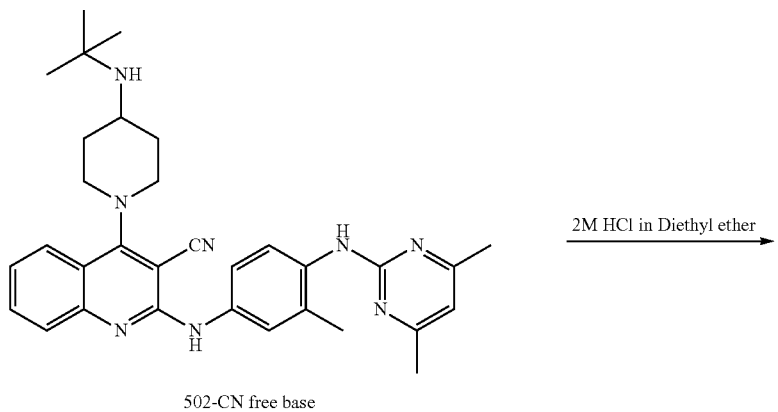

502-CN free base

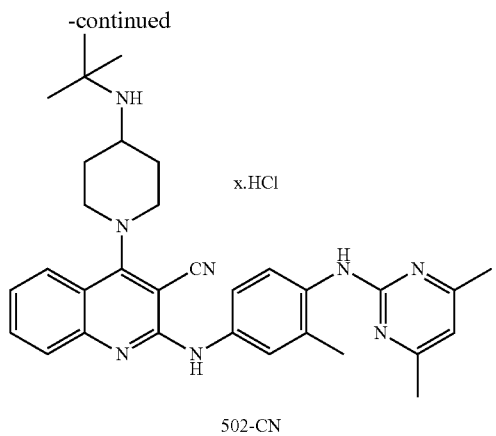

502-CN

To a solution of compound 2-[4-(4,6-dimethyl-2-pyrimidinamino)-3-methyl-phenylamino]-3-cyano-4-(4-tert-butylaminopiperidin-1-yl)-quinoline (70 mg, 0.131 mmol) in 1 ml of DCM was added 2 M HCl in diethyl ether (1.0 ml) and the mixture was stirred at room temperature for 30 min. The reaction mixture was then concentrated under reduced pressure and washed with diethyl ether to give 60 mg (yield 81%) of an off-white solid corresponding 2-[4-(4,6-dimethyl-2-pyrimidinamino)-3-methyl-phenylamino]-3-cyano-4-(4-tert-butylaminopiperidin-1-yl)-quinoline hydrochloride salt.

Mass: (ES+) $C_{32}H_{39}ClN_8$ required 569.2; found 535.3 [M−HCl+H], HPLC/MS method 6

Preparation of Compound of Example 510-CN, 2-[4-(4-methyl-6-methoxypyrimidin-2-ylamino)-3-methylphenylamino]-3-cyano-4-(4-tert-butylaminopiperidin-1-yl)quinoline Hydrochloride Salt

Synthesis of 2-chloro-4-methoxy-6-methylpyrimidine, Intermediate 510-CN-I-1

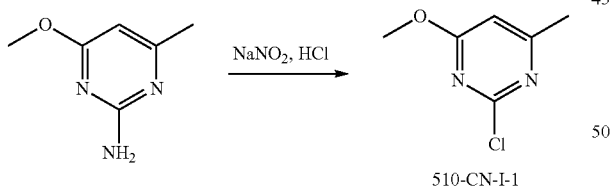

510-CN-I-1

To a solution 2-amino-4-methoxy-6-methylpyrimidine (5 g, 35.97 mmol) in aqueous concentrated HCl (50 ml) was added NaNO$_2$ (2.97 g, 43.16 mmol) in water (5 ml) slowly drop by drop over a period 30 min at 0° C. and then the reaction mixture was stirred at room temperature for 1 hour. Then, the reaction mixture was quenched with 10 N sodium hydroxide solution then insoluble material was, filtered and filtrate was partitioned between brine and AcOEt and the aqueous layer was extracted with AcOEt. The combined organic layers were dried over Na$_2$SO$_4$, filtered and concentrated under reduced pressure to give a brown oil. The crude compound which upon purification by flash chromatography using (silica-gel: 100-200 mesh, AcOEt-petroleum ether; 10:90→15:85) gave 600 mg (yield 8%) of a white solid corresponding to 2-chloro-4-methoxy-6-methylpyrimidine.

Synthesis of 4-methoxy-6-methyl-N-(2-methyl-5-nitrophenyl)pyrimidin-2-amine, Intermediate 510-CN-I-2

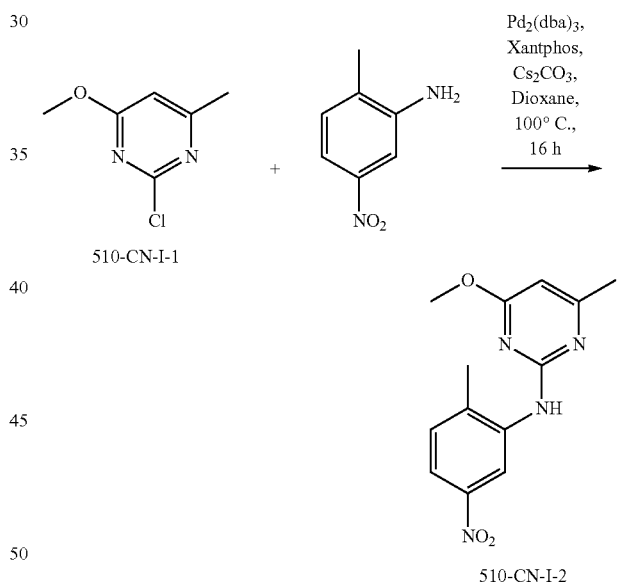

510-CN-I-2

To a solution under nitrogen gas of compound 510-CN-I-1 (600 mg, 3.797 mmol) in 1,4-dioxane (15 ml), compound-3 (578 mg, 3.797 mmol) and cesium carbonate (2.148 g, 6.592 mmol) were added. The resulting mixture was degassed 30 min with Argon gas, then Xantphos (440 mg, 0.759 mmol) and Pd$_2$(dba) 3 (348 mg, 0.379 mmol) were added and the reaction mixture was stirred at 100° C. for 16 h. The reaction mixture was then cooled to room temperature, filtered and concentrated under reduced pressure. The residue was partitioned between brine and AcOEt and the aqueous layer was extracted with AcOEt. The combined organic layers were dried over Na$_2$SO$_4$, filtered and concentrated under reduced pressure to give a brown oil. The crude compound was purified by flash chromatography using (silica-gel: 100-200 mesh, AcOEt-petroleum ether; 70%) to give 0.3 g (yield 28.8%) of a pale yellow solid corresponding to 4-methoxy-6-methyl-N-(2-methyl-5-nitrophenyl)pyrimidin-2-amine.

Mass: (ES+) $C_{13}H_{14}N_4O_3$ required 274.11; found 275.1 [M+H], HPLC/MS method 8.

Synthesis of $N^1$-(4-methoxy-6-methylpyrimidin-2-yl)-6-methylbenzene-1,3-diamine, Intermediate 510-CN-I-3

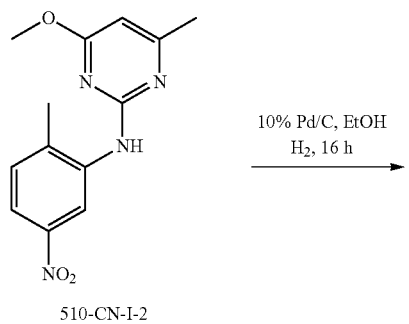

510-CN-I-2

10% Pd/C, EtOH
$H_2$, 16 h

510-CN-I-3

To a solution of compound 510-CN-I-2 (0.3 g, 1.006 mmol) in EtOH (30 ml) was added 10% Pd/C (30 mg). The resulting mixture was stirred under hydrogen (1 bar) for 16 h. Catalyst was filtered off, washed with EtOH and solvent was concentrated under reduced pressure to give 0.20 g of a pale brown solid corresponding to $N^1$-(4-methoxy-6-methylpyrimidin-2-yl)-6-methylbenzene-1,3-diamine. The crude product was used in the next step without further purification.

Synthesis of Compound 510-CN Free Base, 2-[(4-methyl-6-methoxypyrimidin-2-ylamino)-3-methylphenylamino]-3-cyano-4-(4-tert-butylaminopiperidin-1-yl)quinoline

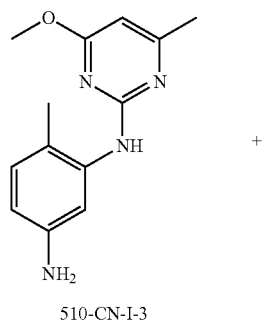

510-CN-I-3

+

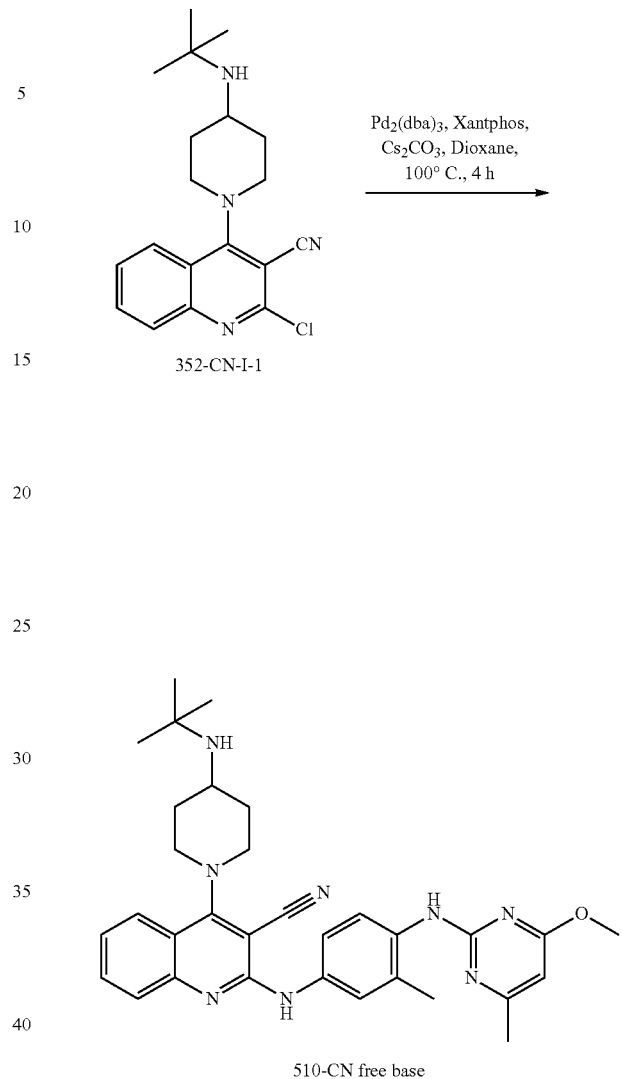

352-CN-I-1

Pd$_2$(dba)$_3$, Xantphos,
Cs$_2$CO$_3$, Dioxane,
100° C., 4 h

510-CN free base

To a solution under nitrogen gas of compound 510-CN-I-3 (0.2 g, 0.585 mmol) in 1,4-dioxane (10 ml) was added 2-chloro-3-cyano-4-(4-tert-butylaminopiperidin-1-yl)quinoline, intermediate 352-CN-I-1 (0142 g, 0.585 mmol) and cesium carbonate (381 mg, 1.169 mmol). The resulting mixture was degassed 30 min with Ar gas, then Xantphos (68 mg, 0.1169 mmol) and Pd$_2$(dba)$_3$ (54 mg, 0.0585 mmol) were added and the reaction mixture was stirred at 100° C. for 4 h. The reaction mixture was then cooled to room temperature, filtered and concentrated under reduced pressure. The residue was partitioned between brine and AcOEt and the aqueous layer was extracted with AcOEt. The combined organic layers were dried over Na$_2$SO$_4$, filtered and concentrated under reduced pressure to give a brown oil. The crude compound which upon purification by flash chromatography using (silica-gel: 100-200 mesh, AcOEt-petroleum ether; 10:90→15:85) gave 90 mg (yield 28%) of a white solid corresponding to 2-[4-(4-methyl-6-methoxypyrimidin-2-ylamino)-3-methylphenylamino]-3-cyano-4-(4-tert-butylaminopiperidin-1-yl)quinoline.

Mass: (ES+) $C_{32}H_3N_{80}$ required 550.31; found 551.3 [M+H], HPLC/MS method 8.

Synthesis of Compound 510-CN, 2-[4-(4-methyl-6-methoxypyrimidin-2-ylamino)-3-methylphenylamino]-3-cyano-4-(4-tert-butylaminopiperidin-1-yl)quinoline Hydrochloride Salt

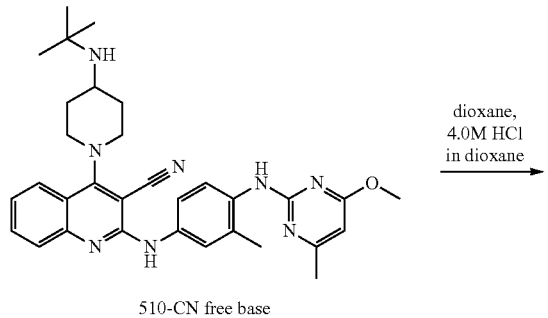

510-CN free base

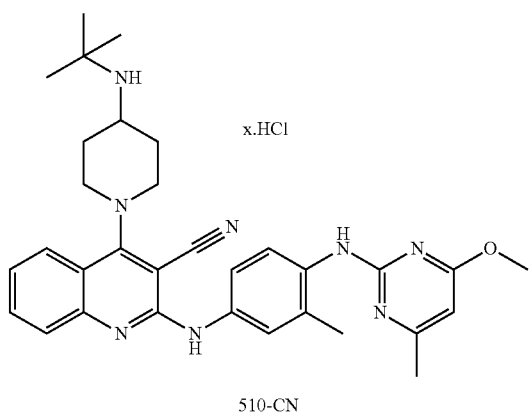

510-CN

To a solution of compound 510-CN free base (90 mg, 0.1636 mmol) in 2 ml of 1,4-dioxane was added 4 M HCl in 1,4-Dioxane (2.0 ml) and the mixture was stirred at room temperature for 30 min. The reaction mixture was concentrated under reduced pressure and washed with diethyl ether to give 80 mg (yield 84%) of an off-white solid corresponding to 2-[4-(4-methyl-6-methoxypyrimidin-2-ylamino)-3-methylphenylamino]-3-cyano-4-(4-tert-butylaminopiperidin-1-yl)quinoline hydrochloride.

Mass: (ES+) $C_{32}H_{39}ClN_8O$ required 586.29; found 551 [M−HCl+H], HPLC/MS method 6

Preparation of Compound 512-CN, 2-[3-methyl-4-(4,6-dimethylfuro[2,3-d]pyrimidin-2-ylamino)phenylamino]-3-cyano-4-(4-tert-butylaminopiperidin-1-yl)quinoline Hydrochloride Salt Synthesis of 2-chloro-4,6-dimethylfuro[2,3-d]pyrimidine, Intermediate 512-CN-I-1

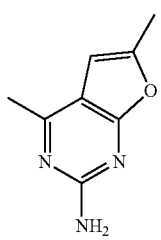 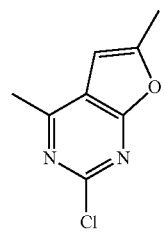

512-CN-I-1

To a solution of 4,6-dimethylfuro[2,3-d]pyrimidin-2-amine in aqueous concentrated HCl (6 ml) was added NaNO$_2$ (0.38 g, 5.521 mmol) in water (1 ml) slowly drop by drop over a period 10 min at 0° C. and the reaction mixture was stirred at room temperature for 3 hours. The reaction mixture was quenched with 10N sodium hydroxide aqueous solution then the resulting solution was filtered off and the filtrate was partitioned between brine and AcOEt and the aqueous layer was extracted with AcOEt. The combined organic layers were dried over Na$_2$SO$_4$, filtered and concentrated under reduced pressure to give a brown oil. The crude compound which upon purification by flash chromatography using (silica-gel: 100-200 mesh, AcOEt-petroleum ether; 10:90→15:85) gave 300 mg (yield 47%) of a white solid corresponding to 2-chloro-4,6-dimethylfuro[2,3-d]pyrimidine.

Synthesis of N-(2-methyl-5-nitrophenyl)-4-(pyridin-3-yl)pyrimidin-2-amine, Intermediate 512-CN-I-2

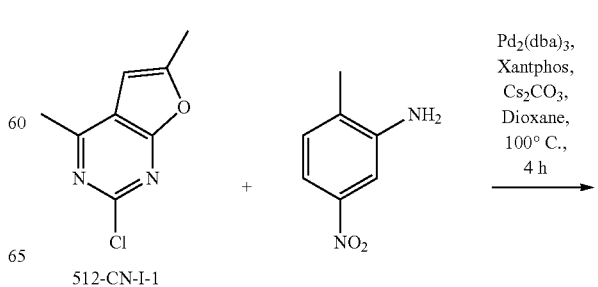

512-CN-I-1

-continued

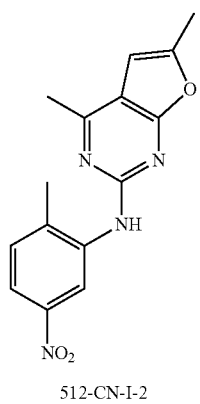

512-CN-I-2

To a solution under nitrogen gas of compound 512-CN-I-1 (300 mg, 1.648 mmol) in 1,4-dioxane (10 ml), 2-amino-4-nitrotoluene (159 mg, 1.648 mmol) and cesium carbonate (1.074 g, 3.296 mmol) were added. The resulting mixture was degassed 30 min with Argon gas, then Xantphos (191 mg, 0.329 mmol) and Pd$_2$(dba)$_3$ (151 mg, 0.1648 mmol) were added and the resulting reaction mixture was stirred at 100° C. for 4 h. The reaction mixture was then cooled to room temperature, filtered and concentrated under reduced pressure. The residue was partitioned between brine and AcOEt and the aqueous layer was extracted with AcOEt. The combined organic layers were dried over Na$_2$SO$_4$, filtered and concentrated under reduced pressure to give a brown oil. The crude compound was purified by flash chromatography using (silica-gel: 100-200 mesh, AcOEt-petroleum ether; 70%) to give 0.3 g (yield 61%) of a pale yellow solid corresponding to 4,6-dimethyl-N-(2-methyl-5-nitrophenyl)furo[2,3-d]pyrimidin-2-amine.

Mass: (ES+) C$_{15}$H$_{14}$N$_4$O$_3$ required 298.11; found 299.1 [M+H], HPLC/MS method 8.

Synthesis of N$^1$-(4,6-dimethylfuro[2,3-d]pyrimidin-2-yl)-6-methylbenzene-1,3-diamine, Intermediate 512-CN-I-3

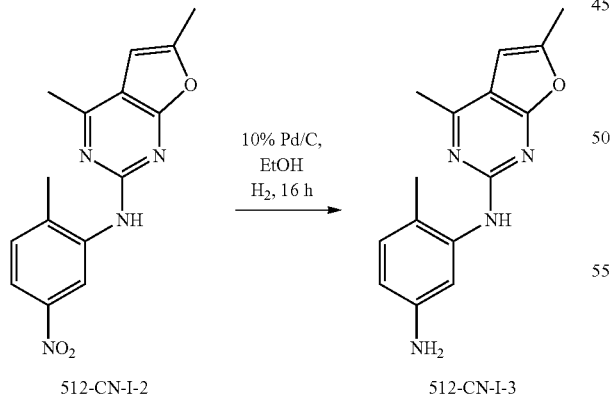

To a solution of compound 512-CN-I-2 (0.3 g, 1.006 mmol) in EtOH (30 ml) was added 10% Pd/C (30 mg). The resulting mixture was stirred under hydrogen (1 bar) for 16 hours. Catalyst was filtered off, washed with EtOH and solvent was concentrated under reduced pressure to give 0.29 g of a pale brown solid corresponding to N-(4,6-dimethylfuro[2,3-d]pyrimidin-2-yl)-6-methylbenzene-1,3-diamine. The crude product was used in the next step without further purification.

Synthesis of Compound 512-CN Free Base, 2-[3-methyl-4-(4,6-dimethylfuro[2,3-d]pyrimidin-2-ylamino)phenylamino]-3-cyano-4-(4-tert-butylaminopiperidin-1-yl)quinoline

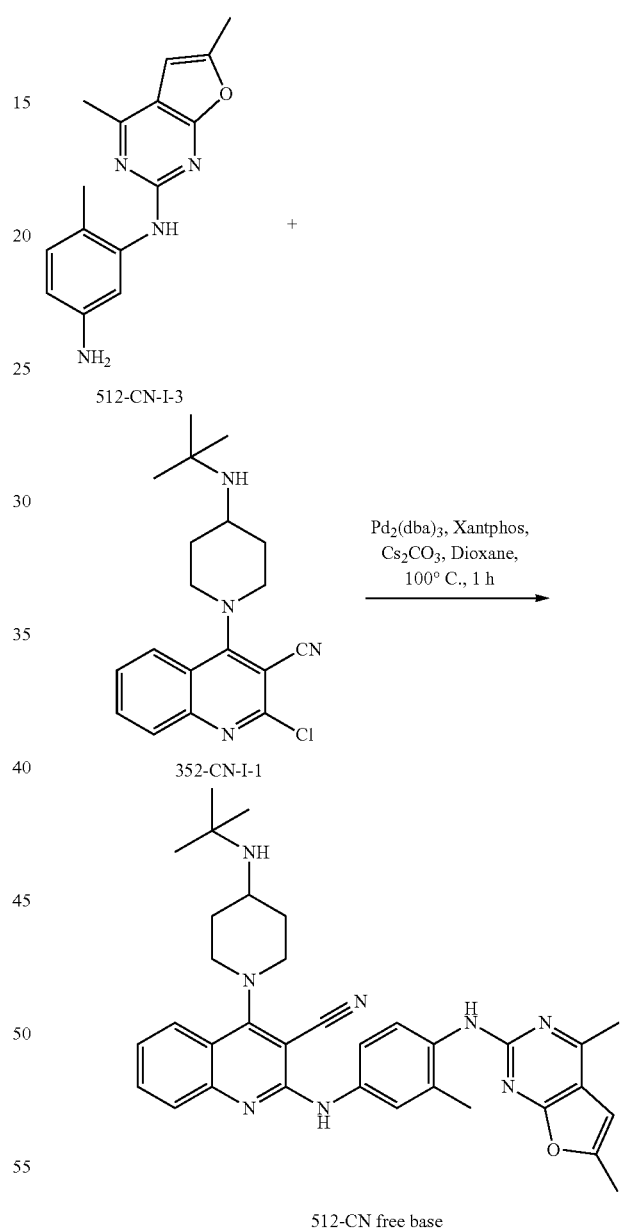

To a solution under nitrogen gas of compound 352-CN-I-1 (0.4 g, 1.169 mmol) in 1,4-dioxane (10 ml) was added compound 512-CN-I-3 (0.313 g, 1.169 mmol) and cesium carbonate (0.953 g, 2.898 mmol). The resulting mixture was degassed 30 min with Ar gas, then Xantphos (135 mg, 0.233 mmol) and Pd$_2$(dba)$_3$ (107 mg, 0.116 mmol) were added and the reaction mixture was stirred at 100° C. for 12 hours. The reaction mixture was then cooled to room temperature, filtered and concentrated under reduced pressure. The residue was partitioned between brine and AcOEt and the aqueous layer was extracted with AcOEt. The combined organic layers were dried over Na₂SO₄, filtered and concentrated under reduced pressure to give a brown oil. The crude compound which upon purification by flash chromatography using (silica-gel: 100-200 mesh, AcOEt-petroleum ether; 10:90→15:85) gave 350 mg (yield 52%) of a white solid corresponding to 2-[3-methyl-4-(4,6-dimethylfuro[2,3-d]pyrimidin-2-ylamino)phenylamino]-3-cyano-4-(4-tert-butylaminopiperidin-1-yl)quinoline.

Mass: (ES+) $C_{34}H_{3}N_{8}O$ required 574.31; found 575.3 [M+H], HPLC/MS method 4.

Synthesis of Compound of Example 512-CN, 2-[3-methyl-4-(4,6-dimethylfuro[2,3-d]pyrimidin-2-ylamino)phenylamino]-3-cyano-4-(4-tert-butylaminopiperidin-1-yl)quinoline Hydrochloride Salt

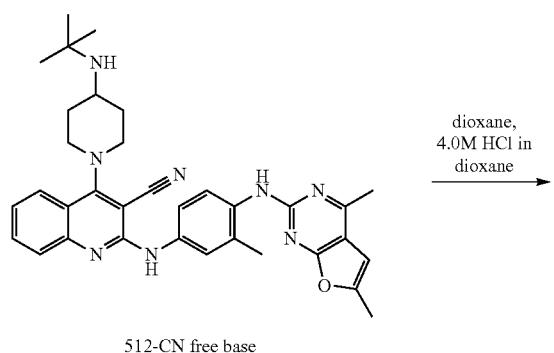

512-CN free base dioxane, 4.0M HCl in dioxane

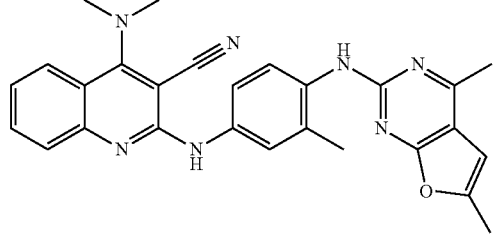

x.HCl

512-CN

To a solution of compound 512-CN free base (100 mg, 0.164 mmol) in 2 ml of 1,4-dioxane was added 4 M HCl in 1,4-Dioxane (2.0 ml) and the mixture was stirred at room temperature for 30 min. The reaction mixture was concentrated under reduced pressure and washed with diethyl ether to give 330 mg (yield 88%) of an off-white solid corresponding to 2-[3-methyl-4-(4,6-dimethylfuro[2,3-d]pyrimidin-2-ylamino)phenylamino]-3-cyano-4-(4-tert-butylaminopiperidin-1-yl)quinoline hydrochloride.

Mass: (ES+) $C_{34}H_{39}ClN_{8}O$ required 610.29; found 575.3 [M−HCl+H], HPLC/MS method 6

Preparation of Compound 522-CN, 2-{3-methyl-4-[2-(pyridin-3-yl)pyrimidin-4-ylamino]phenylamino}-3-cyano-4-(4-tert-butylaminopiperidin-1-yl)quinoline Hydrochloride Salt Synthesis of N-tert-butyl 3-methyl-4-Iodophenylcarbamate, Intermediate 522-CN-I-1

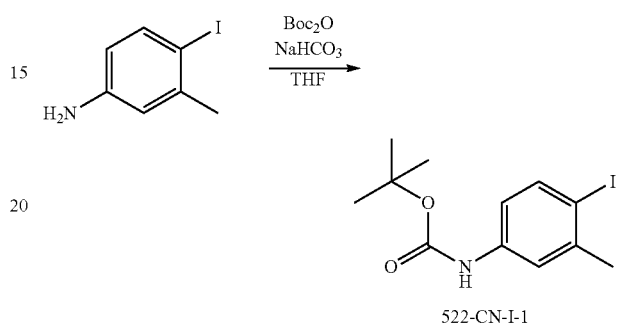

To a solution of 2-iodo-5-aminotoluene (10 g, 43.1 mmol) in THF (200 ml) was added sodium bicarbonate (10.81 g, 128.76 mmol) and Boc₂O (14.09 g, 64.66 mmol) and the reaction mixture was stirred at 50° C. for 12 h. The reaction mixture was then cooled to room temperature, filtered and concentrated under reduced pressure. The residue was partitioned between brine and AcOEt and the aqueous layer was extracted with AcOEt.

The combined organic layers were dried over Na₂SO₄, filtered and concentrated under reduced pressure to give 10 g (yield 69%) of brown solid corresponding to tert-butyl 4-iodo-3-methylphenylcarbamate. The crude product was used in the next step without further purification.

Mass: (ES+) $C_{12}H_{16}INO_{2}$ required 333.02; found 332 [M−H], HPLC/MS method 4.

Synthesis of tert-butyl 3-methyl-4-(2-(pyridin-3-yl)pyrimidin-4-ylamino)phenylcarbamate, Intermediate 522-CN-I-2

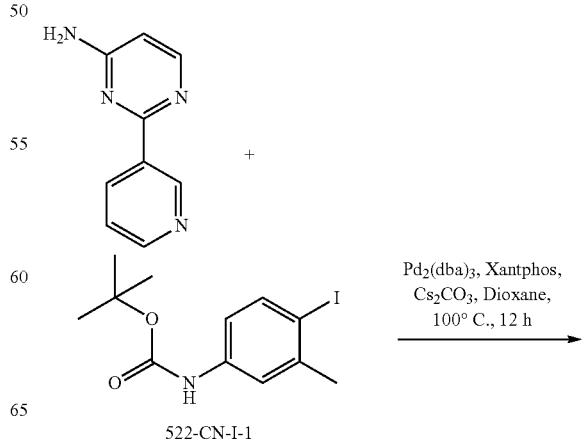

522-CN-I-1

-continued

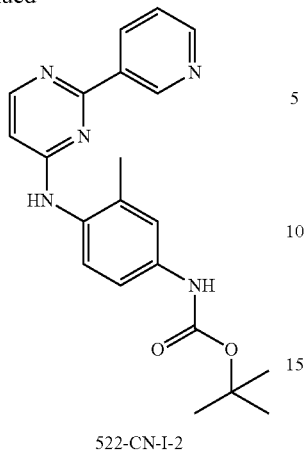

522-CN-I-2

To a solution under nitrogen gas of 2-(pyridin-3-yl)-4-aminopyrimidine (0.4 g, 2.325 mmol) in 1,4-dioxane (8 ml) was added tert-butyl 4-iodo-3-methylphenylcarbamate (1.548 g, 4.651 mmol) and cesium carbonate (2.273 g, 6.976 mmol). The resulting mixture was degassed 30 min with Ar gas, then Xantphos (270 mg, 0.465 mmol) and $Pd_2(dba)_3$ (213 mg, 0.233 mmol) were added and the reaction mixture was stirred at 100° C. for 12 h. The reaction mixture was then cooled to room temperature, filtered and concentrated under reduced pressure. The residue was partitioned between brine and AcOEt and the aqueous layer was extracted with AcOEt. The combined organic layers were dried over $Na_2SO_4$, filtered and concentrated under reduced pressure to give brown oil. The crude compound which upon purification by flash chromatography using (silica-gel: 100-200 mesh, AcOEt-petroleum ether; 10:90→15:85) gave 400 mg (yield 45%) of a brown solid corresponding to tert-butyl 3-methyl-4-(2-(pyridin-3-yl) pyrimidin-4-ylamino) phenylcarbamate.

Mass: (ES+) $C_{21}H_{23}N_5O_2$ required 377; found 378 [M+H], HPLC/MS method 8.

Synthesis of 2-methyl-$N^1$-(2-(pyridin-3-yl)pyrimidin-4-yl)benzene-1,4-diamine, Intermediate 522-CN-I-3

-continued

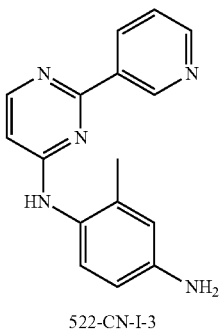

522-CN-I-3

To a solution of compound tert-butyl 3-methyl-4-(2-(pyridin-3-yl) pyrimidin-4-ylamino) phenylcarbamate (400 mg, 1.061 mmol) in 10 ml of 1,4-Dioxane was added 4M HCl in 1,4-dioxane (10.0 ml) and the mixture was stirred at room temperature for 1 hour. The reaction mixture was concentrated under reduced pressure. The residue was partitioned between saturated bicarbonate solution and AcOEt and the aqueous layer was extracted with AcOEt. The combined organic layers were dried over $Na_2SO_4$, filtered and concentrated under reduced pressure to give 250 mg (yield 85%) of an brown solid corresponding to 2-methyl-$N^1$-(2-(pyridin-3-yl)pyrimidin-4-yl)benzene-1,4-diamine. The crude product was used in the next step without further purification.

Mass: (ES+) $C_{16}H_{15}N_5$ required 277.13; found 278 [M+H], HPLC/MS method 8.

Synthesis of Compound 522-CN Free Base, 2-{3-methyl-4-[2-(pyridin-3-yl)pyrimidin-4-ylamino]phenylamino}-3-cyano-4-(4-tert-butylaminopiperidin-1-yl)quinoline

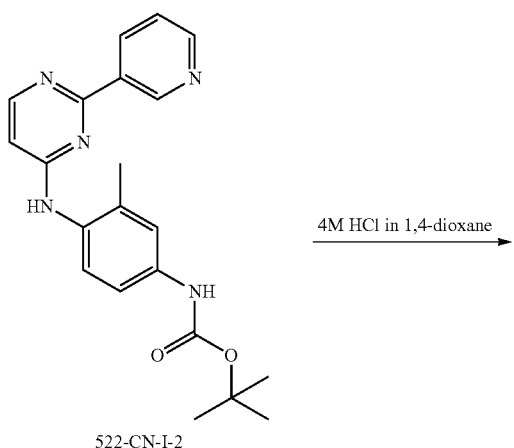

522-CN-I-2

→ 4M HCl in 1,4-dioxane →

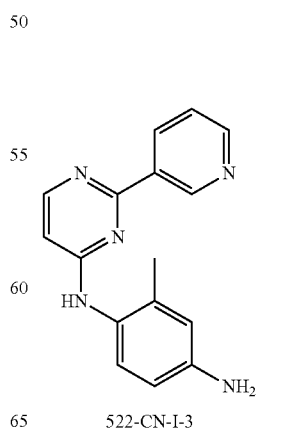

+

522-CN-I-3

-continued

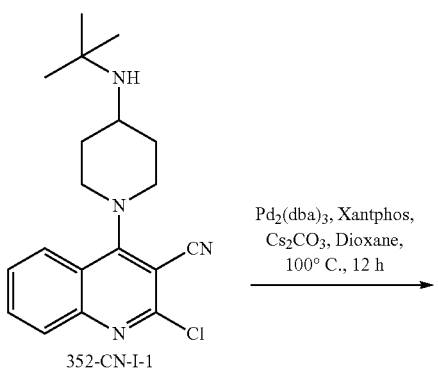

352-CN-I-1

Pd$_2$(dba)$_3$, Xantphos,
Cs$_2$CO$_3$, Dioxane,
100° C., 12 h
→

Synthesis of Compound 522-CN, 2-{3-methyl-4-[2-(pyridin-3-yl)pyrimidin-4-ylamino]phenylamino}-3-cyano-4-(4-tert-butylaminopiperidin-1-yl)quinoline Hydrochloride Salt 522-CN free base 2M HCl in diethyl ether
→

522-CN free base

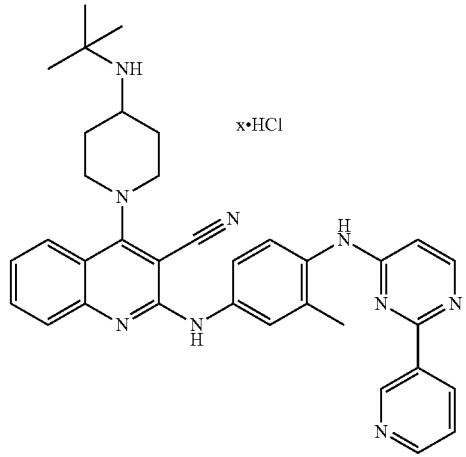

522-CN

To a solution under nitrogen gas of compound 352-CN-I-1 (0.4 g, 1.169 mmol) in 1,4-dioxane (8 ml) was added 2-methyl-N$^1$-(2-(pyridin-3-yl)pyrimidin-4-yl)benzene-1,4-diamine (0.323 g, 1.169 mmol) and cesium carbonate (0.95 g, 2.923 mmol). The resulting mixture was degassed 30 min with Ar gas, then Xantphos (67.6 mg, 0.0117 mmol) and Pd$_2$(dba)$_3$ (107 mg, 0.0117 mmol) were added and the resulting reaction mixture was stirred at 100° C. for 12 h. The reaction mixture was then cooled to room temperature, filtered and concentrated under reduced pressure. The residue was partitioned between brine and AcOEt and the aqueous layer was extracted with AcOEt. The combined organic layers were dried over Na$_2$SO$_4$, filtered and concentrated under reduced pressure to give a brown oil. The crude compound which upon purification by flash chromatography using (silica-gel: 100-200 mesh, AcOEt-petroleum ether; 10:90→15:85) gave 300 mg (yield 58%) of a white solid corresponding to 2-{3-methyl-4-[2-(pyridin-3-yl)pyrimidin-4-ylamino]phenylamino}-3-cyano-4-(4-tert-butylaminopiperidin-1-yl)quinoline Mass: (ES+) C$_{35}$H$_{37}$N$_9$ required 583; found 584 [M+H], HPLC/MS method 4.

To a solution of 2-{3-methyl-4-[2-(pyridin-3-yl)pyrimidin-4-ylamino]phenylamino}-3-cyano-4-(4-tert-butylaminopiperidin-1-yl)quinoline (300 mg, 0.514 mmol) in 3 ml of DCM was added 2 M HCl in diethyl ether (3.0 ml) and the mixture was stirred at room temperature for 30 min. The reaction mixture was concentrated under reduced pressure and washed with diethyl ether to give 230 mg (yield 72%) of an off-white solid corresponding 2-{3-methyl-4-[2-(pyridin-3-yl)pyrimidin-4-ylamino]phenylamino}-3-cyano-4-(4-tert-butylaminopiperidin-1-yl)quinoline hydrochloride.

Mass: (ES+) C$_{35}$H$_{38}$ClN$_9$ required 619.29; found 584.3 [M−HCl+H], HPLC/MS method 6

201

Preparation of Compound 524-CN, 2-{3-methyl-4-[2-(pyridin-3-yl)-5-cyanopyrimidin-4-ylamino]phenylamino}-3-cyano-4-(4-tert-butylaminopiperidin-1-yl)quinoline Hydrochloride Salt Synthesis of tert-butyl 4-(5-cyano-2-(pyridin-3-yl)pyrimidin-4-ylamino)-3-methylphenylcarbamate, Intermediate 524-CN-I-1

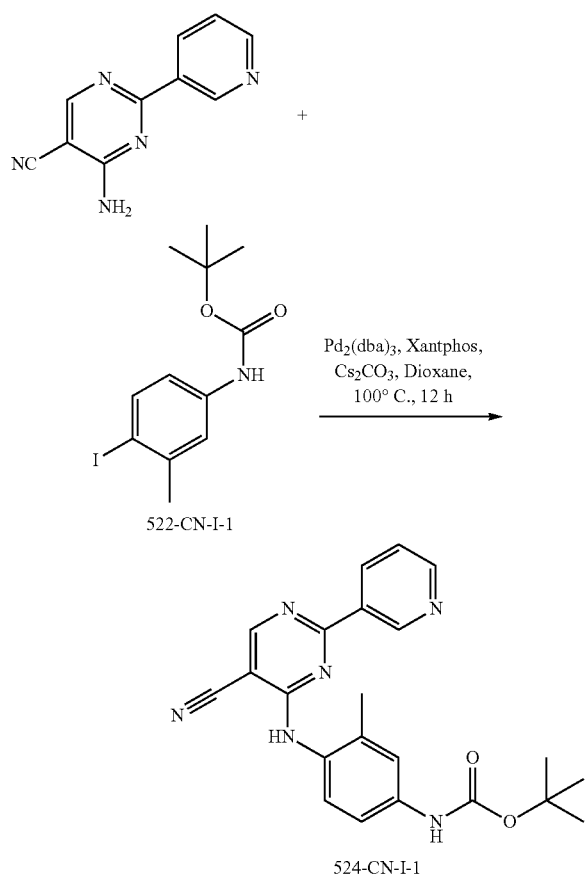

To a solution under nitrogen gas of 4-amino-5-cyano-2-(pyridin-3-yl)pyrimidine (500 mg, 2.538 mmol) in 1,4-dioxane (20 ml), compound 522-CN-I-1 (1.69 g, 5.076 mmol) and cesium carbonate (1.65 g, 5.076 mmol) were added. The resulting mixture was degassed 30 min with Argon gas, then Xantphos (294 mg, 0.507 mmol) and Pd$_2$(dba)$_3$ (232 mg, 0.253 mmol) were added and the reaction mixture was stirred at 100° C. for 12 h. The reaction mixture was then cooled to room temperature, filtered and concentrated under reduced pressure. The residue was partitioned between brine and AcOEt and the aqueous layer was extracted with AcOEt. The combined organic layers were dried over Na$_2$SO$_4$, filtered and concentrated under reduced pressure to give a brown oil. The crude compound was purified by flash chromatography using (silica-gel: 100-200 mesh, AcOEt-petroleum ether; 70%) to give 0.5 g (yield 49%) of a pale yellow solid corresponding to tert-butyl 4-[5-cyano-2-(pyridin-3-yl)pyrimidin-4-ylamino]-3-methylphenylcarbamate.

Mass: (ES+) C$_{22}$H$_{22}$N$_6$O$_2$ required 402.18; found 403.1 [M+H], HPLC/MS method 8.

202

Synthesis of 4-[(4-amino-2-methylphenyl)amino]-2-(pyridin-3-yl)pyrimidine-5-carbonitrile, Intermediate 524-CN-I-2

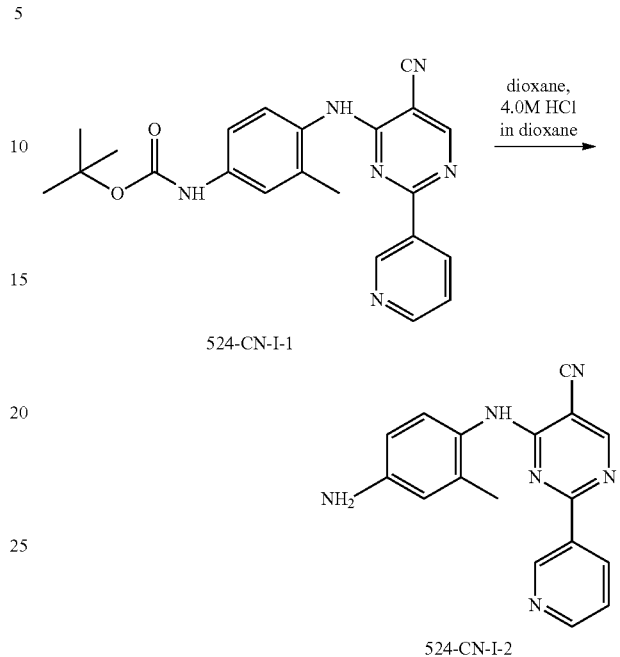

To a solution of compound 524-CN-I-1 (500 mg, 1.243 mmol) in 5 ml of 1,4-Dioxane was added 4 M HCl in 1,4-Dioxane (5.0 ml) and the mixture was stirred at room temperature for 4 h. Then, the reaction mixture was concentrated under reduced pressure. The residue was diluted in water (10 ml), then quenched with solid bicarbonate and the aqueous layer was extracted with AcOEt. The combined organic layers were dried over Na$_2$SO$_4$, filtered and concentrated under reduced pressure to give 0.3 g (yield 79%) of a brown solid corresponding to 4-[(4-amino-2-methylphenyl)amino]-2-(pyridin-3-yl)pyrimidine-5-carbonitrile.

Mass: (ES+) C$_{17}$H$_{14}$N$_6$ required 302.13; found 303.1 [M+H], HPLC/MS method 8.

Synthesis of Compound 524-CN Free Base, 2-{3-methyl-4-[2-(pyridin-3-yl)-5-cyanopyrimidin-4-ylamino]phenylamino}-3-cyano-4-(4-tert-butylaminopiperidin-1-yl)quinoline

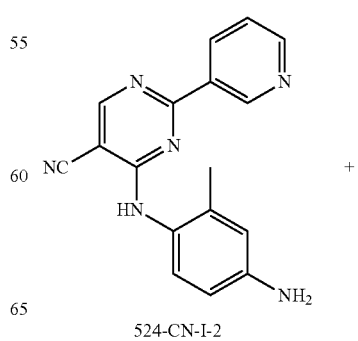

203

-continued

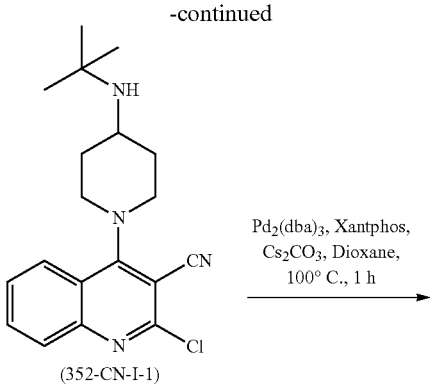

(352-CN-I-1)

Pd₂(dba)₃, Xantphos,
Cs₂CO₃, Dioxane,
100° C., 1 h
→

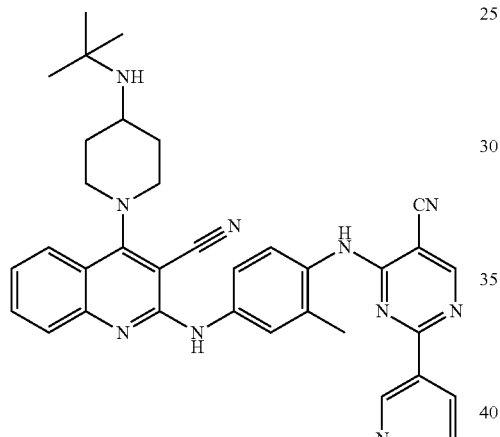

524-CN free base

To a solution under nitrogen gas of compound 352-CN-I-1 (0.4 g, 1.169 mmol) in 1,4-dioxane (10 ml) was added compound 524CN-I-2 (0.35 g, 1.169 mmol) and cesium carbonate (0.953 g, 2.898 mmol). The resulting mixture was degassed 30 min with Ar gas, then Xantphos (135 mg, 0.233 mmol) and Pd₂(dba)₃ (107 mg, 0.1169 mmol) were added and the reaction mixture was stirred at 100° C. for 1 hour. The reaction mixture was then cooled to room temperature, filtered and concentrated under reduced pressure. The residue was partitioned between brine and AcOEt and the aqueous layer was extracted with AcOEt. The combined organic layers were dried over Na₂SO₄, filtered and concentrated under reduced pressure to give a brown oil. The crude compound which upon purification by flash chromatography using (silica-gel: 100-200 mesh, AcOEt-petroleum ether; 10:90→15:85) gave 100 mg (yield 14%) of a white solid corresponding to 2-{3-methyl-4-[2-(pyridin-3-yl)-5-cyanopyrimidin-4-ylamino]phenylamino}-3-cyano-4-(4-tert-butylaminopiperidin-1-yl)quinoline.

Mass: (ES+) $C_{36}H_{36}N_{10}$ required 608.31; found 609 [M+H], HPLC/MS method 4.

204

Synthesis of Compound 524-CN, 2-{3-methyl-4-[2-(pyridin-3-yl)-5-cyanopyrimidin-4-ylamino]phenylamino}-3-cyano-4-(4-tert-butylaminopiperidin-1-yl)quinoline Hydrochloride

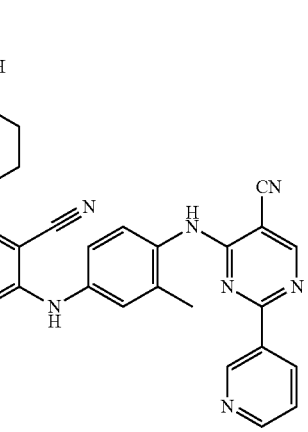

524-CN free base dioxane,
4.0M HCl
in dioxane
→

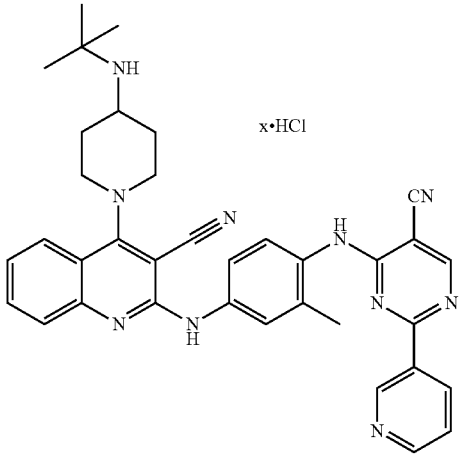

524-CN

To a solution of compound 524-CN free base (100 mg, 0.164 mmol) in 2 ml of 1,4-dioxane was added 4 M HCl in 1,4-Dioxane (2.0 ml) and the mixture was stirred at room temperature for 30 min. The reaction mixture was concentrated under reduced pressure and washed with diethyl ether to give 85 mg (yield 80%) of an off-white solid corresponding to 2-{3-methyl-4-[2-(pyridin-3-yl)-5-cyanopyrimidin-4-ylamino]phenylamino}-3-cyano-4-(4-tert-butylaminopiperidin-1-yl)quinoline hydrochloride.

Mass: (ES+) $C_{36}H_{37}ClN_{10}$ required 644.29; found 609 [M−HCl+H], HPLC/MS method 6

205

Preparation of Compound 532-CN, 2-[4-(4-methyl-pyrimidin-2-ylamino)phenylamino]-3-cyano-4-(4-tert-butylaminopiperidin-1-yl)quinoline Hydrochloride Salt Synthesis of Compound 532-CN Free Base, 2-[4-(4-methylpyrimidin-2-ylamino)phenylamino]-3-cyano-4-(4-tert-butylaminopiperidin-1-yl)quinoline

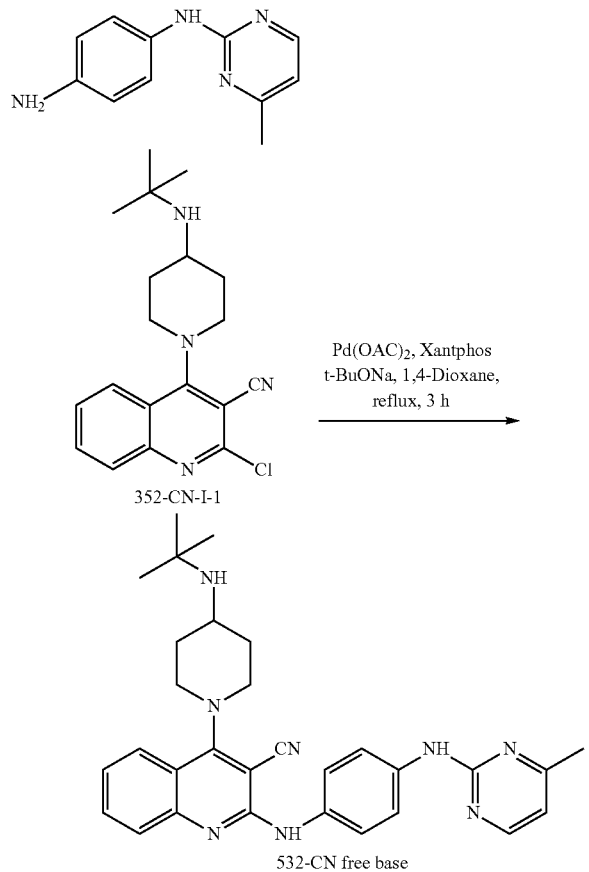

To a solution under nitrogen gas of (4-methylpyrimidin-2-ylamino)-4-phenylamine (0.2 g, 0.585 mmol) in 1,4-dioxane (4 ml) was added compound 352-CN-I-1 (0.175 g, 0.877 mmol) and t-BuONa (0.170 g, 1.754 mmol). The resulting mixture was degassed 30 min with Ar gas, then Xantphos (33.8 mg, 0.0584 mmol) and Pd(OAC)$_2$ (13 mg, 0.0584 mmol) were added and the reaction mixture was stirred at 100° C. for 3 hours. The reaction mixture was then cooled to room temperature, filtered and concentrated under reduced pressure. The residue was partitioned between brine and AcOEt and the aqueous layer was extracted with AcOEt. The combined organic layers were dried over Na$_2$SO$_4$, filtered and concentrated under reduced pressure to give a brown oil. The crude compound which upon purification by flash chromatography using (silica-gel: 100-200 mesh, AcOEt-petroleum ether; 10:90→15:85) gave 50 mg (yield 16.8%) of a white solid corresponding to 2-[4-(4-methylpyrimidin-2-ylamino)phenylamino]-3-cyano-4-(4-tert-butylaminopiperidin-1-yl)quinoline.

Mass: (ES+) C$_{30}$H$_{34}$N$_8$ required 506.29; found 507.22 [M+H], HPLC/MS method 4.

206

Synthesis of Compound 532-CN, 2-[4-(4-methylpyrimidin-2-ylamino)phenylamino]-3-cyano-4-(4-tert-butylaminopiperidin-1-yl)quinoline Hydrochloride Salt

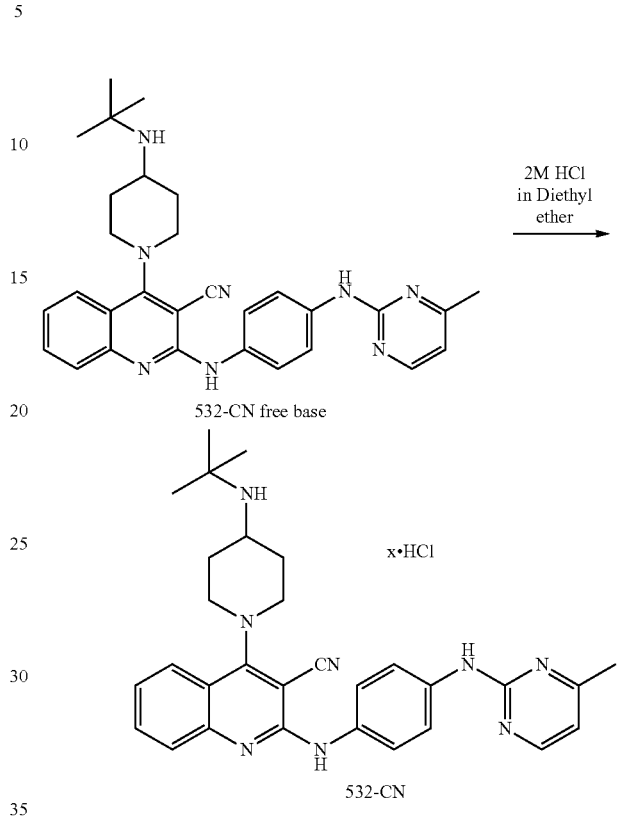

To a solution of compound 532-CN free base (50 mg, 0.0988 mmol) in 1 ml of DCM was added 2 M HCl in diethyl ether (1.0 ml) and the resulting mixture was stirred at room temperature for 30 min. Then, the reaction mixture was concentrated under reduced pressure and washed with diethyl ether to give 40 mg (yield 75%) of an off-white solid corresponding to 2-[4-(4-methylpyrimidin-2-ylamino)phenylamino]-3-cyano-4-(4-tert-butylaminopiperidin-1-yl)quinoline hydrochloride.

Mass: (ES+) C$_{30}$H$_{35}$ClN$_8$ required 542.27; found 507 [M−HCl+H], HPLC/MS method 4

Preparation of Compound 534-CN, 2-[3-methyl-4-(4-trifluoromethylpyrimidin-2-ylamino)phenylamino]-3-cyano-4-(4-tert-butylaminopiperidin-1-yl)quinoline Hydrochloride Salt Synthesis of N-(2-methyl-4-nitrophenyl)-4-(trifluoromethyl)pyrimidin-2-amine Intermediate 534-CN-I-1

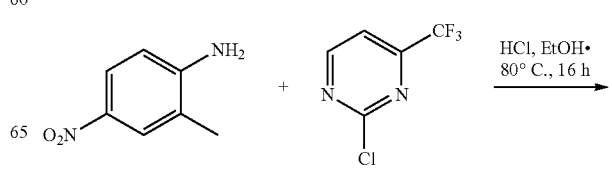

207
-continued

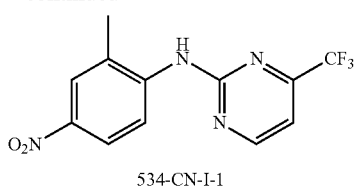

534-CN-I-1

Aqueous concentrated HCl solution was added to a stirred solution of 2-amino-5-nitrotoluene (2 g, 13.15 mmol) and 2-chloro-4-trifluoromethylpyrimidine (2.39 g, 13.15 mmol) in 10% aqueous ethanol. The reaction mixture was stirred at 80° C. for 16 hours. The reaction mixture was then cooled to room temperature, filtered and concentrated under reduced pressure. The residue was partitioned between brine and EtOAc and the aqueous layer was extracted with EtOAc. The combined organic layers were dried over $Na_2SO_4$, filtered and concentrated under reduced pressure to give a yellow solid. The crude compound was purified by flash chromatography using (silica-gel: 100-200 mesh, AcOEt-petroleum ether; 20:80) to give 800 mg (yield 25%) of a yellow solid corresponding to N-(2-methyl-4-nitrophenyl)-4-(trifluoromethyl)pyrimidin-2-amine.

Mass: (ES+) $C_{12}H_9F_3N_4O_2$ required 298.07; found 299.0 [M+H], HPLC/MS method 6.

Synthesis of 2-methyl-$N^1$-(4-(trifluoromethyl)pyrimidin-2-yl)benzene-1,4-diamine, Intermediate 534-CN-I-2

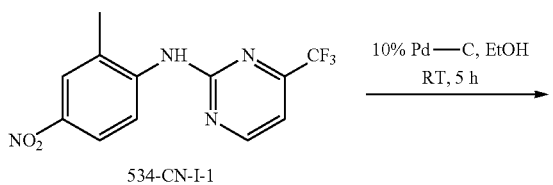

10% Pd—C was added to a stirred solution of compound-534-CN-I-1 (0.8 g 2.684 mmol) in ethanol at room temperature and the reaction mixture was stirred under Hydrogen (50 Psi) at room temperature for 5 hours. Then, the reaction mixture was filtered and concentrated under reduced pressure to give a brown oil. The crude compound was washed with ether to give 500 mg (yield 69.3%) of a yellow solid corresponding to 2-methyl-N-(4-(trifluoromethyl) pyrimidin-2-yl) benzene-1,4-diamine.

Mass: (ES+) $C_{12}H_{11}F_3N_4$ required 268.09.26; found 269.1 [M+H], HPLC/MS method 6.

208

Synthesis of Compound 534-CN Free Base, 2-[3-methyl-4-(4-trifluoromethylpyrimidin-2-ylamino) phenylamino]-3-cyano-4-(4-tert-butylaminopiperidin-1-yl)quinoline

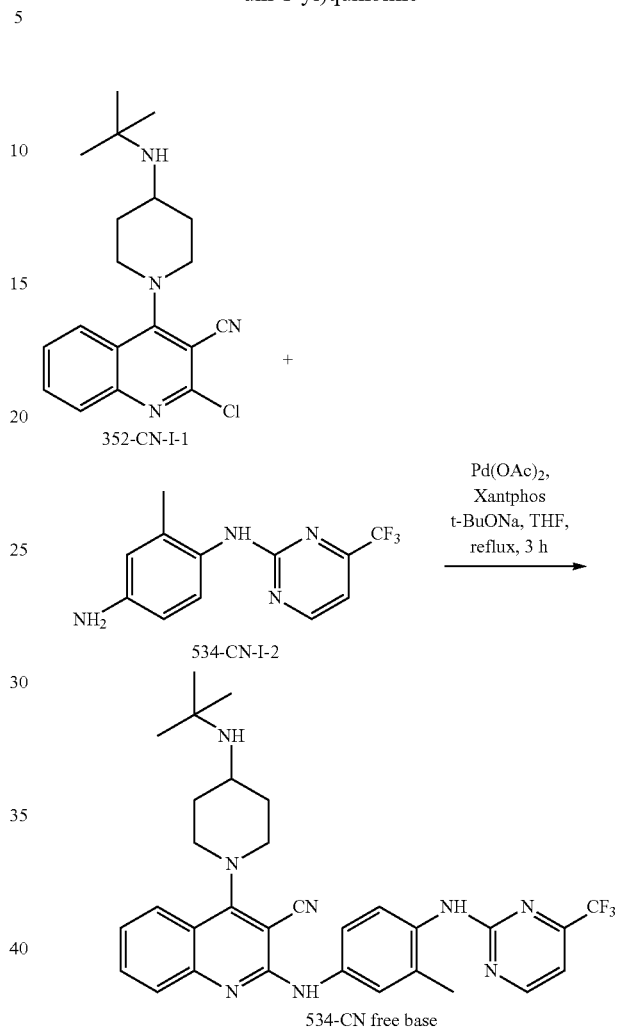

To a solution under nitrogen gas of compound 352-CN-I-1 (0.3 g, 0.875 mmol) in THF (15 ml) was added compound-534-CN-I-2 (0.235 g, 0.8775 mmol) and t-BuONa (0.255 g, 2.625 mmol). The resulting mixture was degassed 30 min with Ar gas, then Xantphos (50.0 mg, 0.087 mmol) and Pd(OAc)$_2$ (10.0 mg, 0.044 mmol) were added and the reaction mixture was stirred at 80° C. for 3 hours. The reaction mixture was then cooled to room temperature, filtered and concentrated under reduced pressure. The residue was partitioned between brine and AcOEt and the aqueous layer was extracted with AcOEt. The combined organic layers were dried over $Na_2SO_4$, filtered and concentrated under reduced pressure to give a brown oil. The crude compound which upon purification by flash chromatography using (silica-gel: 100-200 mesh, 0-10% MeOH:DCM) gave 50 mg (yield 10%) of a white solid corresponding to 2-[3-methyl-4-(4-trifluoromethylpyrimidin-2-ylamino)phenylamino]-3-cyano-4-(4-tert-butylaminopiperidin-1-yl)quinoline.

Mass: (ES+) $C_{31}H_{33}F_3N_8$ required 574.28.26; found 575.2M+H], HPLC/MS method 6.

Synthesis of Compound 534-CN, 2-[3-methyl-4-(4-trifluoromethylpyrimidin-2-ylamino)phenylamino]-3-cyano-4-(4-tert-butylaminopiperidin-1-yl)quinoline Hydrochloride Salt

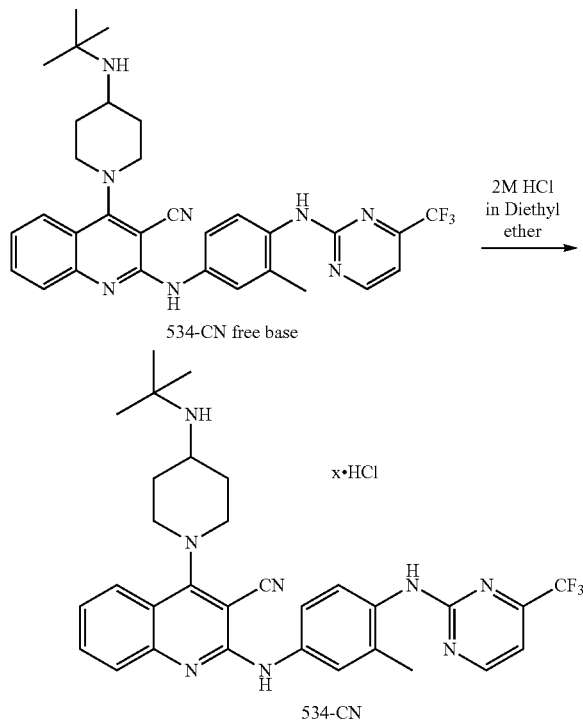

To a solution of compound 534-CN free base (50 mg, 574.28 mmol) in 1 ml of DCM was added 2 M HCl in diethyl ether (1.0 ml) and the resulting mixture was stirred at room temperature for 30 min. Then, the reaction mixture was concentrated under reduced pressure and washed with diethyl ether to give 40 mg (yield 71%) of an off-white solid of 2-[3-methyl-4-(4-trifluoromethylpyrimidin-2-ylamino)phenylamino]-3-cyano-4-(4-tert-butylaminopiperidin-1-yl)quinoline hydrochloride.

Mass: (ES+) $C_{31}H_{34}F_3ClN_8$ required 610.25; found 575.2 (M−HCl+H), HPLC method 4.

Preparation of Compound of Example 538-CN, 2-[3-(4-trifluoromethylpyrimidin-2-ylamino)-4-methyl-phenylamino]-3-cyano-4-(4-tertbutylaminopiperidin-1-yl)-quinoline Hydrochloride Salt

Synthesis of N-(2-methyl-5-nitrophenyl)-4-(trifluoromethyl)pyrimidin-2-amine, Intermediate 538-CN-I-1

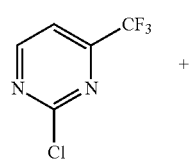

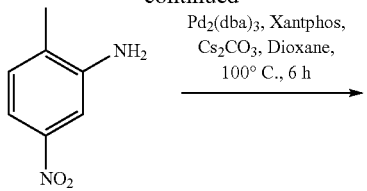

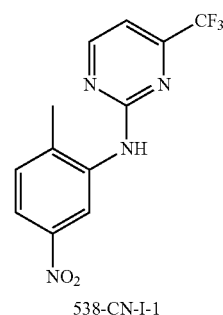

To a solution under nitrogen gas of 2-chloro-4-(trifluoromethyl)pyrimidine (1.0 g, 5.47 mmol) in 1,4-dioxane (20 ml) were added 2-methyl-5-nitroaniline (1.0 g, 6.5 mmol) and cesium carbonate (4.64 g, 14.25 mmol). The resulting mixture was degassed 30 min with Argon gas, then Xantphos (330 mg, 0.57 mmol) and $Pd_2(dba)_3$ (520 mg, 0.57 mmol) were added and the reaction mixture was stirred at 100° C. for 6 hours. The reaction mixture was then cooled to room temperature, filtered and concentrated under reduced pressure. The residue was partitioned between brine and AcOEt and the aqueous layer was extracted with AcOEt. The combined organic layers were dried over $Na_2SO_4$, filtered and concentrated under reduced pressure to give a brown oil. The crude compound was purified by flash chromatography using (silica-gel: 100-200 mesh, AcOEt-petroleum ether; 30%) to give 0.5 g (yield 31%) of a pale yellow solid corresponding to N-(2-methyl-5-nitrophenyl)-4-(trifluoromethyl)pyrimidin-2-amine.

Mass: (ES+) $C_{12}H_9F_3N_4O_2$ required 298; found 299 [M+H], HPLC/MS method 4.

Synthesis of 6-methyl-$N^1$-[4-(trifluoromethyl)pyrimidin-2-yl]benzene-1,3-diamine, Intermediate 538-CN-I-2

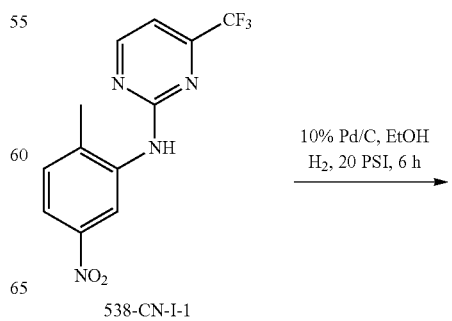

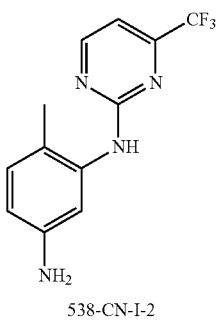

538-CN-I-2

To a solution of N-(2-methyl-5-nitrophenyl)-4-(trifluoromethyl) pyrimidin-2-amine (0.5 g, 1.67 mmol) in EtOH (15 ml) was added 10% Pd/C (50 mg). The resulting mixture was stirred under hydrogen (1 bar) for 6 hour. Catalyst was filtered off, washed with EtOH and solvent was concentrated under reduced pressure to give 0.35 g (yield 77.7%) of a pale brown solid corresponding to 6-methyl-$N^1$-(4-(trifluoromethyl)pyrimidin-2-yl)benzene-1,3-diamine.

Mass: (ES+) $C_{12}H_{11}F_3N_4$ required 268; found 269 [M+H], HPLC/MS method 2.

Synthesis of Compound 538-CN Free Base, 2-[3-(4-trifluoromethylpyrimidin-2-ylamino)-4-methyl-phenylamino]-3-cyano-4-(4-tert-butylaminopiperidin-1-yl)-quinoline

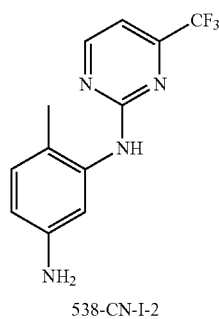

538-CN-I-2

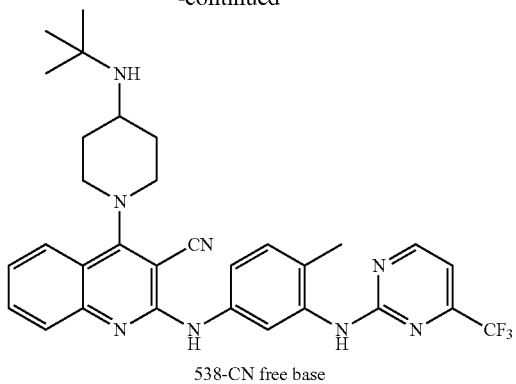

538-CN free base

To a solution under nitrogen gas of 2-[3-(4-trifluoromethyl-2-pyrimidinamino)-4-methyl-phenylamino]-3-cyano-4-(4-tert-butylaminopiperidin-1-yl)-quinoline 352-CN-I-1 (0.45 g, 1.3 mmol) in 1,4-dioxane (25 ml), 6-methyl-$N^1$-(4-(trifluoromethyl)pyrimidin-2-yl)benzene-1,3-diamine 538-CN-I-2 (0.35 g, 1.3 mmol) and t-BuONa (312 mg, 3.25 mmol) were added. The resulting mixture was degassed 30 min with Argon gas, then Xphos (62 mg, 0.13 mmol) and Pd(OAc)$_2$ (29 mg, 0.13 mmol) were added and the reaction mixture was stirred at 100° C. for 16 hours. The reaction mixture was then cooled to room temperature, filtered and concentrated under reduced pressure. The residue was partitioned between brine and AcOEt and the aqueous layer was extracted with AcOEt. The combined organic layers were dried over Na$_2$SO$_4$, filtered and concentrated under reduced pressure to give a brown oil. The crude compound which upon purification by twice flash chromatography using (silica-gel: 100-200 mesh, 4% MeOH—CH$_2$Cl$_2$) gave 30 mg (yield 4%) of a pale brown solid corresponding to 2-[3-(4-trifluoromethyl-2-pyrimidinamino)-4-methyl-phenylamino]-3-cyano-4-(4-tert-butylaminopiperidin-1-yl)-quinoline.

Mass: (ES+) $C_{31}H_{33}F_3N_8$ required 574; found 575 [M+H], HPLC method 2.

Synthesis of Compound 538-CN, 2-[3-(4-trifluoromethylpyrimidin-2-ylamino)-4-methyl-phenylamino]-3-cyano-4-(4-tert-butylaminopiperidin-1-yl)-quinoline Hydrochloride Salt

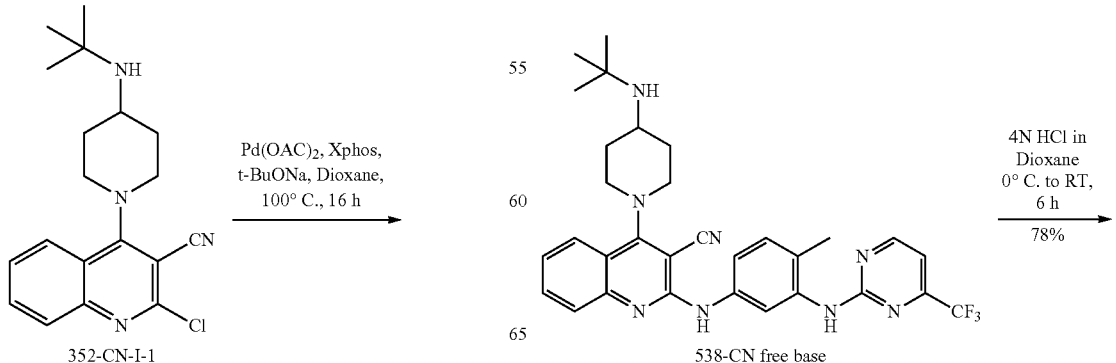

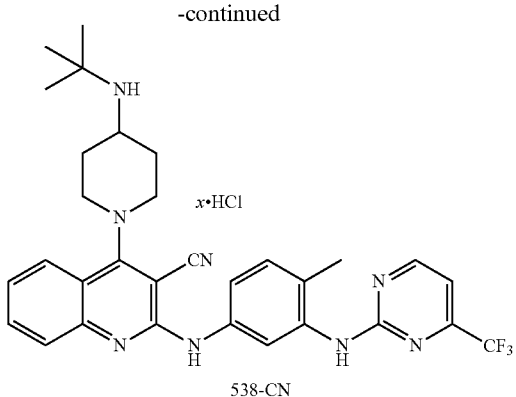

538-CN

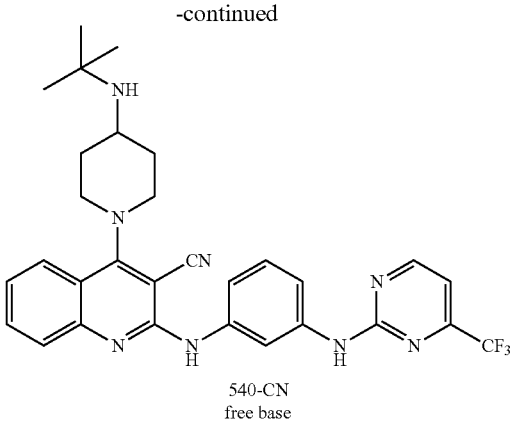

540-CN
free base

To a solution of 2-[3-(4-trifluoromethyl-2-pyrimidinamino)-4-methyl-phenylamino]-3-cyano-4-(4-tert-butylaminopiperidin-1-yl)-quinoline (0.03 g, 0.05 mmol) in 5 ml of 1,4-dioxane was added 4M HCl in 1,4-dioxane (5.0 ml) at 0° C. and the mixture was stirred at room temperature for 6 hours. The reaction mixture was then concentrated under reduced pressure and washed with diethyl ether to give 25 mg (yield 78%) of an off-white solid corresponding to 2-[3-(4-trifluoromethyl-2-pyrimidinamino)-4-methyl-phenylamino]-3-cyano-4-(4-tert-butylaminopiperidin-1-yl)-quinoline hydrochloride.

Mass: (ES+) $C_{31}H_{34}ClF_3N_8$ required 574 (M−HCl); found 575 [(M−HCl)+H]+, HPLC/MS method 5

Preparation of Compound 540-CN, 2-[3-(4-trifluoromethylpyrimidin-2-ylamino)phenylamino]-3-cyano-4-(4-tert-butylaminopiperidin-1-yl)quinoline Hydrochloride Salt Synthesis of 2-[3-(4-trifluoromethylpyrimidin-2-ylamino)phenylamino]-3-cyano-4-(4-tert-butylaminopiperidin-1-yl)quinoline, Compound of Example 540-CN Free Base To a solution under nitrogen gas of compound 352-CN-I-1 (0.2 g, 0.585 mmol) in 1,4-dioxane (4 ml) was added compound-540-Me-I-1 (0.222 g, 0.877 mmol) and t-BuONa (0.170 g, 1.754 mmol). The resulting mixture was degassed 30 min with Ar gas, then Xantphos (33.8 mg, 0.0584 mmol) and Pd(OAC)$_2$ (13 mg, 0.0584 mmol) were added and the reaction mixture was stirred at 100° C. for 3 hours. The reaction mixture was then cooled to room temperature, filtered and concentrated under reduced pressure. The residue was partitioned between brine and AcOEt and the aqueous layer was extracted with AcOEt. The combined organic layers were dried over Na$_2$SO$_4$, filtered and concentrated under reduced pressure to give a brown oil. The crude compound which upon purification by flash chromatography using (silica-gel: 100-200 mesh, AcOEt-petroleum ether; 10:90→15:85) gave 70 mg (yield 21%) of a white solid corresponding to 2-[3-(4-trifluoromethylpyrimidin-2-ylamino)phenylamino]-3-cyano-4-(4-tert-butylaminopiperidin-1-yl)quinoline.

Mass: (ES+) $C_{30}H_{31}F_3N_8$ required 560.26; found 561.22 [M+H], HPLC/MS method 4.

Synthesis of Compound 540-CN, 2-[3-(4-trifluoromethylpyrimidin-2-ylamino)phenylamino]-3-cyano-4-(4-tert-butylaminopiperidin-1-yl)quinoline Hydrochloride Salt

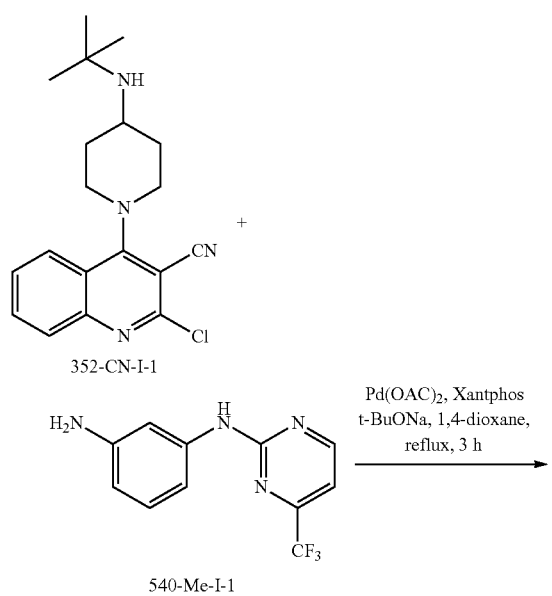

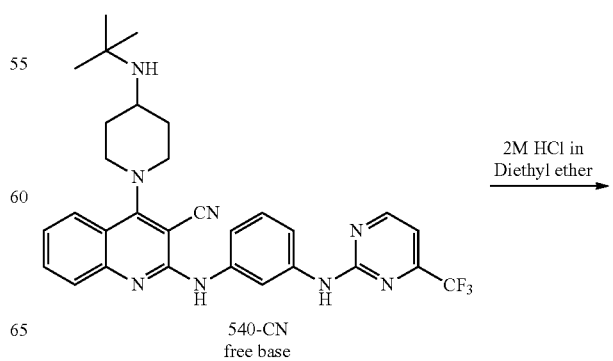

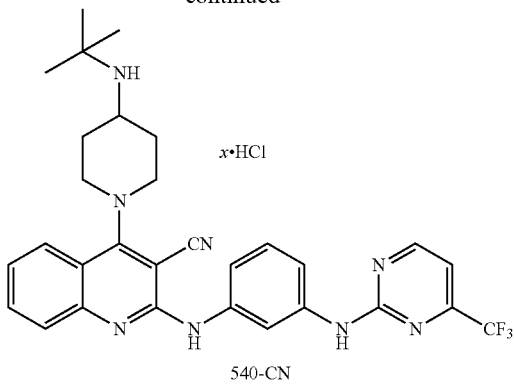

540-CN

To a solution of compound 540-CN free base (70 mg, 0.125 mmol) in 2 ml of DCM was added 2 M HCl in diethyl ether (2.0 ml) and the mixture was stirred at room temperature for 30 min. Then, the reaction mixture was concentrated under reduced pressure and washed with diethyl ether to give 67 mg (yield 90%) of an off-white solid corresponding to 2-[3-(4-trifluoromethylpyrimidin-2-ylamino)phenylamino]-3-cyano-4-(4-tert-butylaminopiperidin-1-yl)quinoline hydrochloride.

Mass: (ES+) $C_{30}H_{32}ClF_3N_8$ required 596; found 559 [M−HCl−H]+, HPLC/MS method 4

Preparation of Compound 3131-CN, 2-[4-(4-(pyridin-3-yl)pyrimidin-2-ylamino)-3-methylphenylamino]-3-cyano-4-(4-tert-butylaminopiperidin-1-yl)quinoline Hydrochloride Salt Synthesis of N-(2-methyl-4-nitrophenyl)-4-(pyridin-3-yl)pyrimidin-2-amine, Intermediate 3131-CN-I-1

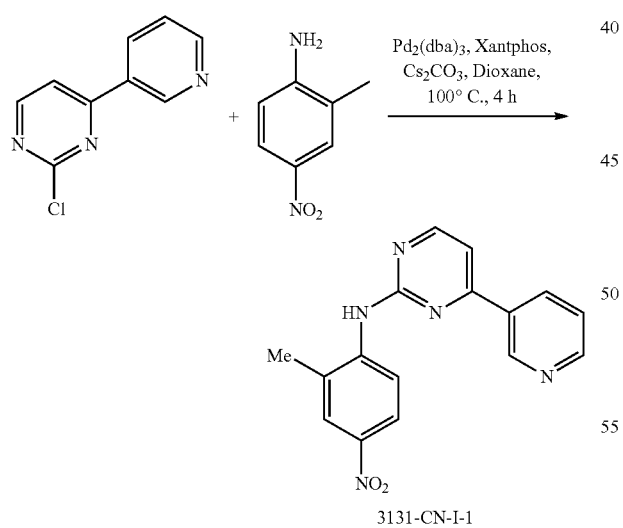

3131-CN-I-1

To a solution under nitrogen gas of 4-(pyridin-3-yl)-2-chloropyrimidine (200 mg, 1.047 mmol) in 1,4-dioxane (10 ml) were added 2-methyl-4-nitroaniline (159 mg, 1.047 mmol) and cesium carbonate (682 mg, 2.094 mmol). The resulting mixture was degassed 30 min with Argon gas, then Xantphos (61 mg, 0.1047 mmol) and Pd₂(dba)₃ (96 mg, 0.1047 mmol) were added and the reaction mixture was stirred at 100° C. for 4 hours. The reaction mixture was then cooled to room temperature, filtered and concentrated under reduced pressure. The residue was partitioned between brine and AcOEt and the aqueous layer was extracted with AcOEt. The combined organic layers were dried over Na₂SO₄, filtered and concentrated under reduced pressure to give a brown oil. The crude compound was purified by flash chromatography using (silica-gel: 100-200 mesh, AcOEt-petroleum ether; 70%) to give 0.2 g (yield 62%) of a pale yellow solid corresponding to N-(2-methyl-4-nitrophenyl)-4-(pyridin-3-yl)pyrimidin-2-amine.

Mass: (ES+) $C_{16}H_{13}N_5O_2$ required 307.11; found 308.1 [M+H], method 8.

Synthesis of 2-methyl-N-(4-(pyridin-3-yl)pyrimidin-2-yl) benzene-1,4-diamine, Intermediate 3131-CN-I-2

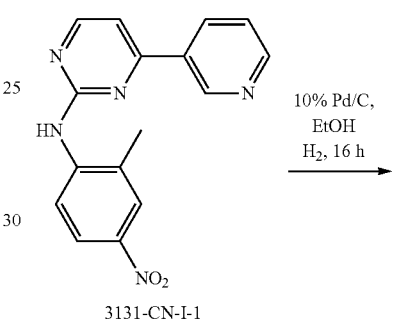

3131-CN-I-1

3131-CN-I-2

To a solution of compound 3131-CN-I-2 (0.2 g, 0.651 mmol) in EtOH (20 ml) was added 10% Pd/C (20 mg). The resulting mixture was stirred under hydrogen (1 bar) for 16 hours. Catalyst was filtered off, washed with EtOH and solvent was concentrated under reduced pressure to give 0.15 g (yield 83%) of a pale brown solid corresponding to 2-methyl-N¹-(4-(pyridin-3-yl)pyrimidin-2-yl)benzene-1,3-diamine.

Mass: (ES+) $C_{16}H_{15}N_5$ required 277.13; found 278 [M+H], HPLC/MS method 8.

217

Synthesis of Compound 3131-CN Free Base, 2-{4-[4-(pyridin-3-yl)pyrimidin-2-ylamino]-3-methylphenylamino}-3-cyano-4-(4-tert-butylaminopiperidin-1-yl)quinoline

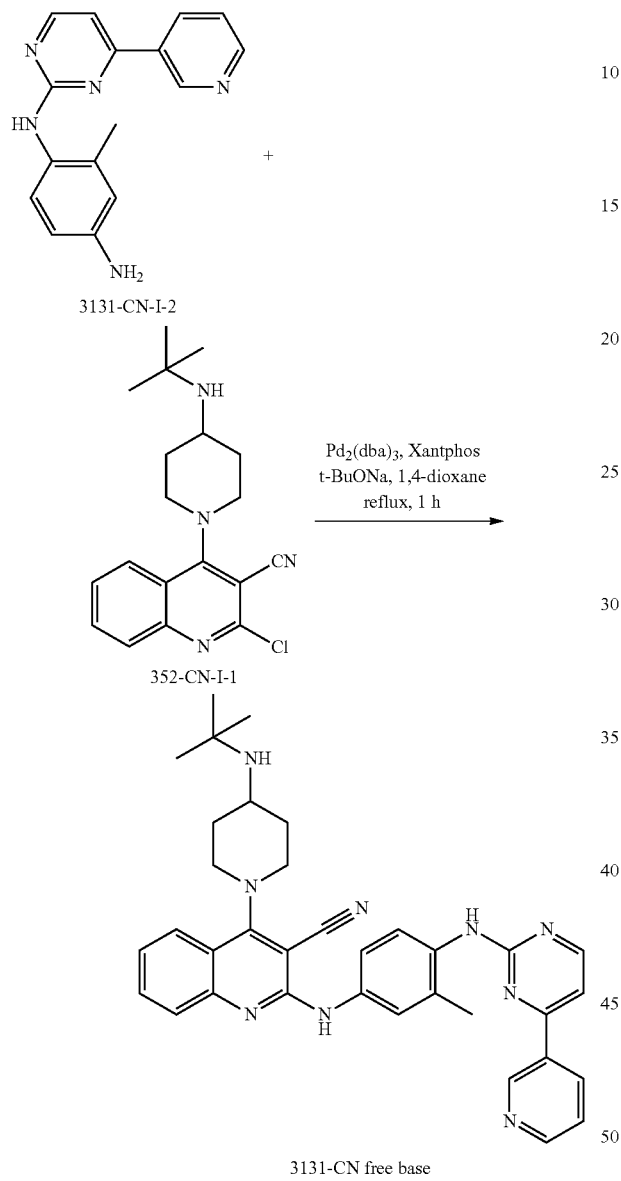

To a solution under nitrogen gas of 352-CN-I-1 (0.2 g, 0.585 mmol) in 1,4-dioxane (4 ml) was added 3131-CN-I-2 (0.16 g, 0.585 mmol) and t-BuONa (0.170 g, 1.754 mmol). The resulting mixture was degassed 30 min with Ar gas, then Xantphos (33.8 mg, 0.0584 mmol) and Pd$_2$ (dba) 3 (53.5 mg, 0.0584 mmol) were added and the reaction mixture was stirred at 100° C. for 3 hours. The reaction mixture was then cooled to room temperature, filtered and concentrated under reduced pressure. The residue was partitioned between brine and AcOEt and the aqueous layer was extracted with AcOEt. The combined organic layers were dried over Na$_2$SO$_4$, filtered and concentrated under reduced pressure to give a brown oil. The crude compound which upon purification by flash chromatography using (silica-gel: 100-200 mesh,

218

AcOEt-petroleum ether; 10:90→15:85) gave 40 mg (yield 12%) of a white solid corresponding to 2-[4-(4-(pyridin-3-yl)pyrimidin-2-ylamino)-3-methylphenylamino]-3-cyano-4-(4-tert-butylaminopiperidin-1-yl)quinoline.

Mass: (ES+) $C_{35}H_{37}N_9$ required 583.32; found 584.22 [M+H], HPLC/MS method 8.

Synthesis of Compound 3131-CN, 2-[4-(4-(pyridin-3-yl)pyrimidin-2-ylamino)-3-methylphenylamino]-3-cyano-4-(4-tert-butylaminopiperidin-1-yl)quinoline Hydrochloride Salt

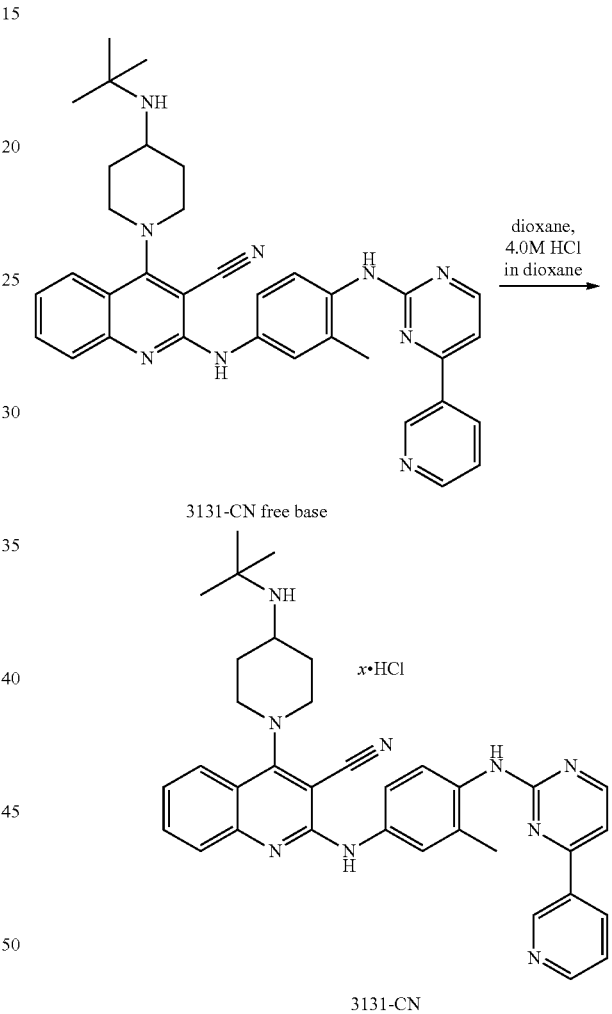

To a solution of 2-{4-[4-(pyridin-3-yl)pyrimidin-2-ylamino]-3-methylphenylamino}-3-cyano-4-(4-tert-butylaminopiperidin-1-yl)quinoline (40 mg, 0.103 mmol) in 1 ml of dioxane was added 4M HCl 1,4-dioxane (1.0 ml) and the mixture was stirred at room temperature for 30 min. The reaction mixture was concentrated under reduced pressure and washed with diethyl ether to give 30 mg (yield 71%) of an off-white solid corresponding to 2-{4-[4-(pyridin-3-yl)pyrimidin-2-ylamino]-3-methylphenylamino}-3-cyano-4-(4-tert-butylaminopiperidin-1-yl)quinoline hydrochloride.

Mass: (ES+) $C_{35}H_{38}ClN_9$ required 619.29; found 584 [M−HCl+H], HPLC/MS method 6.

Preparation of Compound of example 540-F, 2-[3-(4-trifluoromethylpyrimidin-2-ylamino)phenylamino]-3-fluoro-4-(4-tert-butylaminopiperidin-1-yl)quinoline Hydrochloride Synthesis of 2-[3-(4-trifluoromethylpyrimidin-2-ylamino)phenylamino]-3-fluoro-4-chloroquinoline, Intermediate 540-F-I-1

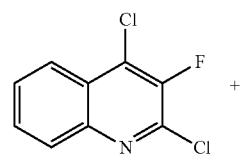

+

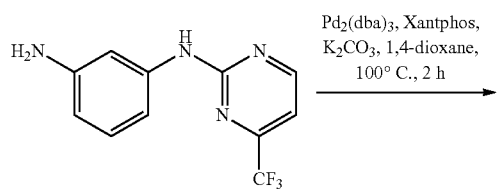

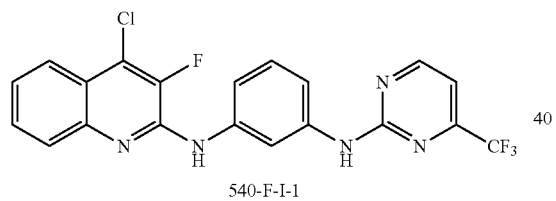

To a solution under nitrogen gas of 2,4-dichloro-3-fluoroquinoline (0.1 g, 0.465 mmol) in 1,4-dioxane (4 ml) were added compound intermediate 540-Me-I-1 (141.7 mg, 0.558 mmol) and $K_2CO_3$ (0.158 g, 1.145 mmol). The resulting mixture was degassed 5 min with Ar gas, then Xantphos (26.9 mg, 0.046 mmol) and $Pd_2(dba)3$ (21.3 mg, 0.023 mmol) were added and the reaction mixture was stirred at 100° C. for 2 hours. The reaction mixture was then cooled to room temperature, filtered and concentrated under reduced pressure. The residue was partitioned between brine and AcOEt and the aqueous layer was extracted with AcOEt. The combined organic layers were dried over $Na_2SO_4$, filtered and concentrated under reduced pressure to give a brown oil. The crude compound which upon purification by flash chromatography using (silica-gel: 100-200 mesh, AcOEt-pet ether; 10:90→15:85) gave 110 mg (yield 55%) of a white solid corresponding to 2-[3-(4-trifluoromethylpyrimidin-2-ylamino)phenylamino]-3-fluoro-4-chloroquinoline.

Mass: (ES+) $C_{20}H_{12}ClF_4N_5$ required 433.07; found 434.1 [M+H], HPLC/MS method 4.

Synthesis of Compound 540-F Free Base, 2-[3-(4-trifluoromethylpyrimidin-2-ylamino)phenylamino]-3-fluoro-4-(4-tert-butylaminopiperidin-1-yl)quinoline Hydrochloride

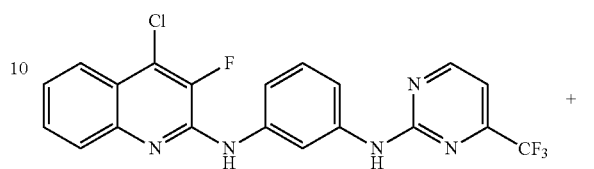

+

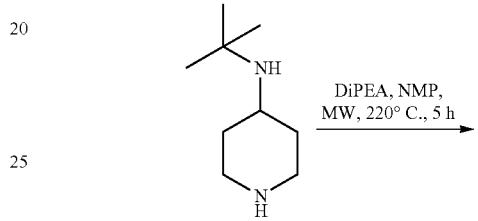

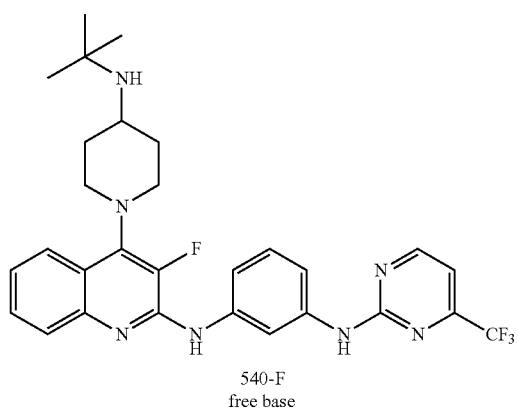

To a solution of compound 540-F-I-1 (100 mg, 0.230 mmol) in 2 ml of NMP were added 4-(tert-butylamino)piperidine (108 mg, 0.692 mmol) followed by DiPEA (0.06 ml, 0.345 mmol) and the resulting mixture was stirred in microwave at 220° C. for 5 hours. Then, the reaction mixture was cooled to room temperature, diluted with ice-water and AcOEt, and the aqueous layer was extracted with AcOEt. The combined organic layers were dried over $Na_2SO_4$, filtered and concentrated under reduced pressure to give off white solid. The obtained solid was purified by the flash chromatography using (silica-gel: 100-200 mesh, MeOH—DCM; 05:95→10:90) to give 0.4 g (yield 31%) of an off-white solid corresponding to give 2-[3-(4-trifluoromethylpyrimidin-2-ylamino)phenylamino]-3-fluoro-4-(4-tert-butylaminopiperidin-1-yl)quinoline.

Mass: (ES+) $C_{29}H_{31}F_4N_7$ required 553.26; found 554.2 [M+H], HPLC/MS method 4.

Synthesis of Compound 540-F, 2-[3-(4-trifluoromethylpyrimidin-2-ylamino)phenylamino]-3-fluoro-4-(4-tert-butylaminopiperidin-1-yl)quinoline Hydrochloride Salt

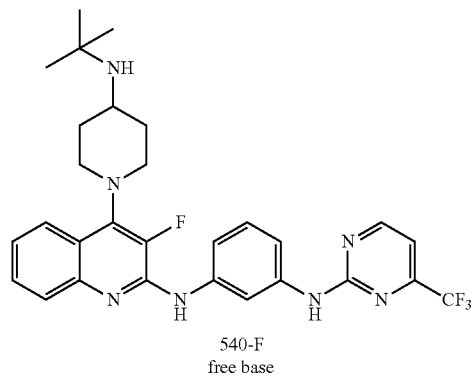

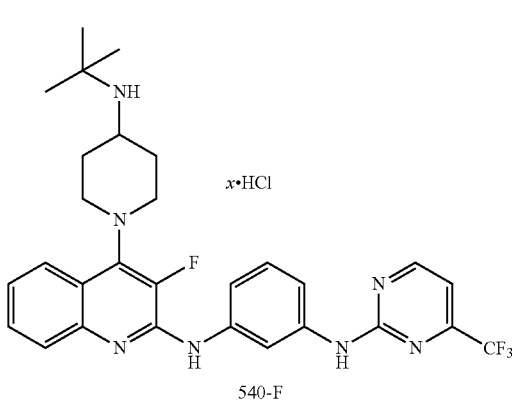

To a solution of compound 540-F free base (40 mg, 0.072 mmol) in 2 ml of DCM was added 2 M HCl in Ethanol (2.0 ml) and the mixture was stirred at room temperature for 30 min. The reaction mixture was concentrated under reduced pressure and washed with diethyl ether to give 40 mg (yield 95%) of an yellow solid corresponding to 2-[3-(4-trifluoromethylpyrimidin-2-ylamino)phenylamino]-3-fluoro-4-(4-tert-butylaminopiperidin-1-yl)quinoline hydrochloride salt.

Mass: (ES+) $C_{29}H_{32}ClF_4N_7$ required 553.26; found 554.3 [M−HCl+H], HPLC/MS method 4.

Additional Examples of Chemical Synthesis

General Procedure GP-1

The present general procedure GP-1 may be used to prepare certain compounds of formula III, in particular for compounds of formula III'-a below:

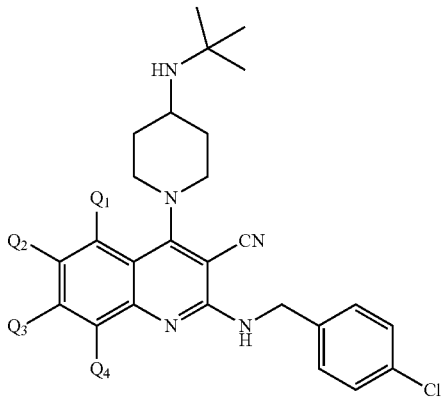

Wherein $Q_1$, $Q_2$, $Q_3$ and $Q_4$ are each independently H, substituted or unsubstituted alkyl, or substituted or unsubstituted alkoxy

Synthesis of ethyl 2-cyano-3-oxo-3-(arylamino) propanoates (3)

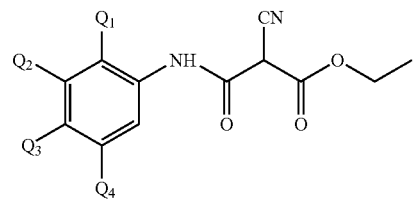

Wherein $Q_1$, $Q_2$, $Q_3$ and $Q_4$ are each independently as defined above under the general formula III'-a.

To a solution under nitrogen gas of aryl isocyanates (1) (1.0 mmol) in DMF was added ethyl 2-cyanoacetate (2) (1.2 mmol) and followed the addition of $Et_3N$ (2.5 mmol). The reaction mixture was stirred at RT for 3 h. The reaction mixture was then poured into crushed ice water, filtered and washed with n-pentane to give solid product corresponding to ethyl 2-cyano-3-oxo-3-(arylamino) propanoates (3) in 50-65% yield.

Synthesis of 2, 4-dioxo-1, 2, 3, 4-tetrahydroquinoline-3-carbonitrile derivatives (4)

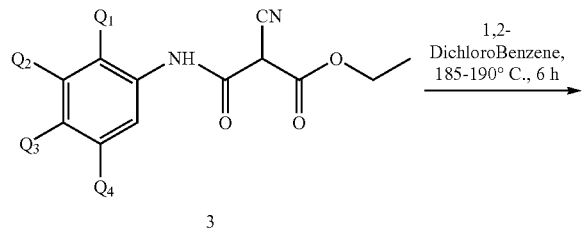

Wherein $Q_1$, $Q_2$, $Q_3$ and $Q_4$ are each independently as defined above under the general formula III'-a.

To a solution under nitrogen gas of ethyl 2-cyano-3-oxo-3-(arylamino) propanoates (3)(1.0 mmol) in 1,2-dichlorobenzene was heated at 185-190° C. for 6 h. The reaction mixture was then cooled to RT, filtered and washed with EtOH to give solid compound corresponding to the desired compound (4) (2,4-dioxo-1,2,3,4-tetrahydroquinoline-3-carbonitrile) (4) in at least 70% (e.g. 72-85%) yield.

Synthesis of 2, 4-dichloro-quinoline-3-carbonitrile derivatives (5)

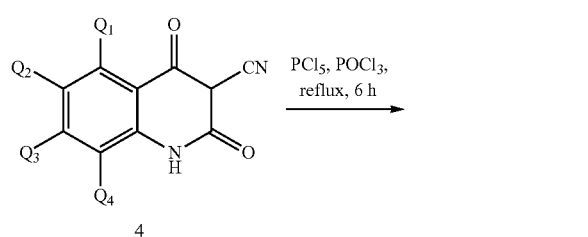

Wherein $Q_1$, $Q_2$, $Q_3$ and $Q_4$ are each independently as defined above under the general formula III'-a.

To a solution, stirred under nitrogen gas, of 2,4-dioxo-1, 2, 3, 4-tetrahydroquinoline-3-carbonitrile derivative (4) (1.0 mmol) in $POCl_3$, $PCl_5$ (0.80 g, 0.7 mmol) was added under nitrogen atmosphere, heated to reflux for 6 h. The reaction mixture was then cooled to RT, and then evaporated under reduced pressure to give a residue. The resulted residue was triturated with cold water (less than 15° C.), filtered and washed with n-pentane to afford the compound (5) (2,4-dichloro-quinoline-3-carbonitrile derivative) as pale yellow solid in at least 50% (e.g. 57-69%) yield.

Synthesis of 2-chloro-3-cyano-4-[4-(tert-butylamino) piperidin-1-yl]quinoline derivatives (7a)

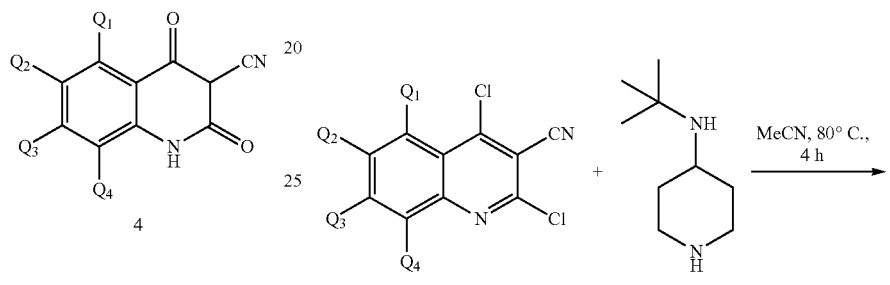

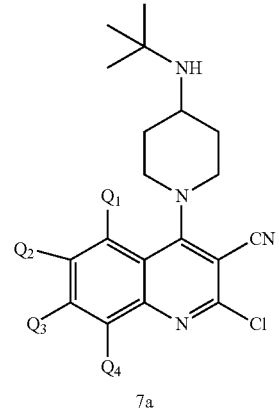

Wherein $Q_1$, $Q_2$, $Q_3$ and $Q_4$ are each independently as defined above under the general formula III'-a.

To a solution, stirred under nitrogen gas, of compound (5) (2, 4-dichloro-8-quinoline-3-carbonitrile derivative) (1.0 mmol) in MeCN was added N-tert-butylpiperidin-4-amine (6a) (1.2 mmol). The reaction mixture was stirred at 80° C. for 4 h. The reaction mixture was then cooled to RT, filtered and washed with MeCN to give compound (7a) (2-chloro-3-cyano-4-[4-(tert-butylamino) piperidin-1-yl]quinoline_derivative) a solid product in at least 50% (e.g. 58-78%) yield.

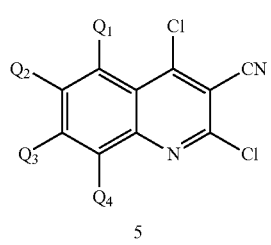

225

Synthesis of Compounds of Formula II'-a (2-(4-chlorobenzylamino)-3-cyano-4-[4-(tert-butylamino)piperidin-1-yl]quinoline Derivatives)

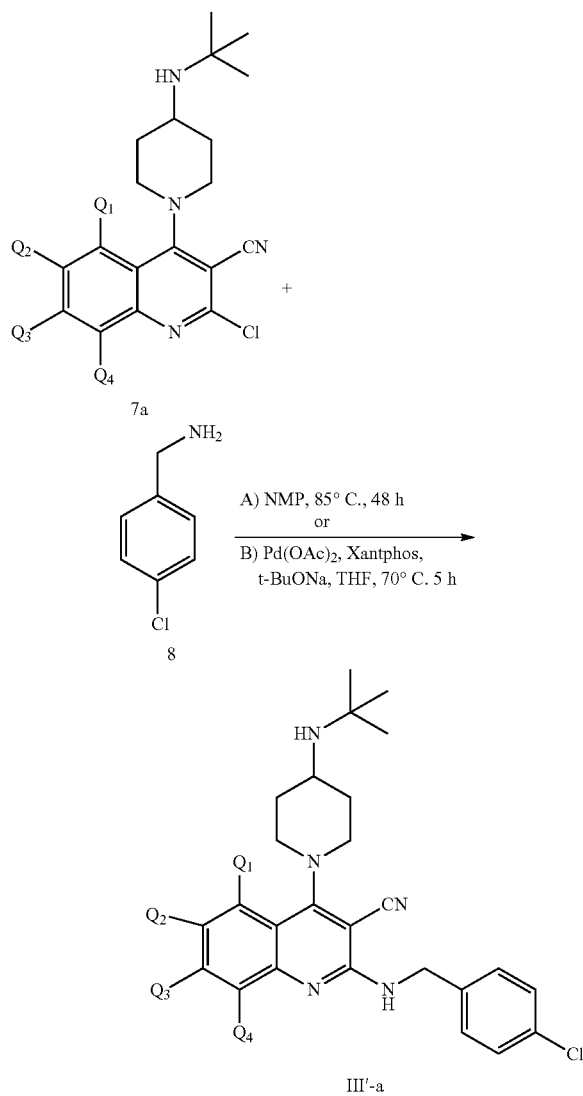

226

Reaction Under Conditions A (NMP, 85° C., 48 h):

To a solution, stirred under nitrogen gas, of compound (7a) (2-chloro-3-cyano-4-[4-(tert-butylamino)piperidin-1-yl]quinoline derivative) (1.0 mmol) in NMP (4 ml) was added 4-chlorobenzylamine (8) (4.0 mmol). The resulting mixture was stirred at 80° C. for 48 h. The reaction mixture was then cooled to RT, concentrated under reduced pressure. The residue was partitioned between brine and EtOAc and the aqueous layer was extracted with EtOAc. The combined organic layers were dried over $Na_2SO_4$, filtered and concentrated under reduced pressure to give a solid residue. The latter was subjected to purification by Prep HPLC to give the desired compound (III'-a) (2-(4-chlorobenzylamino)-3-cyano-4-[4-(tert-butylamino) piperidin-1-yl]quinoline derivative) as a solid product in at least 20% yield.

Reaction Under Conditions B ($Pd(OAc)_2$, Xantphos, t-BuONa, THF, 70° C. 5 h)

To a solution, stirred under nitrogen gas, of compound 7a (2-chloro-4-[4-(tert-butylamino) piperidin-1-yl]-3-cyano-quinoline derivative) (1.0 mmol) in THF was added 4-chlorobenzylamine (8) (1.3 mmol) and t-BuONa (3.0 mmol). The resulting mixture was degassed 30 min with Ar gas, then Xantphos (0.1 mmol) and $Pd(OAc)_2$ (0.1 mmol) were added and the reaction mixture was stirred at 70° C. for 5 h. The reaction mixture was then cooled to RT, filtered and concentrated under reduced pressure. The residue was partitioned between brine and EtOAc and the aqueous layer was extracted with was extracted with EtOAc. The combined organic layers were dried over $Na_2SO_4$, filtered and concentrated under reduced pressure to give crude compound. The crude compounds were purified by Prep.HPLC to give the corresponding compound of formula III'-a (2-chloro-3-cyano-4-[4-(tert-butylamino)piperidin-1-yl]-quinoline derivative) as solids in at least 10% yield.

The compounds in table below are prepared according to the general procedure GP-1:

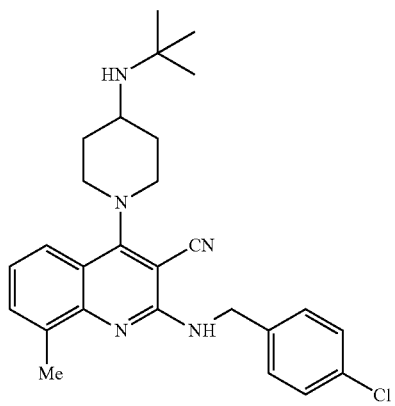

2-(4-chlorobenzylamino)-3-cyano-4-[4-(tert-butylamino)piperidin-1-yl]-8-methylquinoline (414-CN)

414

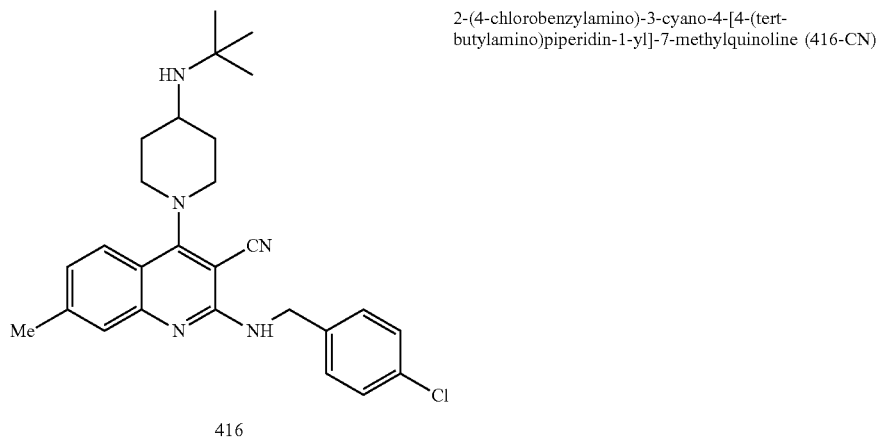

2-(4-chlorobenzylamino)-3-cyano-4-[4-(tert-butylamino)piperidin-1-yl]-7-methylquinoline (416-CN)

416

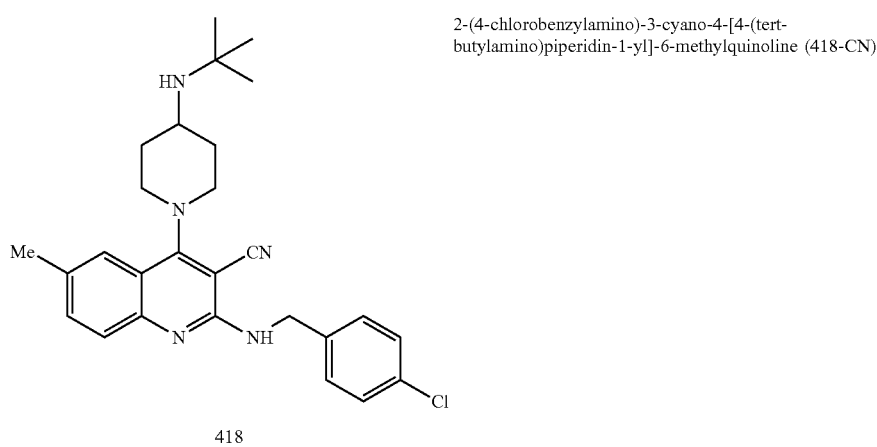

2-(4-chlorobenzylamino)-3-cyano-4-[4-(tert-butylamino)piperidin-1-yl]-6-methylquinoline (418-CN)

418

General Procedure GP-2

The present procedure GP-2 may be used to prepare certain compounds of the general formula II, in particular for compounds of the general formula II-a below:

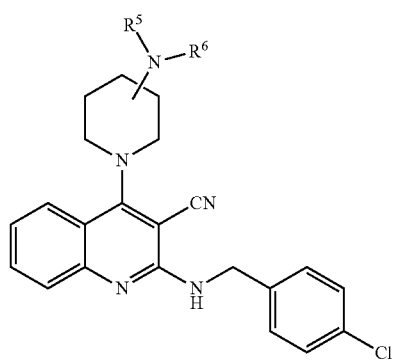

Wherein $R^5$ and $R^6$ are as defined under the general formula II.

Synthesis of 3- or 4-Substituted aminopiperidine Derivatives (6)

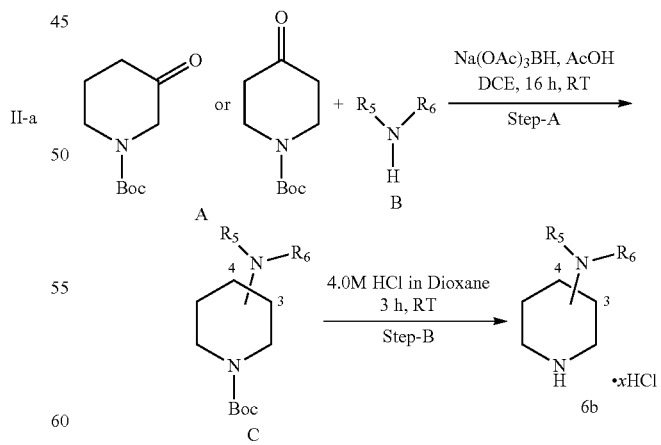

$R^5$ and $R^6$ are as defined under the general formula II.

Step-A:

To a stirred solution, under nitrogen gas, of tert-butyl-3- or 4-oxopiperidine-1-carboxylate (A) (1.0 mmol) and amine (B) (1.5 mmol) in DCE was added acetic acid (0.1 mmol) at 0° C. After 10 min, sodium triacetoxyborohydride (3.0 mmol) was added to the reaction mixture at the same temperature and allowed to stir at room temperature for 16 h. Then, the reaction completion was checked by TLC, TLC indicates the consumption of the starting material and the reaction mixture was quenched with aqueous 1N NaOH and allowed to stir at room temperature for 10 min. Then, the aqueous layer was extracted with ethyl acetate. The combined organic layers were washed with brine, dried over sodium sulfate, filtered and concentrated under reduced pressure. Then, the crude material was purified by column chromatography (Silica gel (60-120 mesh), eluting from 0% to 100% EtOAc in Petroleum ether to afford 3- or 4-amino Boc piperidine C in at least 30% (30-60%) yield.

Step-B:

To a solution, stirred under nitrogen gas, of 4 amino Boc piperidine C (1.0 mmol) in DCM (5 ml) was added at 0° C. a 4 N solution of HCl in Dioxane (8 mL). Then, the reaction mixture was stirred for 3 h at room temperature. Then, the reaction completion was checked by TLC, TLC indicates the consumption of the starting material and the solvent was removed under reduced pressure. The resulting crude material was washed with diethyl ether and dried to give compound (6b) (3- or 4-aminopiperidine) as hydrochloride salt and as a solid compound in at least 60 (e.g. 65-95%) yield.

Synthesis of Compounds (7b) (2-chloro-3-cyano-4-(Substituted 3- or 4-aminopiperidine-1-yl)quinoline)

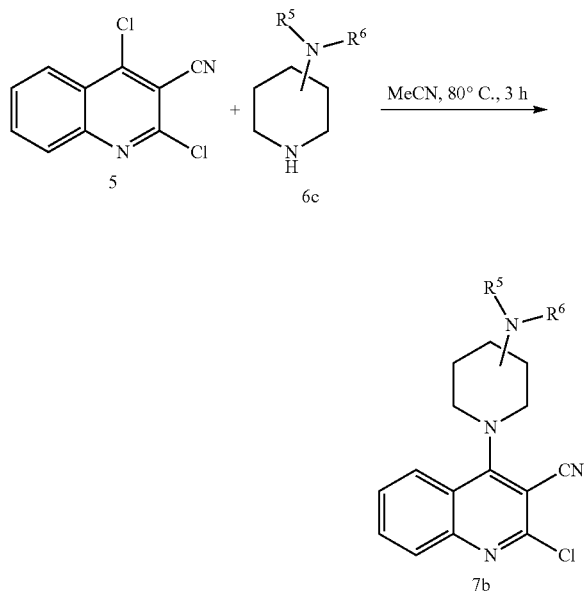

$R^5$ and $R^6$ are as defined under the general formula II.

To a solution under nitrogen gas of 2, 4-dichloro-3-cyanoquinoline (5) (1.0 mmol) in MeCN was added the substituted 3- or 4-aminopiperidine (6c) (1.2 mmol). The reaction mixture was stirred at 80° C. for 3 h. The reaction mixture was then cooled to RT, filtered and washed with MeCN to give a solid compound corresponding to 2-chloro-3-cyano-4-(3- or 4-substituted aminopiperidine-1-yl)quinoline (7b) in at least 30% (e.g. 35-87%) yield.

Note:

TEA was used as base in case of aminopiperidine (6c) was used as HCl salt (6b) in the reaction, in order to neutralize the HCl in the reaction mixture.

Synthesis of the Compounds of Formula II-a (2-(4-chlorobenzylamino)-3-cyano-4-(3- or 4-Substituted aminopiperidine-1-yl)quinoline)

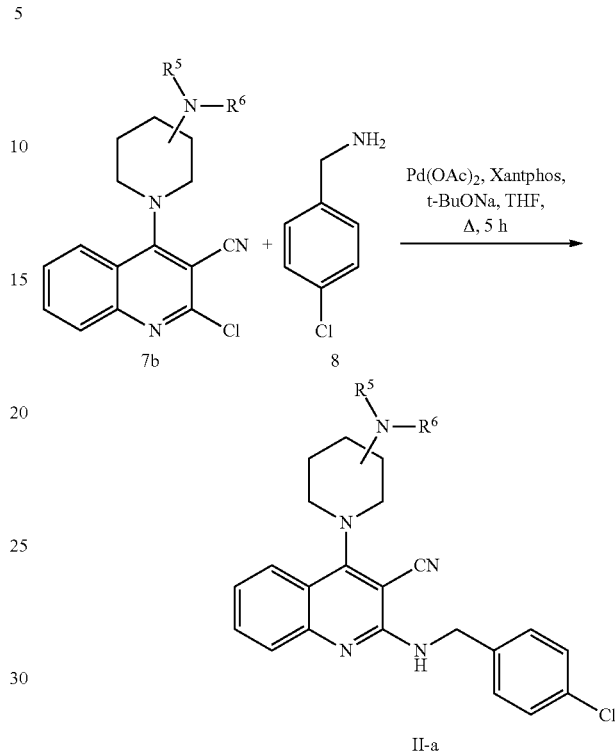

To a stirred solution under nitrogen gas of compound (7b) (2-chloro-3-cyano-4-(3- or 4-substituted aminopiperidin-1-yl)quinoline) (1.0 mmol) in THF (4 ml) was added 4-chlorobenzylamine (8) (1.5 mmol) and t-BuONa (3.0 mmol). The resulting mixture was degassed 10 min with Ar gas, then Xantphos (0.1 mmol) and Pd(OAc)$_2$ (0.1 mmol) were added and the reaction mixture was stirred at 70-80° C. for 5 h. The reaction mixture was then cooled to RT, filtered and concentrated under reduced pressure. The residue was partitioned between brine and EtOAc and the aqueous layer was extracted with EtOAc. The combined organic layers were dried over Na$_2$SO$_4$, filtered and concentrated under reduced pressure to give a brown solid. The latter was purified by flash chromatography using (silica-gel: 100-200 mesh, MeOH-DCM; 0%→10%) or Prep HPLC to give the desired compound of formula (II-a) (2-(4-chlorobenzylamino)-3-cyano-4-(3- or 4-substituted aminopiperidine-1-yl)quinoline) as a solid compound in at least 5% (e.g. 6-50%) yield.

Note:

In some examples for compound 6c, the group $R^5$ and/or $R^6$ may be H. For these examples, the corresponding amine function (—NH$_2$ or —NH—R$^4$ or —NH—R$^5$) may be protected by any suitable protecting group (e.g. tertiary butoxy carbonyl (Boc), benzyloxy carbamate (Cbz) group). Thus, the corresponding compounds II-a will have a N-protected amine function on the piperidine cycle. The conversion of these compounds II-a into the corresponding free base forms may be carried out using any suitable deprotection techniques known in the art.

The compounds in table below are prepared according to the general procedure GP-2

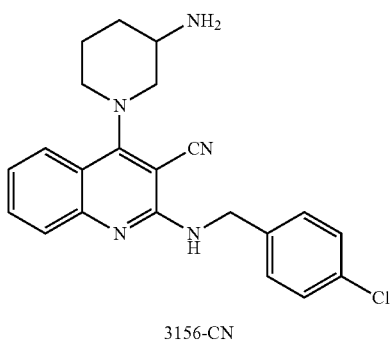 [SMILES: N#Cc1c(NCc2ccc(Cl)cc2)nc2ccccc2c1N1CCCC(N)C1]
2-(4-chlorobenzylamino)-3-cyano-4-(3-aminopiperidin-1-yl)quinoline (3156-CN)
3156-CN
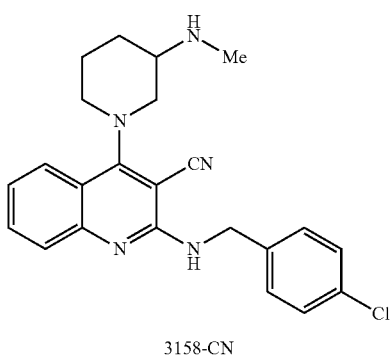 [SMILES: CNC1CCCN(c2c(C#N)c(NCc3ccc(Cl)cc3)nc3ccccc23)C1]
2-(4-chlorobenzylamino)-3-cyano-4-[3-(methylamino)piperidin-1-yl]quinoline (3158-CN)
3158-CN
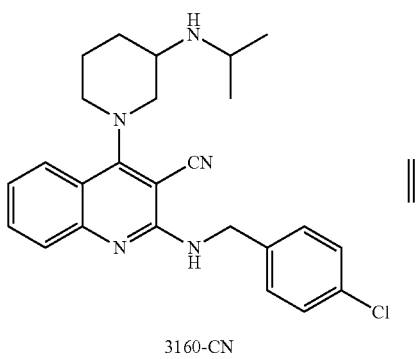
2-(4-chlorobenzylamino)-3-cyano-4-[3-(isopropylamino)piperidin-1-yl]quinoline (3160-CN)
3160-CN
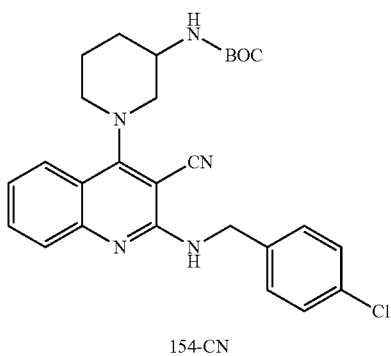 [SMILES: CC(C)(C)OC(=O)NC1CCCN(c2c(C#N)c(NCc3ccc(Cl)cc3)nc3ccccc23)C1]
{[(tetrahydro-2H-pyra-4-yl)methyl]amino}-3-fluoro-4-[4-(tert-butylamino)piperidin-1-yl]quinoline (154-CN)
154-CN -continued
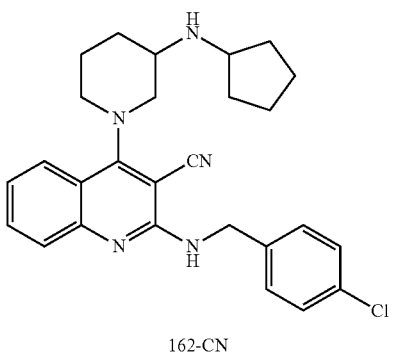 [SMILES: N#Cc1c(NCc2ccc(Cl)cc2)nc2ccccc2c1N1CCCC(NC2CCCC2)C1]
162-CN
2-(4-chlorobenzylamino)-3-cyano-4-[3-(cyclopentylamino)piperidin-1-yl]quinoline (162-CN)
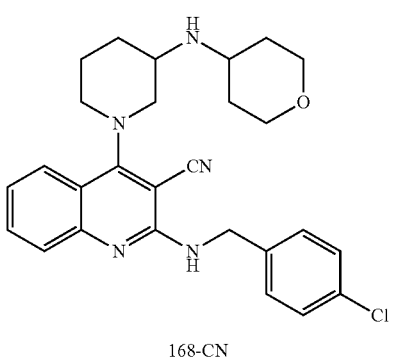 [SMILES: N#Cc1c(NCc2ccc(Cl)cc2)nc2ccccc2c1N1CCCC(NC2CCOCC2)C1]
168-CN
2-(4-chlorobenzylamino)-3-cyano-4-[3-(4-methylpiperazin-1-yl)piperidin-1-yl]quinoline (168-CN)
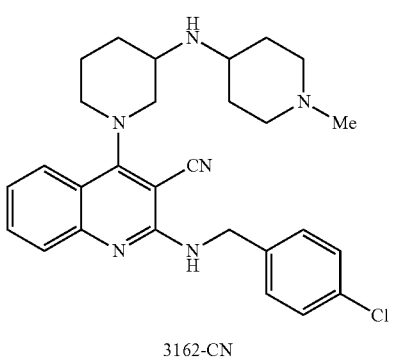 [SMILES: CN1CCC(NC2CCCN(c3c(C#N)c(NCc4ccc(Cl)cc4)nc4ccccc34)C2)CC1]
3162-CN
2-(4-chlorobenzylamino)-3-cyano-4-{3-[(1-methylpiperidin-4-yl)amino]piperidin-1-yl}quinoline (3162-CN)
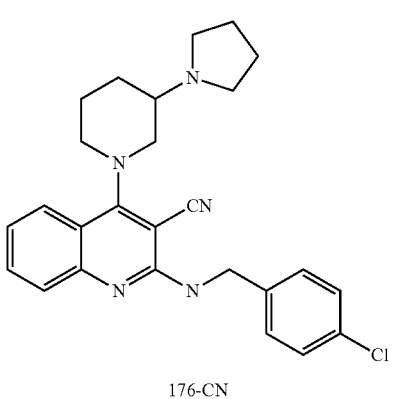 [SMILES: N#Cc1c(NCc2ccc(Cl)cc2)nc2ccccc2c1N1CCCC(N2CCCC2)C1]
176-CN
2-(4-chlorobenzylamino)-3-cyano-4-[3-(pyrrolidin-1-yl)piperidin-1-yl]quinoline (176-CN)

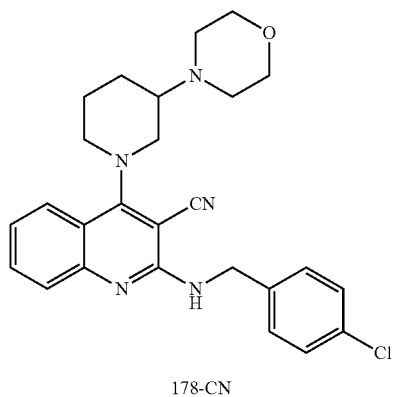 [SMILES: N#Cc1c(NCc2ccc(Cl)cc2)nc2ccccc2c1N1CCCC(N2CCOCC2)C1]
178-CN
2-(4-chlorobenzylamino)-3-cyano-4-[3-(morpholino)piperidin-1-yl]quinoline (178-CN)
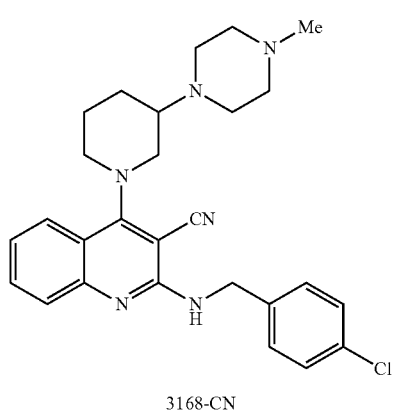 [SMILES: CN1CCN(C2CCCN(c3c(C#N)c(NCc4ccc(Cl)cc4)nc4ccccc34)C2)CC1]
3168-CN
2-(4-chlorobenzylamino)-3-cyano-4-[3-(4-methylpiperazin-1-yl)piperidin-1-yl]quinoline (3168-CN)
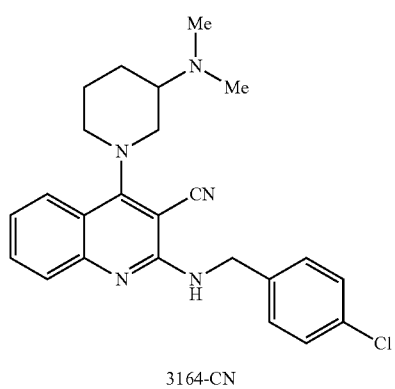 [SMILES: CN(C)C1CCCN(c2c(C#N)c(NCc3ccc(Cl)cc3)nc3ccccc23)C1]
3164-CN
2-(4-chlorobenzylamino)-3-cyano-4-[3-(dimethylamino)piperidin-1-yl]quinoline (3164-CN)
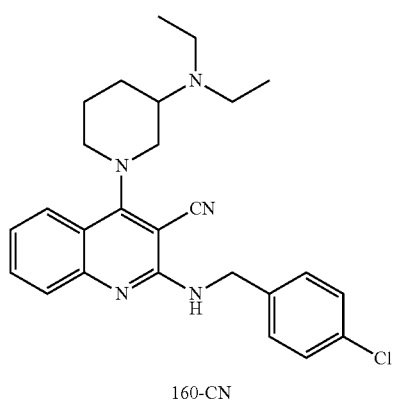 [SMILES: CCN(CC)C1CCCN(c2c(C#N)c(NCc3ccc(Cl)cc3)nc3ccccc23)C1]
160-CN
2-(4-chlorobenzylamino)-3-cyano-4-[3-(diethylamino)piperidin-1-yl]quinoline (160-CN)

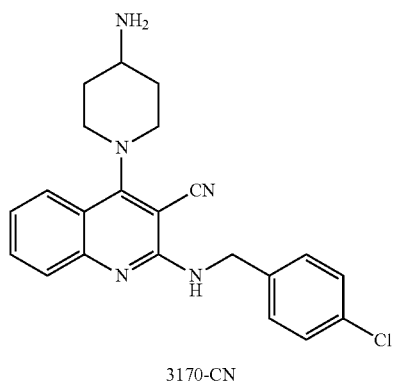 [SMILES: N#Cc1c(NCc2ccc(Cl)cc2)nc2ccccc2c1N1CCC(N)CC1]
2-(4-chlorobenzylamino)-3-cyano-4-(4-aminopiperidin-1-yl)quinoline (3170-CN)
3170-CN
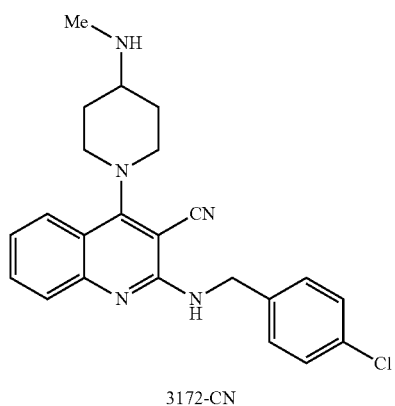 [SMILES: CNC1CCN(c2c(C#N)c(NCc3ccc(Cl)cc3)nc3ccccc23)CC1]
2-(4-chlorobenzylamino)-3-cyano-4-[4-(methylamino)piperidin-1-yl]quinoline (3172-CN)
3172-CN
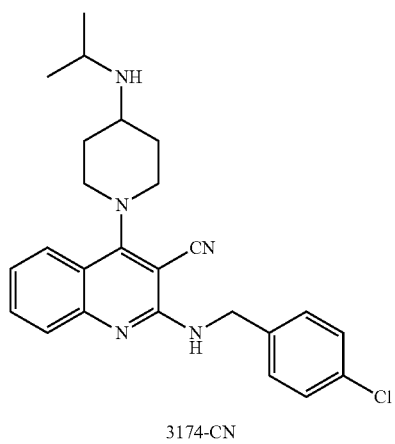 [SMILES: CC(C)NC1CCN(c2c(C#N)c(NCc3ccc(Cl)cc3)nc3ccccc23)CC1]
2-(4-chlorobenzylamino)-3-cyano-4-[4-(iso-propylamino)piperidin-1-yl]quinoline (3174-CN)
3174-CN

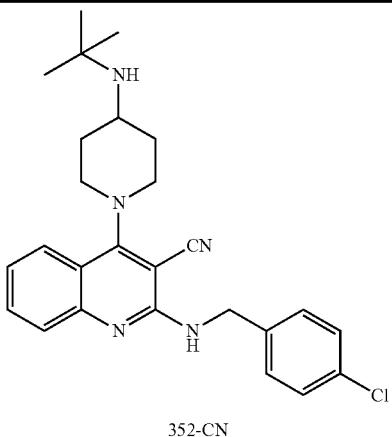
2-(4-chlorobenzylamino)-3-cyano-4-[4-(tert-butylamino)piperidin-1-yl]quinoline (352-CN)
352-CN
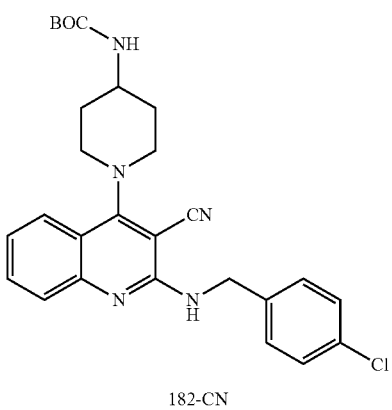 [SMILES: CC(C)(C)OC(=O)NC1CCN(c2c(C#N)c(NCc3ccc(Cl)cc3)nc3ccccc23)CC1]
2-(4-chlorobenzylamino)-3-cyano-4-{4-[(tert-butyloxycarbonyl)amino]piperidin-1-yl}quinoline (182-CN)
182-CN
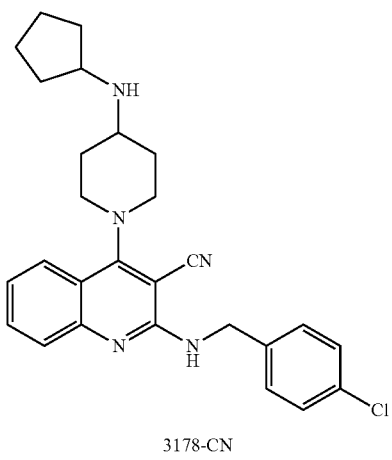 [SMILES: N#Cc1c(NCc2ccc(Cl)cc2)nc2ccccc2c1N1CCC(NC2CCCC2)CC1]
2-(4-chlorobenzylamino)-3-cyano-4-[4-(cyclopentylamino)piperidin-1-yl]quinoline (3178-CN)
3178-CN

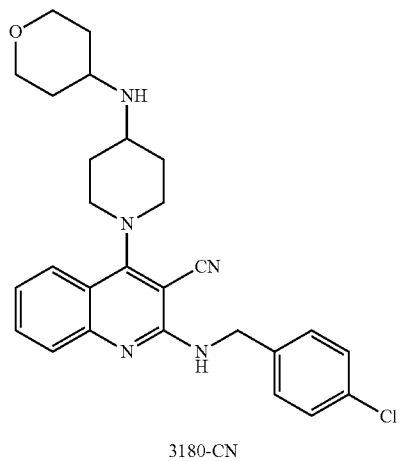 [SMILES: N#Cc1c(NCc2ccc(Cl)cc2)nc2ccccc2c1N1CCC(NC2CCOCC2)CC1]
2-(4-chlorobenzylamino)-3-cyano-4-{4-[(tetrahydro-2H-pyran-4-yl)amino]piperidin-1-yl}quinoline (3180-CN)
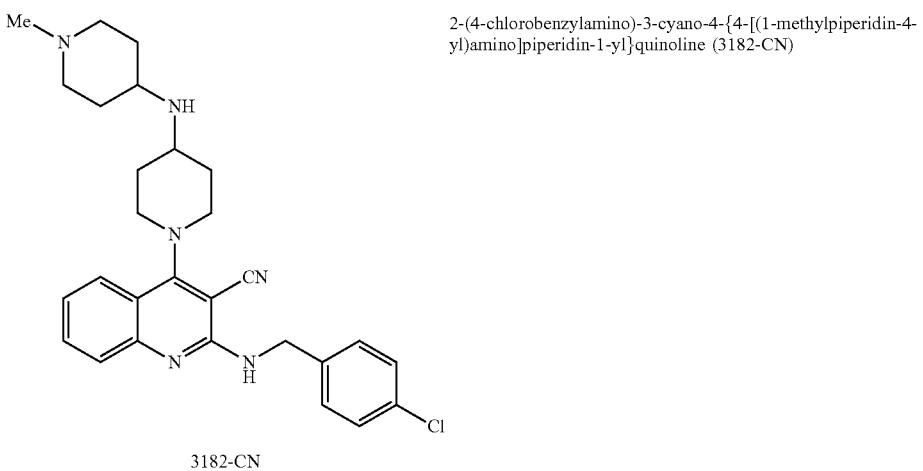
2-(4-chlorobenzylamino)-3-cyano-4-{4-[(1-methylpiperidin-4-yl)amino]piperidin-1-yl}quinoline (3182-CN)
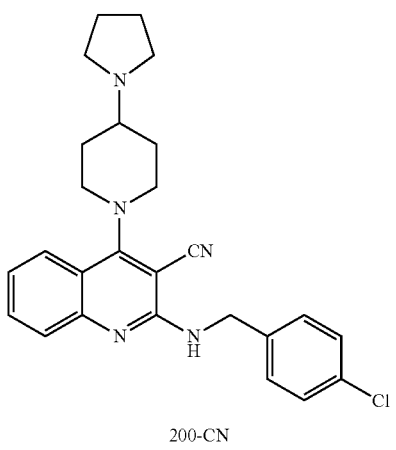 [SMILES: N#Cc1c(NCc2ccc(Cl)cc2)nc2ccccc2c1N1CCC(N2CCCC2)CC1]
2-(4-chlorobenzylamino)-3-cyano-4-[4-(pyrrolidin-1-yl)piperidin-1-yl]quinoline (200-CN)

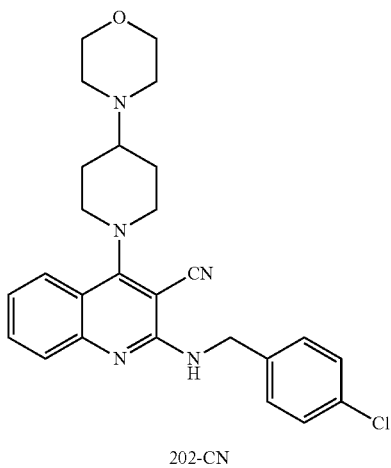 [SMILES: N#Cc1c(NCc2ccc(Cl)cc2)nc2ccccc2c1N1CCC(N2CCOCC2)CC1]
202-CN
2-(4-chlorobenzylamino)-3-cyano-4-[4-(morpholino)piperidin-1-yl]quinoline (202-CN)
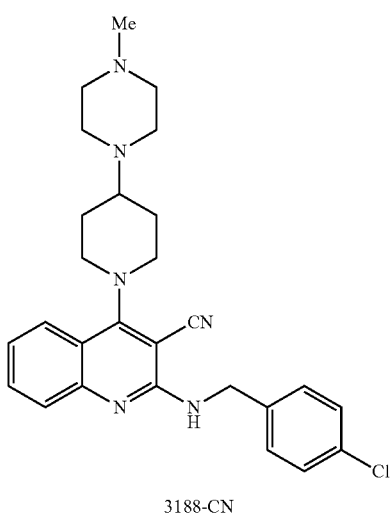 [SMILES: CN1CCN(C2CCN(c3c(C#N)c(NCc4ccc(Cl)cc4)nc4ccccc34)CC2)CC1]
3188-CN
2-(4-chlorobenzylamino)-3-cyano-4-[4-(4-methylpiperazin-1-yl)piperidin-1-yl]quinoline (3188-CN)
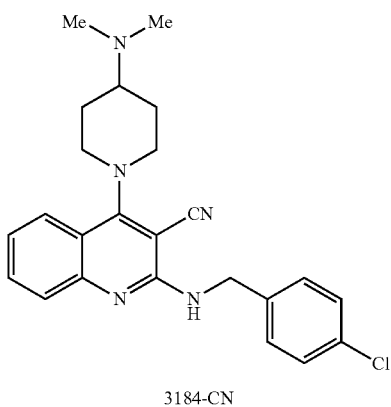 [SMILES: CN(C)C1CCN(c2c(C#N)c(NCc3ccc(Cl)cc3)nc3ccccc23)CC1]
3184-CN
2-(4-chlorobenzylamino)-3-cyano-4-[4-(dimethylamino)piperidin-1-yl]quinoline (3184-CN)

2-(4-chlorobenzylamino)-3-cyano-4-[4-(diethylamino)piperidin-1-yl]quinoline (184-CN)

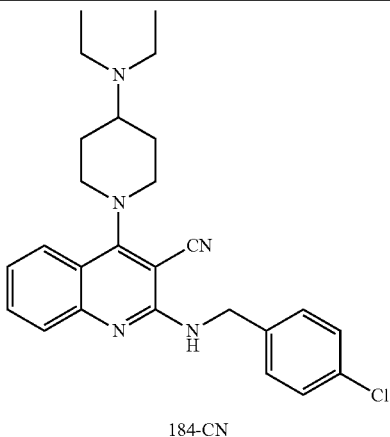

184-CN

General Procedure GP-3

The present procedure GP-3 may be used to prepare certain compounds of the general formula II, in particular compounds of the general formula II-b below:

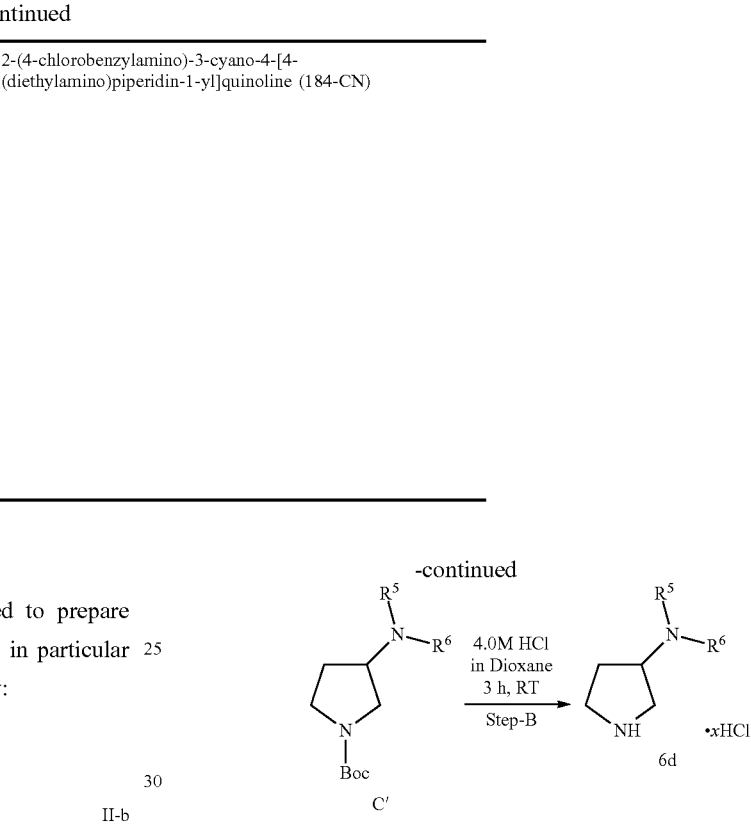

II-b wherein $R^5$ and $R^6$ are as defined under the general formula II

Synthesis of Compounds (6d) (3-Substituted aminopyrrolidin Derivatives)

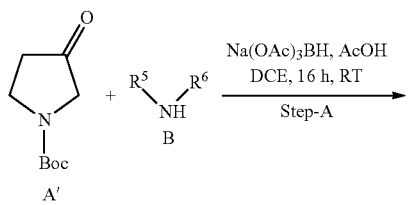

$R^5$ and $R^6$ are as defined under the general formula II

Step-A:

To a solution, stirred under nitrogen gas, of tert-butyl-3-oxopyrrolidine-1-carboxylate (A') (1.0 mmol) and amine (B) (1.5 mmol) in DCE was added acetic acid (0.1 mmol) at 0° C. After 10 min, Sodium triacetoxyborohydride (3.0 mmol) was added to the reaction mixture at the same temperature and allowed to stir at room temperature for 16 h. Then, the reaction completion was checked by TLC, TLC indicates the consumption of the starting material and the reaction mixture was quenched in 1N aqueous NaOH allowed to stir at room temperature for 10 min and the aqueous layer was then extracted with Ethyl acetate. The combined organic layers were washed with brine, dried over sodium sulfate, filtered and concentrated under reduced pressure. Then, the crude material was purified by column chromatography (Silica gel (60-120 mesh), eluting 0 to 100% of EtOAc in Petroleum ether to afford the desired compound (C') (Boc protected pyrrolidine) in at least 40% (e.g. 43-77%) yield.

Step-B:

To a solution under nitrogen gas of compound (C') (Boc protected pyrrolidine) (1.0 mmol) in DCM (5 ml) was added a 4N HCl solution in Dioxane (8 mL) at 0° C. Then, the reaction mixture was stirred for 3 h at room temperature. Then, the reaction completion was checked by TLC, TLC indicates the consumption of the starting material and the solvents removed under reduced pressure. The resulting crude material was washed with diethyl ether and then dried to give the desired compound (6d) (3-aminopyrrolidine derivative) as hydrochloride salt and as solid compound in at least 80% (e.g. 85-90%) yield.

Synthesis of Compounds (7c) (2-chloro-3-cyano-4-(3-amino pyrrolidin-1-yl)quinoline Derivatives)

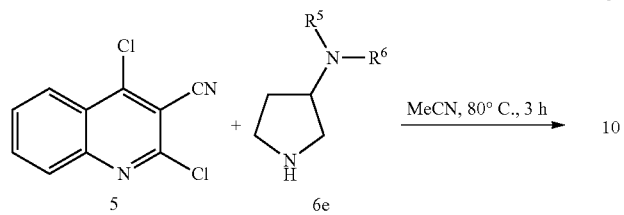

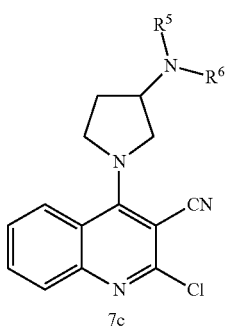

R⁵ and R⁶ are as defined under the general formula II

To a solution under nitrogen gas of 2, 4-dichloro-3-cyanoquinoline (5) (1.0 mmol) in MeCN (5 ml) was added compound 6e (1.0 mmol). The reaction mixture was stirred at 80° C. for 3 h. The reaction mixture was then cooled to RT, filtered and washed with MeCN to give solid compound (7c) corresponding to 2-chloro-3-cyano-4-(3-aminopyrrolidin-1-yl)quinoline derivatives in at least 50% (e.g. 59-89%) yield.

Note:

triethylamine (TEA) was used as base in case of intermediates (6e) were obtained in hydrochloride salt form (6d) in order to neutralize the HCl in the reaction mixture.

Synthesis of Compounds of Formula (II-b): 2-(4-chlorobenzylamino)-3-cyano-4-(3-aminopyrrolidin-1-yl)quinoline Derivatives

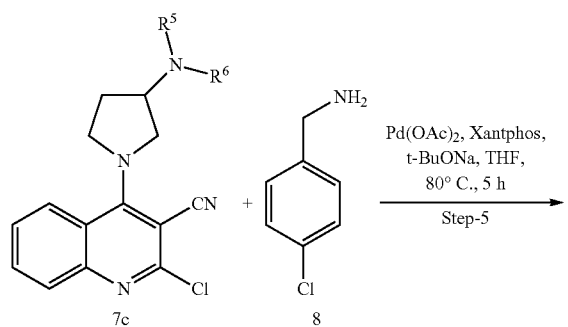

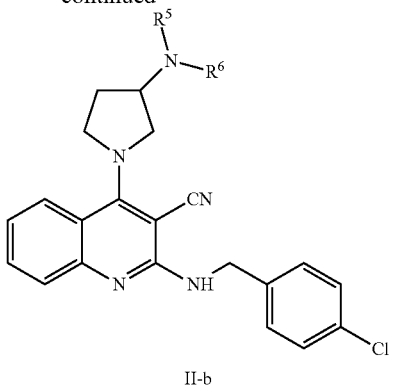

R⁵ and R⁶ are as defined under the general formula II

To a solution under nitrogen gas of the compound (7c) (2-chloro-3-cyano-4-(3-aminopyrrolidin-1-yl)quinoline derivative) (1.0 mmol) in THF (4 ml) was added 4-chlorobenzylamine (8) (1.5 mmol) and t-BuONa (3.0 mmol). The resulting mixture was degassed 10 min with Ar gas, then Xantphos (0.1 mmol) and Pd(OAc)₂ (0.1 mmol) were added and the reaction mixture was stirred at 80° C. for 5 h. The reaction mixture was then cooled to RT, filtered and concentrated under reduced pressure. The residue was partitioned between brine and EtOAc and the aqueous layer was extracted with EtOAc. The combined organic layers were dried over Na₂SO₄, filtered and concentrated under reduced pressure to give brown solids. The crude compound which upon purification by flash chromatography (silica-gel: 100-200 mesh, MeOH-DCM; 0%→10%) or Prep HPLC gave compounds of formula II-b [2-(4-chlorobenzylamino)-3-cyano-4-(3-aminopyrrolidin-1-yl)quinoline derivatives] as a solid compound in at least 5% (e.g. 6-32%) yield.

Note:

In some examples for compound 6e, the group R⁵ and/or R⁶ may be H. For these examples, the corresponding amine function (—NH₂ or —NH—R⁴ or —NH—R⁵) may be protected by any suitable protecting group (e.g. tertiary butoxy carbonyl (Boc), benzyloxy carbamate (Cbz) group). Thus, the corresponding compounds II-b will have a N-protected amine function on the pyrolidine cycle. The conversion of these compounds II-b into the corresponding free base forms may be carried out using any suitable deprotection techniques known in the art.

The compounds in table below are prepared according to the general procedure GP-3:

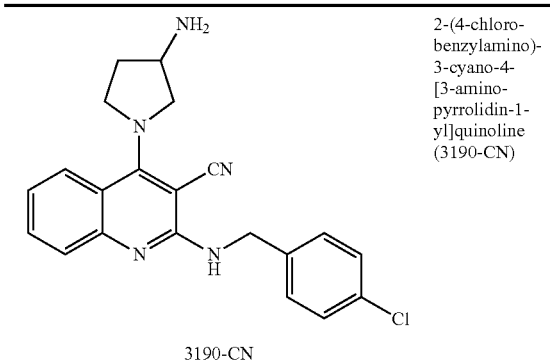

2-(4-chlorobenzylamino)-3-cyano-4-[3-aminopyrrolidin-1-yl]quinoline (3190-CN)

3190-CN

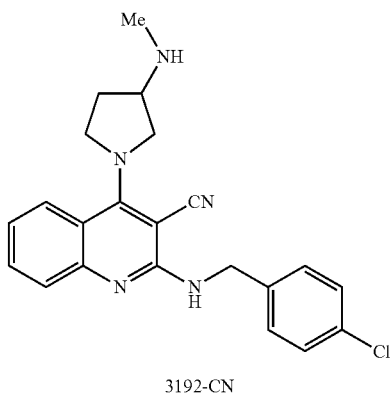 [SMILES: CNC1CCN(c2c(C#N)c(NCc3ccc(Cl)cc3)nc3ccccc23)C1]

3192-CN 2-(4-chloro-benzylamino)-3-cyano-4-[3-(methylamino)pyrrolidin-1-yl]quinoline (3192-CN)

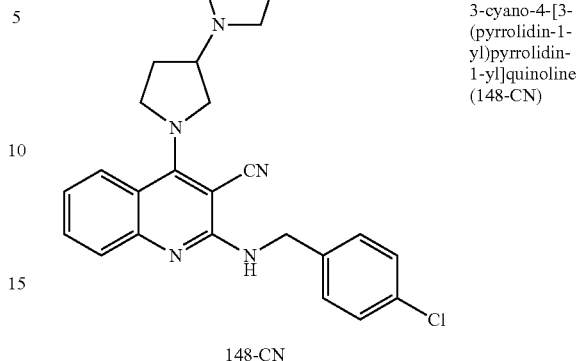

148-CN 2-(4-chloro-benzylamino)-3-cyano-4-[3-(pyrrolidin-1-yl)pyrrolidin-1-yl]quinoline (148-CN)

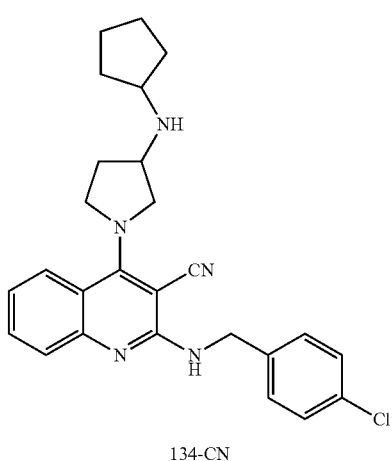 [SMILES: N#Cc1c(NCc2ccc(Cl)cc2)nc2ccccc2c1N1CCC(NC2CCCC2)C1]

134-CN 2-(4-chloro-benzylamino)-3-cyano-4-[3-(cyclopentylamino)pyrrolidin-1-yl]quinoline (134-CN)

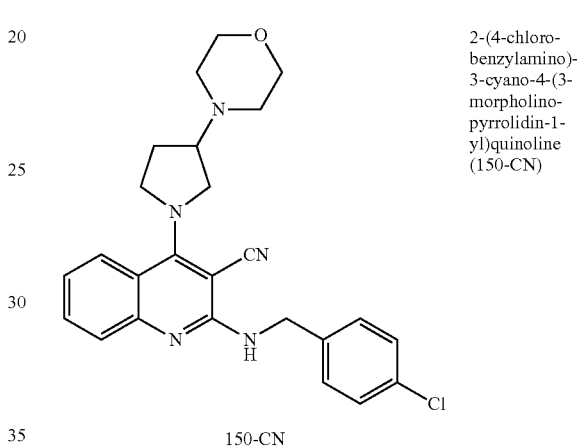

150-CN 2-(4-chloro-benzylamino)-3-cyano-4-(3-morpholinopyrrolidin-1-yl)quinoline (150-CN)

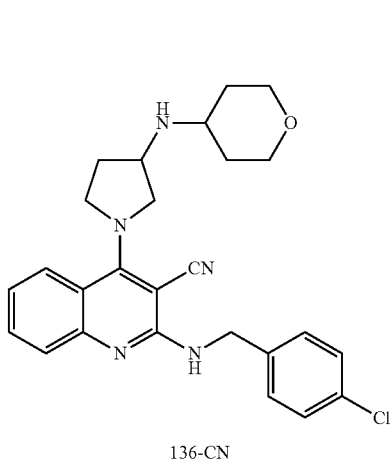 [SMILES: N#Cc1c(NCc2ccc(Cl)cc2)nc2ccccc2c1N1CCC(NC2CCOCC2)C1]

136-CN 2-(4-chloro-benzylamino)-3-cyano-4-{3-[(tetrahydro-2H-pyran-4-yl)-amino]pyrrolidin-1-yl}quinoline (136-CN)

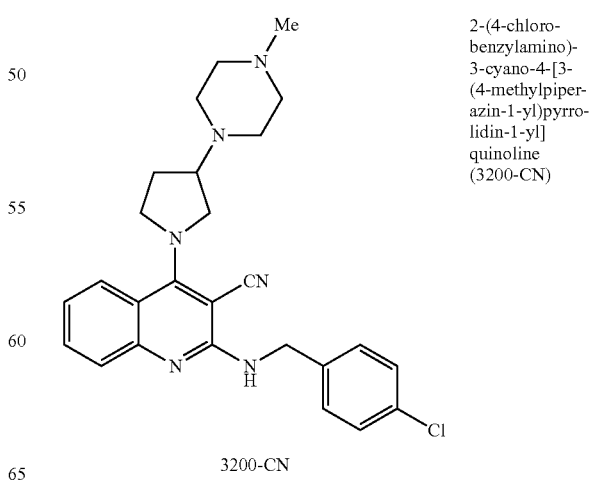

3200-CN 2-(4-chloro-benzylamino)-3-cyano-4-[3-(4-methylpiperazin-1-yl)pyrrolidin-1-yl]quinoline (3200-CN)

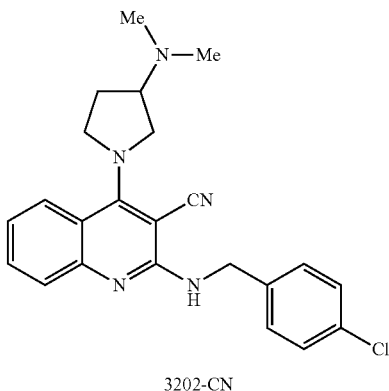 [SMILES: CN(C)C1CCN(c2c(C#N)c(NCc3ccc(Cl)cc3)nc3ccccc23)C1]

2-(4-chloro-benzylamino)-3-cyano-4-[3-(dimethylamino)pyrrolidin-1-yl]quinoline (3202-CN)

3202-CN

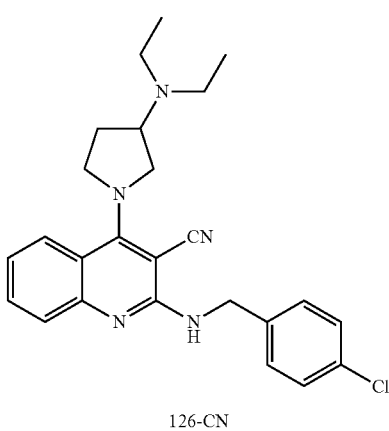 [SMILES: CCN(CC)C1CCN(c2c(C#N)c(NCc3ccc(Cl)cc3)nc3ccccc23)C1]

2-(4-chloro-benzylamino)-3-cyano-4-[3-(diethylamino)pyrrolidin-1-yl]quinoline (126-CN)

126-CN

General Procedure GP-4

The present procedure GP-4 may be used to prepare certain compounds of the general formula II, in particular of the general formula II-c below:

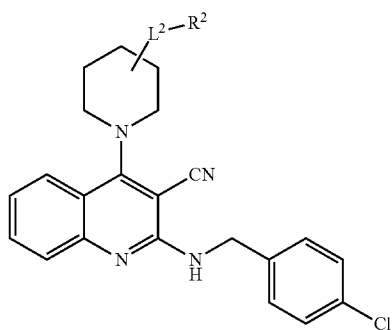

II-c

Wherein $L^2$ is a single bond, and $R^2$ is substituted or unsubstituted aryloxy, or substituted or unsubstituted heteroaryloxy.

Synthesis of Intermediate 6e

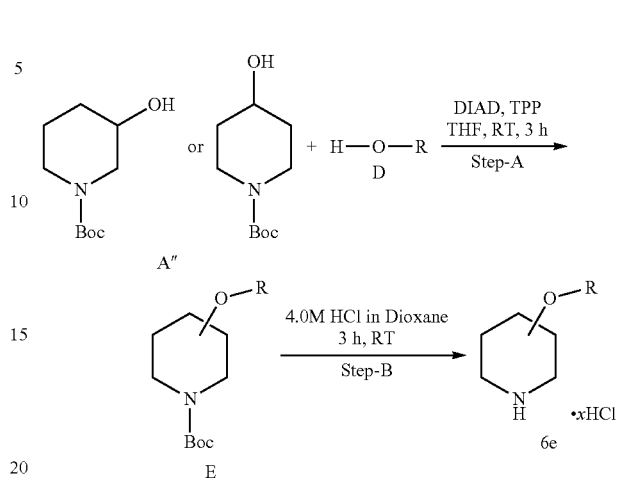

wherein R—O (=$R^2$) is substituted or unsubstituted aryloxy, or substituted or unsubstituted heteroaryloxy.

Step-A:

To a solution under nitrogen gas of compound A" (3- or 4-Boc piperidinol) (1.0 mmol) and arylhydroxyl or heteroarylhydroxyl (D) (1.0 mmol) in THF (20 ml) followed by addition of DIAD (1.1 mmol) and triphenyl phosphine (1.1 mmol) at 0° C. The reaction mixture was stirred at room temperature for overnight. Then, the reaction completion was checked by TLC, TLC indicates the consumption of the starting material and the reaction mixture was quenched with aqueous 1N NaOH and allowed stirred at room temperature for 10 min. Then, the aqueous layer was extracted with Ethyl acetate. The combined organic layers were washed with brine, dried over sodium sulfate, filtered and concentrated under reduced pressure. Then, the crude material was purified by column chromatography (Silica gel (60-120 mesh), eluting from 0% to 100% EtOAc in Petroleum ether to give intermediate E (3- or 4-aryloxy or 3- or 4-heterparyloxy Boc-piperidine) in at least 30% (e.g. 38-75%) yield.

Step-B:

To a solution under nitrogen gas of the intermediate E (3- or 4-aryloxy or 3- or 4-heterparyloxy Boc-piperidine) (1.0 mmol) in DCM (5 ml) was added at 0° C. a 4N HCl solution in Dioxane (8 mL). Then, the reaction mixture was stirred for 3 h at room temperature. Then, the reaction completion was checked by TLC, TLC indicated the consumption of the starting material and the solvents removed under reduced pressure. The resulting crude material were washed with di-ethyl ether and dried under vacuum to give the desired intermediate (6e) (3- or 4-aryloxy or 3- or 4-heteroaryloxy piperidine derivative) as hydrochloride salt and as solid compound in at least 50% yield (60-100%).

Synthesis of Intermediate 7d

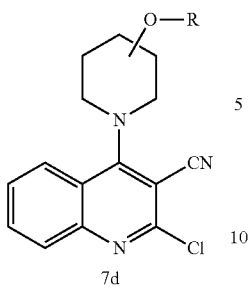

wherein R—O (=R$^2$) is substituted or unsubstituted aryloxy, or substituted or unsubstituted heteroaryloxy.

To a solution under nitrogen gas of 2,4-dichloro-3-cyanoquinoline (5) (1.0 mmol) in MeCN was added the intermediate (6f) (3 or 4-aryloxy or 3-,4-heteroaryloxy piperidine derivatives) (1.5 mmol). The reaction mixture was stirred at 70-80° C. for 3 h. The reaction mixture was then cooled to RT, filtered and washed with MeCN to give the desired intermediate (7d) (2-chloro-3-cyano-4-(3- or 4-aryloxy/heteroaryloxy piperidin-1-yl)quinoline derivative) as solid compound in at least 45% (e.g. 51-78%) yield.

Note:

TEA was used as base in case of compound (6f) was used as salt form (6e) in order to neutralize the HCl from reaction mixture.

Synthesis of the Compounds of Formula II-c [2-(4-chlorobenzylamino)-3-cyano-4-(3- or 4-aryloxy-piperidin-1-yl)quinoline or 2-(4-chlorobenzy-lamino)-3-cyano-4-(3- or 4-heteroaryloxy-piperidin-1-yl) quinoline]

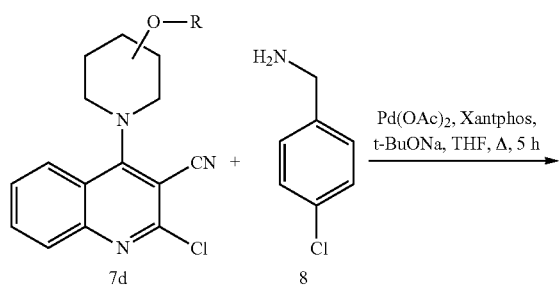

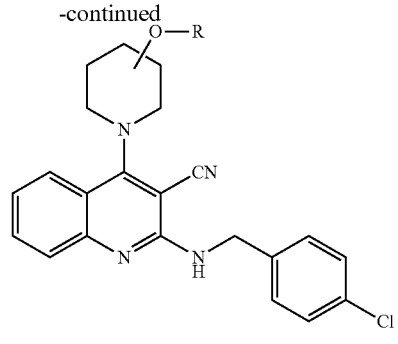

wherein R—O (=R$^2$) is substituted or unsubstituted aryloxy, or substituted or unsubstituted heteroaryloxy.

To a solution under nitrogen gas of compound (7d) (2-chloro-3-cyano-4-(3- or 4-aryloxy/heteroaryloxy piperidin-1-yl)quinoline derivatives) (1.0 mmol) in THF (4 ml) was added 4-chloro benzylamine (8) (1.5 mmol) and t-BuONa (3.0 mmol). The resulting mixture was degassed 10 min with Ar gas, then Xantphos (0.1 mmol) and Pd(OAc)$_2$ (0.1 mmol) were added and the reaction mixture was stirred under reflux for 5 h. The reaction mixture was then cooled to RT, filtered and concentrated under reduced pressure. The residue was partitioned between brine and EtOAc and the aqueous layer was extracted with EtOAc. The combined organic layers were dried over Na$_2$SO$_4$, filtered and concentrated under reduced pressure to give a brown solid.

Each crude compound was purified by flash chromatography using (silica-gel: 100-200 mesh, MeOH-DCM; 0%→10%) or by Prep HPLC to give the corresponding desired compound of formula II-c [2-(4-chlorobenzy-lamino)-3-cyano-4-(3- or 4-aryloxy-piperidin-1-yl)quinoline or 2-(4-chlorobenzylamino)-3-cyano-4-(3- or 4-heteroaryloxy-piperidin-1-yl)quinoline] as a solid compound in at least 9% (e.g. 9%-38%) yield.

The compounds in table below are prepared according to the general procedure GP-4:

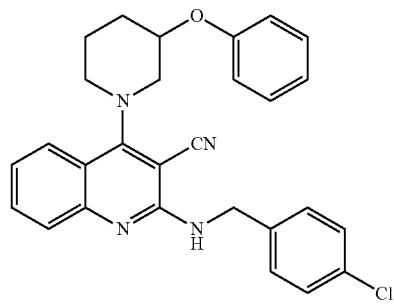

2-(4-chlorobenzylamino)-3-cyano-4-(3-phenoxypiperidin-1-yl)quinoline (3206-CN)

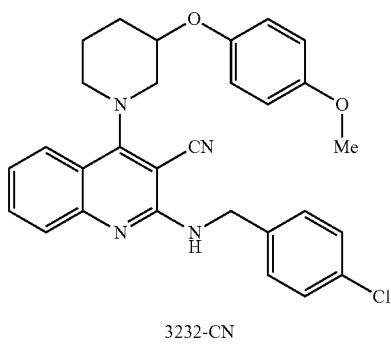 [SMILES: COc1ccc(OC2CCCN(c3c(C#N)c(NCc4ccc(Cl)cc4)nc4ccccc34)C2)cc1]
2-(4-chlorobenzylamino)-3-cyano-4-[3-(4-methoxyphenoxy)piperidin-1-yl]quinoline (3232-CN)
3232-CN
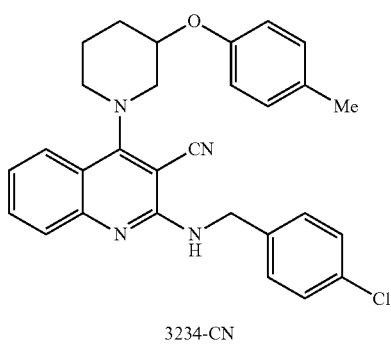 [SMILES: Cc1ccc(OC2CCCN(c3c(C#N)c(NCc4ccc(Cl)cc4)nc4ccccc34)C2)cc1]
2-(4-chlorobenzylamino)-3-cyano-4-[3-(4-methylphenoxy)piperidin-1-yl]quinoline (3234-CN)
3234-CN
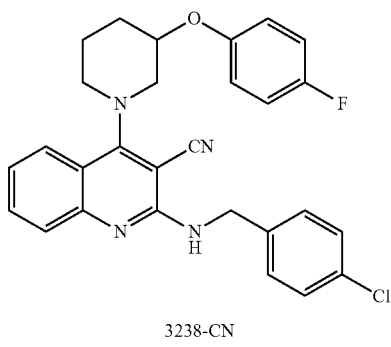 [SMILES: N#Cc1c(NCc2ccc(Cl)cc2)nc2ccccc2c1N1CCCC(Oc2ccc(F)cc2)C1]
2-(4-chlorobenzylamino)-3-cyano-4-[3-(4-fluorophenoxy)piperidin-1-yl]quinoline (3238-CN)
3238-CN
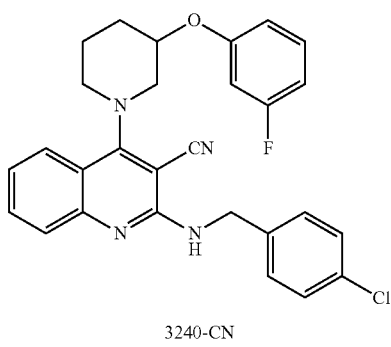 [SMILES: N#Cc1c(NCc2ccc(Cl)cc2)nc2ccccc2c1N1CCCC(Oc2cccc(F)c2)C1]
2-(4-chlorobenzylamino)-3-cyano-4-[3-(3-fluorophenoxy)piperidin-1-yl]quinoline (3240-CN)
3240-CN

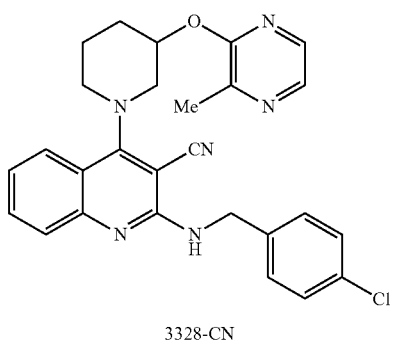 [SMILES: Cc1nccnc1OC1CCCN(c2c(C#N)c(NCc3ccc(Cl)cc3)nc3ccccc23)C1]
2-(4-chlorobenzylamino)-3-cyano-4-{3-[(3-methylpyrazin-2-yl)oxy]piperidin-1-yl}quinoline (3328-CN)
3328-CN
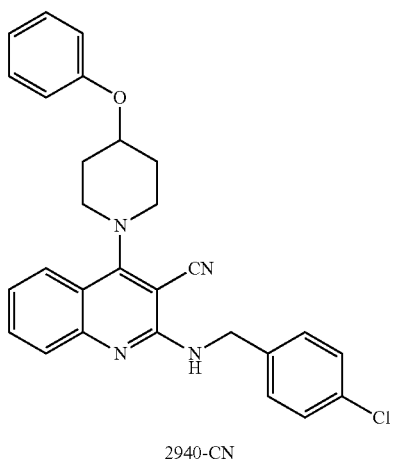 [SMILES: N#Cc1c(NCc2ccc(Cl)cc2)nc2ccccc2c1N1CCC(Oc2ccccc2)CC1]
2-(4-chlorobenzylamino)-3-cyano-4-(4-phenoxypiperidin-1-yl)quinoline (2940-CN)
2940-CN
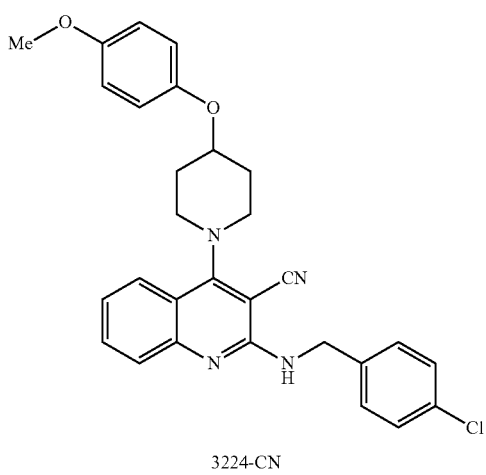 [SMILES: COc1ccc(OC2CCN(c3c(C#N)c(NCc4ccc(Cl)cc4)nc4ccccc34)CC2)cc1]
2-(4-chlorobenzylamino)-3-cyano-4-[4-(4-methoxyphenoxy)piperidin-1-yl]quinoline (3224-CN)
3224-CN -continued
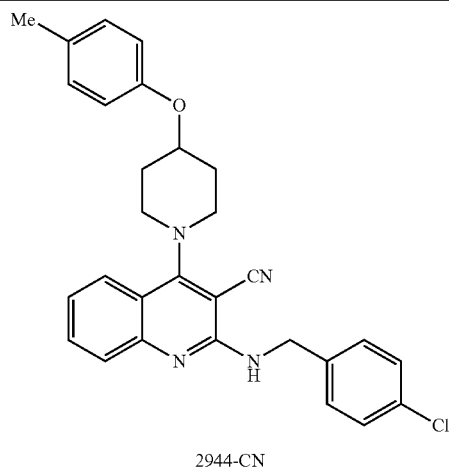
2944-CN
2-(4-chlorobenzylamino)-3-cyano-4-[4-(p-tolyloxy)piperidin-1-yl]quinoline (2944-CN)
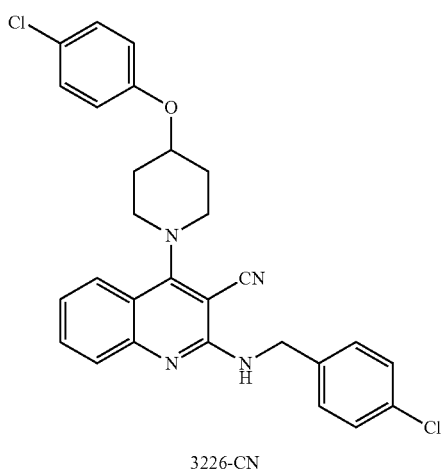 [SMILES: N#Cc1c(NCc2ccc(Cl)cc2)nc2ccccc2c1N1CCC(Oc2ccc(Cl)cc2)CC1]
3226-CN
2-(4-chlorobenzylamino)-3-cyano-4-[4-(4-chlorophenoxy)piperidin-1-yl]quinoline (3226-CN)
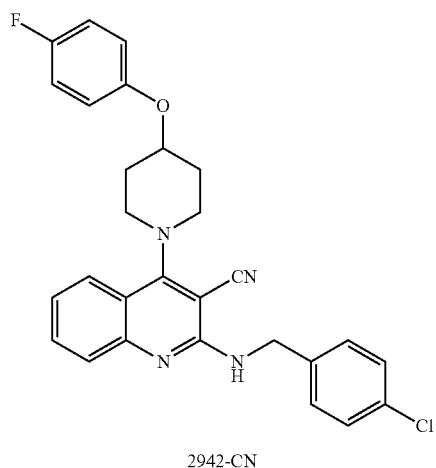 [SMILES: N#Cc1c(NCc2ccc(Cl)cc2)nc2ccccc2c1N1CCC(Oc2ccc(F)cc2)CC1]
2942-CN
2-(4-chlorobenzylamino)-3-cyano-4-[4-(4-fluorophenoxy)piperidin-1-yl]quinoline (2942-CN)

-continued
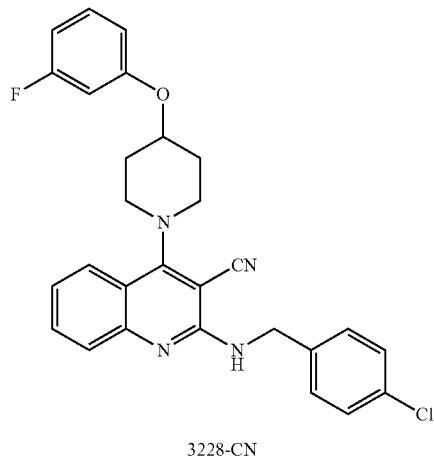 [SMILES: N#Cc1c(NCc2ccc(Cl)cc2)nc2ccccc2c1N1CCC(Oc2cccc(F)c2)CC1]
3228-CN
2-(4-chlorobenzylamino)-3-cyano-4-[4-(3-fluorophenoxy)piperidin-1-yl]quinoline (3228-CN)
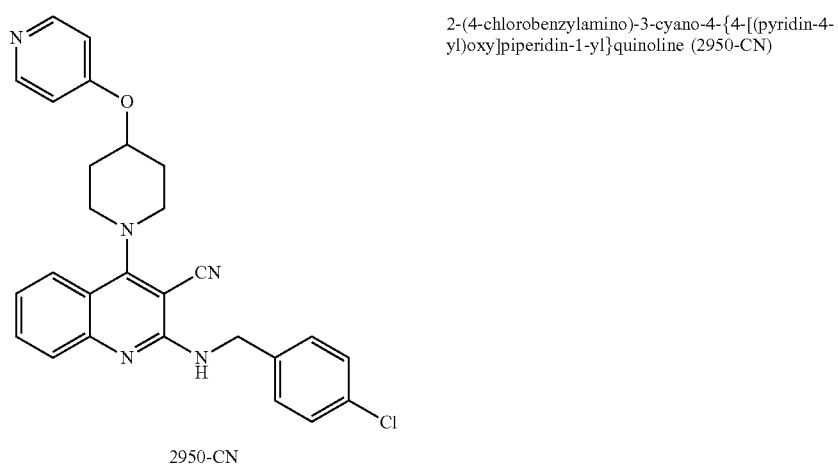
2950-CN
2-(4-chlorobenzylamino)-3-cyano-4-{4-[(pyridin-4-yl)oxy]piperidin-1-yl}quinoline (2950-CN)
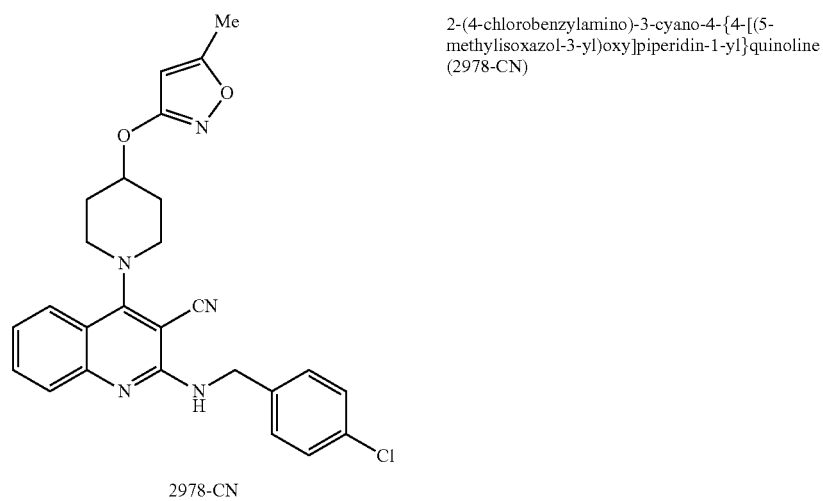
2978-CN
2-(4-chlorobenzylamino)-3-cyano-4-{4-[(5-methylisoxazol-3-yl)oxy]piperidin-1-yl}quinoline (2978-CN)

| | 2-(4-chlorobenzylamino)-3-cyano-4-{4-[(3-methylpyrazin-2-yl)oxy]piperidin-1-yl}quinoline (2970-CN) |
|---|---|
| 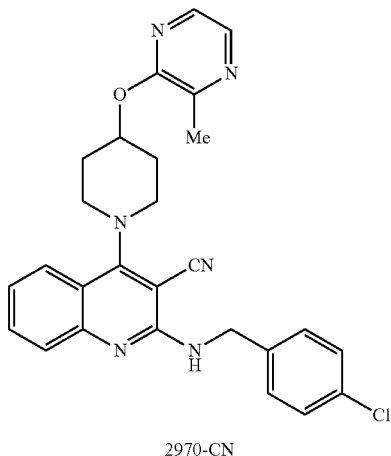 [SMILES: Cc1nccnc1OC1CCN(c2c(C#N)c(NCc3ccc(Cl)cc3)nc3ccccc23)CC1] 2970-CN | |

General Procedure GP-5

The present general procedure GP-5 may be used to prepare certain compounds of the general formula IV, in particular compounds of the general formula IV-a below:

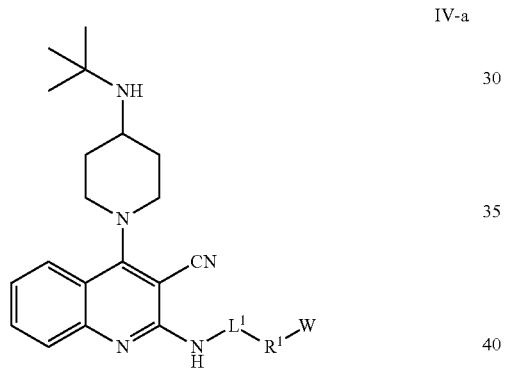

IV-a wherein:
$L^1$ is a single bond,
$R^1$ is substituted or unsubstituted aryl, substituted or unsubstituted heteroaryl, substituted or unsubstituted arylene, or substituted or unsubstituted heteroarylene,
W is H, halo, substituted or unsubstituted alkyl, substituted or unsubstituted alkoxy, substituted or unsubstituted aryloxy, substituted or unsubstituted heteroaryloxy, substituted or unsubstituted arylamino, or substituted or unsubstituted heteroarylamino.

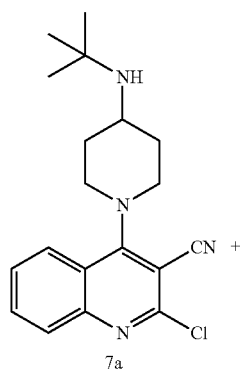

7a

+

$$W\!-\!R^1\!-\!NH_2$$
10

A) Pd(OAc)$_2$, Xantphos, t-BuONa, THF, 80° C., 5 h
or
B) Pd(dba)$_2$, Xantphos, Cs$_2$CO$_3$, Dioxane Reflux, 3 h

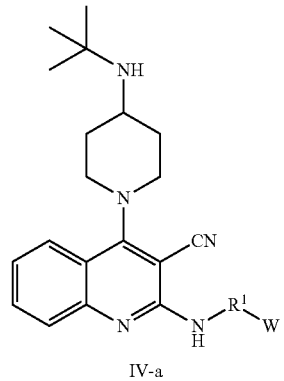

IV-a

Reaction Un Conditions A:

To a solution under nitrogen gas of 2-chloro-3-cyano-4-[4-(tert-butylamino)piperidin-1-yl]quinoline 7a (1.0 mmol) in THF was added the amine compound 10 (arylamine or heteroarylamine) (1.5 mmol) and t-BuONa (3.0 mmol). The resulting mixture was degassed 30 min with Ar gas, then Xantphos (0.1 mmol) and Pd(OAc)$_2$ (0.1 mmol) were added and the reaction mixture was stirred at 80° C. for 3-5 h. The reaction mixture was then cooled to RT, filtered and concentrated under reduced pressure. The residue was partitioned between brine and EtOAc and the aqueous layer was extracted with EtOAc. The combined organic layers were dried over Na$_2$SO$_4$, filtered and concentrated under reduced pressure to give a brown solid.

The crude compound was subjected to purification by flash chromatography using (silica-gel: 230-400 mesh, MeOH-DCM; 0%→10%) or by Prep HPLC to give the corresponding desired compound of formula IV-a (2-substituted arylamino-3-cyano-4-[4-(tert-butylamino)piperidin-1-yl]quinoline or 2-substituted heteroarylamino-3-cyano-4-[4-(tert-butylamino)piperidin-1-yl]quinoline) as solid compound in at least 5% (e.g. 5-43%) yield.

Reaction Under Condition B:

To a solution under nitrogen gas of compound 7a (2-chloro-3-cyano-4-[4-(tert-butylamino)piperidin-1-yl]quinoline) (1.0 mmol) in dioxane was added the amine compound 10 (aryl- or heteroarylamine) (1.5 mmol) and $Cs_2CO_3$ (3.0 mmol). The resulting mixture was degassed 30 min with Ar gas, then Xantphos (0.1 mmol) and $Pd_2(dba)_3$. (0.05 mmol) were added and the reaction mixture was stirred under reflux for 3-5 h. The reaction mixture was then cooled to RT, filtered and concentrated under reduced pressure. The residue was partitioned between brine and EtOAc and the aqueous layer was extracted with EtOAc. The combined organic layers were dried over $Na_2SO_4$, filtered and concentrated under reduced pressure to give a brown solid. The crude compound was subjected to purification by flash chromatography using (silica-gel: 230-400 mesh, MeOH-DCM; 0%→10%) or Prep HPLC to give the corresponding desired compound of formula IV-a (2-substituted arylamino-3-cyano-4-[4-(tert-butylamino)piperidin-1-yl]quinoline or 2-substituted heteroarylamino-3-cyano-4-[4-(tert-butylamino)piperidin-1-yl]quinoline) as solid compound in at least 20% (25-30%) yield.

The compounds in table below are prepared according to the general procedure GP-5:

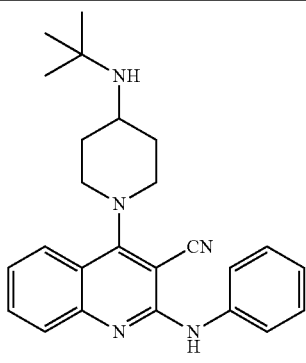

2-(phenylamino)-3-cyano-4-[4-(tert-butylamino)piperidin-1-yl]quinoline (3246-CN),

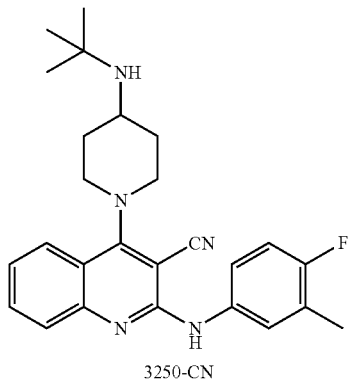 [SMILES: Cc1cc(Nc2nc3ccccc3c(N3CCC(NC(C)(C)C)CC3)c2C#N)ccc1F]

2-(3-methyl-4-fluorophenylamino)-3-cyano-4-[4-(tert-butylamino)piperidin-1-yl]quinoline (3250-CN),

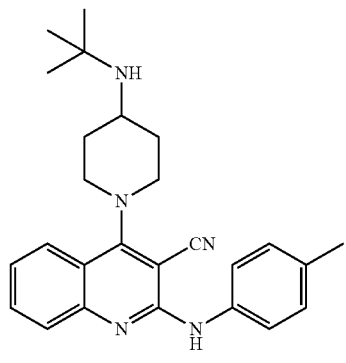

2-(4-methylphenylamino)-3-cyano-4-[4-(tert-butylamino)piperidin-1-yl]quinoline (3248-CN),

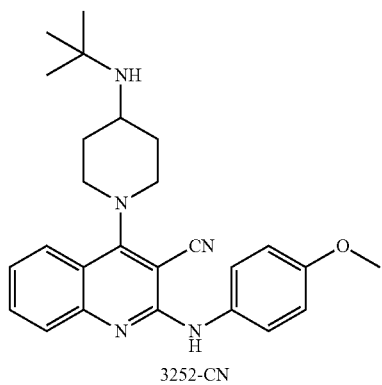 [SMILES: COc1ccc(Nc2nc3ccccc3c(N3CCC(NC(C)(C)C)CC3)c2C#N)cc1]
3252-CN
2-(4-methoxyphenylamino)-3-cyano-4-[4-(tert-butylamino)piperidin-1-yl]quinoline (3252-CN),
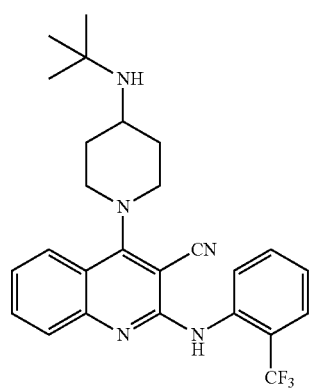
3254-CN
2-(2-trifluoromethylphenylamino)-3-cyano-4-[4-(tert-butylamino)piperidin-1-yl]quinoline (3254-CN),
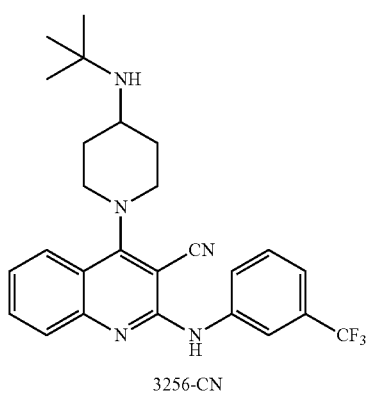 [SMILES: CC(C)(C)NC1CCN(c2c(C#N)c(Nc3cccc(C(F)(F)F)c3)nc3ccccc23)CC1]
3256-CN
2-(3-trifluoromethylphenylamino)-3-cyano-4-[4-(tert-butylamino)piperidin-1-yl]quinoline (3256-CN),
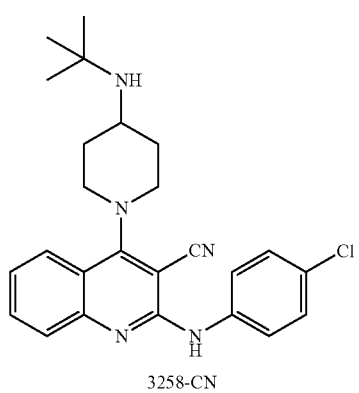 [SMILES: CC(C)(C)NC1CCN(c2c(C#N)c(Nc3ccc(Cl)cc3)nc3ccccc23)CC1]
3258-CN
2-(4-chlorophenylamino)-3-cyano-4-[4-(tert-butylamino)piperidin-1-yl]quinoline (3258-CN),

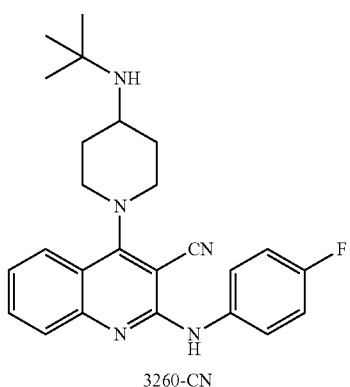 [SMILES: CC(C)(C)NC1CCN(c2c(C#N)c(Nc3ccc(F)cc3)nc3ccccc23)CC1]
2-(4-fluorophenylamino)-3-cyano-4-[4-(tert-butylamino)piperidin-1-yl]quinoline (3260-CN),
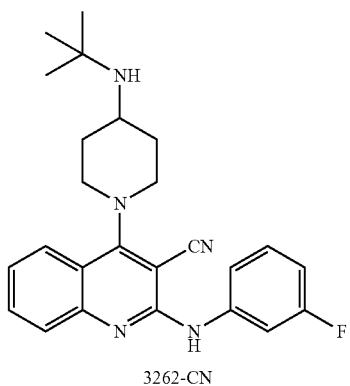 [SMILES: CC(C)(C)NC1CCN(c2c(C#N)c(Nc3cccc(F)c3)nc3ccccc23)CC1]
2-(3-fluorophenylamino)-3-cyano-4-[4-(tert-butylamino)piperidin-1-yl]quinoline (3262-CN),
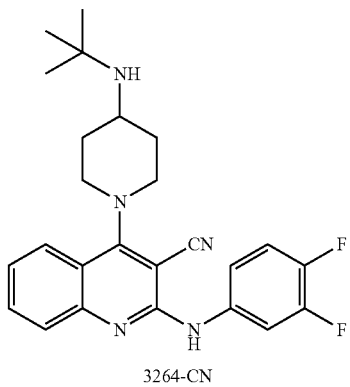 [SMILES: CC(C)(C)NC1CCN(c2c(C#N)c(Nc3ccc(F)c(F)c3)nc3ccccc23)CC1]
2-(3,4-difluorophenylamino)-3-cyano-4-[4-(tert-butylamino)piperidin-1-yl]quinoline (3264-CN),
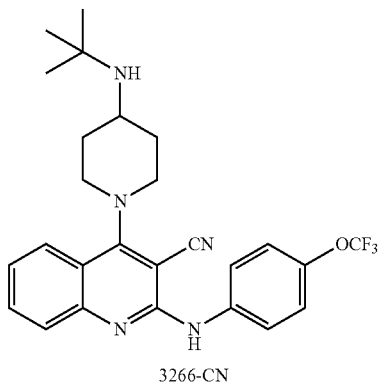 [SMILES: CC(C)(C)NC1CCN(c2c(C#N)c(Nc3ccc(OC(F)(F)F)cc3)nc3ccccc23)CC1]
2-[4-(trifluoromethyloxy)phenylamino]-3-cyano-4-[4-(tert-butylamino)piperidin-1-yl]quinoline (3266-CN),

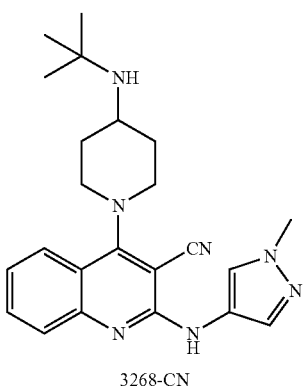 [SMILES: Cn1cc(Nc2nc3ccccc3c(N3CCC(NC(C)(C)C)CC3)c2C#N)cn1]
3268-CN
2-[(1-methyl-1H-pyrazol-4-yl)amino]-3-cyano-4-[4-(tert-butylamino)piperidin-1-yl]quinoline (3268-CN),
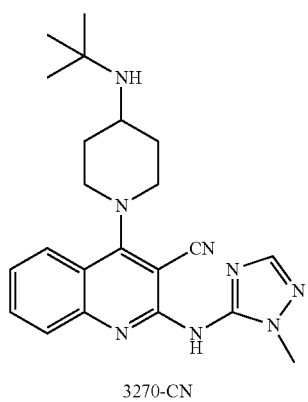 [SMILES: Cn1ncnc1Nc1nc2ccccc2c(N2CCC(NC(C)(C)C)CC2)c1C#N]
3270-CN
2-[(1-methyl-1H-1,2,4-triazol-5-yl)amino]-3-cyano-4-[4-(tert-butylamino)piperidin-1-yl]quinoline (3270-CN),
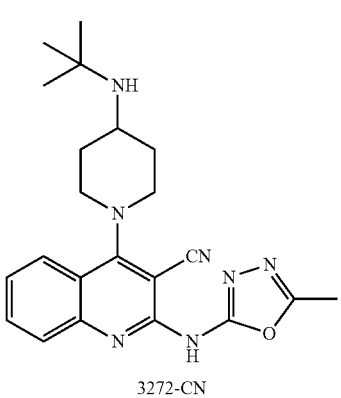 [SMILES: Cc1nnc(Nc2nc3ccccc3c(N3CCC(NC(C)(C)C)CC3)c2C#N)o1]
3272-CN
2-[(5-methyl-1,3,4-oxadiazol-2-yl)amino]-3-cyano-4-[4-(tert-butylamino)piperidin-1-yl]quinoline (3272-CN)
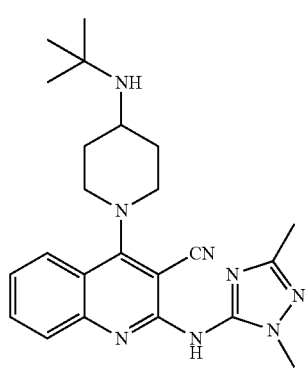
3274-CN
2-[(1,3-dimethyl-1H-1,2,4-triazol-5-yl)amino]-3-cyano-4-[4-(tert-butylamino)piperidin-1-yl]quinoline (3274-CN)

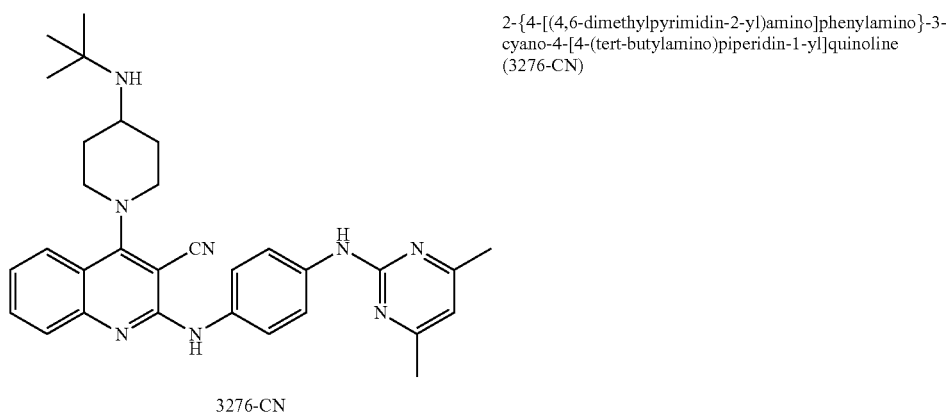
2-{4-[(4,6-dimethylpyrimidin-2-yl)amino]phenylamino}-3-cyano-4-[4-(tert-butylamino)piperidin-1-yl]quinoline (3276-CN)
3276-CN
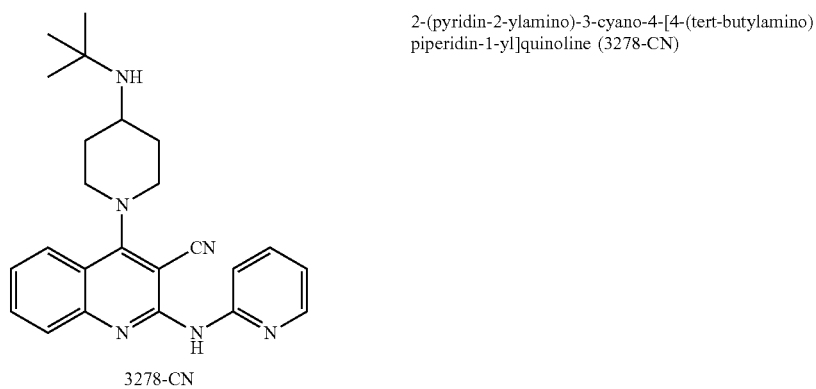
2-(pyridin-2-ylamino)-3-cyano-4-[4-(tert-butylamino)piperidin-1-yl]quinoline (3278-CN)
3278-CN
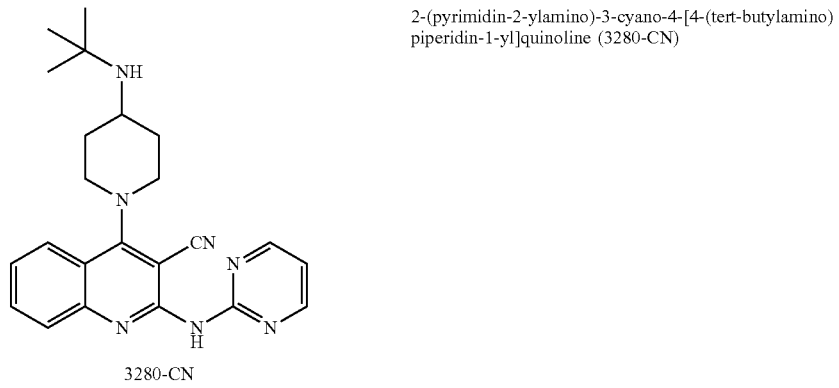
2-(pyrimidin-2-ylamino)-3-cyano-4-[4-(tert-butylamino)piperidin-1-yl]quinoline (3280-CN)
3280-CN
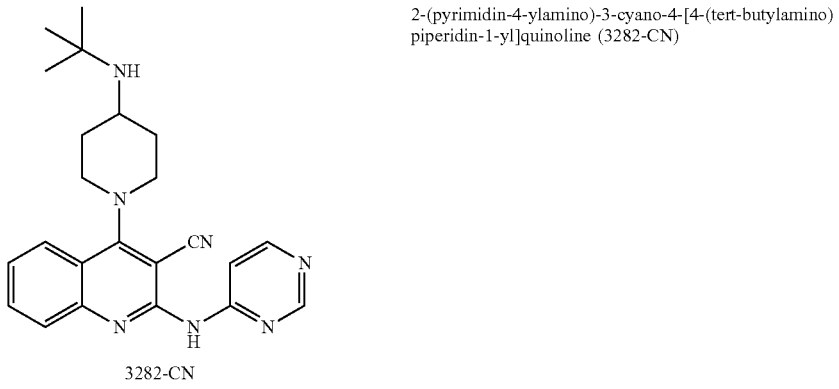
2-(pyrimidin-4-ylamino)-3-cyano-4-[4-(tert-butylamino)piperidin-1-yl]quinoline (3282-CN)
3282-CN

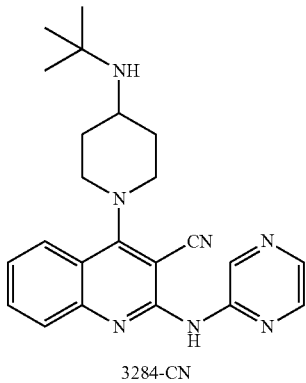 [SMILES: CC(C)(C)NC1CCN(c2c(C#N)c(Nc3cnccn3)nc3ccccc23)CC1]

2-(pyrazin-2-ylamino)-3-cyano-4-[4-(tertbutylamino)piperidin-1-yl]quinoline (3284-CN)

3284-CN

General Procedure GP-6

The following procedure GP-6 may be used to prepare certain compounds formula IV, in particular compounds of formula IV-b below:

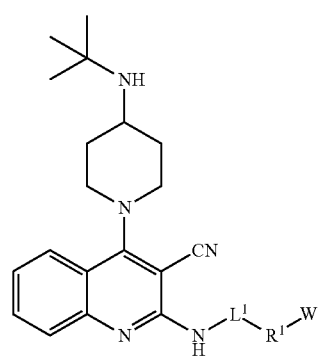

IV-b

Wherein:
$L^1$ is substituted or unsubstituted alkylene, substituted or unsubstituted alkenylene, or substituted or unsubstituted alkynylene; and $R^1$ is substituted or unsubstituted aryl or substituted or unsubstituted heteroaryl; and W is H.

Synthesis of Compound of Formula IV-b (2-Substituted amino-3-cyano-4-[4-(tert-butylamino)piperidin-1-yl]quinoline Derivatives)

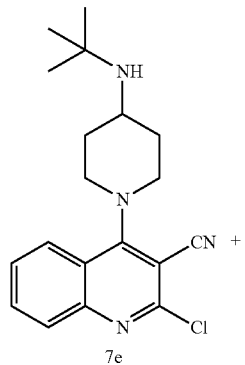

7e

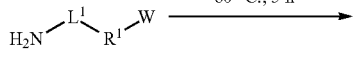

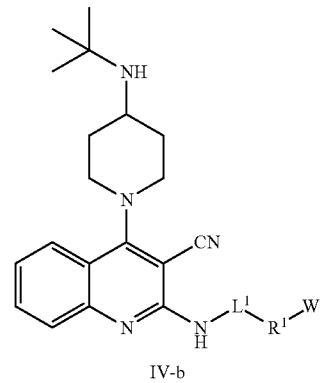

IV-b wherein $L^1$, $R^1$ and W are as defined above under formula VI-b

Example for compounds where $L^1$ is methylene:

To a solution under nitrogen gas of 2-chloro-3-cyano-4-[4-(tert-butylamino)piperidin-1-yl]quinoline 7e (1.0 mmol) in THF (4 ml) was added arylmethylamine or heteroarylmethylamine 9 (1.5 mmol) and t-BuONa (3.0 mmol). The resulting mixture was degassed 30 min with Ar gas, then Xantphos (0.1 mmol) and Pd(OAc)$_2$ (0.1 mmol) were added and the reaction mixture was stirred at 80° C. for 5 h. The reaction mixture was then cooled to RT, filtered and concentrated under reduced pressure. The residue was partitioned between brine and EtOAc and the aqueous layer was extracted with EtOAc. The combined organic layers were dried over Na$_2$SO$_4$, filtered and concentrated under reduced pressure to give a brown solid.

The crude compound was purified by flash chromatography using (silica-gel: 230-400 mesh, MeOH-DCM; 0%→10%) or Prep HPLC to give the corresponding desired compound of formula IV-b (2-substituted arylmethylamino-3-cyano-4-[4-(tert-butylamino)piperidin-1-yl]quinoline or 2-substituted heteroarylmethylamino-3-cyano-4-[4-(tert-butylamino)piperidin-1-yl]quinoline as solid compounds in at least 5% (e.g. 7-25%) yield.

The compounds in table below are prepared according to the general procedure GP-6:

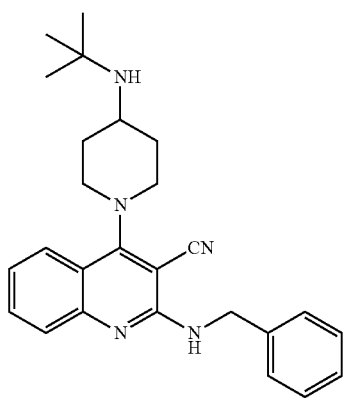
3286-CN
2-(benzylamino)-3-cyano-4-[4-(tert-butylamino)piperidin-1-yl]quinoline (3286-CN)
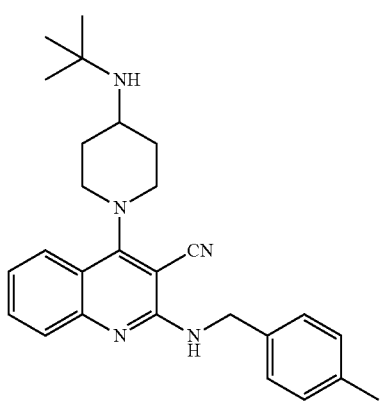
3288-CN
2-(4-methylbenzylamino)-3-cyano-4-[4-(tert-butylamino)piperidin-1-yl]quinoline (3288-CN)
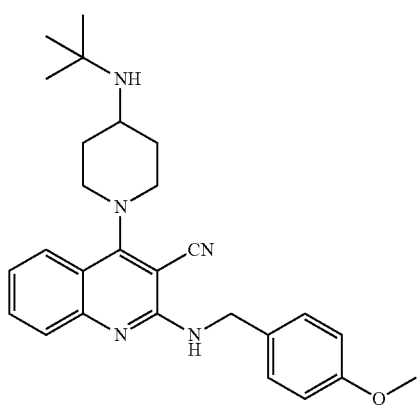
3290-CN
2-(4-methoxybenzylamino)-3-cyano-4-[4-(tert-butylamino)piperidin-1-yl]quinoline (3290-CN)

-continued
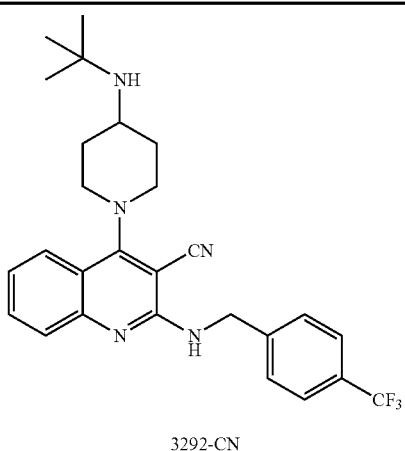
3292-CN
2-[4-(trifluoromethyl)benzylamino]-3-cyano-4-[4-(tert-butylamino)piperidin-1-yl]quinoline (3292-CN)
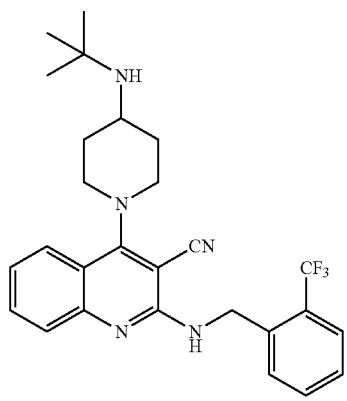
3298-CN
2-[4-(trifluoromethyl)benzylamino]-3-cyano-4-[4-(tert-butylamino)piperidin-1-yl]quinoline (3298-CN)
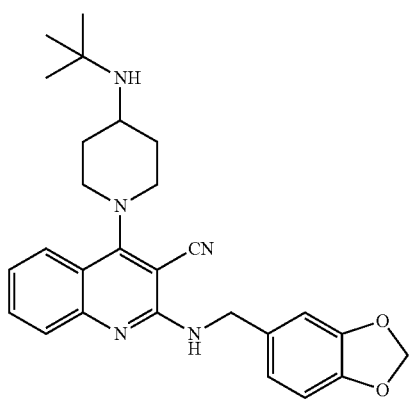
3300-CN
2-[(benzo[d][1,3]dioxol-5-ylmethyl)amino]-3-cyano-4-[4-(tert-butylamino)piperidin-1-yl]quinoline (3300-CN)

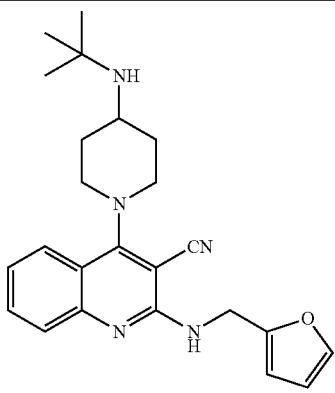
3302-CN
2-[(furan-2-ylmethyl)amino]-3-cyano-4-[4-(tert-butylamino)piperidin-1-yl]quinoline (3302-CN)
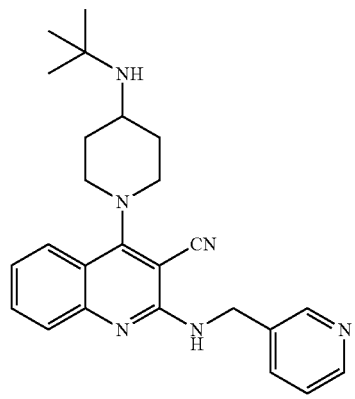
3304-CN
2-[(pyridin-3-ylmethyl)amino]-3-cyano-4-[4-(tert-butylamino)piperidin-1-yl]quinoline (3304-CN)
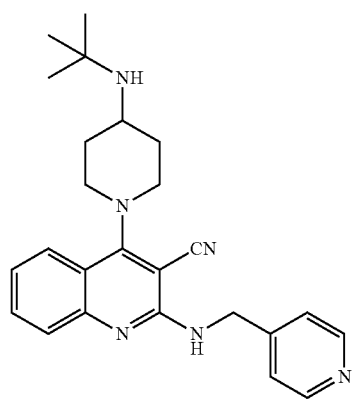
3306-CN
2-[(pyridin-4-ylmethyl)amino]-3-cyano-4-[4-(tert-butylamino)piperidin-1-yl]quinoline (3306-CN)

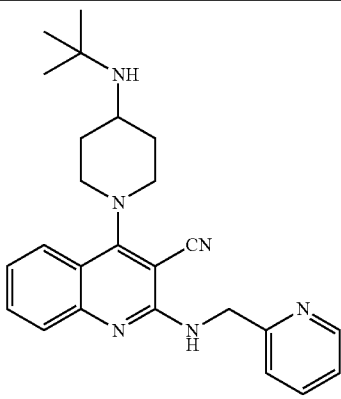

2-[(pyridin-2-ylmethyl)amino]-3-cyano-4-[4-(tert-butylamino)piperidin-1-yl]quinoline (3308-CN)

3308-CN

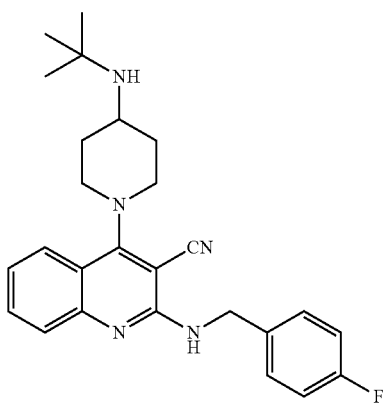

2-(4-fluorobenzylamino)-3-cyano-4-[4-(tert-butylamino)piperidin-1-yl]quinoline (240-CN)

240-CN

General Procedure GP-7

The following procedure GP-7 may be used to prepare certain compounds of formula II, in particular compounds of formula II-d below:

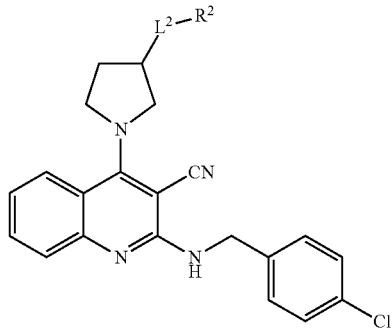

II-d wherein $L^2$ is a single bond, and $R^2$ is substituted or unsubstituted aryloxy, or substituted or unsubstituted heteroaryloxy.

Synthesis of Compound 6h
(3-aryloxy/heteroaryloxypyrrolidine HCl Salts)

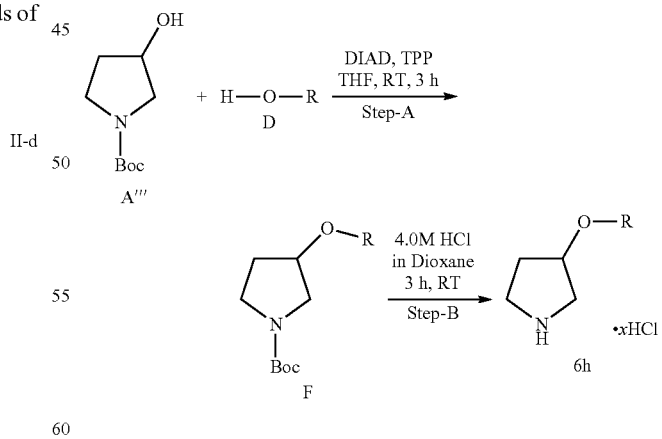

wherein R—O (=$R^2$) is substituted or unsubstituted aryloxy, or substituted or unsubstituted heteroaryloxy.

Step-A:

To a solution under nitrogen gas of N-Boc pyrrolidin-3-ol A''' (1.0 mmol) and hydroxylaryl or hydroxyheteroaryl D (1.0 mmol) in THF (20 ml) was added DIAD (1.1 mmol) and triphenyl phosphine (1.1 mmol) at 0° C. Then, the reaction mixture was allowed to stir at room temperature for overnight. Then, the reaction completion was checked by TLC, TLC indicates the consumption of the starting material and the reaction mixture was quenched with 1N aqueous NaOH solution and allowed to stir at room temperature for 10 min. Then, the aqueous layer was extracted with Ethyl acetate. The combined organic layers sere washed with brine, dried over Na₂SO₄, filtered and concentrated under reduced pressure. Then, the crude material was purified by column chromatography (Silica gel (60-120 mesh), eluting from 0% to 100% EtOAc in Petroleum ether to afford compound F (N-Boc 3-aryloxy/heteroaryloxypyrrolidine) in at least 20% (e.g. 25-67%) yield.

Step-B:

To a solution under nitrogen gas of compound F (N-Boc 3-aryloxy/heteroaryloxypyrrolidine) (1.0 mmol) in DCM (5 ml) was added at 0° C., a 4N HCl solution in Dioxane (8 mL). Then, the reaction mixture was stirred for 3 h at room temperature. Then, the reaction completion was checked by TLC, TLC indicates the consumption of the starting material and the solvents were removed under reduced pressure. The resulting crude material was washed with di-ethyl ether and dried to obtain compound 6h (3-aryloxy/heteroaryloxypyrrolidine) as hydrochloride salt form and as a solid compound in at least 70% (e.g. 81-95%) yield.

Synthesis of Intermediate 7e (2-chloro-3-cyano-4-(3-aryloxy or 3-heteroaryloxypyrrolidin-1-yl)quinoline)

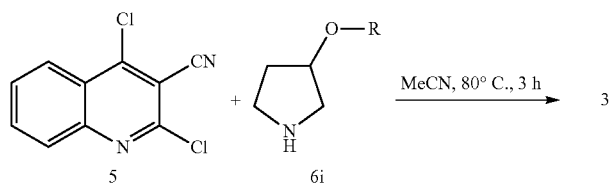

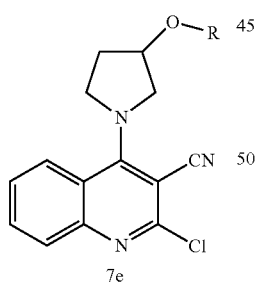

wherein R—O (═R²) is substituted or unsubstituted aryloxy, or substituted or unsubstituted heteroaryloxy.

To a solution under nitrogen gas of 2,4-dichloro-3-cyanoquinoline 5 (1.0 mmol) in MeCN was added the amine compound 6i (3-aryloxy or 3-heteroaryloxypyrrolidine) (1.0 mmol). The reaction mixture was allowed to stir at 80° C. for 3 h. The reaction mixture was then cooled to RT, filtered and washed with MeCN to give a solid compound corresponding to the intermediate 7e (2-chloro-3-cyano-4-(3-aryloxy or 3-heteroaryloxypyrrolidin-1-yl)quinoline) in at least 40% (e.g. 46-88%) yield.

Note:

TEA was used as base in case of the amine compound 6i (3-aryloxy or 3-heteroaryloxypyrrolidine) was used as in the form of HCl salt 6 h in order to neutralize HCl from the reaction mixture.

Synthesis of the Compounds of Formula II-d (2-(4-chlorobenzylamino)-3-cyano-4-(3-aryloxy or 3-heteroaryloxypyrrolidin-1-yl)quinolines)

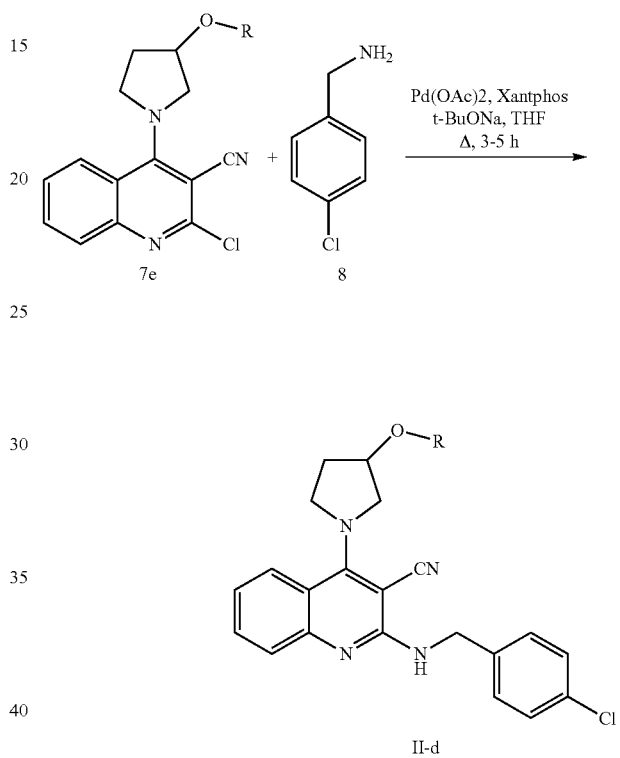

wherein R—O (═R²) is substituted or unsubstituted aryloxy, or substituted or unsubstituted heteroaryloxy To a solution under nitrogen gas of the intermediate 7e (2-chloro-3-cyano-4-(3-aryloxy/heteroaryloxypyrrolidin-1-yl)quinoline) (1.0 mmol) in THF (4 ml) was added 4-chlorobenzylamine 8 (1.5 mmol) and t-BuONa (3.0 mmol). The resulting mixture was degassed 10 min with Ar gas, then Xantphos (0.1 mmol) and Pd(OAc)₂ (0.1 mmol) were added and the reaction mixture was allowed to stir under reflux for 3-5 h. The reaction mixture was then cooled to RT, filtered and concentrated under reduced pressure. The residue was partitioned between brine and EtOAc and the aqueous layer was extracted with EtOAc. The combined organic layers were dried over Na₂SO₄, filtered and concentrated under reduced pressure to give a brown solid. The crude compound was purified by flash chromatography (using silica-gel: 100-200 mesh, MeOH-DCM: 0%→10%) to give the compound II-d (2-(4-chlorobenzylamino)-3-cyano-4-(3-aryloxy or 3-heteroaryloxypyrrolidin-1-yl)quinoline) as an solid compound in at least 3% (e.g. 3-41%) yield.

The compounds in table below are prepared according to the general procedure GP-7:

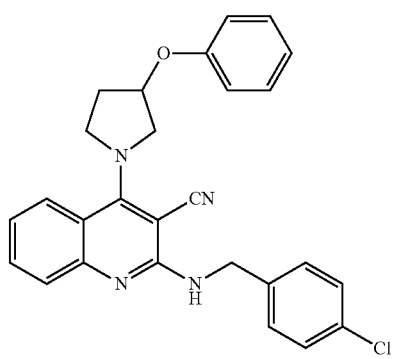
2-(4-chlorobenzylamino)-3-cyano-4-(3-phenoxypyrrolidin-1-yl)quinoline (3330-CN)
3330-CN
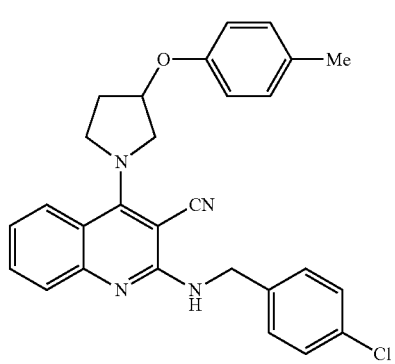
2-(4-chlorobenzylamino)-3-cyano-4-[3-(4-methylphenoxy)pyrrolidin-1-yl]quinoline (3332-CN)
3332-CN
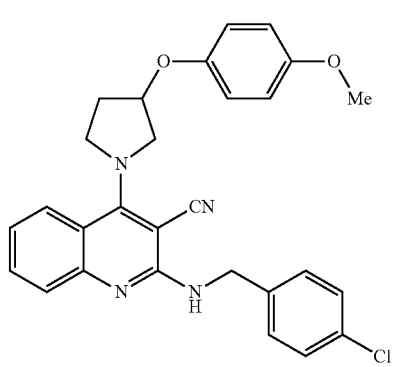
2-(4-chlorobenzylamino)-3-cyano-4-[3-(4-methoxyphenoxy)pyrrolidin-1-yl]quinoline (3334-CN)
3334-CN
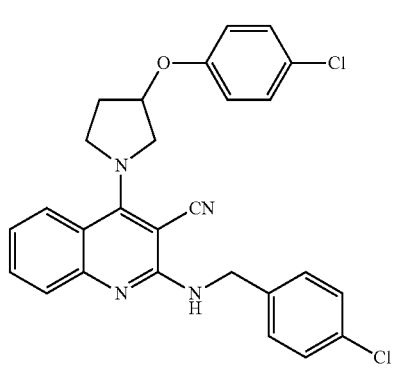
2-(4-chlorobenzylamino)-3-cyano-4-[3-(4-chlorophenoxy)pyrrolidin1--yl]quinoline (3336-CN)
3336-CN -continued
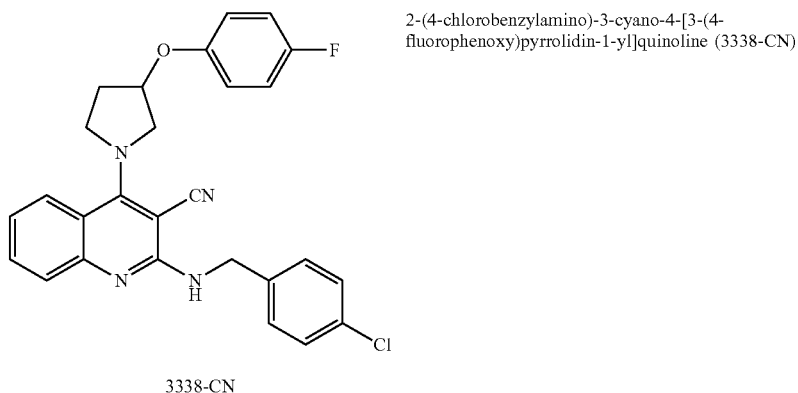
3338-CN
2-(4-chlorobenzylamino)-3-cyano-4-[3-(4-fluorophenoxy)pyrrolidin-1-yl]quinoline (3338-CN)
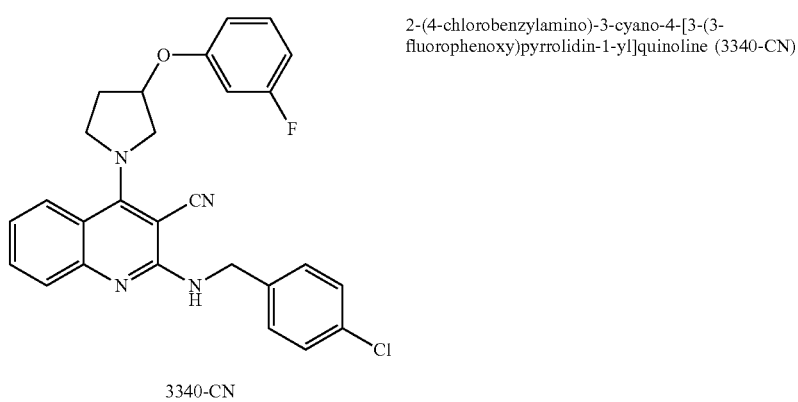
3340-CN
2-(4-chlorobenzylamino)-3-cyano-4-[3-(3-fluorophenoxy)pyrrolidin-1-yl]quinoline (3340-CN)
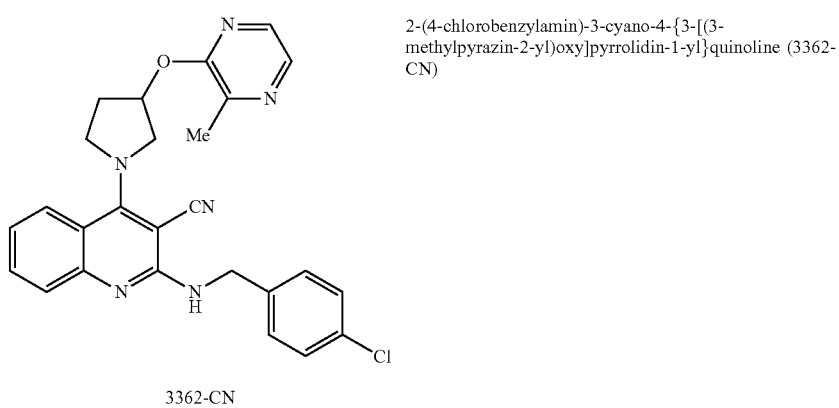
3362-CN
2-(4-chlorobenzylamin)-3-cyano-4-{3-[(3-methylpyrazin-2-yl)oxy]pyrrolidin-1-yl}quinoline (3362-CN)
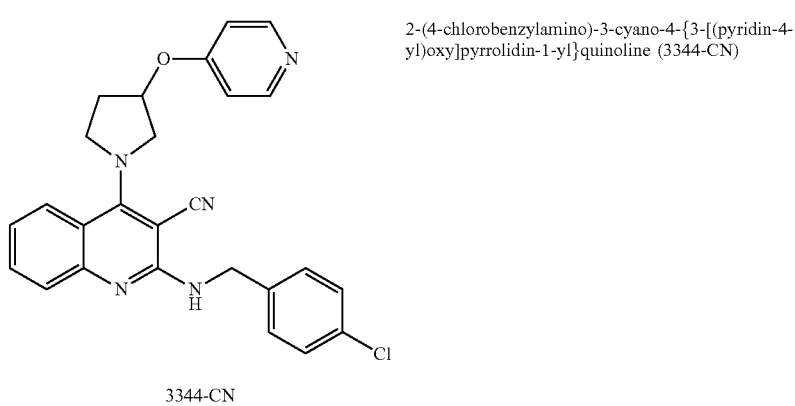
3344-CN
2-(4-chlorobenzylamino)-3-cyano-4-{3-[(pyridin-4-yl)oxy]pyrrolidin-1-yl}quinoline (3344-CN)

Analytical Data

TABLE 7

Analytical data

| ID | HPLC/MS[a] | Rt[b] (min) | [M − HCl] MH+ (Da) | HPLC/UV[c] | Rt[b] (min) | $^1$H NMR[d] | $^{13}$C NMR[e] | IR cm[−1] |
|---|---|---|---|---|---|---|---|---|
| 116 | 1 | 2.78 | 393 | | | 1 | | |
| 118 | 1 | 3.39 | 409 | | | 1 | | |
| 212 | 1 | 3.35 | 437 | | | 1 | | |
| 214 | 1 | 3.16 | 451 | | | 1 | | |
| 216 | 1 | 3.33 | 465 | | | 1 | | |
| 220 | 1 | 3.38 | 479 | | | 1 | | |
| 348 | 2 | 1.13 | 441 | 3 | 7.16 | 2 | | X |
| 350 | 2 | 0.99 | 437 | 3 | 7.15 | 2 | | X |
| 354 | 2 | 1.68 | 481 | 3 | 7.69 | 2 | X | X |
| 564 | 2 | 1.0 | 564 | 3 | 7.20 | 2 | 2 | X |
| 568 | 2 | 1.01 | 455 | 3 | 6.85 | 2 | X | X |
| 572 | 2 | 1.02 | 455 | 3 | 7.87 | 2 | 2 | X |
| 580 | 2 | 0.96 | 455 | 3 | 6.52 | 2 | X | X |
| 1598 | 1 | 3.74 | 409 | | | 1 | | |
| 1604 | 1 | 4.06 | 451 | | | 1 | | |
| 1648 | 1 | 3.93 | 449 | | | 1 | | |
| 1656 | 1 | 3.38 | 478 | | | 1 | | |
| 2308 | 1 | 3.71 | 368 | | | 1 | | |
| 2310 | 1 | 4.01 | 382 | | | 1 | | |
| 2380 | 1 | 3.92 | 368 | | | 1 | | |
| 2916 | 1 | 3.72 | 368 | | | 1 | | |
| 2916 | 2 | 2.52 | 368 | 3 | 6.92 | 2 | 2 | X |
| 2918 | 1 | 4.39 | 410 | | | 1 | | |
| 2940 | 1 | 4.54 | 444 | | | 1 | | |
| 2946 | 1 | 4.63 | 458 | | | 1 | | |
| 2950 | 1 | 3.34 | 445 | | | 1 | | |
| 2962 | 1 | 4.08 | 446 | | | 1 | | |
| 2988 | 1 | 3.63 | 354 | | | 1 | | |
| 3012 | 1 | 4.28 | 430 | | | 1 | | |
| 3026 | 1 | 4.22 | 431 | | | 1 | | |
| 3060 | 1 | 3.65 | 354 | | | 1 | | |
| 3098 | 1 | 4.17 | 431 | | | 1 | | |
| 532-Me | 6 | 1.26 | 496 | 3 | 6.00 | 2 | | |
| 540-Me | 4 | 1.63 | 550 | 3 | 7.01 | 2 | | X |
| 352-CN | 2 | 1.83 | 446 | 3 | 7.53 | 2 | | X |
| 498-CN | 4 | 1.65 | 598 | 4 | 6.10 | 2 | | |
| 500-CN | 2 | 1.05 | 521 | 3 | 6.06 | 1 | | |
| 502-CN | 2 | 1.40 | 535[#] | 3 | 6.57 | 1 | | X |
| 510-CN | 6 | 1.37 | 276 | 3 | 6.96 | 2 | | X |
| 512-CN | 6 | 1.52 | 575 | 3 | 7.11 | 2 | | X |
| 522-CN | 6 | 1.34 | 584 | 3 | 5.94 | 2 | | X |
| 524-CN | 6 | 1.49 | 609 | 3 | 6.36 | 2 | | |
| 532-CN | 2 | 1.63 | 505 | 3 | 5.89 | 2 | | X |
| 534-CN | 4 | 1.82 | 575 | 3 | 6.90 | 2 | | X |
| 538-CN | 2 | 2.80 | 575 | 3 | 7.27 | 1 | | X |
| 540-CN | 2 | 1.85 | 559 | 3 | 7.21 | 2 | | X |
| 3131CN | 6 | 1.39 | 584 | 3 | 5.80 | 2 | | X |
| 540-F | 4 | 1.61 | 554 | 3 | 7.54 | 2 | | X |
| 204-F | 10 | 1.60 | 425 | 9 | 4.48 | 2 | 2 | X |
| 240-CN | 10 | 1.78 | 432 | 9 | 4.59 | 2 | 2 | X |
| 414-CN | 10 | 2.19 | 462 | 9 | 5.50 | 2 | 2 | X |
| 416-CN | 10 | 1.91 | 462 | 9 | 5.24 | 2 | 2 | X |
| 418-CN | 10 | 1.94 | 462 | 9 | 5.13 | 2 | 2 | X |
| 3156-CN | 10 | 1.82 | 392 | 9 | 4.68 | 2 | 2 | X |
| 3158-CN | 10 | 1.89 | 406 | 9 | 4.63 | 2 | — | X |
| 3160-CN | 10 | 1.93 | 434 | 9 | 5.14 | 2 | 2 | X |
| 154-CN | 10 | 2.43 | 492 | 9 | 6.25 | 2 | 2 | X |
| 162-CN | 10 | 2.01 | 460 | 9 | 5.48 | 2 | 2 | X |
| 168-CN | 10 | 1.97 | 476 | 9 | 5.39 | 2 | 2 | X |
| 3162-CN | 10 | 2.09 | 489 | 9 | 4.69 | 2 | 2 | X |
| 176-CN | 10 | 1.95 | 446 | 9 | 5.36 | 2 | 2 | X |
| 178-CN | 10 | 1.78 | 462 | 9 | 5.78 | 2 | 2 | X |
| 3168-CN | 10 | 1.81 | 475 | 9 | 5.10 | 2 | 2 | X |
| 3164-CN | 10 | 1.92 | 420 | 9 | 5.21 | 2 | 2 | X |
| 160-CN | 10 | 1.95 | 448 | 9 | 5.50 | 2 | 2 | X |
| 3170-CN | 10 | 1.73 | 392 | 9 | 4.48 | 2 | 2 | X |

TABLE 7-continued

| | | Analytical data | | | | | | |
|---|---|---|---|---|---|---|---|---|
| ID | HPLC/MS[a] | Rt[b] (min) | [M − HCl] MH+ (Da) | HPLC/UV[c] | Rt[b] (min) | $^1$H NMR[d] | $^{13}$C NMR[e] | IR cm$^{-1}$ |
| 3172-CN | 10 | 1.77 | 406 | 9 | 4.79 | 2 | 2 | X |
| 3174-CN | 10 | 1.84 | 434 | 9 | 4.88 | 2 | 2 | X |
| 352-CN | 10 | 1.84 | 448 | 9 | 4.76 | 2 | 2 | X |
| 182-CN | 10 | 2.36 | 492 | 9 | 6.17 | 2 | 2 | X |
| 3178-CN | 10 | 1.89 | 460 | 9 | 5.00 | 2 | 2 | X |
| 3180-CN | 10 | 1.83 | 476 | 9 | 4.97 | 2 | 2 | X |
| 3182-CN | 11 | 6.16 | 487[#] | 9 | 4.58 | 2 | 2 | X |
| 200-CN | 10 | 1.83 | 446 | 12 | 4.86 | 2 | 2 | X |
| 202-CN | 10 | 1.90 | 462 | 12 | 11.25 | 2 | 2 | X |
| 3188-CN | 13 | 3.05 | 476 | 9 | 4.89 | 2 | 2 | X |
| 3184-CN | 10 | 1.53 | 406 | 9 | 5.32 | 2 | 2 | X |
| 184-CN | 10 | 1.86 | 448 | 9 | 4.68 | 2 | 2 | X |
| 3190-CN | 11 | 6.08 | 378 | 9 | 4.96 | 2 | 2 | X |
| 3192-CN | 10 | 1.51 | 392 | 9 | 5.59 | 2 | 2 | X |
| 134-CN | 10 | 1.64 | 446 | 9 | 5.47 | 2 | 2 | X |
| 136-CN | 11 | 6.45 | 462 | 9 | 5.15 | 2 | 2 | X |
| 148-CN | 10 | 1.55 | 432 | 9 | 5.48 | 2 | 2 | X |
| 150-CN | 10 | 1.59 | 448 | 9 | 5.38 | 2 | 2 | X |
| 3200-CN | 10 | 1.52 | 461 | 9 | 4.79 | 2 | 2 | X |
| 3202-CN | 10 | 1.53 | 406 | 9 | 5.31 | 2 | 2 | X |
| 126-CN | 10 | 1.63 | 434 | 9 | 5.56 | 2 | 2 | X |
| 3206-CN | 10 | 2.59 | 469 | 9 | 6.60 | 2 | 2 | X |
| 3232-CN | 10 | 2.51 | 499 | 9 | 6.46 | 2 | 2 | X |
| 3234-CN | 10 | 2.66 | 483 | 9 | 7.41 | 2 | 2 | X |
| 3238-CN | 10 | 2.57 | 487 | 9 | 6.57 | 2 | 2 | X |
| 3240-CN | 10 | 2.62 | 487 | 9 | 6.23 | 2 | 2 | X |
| 3328-CN | 10 | 2.43 | 485 | 9 | 6.23 | 2 | 2 | X |
| 2940-CN | 10 | 2.57 | 469 | 9 | 6.63 | 2 | 2 | X |
| 3224-CN | 10 | 2.53 | 499 | 9 | 6.53 | 2 | 2 | X |
| 2944-CN | 10 | 2.66 | 483 | 9 | 6.91 | 2 | 2 | X |
| 3226-CN | 11 | 2.68 | 503 | 9 | 6.87 | 2 | 2 | X |
| 2942-CN | 10 | 2.53 | 487 | 9 | 6.62 | 2 | 2 | X |
| 3228-CN | 10 | 2.60 | 487 | 9 | 6.69 | 2 | 2 | X |
| 2950-CN | 10 | 1.92 | 470 | 9 | 5.68 | 2 | 2 | X |
| 2978-CN | 14 | 2.95 | 474 | 9 | 6.19 | 2 | 2 | X |
| 2970-CN | 10 | 2.42 | 485 | 9 | 6.30 | 2 | 2 | X |
| 3330-CN | 10 | 2.08 | 455 | 9 | 6.30 | 2 | 2 | X |
| 3332-CN | 10 | 2.15 | 469 | 9 | 6.50 | 2 | 2 | X |
| 3334-CN | 10 | 2.04 | 485 | 9 | 6.19 | 2 | 2 | X |
| 3336-CN | 10 | 2.16 | 489 | 9 | 6.53 | 2 | 2 | X |
| 3338-CN | 10 | 2.08 | 473 | 9 | 6.30 | 2 | 2 | X |
| 3340-CN | 10 | 2.10 | 473 | 9 | 6.26 | 2 | 2 | X |

TABLE 7-continued

| | Analytical data | | | | | | | |
|---|---|---|---|---|---|---|---|---|
| ID | HPLC/MS[a] | Rt[b] (min) | [M − HCl] MH+ (Da) | HPLC/UV[c] | Rt[b] (min) | $^1$H NMR[d] | $^{13}$C NMR[e] | IR cm$^{-1}$ |
| 3362-CN | 10 | 1.90 | 471 | 9 | 5.89 | 2 | 2 | X |
| 3344-CN | 10 | 1.55 | 456 | 9 | 5.39 | 2 | — | X |
| 3246-CN | 10 | 1.70 | 400 | 9 | 4.42 | 2 | 2 | X |
| 3248-CN | 10 | 1.77 | 414 | 9 | 4.61 | 2 | 2 | X |
| 3250-CN | 10 | 1.84 | 432 | 9 | 5.09 | 2 | 2 | X |
| 3252-CN | 10 | 1.58 | 430 | 9 | 4.28 | 2 | 2 | X |
| 3254-CN | 10 | 1.96 | 468 | 9 | 4.63 | 2 | 2 | X |
| 3256-CN | 10 | 2.04 | 468 | 9 | 5.29 | 2 | 2 | X |
| 3258-CN | 11 | 6.91 | 434 | 9 | 4.92 | 2 | 2 | X |
| 3260-CN | 10 | 1.75 | 418 | 9 | 4.47 | 2 | 2 | X |
| 3262-CN | 10 | 1.88 | 418 | 9 | 4.51 | 2 | 2 | X |
| 3264-CN | 10 | 1.92 | 436 | 9 | 4.55 | 2 | 2 | X |
| 3266-CN | 10 | 2.08 | 484 | 9 | 5.04 | 2 | 2 | X |
| 3268-CN | 10 | 1.60 | 404 | 9 | 3.37 | 2 | 2 | X |
| 3270-CN | 10 | 1.59 | 405 | 9 | 3.40 | 2 | 2 | X |
| 3274-CN | 10 | 1.60 | 419 | 9 | 3.57 | 2 | 2 | X |
| 3276-CN | 10 | 1.65 | 521 | 9 | 4.36 | 2 | 2 | X |
| 3278-CN | 10 | 1.37 | 401 | 9 | 3.78 | 2 | 2 | X |
| 3280-CN | 10 | 1.29 | 402 | 9 | 3.00 | 2 | — | X |
| 3282-CN | 10 | 1.37 | 402 | 9 | 3.23 | 2 | 2 | X |
| 3284-CN | 10 | 1.49 | 402 | 9 | 3.72 | 2 | 2 | X |
| 3286-CN | 10 | 1.71 | 414 | 9 | 4.70 | 2 | 2 | X |
| 3288-CN | 10 | 1.83 | 428 | 9 | 4.89 | 2 | 2 | X |
| 3290-CN | 10 | 1.65 | 444 | 9 | 4.38 | 2 | 2 | X |
| 3292-CN | 10 | 2.00 | 482 | 9 | 5.12 | 2 | 2 | X |
| 3298-CN | 10 | 2.03 | 482 | 9 | 4.86 | 2 | 2 | X |
| 3300-CN | 10 | 1.66 | 458 | 9 | 4.66 | 2 | 2 | X |
| 3302-CN | 10 | 1.57 | 404 | 9 | 4.58 | 2 | 2 | X |
| 3304-CN | 10 | 1.34 | 415 | 9 | 3.89 | 2 | 2 | X |
| 3306-CN | 10 | 1.32 | 415 | 9 | 3.92 | 2 | 2 | X |
| 3308-CN | 10 | 1.39 | 415 | 9 | 3.97 | 2 | 2 | X |

[a] HPLC/MS analytical method used,
[b] Rt: Retention time in minute,
[c] HPLC/UV analytical method used,
[d] NMR $^1$H method,
[e] NMR $^{13}$C method,
[M − 2 HCl] MH+, the cross "X" in column of IR or NMR, means that corresponding data are available.

III. Biological Evaluation

Example 5: Activity Profile of Compounds of the Present Invention in HepG2, Huh-7, HCT-116, A375, MOLM-14, 786-O Cell Lines Cell Culture:

All cell lines were maintained in medium containing 1% penicillin-streptomycin (Dutscher, P06-07100) and 10% Fetal Bovine Serum (Hyclone Dutscher, RZK35922) cultured at 37° C. with 5% $CO_2$. HepG2 (hepatocellular carcinoma), cell line was cultured in Dulbecco's modified Eagle's medium low glucose (Gibco, 21885025), Huh7 (hepatocellular carcinoma), HCT-116 (colorectal carcinoma), PANC-1 (prancreatic carcinoma) and A375 (malignant melanoma) cell lines were cultured in Dulbecco's modified Eagle's medium (Dutscher, L0103). MOLM-14 (acute myeloid leukemia) cell line was maintained in MEM alpha medium (Gibco, 22561-021). 786-0 (renal adenocarcinoma) cell lines were maintained in RPMI 1640 medium (Dutscher, L0498).

Cell Viability Assay:

Cell viability was measured using the CellTiter-Glo® luminescent cell viability assay as described by the manufacturer (Promega, Ref G7571) using an Infinite $F_{200}$Pro luminometer (Tecan). Briefly, for adherent cells, cells were plated onto 96-well plates (white with clear bottom) in 90 µL of media per well and were allowed to grow overnight before the assay. For cells growing in suspension, cells were plated onto 96-well plates 1 h before the assay. The number of cells seeded per well is indicated in the table 8 below:

TABLE 8

Number of cells seeded per well for cell viability assays

| Entry | Cell lines | Cells number per well |
|---|---|---|
| 1 | HCT-116 | 2,000 |
| 2 | A375 | 1,600 |
| 3 | Huh7 | 10,000 |
| 4 | HepG2 | 7,500 |
| 5 | MOLM-14 | 10,000 |
| 6 | 786-O | 1,250 |
| 7 | PANC-1 | 5000 |

Compounds were resuspended in $H_2O$ or DMSO and added at different concentrations to each well, and cell cultures were incubated for 72 h. Each diluent ($H_2O$ or DMSO) were used as a control, and all compounds were tested in a constant percentage of $H_2O$ or DMSO. On the day of the reading, plates are equilibrated 30 min at room temperature before the addition of 100 µL of CellTiter-Glo® and luminescence was measured using an Infinite $F_{200}$Pro (Tecan). % cell viability were expressed as a percentage of the signal obtained for cell cultures treated with diluent. $EC_{50}$ values were determined as the dose of compound required to reduce luminescent values to 50% of the signal obtained for cell cultures treated with diluent. The experimental data were analyzed using a computer program, Graphpad Prism v5 (GraphPad Software, Inc. La Jolla, Calif.). All points were at least done in duplicate.

Tables 9 and 9a below shows the $EC_{50}$ ranges of compounds as determined by the above method when tested against the following cancer cell lines: MOLM-14; A375; HCT-116; Huh7; PANC-1; 786-0; HepG2, respectively.

The results are shown in below:
A represents an $EC_{50}$ value in the range of ≤10 µM to >5 µM
B represents an $EC_{50}$ value in the range of ≤5 µM to >0.5 µM
C represents an $EC_{50}$ value in the range of ≤0.5 µM to >0.05 µM

TABLE 9

Example of growth inhibition assay of MOLM14, A375, HCT-166, Huh7, 786-O and HepG2 cell lines ($EC_{50}$, µM)

| Compound ID | MOLM-14 | A375 | HCT-116 | Huh7 | 786-O | HepG2 |
|---|---|---|---|---|---|---|
| 116 | B | B | B | B | B | B |
| 118 | A | A | A | A | B | A |
| 212 | A | B | B | A | A | B |
| 348 | B | B | B | A | B | B |
| 350 | A | B | B | A | B | B |
| 352 | B | B | B | A | B | A |
| 354 | B | B | B | B | B | A |
| 500CN | A | A | B | A | A | A |
| 502CN | A | B | B | A | B | B |
| 532CN | A | B | B | A | B | A |
| 538CN | A | B | B | A | A | B |
| 540CN | B | B | B | B | B | A |
| 564 | B | B | B | A | B | B |
| 568 | B | B | B | A | B | B |
| 572 | B | B | B | B | B | B |
| 580 | B | B | B | ND | B | B |
| 1598 | A | A | B | B | A | B |
| 1604 | A | A | A | B | A | B |
| 1648 | ND | ND | ND | B | ND | ND |
| 1656 | B | B | B | B | B | B |
| 2308 | B | B | A | B | A | B |
| 2310 | B | B | B | B | B | B |
| 2380 | B | B | B | B | A | B |
| 2916 | ND | A | A | B | A | B |
| 2918 | B | A | B | A | A | B |
| 2940 | B | B | B | A | B | B |
| 2946 | A | B | A | A | A | A |
| 2950 | B | B | B | B | B | B |
| 2958 | B | A | A | B | A | B |
| 2988 | B | B | A | B | B | B |
| 3012 | B | B | B | B | B | B |
| 3026 | B | B | B | B | B | B |
| 3060 | B | B | B | B | A | B |
| 3098 | B | B | B | B | B | B |
| 240F | A | A | A | A | A | A |
| 240CN | A | B | B | B | A | B |
| 414CN | B | B | B | B | B | B |
| 416CN | B | B | B | B | B | B |
| 418CN | B | B | B | B | B | B |
| 3156CN | A | B | B | B | B | B |
| 3158CN | A | B | B | A | A | B |
| 3160CN | A | B | B | A | A | B |
| 162CN | B | B | B | B | B | B |
| 168CN | A | B | A | A | A | A |
| 3162CN | B | B | B | B | B | B |
| 3168CN | A | B | B | B | B | A |
| 3170CN | B | B | B | B | B | B |
| 3172CN | B | B | B | B | B | B |
| 3174CN | B | B | B | B | B | B |
| 3178CN | B | B | B | B | B | B |
| 3180CN | A | A | A | A | A | A |
| 3182CN | B | B | B | B | C | B |
| 200CN | B | B | B | A | B | A |
| 3188CN | B | B | B | B | B | B |
| 3184CN | B | B | B | B | B | B |
| 184CN | A | B | A | A | A | A |
| 3190CN | A | A | A | A | A | A |
| 3192CN | A | B | B | B | B | B |
| 3200CN | A | A | A | A | A | A |
| 3246CN | A | B | B | B | A | B |
| 3250CN | A | B | B | A | B | B |
| 3252CN | B | B | B | A | B | A |
| 3254CN | A | B | B | B | B | B |
| 3258CN | B | B | B | B | B | B |
| 3260CN | A | B | B | A | B | B |

TABLE 9-continued

Example of growth inhibition assay of MOLM14, A375, HCT-166, Huh7, 786-O and HepG2 cell lines (EC$_{50}$, μM)

| Compound ID | MOLM-14 | A375 | HCT-116 | Huh7 | 786-O | HepG2 |
|---|---|---|---|---|---|---|
| 3262CN | A | A | B | A | B | A |
| 3264CN | B | ND | B | B | B | B |
| 3270CN | B | B | ND | A | A | B |
| 3276CN | B | B | B | B | B | B |
| 3286CN | A | B | A | A | A | A |
| 3288CN | B | B | B | B | B | B |
| 3290CN | A | B | B | B | A | B |
| 3292CN | A | B | B | B | B | B |
| 3298CN | B | B | B | B | B | B |
| 3300CN | A | B | B | A | A | A |

TABLE 9a

Example of growth inhibition assay of PANC-1 cell line (EC$_{50}$, μM)
PANC-1 Cell line (EC$_{50}$)

| Compound ID | EC$_{50}$ |
|---|---|
| 240F | A |
| 240CN | A |
| 414CN | A |
| 416CN | A |
| 418CN | A |
| 3156CN | A |
| 3158CN | A |
| 3160CN | A |
| 168CN | A |
| 3168CN | A |
| 3170CN | A |
| 3172CN | A |
| 3174CN | A |
| 3178CN | A |
| 3180CN | A |
| 200CN | A |
| 3188CN | A |
| 3184CN | A |
| 184CN | A |
| 3192CN | A |
| 3246CN | A |
| 3250CN | A |
| 3252CN | A |
| 3254CN | A |
| 3260CN | A |
| 3286CN | A |
| 3288CN | A |
| 3290CN | A |
| 3292CN | A |
| 3298CN | A |
| 3300CN | A |

TABLE 10

Example of growth inhibition assay of MOLM14, A375, HCT-166, Huh7, 786-O and HepG2 cell lines (Double screening testing concentrations, 4 and 10 μM)

Cell lines, % Cell viability at 10 μM and 4 μM

| ID | MOLM-14 10 μM | MOLM-14 4 μM | A375 10 μM | A375 4 μM | HCT-116 10 μM | HCT-116 4 μM | Huh7 10 μM | Huh7 4 μM | 786-O 10 μM | 786-O 4 μM | HepG 10 μM | HepG 4 μM |
|---|---|---|---|---|---|---|---|---|---|---|---|---|
| 214 | 16.4 | 26.8 | 0.4 | 0.4 | 0.3 | 0.2 | 0.4 | 43.0 | 0.4 | 6.5 | 0.4 | 0.3 |
| 216 | 0.5 | 86.7 | 0.4 | 78.1 | 0.3 | 15.5 | 0.5 | 74.1 | 0.5 | 78.4 | 0.4 | 30.4 |
| 220 | 52.6 | 78.9 | 0.3 | 76.3 | 0.3 | 60.9 | 0.3 | 81.5 | 0.4 | 74.6 | 31 | 79.6 |
| 498CN | 0.2 | 0.3 | 0.1 | 0.2 | 0.1 | 0.2 | 0.2 | 58.5 | 0.1 | 0.2 | 0.1 | 0.2 |
| 510CN | 0.2 | 74.5 | 0.1 | 57.4 | 0.1 | 24.8 | 0.3 | 62.6 | 0.1 | 2.8 | 0.1 | 54.6 |
| 512CN | 0.3 | 0.2 | 0.2 | 0.3 | 0.2 | 0.2 | 0.3 | 0.2 | 0.2 | 0.2 | 0.2 | 0.2 |
| 522CN | 0.3 | 0.3 | 0.3 | 0.3 | 0.2 | 0.3 | 0.4 | 0.4 | 0.2 | 0.2 | 0.2 | 0.3 |
| 532Me | 0.4 | 65.5 | 0.3 | 23.3 | 0.3 | 16.0 | 0.5 | 55.9 | 0.3 | 0.3 | 0.3 | 12.3 |
| 534CN | 0.3 | 0.4 | 0.2 | 0.4 | 0.2 | 0.4 | 0.4 | 49.1 | 0.2 | 2.1 | 0.2 | 13.0 |
| 540F | 0.3 | 8.8 | 0.3 | 0.4 | 0.3 | 0.4 | 59.4 | 43.3 | 0.3 | 0.8 | 0.2 | 0.3 |
| 540Me | 0.3 | 63.1 | 0.1 | 1.6 | 0.1 | 0.4 | 0.2 | 63.9 | 0.1 | 2.6 | 0.1 | 38.3 |
| 3131CN | 7.3 | 80.1 | 0.1 | 79.4 | 0.1 | 63.9 | 69.8 | 87.0 | 0.1 | 42.6 | 0.1 | 80.6 |
| 240F | 50.8 | 83.4 | 0.2 | 73.6 | 0.2 | 49.6 | 2.5 | 70.5 | 28.7 | 94.7 | 0.1 | 46.1 |
| 240CN | 0.5 | 100 | 0.3 | 64.5 | 0.3 | 55.2 | 0.4 | 80.0 | 0.7 | 77.2 | 0.4 | 86.7 |
| 414CN | 0.3 | 0.5 | 0.4 | 0.3 | 0.3 | 0.3 | 0.5 | 79.8 | 0.3 | 0.7 | 0.5 | 9.0 |
| 416CN | 0.4 | 37.9 | 0.4 | 0.4 | 0.3 | 0.3 | 0.6 | 75.5 | 0.3 | 0.4 | 0.5 | 61.9 |
| 418CN | 0.3 | 3.8 | 0.3 | 0.3 | 0.2 | 0.2 | 0.2 | 50.5 | 0.2 | 0.9 | 0.2 | 5.0 |
| 3156CN | 0.6 | 92.8 | 0.4 | 10.0 | 0.5 | 52.0 | 0.6 | 83.0 | 0.6 | 77.8 | 0.5 | 32.6 |
| 3158CN | 0.6 | 91.5 | 0.3 | 70.9 | 0.4 | 74.2 | 0.5 | 86.4 | 0.5 | 88.4 | 0.4 | 84.6 |
| 3160CN | 0.6 | 88.7 | 0.4 | 18.2 | 0.4 | 57.7 | 0.5 | 80.8 | 0.5 | 65.2 | 0.5 | 62.1 |
| 154CN | 113 | 112 | 88.5 | 96.2 | 87.2 | 98.8 | 93.5 | 101 | 82.3 | 94.1 | 97.5 | 105 |
| 162CN | 0.3 | 45.6 | 0.2 | 0.4 | 0.1 | 0.8 | 0.2 | 37.1 | 0.2 | 12.0 | 0.1 | 0.3 |
| 168CN | 0.4 | 74.5 | 0.4 | 74.0 | 0.2 | 60.7 | 0.5 | 83.0 | 0.3 | 74.2 | 0.4 | 79.8 |
| 3162CN | 0.3 | 0.5 | 0.2 | 0.4 | 0.2 | 0.3 | 0.2 | 0.5 | 0.3 | 0.5 | 0.2 | 0.3 |
| 176CN | 75.2 | 95.6 | 65.4 | 114 | 42.7 | 84.3 | 64.7 | 96.4 | 39.3 | 89.8 | 60.2 | 93.0 |
| 178CN | 106 | 123 | 80.2 | 95.5 | 77.0 | 95.7 | 81.9 | 95.3 | 88.9 | 99.6 | 97.5 | 101 |
| 3168CN | 0.8 | 105 | 0.8 | 61.0 | 0.5 | 40.7 | 0.7 | 80.1 | 0.6 | 75.4 | 0.6 | 87.8 |
| 3164CN | 74.6 | 113 | 39.3 | 89.2 | 38.4 | 91.2 | 51.1 | 91.9 | 64.1 | 97.1 | 52.9 | 101 |
| 160CN | 94.5 | 106 | 47.9 | 86.6 | 47.3 | 86.4 | 62.3 | 89.5 | 40.0 | 94.9 | 48.3 | 94.5 |
| 3170CN | 0.4 | 84.2 | 0.3 | 0.5 | 0.2 | 0.7 | 0.4 | 79.4 | 0.4 | 36.5 | 0.3 | 0.6 |
| 3172CN | 0.4 | 0.5 | 0.3 | 0.4 | 0.1 | 0.2 | 0.4 | 30.7 | 0.3 | 0.5 | 0.4 | 0.5 |
| 3174CN | 0.3 | 24.4 | 0.2 | 0.3 | 0.1 | 0.3 | 0.3 | 62.9 | 0.2 | 3.6 | 0.2 | 0.5 |

TABLE 10-continued

Example of growth inhibition assay of MOLM14, A375, HCT-166, Huh7, 786-O and HepG2 cell lines (Double screening testing concentrations, 4 and 10 μM)

Cell lines, % Cell viability at 10 μM and 4 μM

| ID | MOLM-14 10 μM | MOLM-14 4 μM | A375 10 μM | A375 4 μM | HCT-116 10 μM | HCT-116 4 μM | Huh7 10 μM | Huh7 4 μM | 786-O 10 μM | 786-O 4 μM | HepG 10 μM | HepG 4 μM |
|---|---|---|---|---|---|---|---|---|---|---|---|---|
| 352CN | 0.6 | 76.9 | 0.5 | 29.1 | 0.5 | 43.9 | 0.6 | 73.2 | 0.5 | 52.4 | 0.6 | 71.2 |
| 182CN | 48.7 | 86.9 | 90.2 | 94.4 | 47.7 | 66.9 | 76.2 | 86.0 | 83.9 | 89.9 | 89.8 | 91.6 |
| 3178CN | 0.7 | 90.4 | 0.5 | 0.4 | 0.4 | 0.3 | 0.6 | 58.8 | 0.5 | 1.3 | 0.5 | 6.0 |
| 3180CN | 22.7 | 92.3 | 0.3 | 88.6 | 0.2 | 59.5 | 0.4 | 76.5 | 0.4 | 69.7 | 0.4 | 78.4 |
| 3182CN | 0.4 | 0.6 | 0.4 | 0.5 | 0.3 | 0.5 | 0.4 | 0.6 | 0.4 | 0.6 | 0.3 | 0.5 |
| 200CN | 0.4 | 92.7 | 0.4 | 65.9 | 0.5 | 78.1 | 0.7 | 83.1 | 2.2 | 74.8 | 0.9 | 90.8 |
| 202CN | 64.2 | 112 | 79.2 | 96.9 | 33.5 | 65.8 | 56.1 | 83.6 | 51.9 | 66.3 | 51.1 | 80.2 |
| 3188CN | 0.7 | 108 | 0.4 | 52.8 | 0.5 | 42.9 | 0.6 | 85.2 | 0.5 | 64.0 | 0.6 | 82.7 |
| 3184CN | 0.6 | 71.8 | 0.5 | 59.5 | 0.5 | 60.5 | 0.6 | 77.4 | 0.7 | 54.1 | 0.7 | 72.9 |
| 184CN | 0.7 | 95.1 | 0.8 | 53.7 | 0.9 | 65.7 | 0.7 | 74.7 | 1.1 | 72.6 | 0.8 | 72.4 |
| 3190CN | 2.1 | 78.1 | 0.8 | 87.3 | 0.4 | 75.2 | 1.3 | 92.7 | 1.6 | 90.6 | 16.0 | 95.5 |
| 3192CN | 0.3 | 0.6 | 0.4 | 104 | 0.2 | 57.3 | 0.4 | 78.0 | 0.2 | 0.4 | 0.4 | 59.5 |
| 134CN | 89.5 | 100 | 29.1 | 79.9 | 50.6 | 88.5 | 70.5 | 85.3 | 64.0 | 92.8 | 81.3 | 101 |
| 136CN | 32.0 | 95.7 | 17.4 | 110 | 17.4 | 73.3 | 50.5 | 87.6 | 21.8 | 75.7 | 44.1 | 88.6 |
| 148CN | 94.7 | 92.9 | 93.2 | 94.1 | 92.2 | 93.5 | 80.8 | 91.9 | 67.0 | 88.2 | 91.9 | 104 |
| 150CN | 114 | 109 | 96.8 | 97.9 | 95.1 | 99.5 | 90.4 | 93.8 | 91.4 | 96.1 | 103 | 100 |
| 3200CN | 0.4 | 97.1 | 0.3 | 47.3 | 0.4 | 35.1 | 0.4 | 80.6 | 0.4 | 41.7 | 0.3 | 71.8 |
| 3202CN | 82.6 | 98.7 | 70.5 | 84.5 | 62.4 | 93.7 | 61.5 | 91.1 | 74.7 | 92.9 | 81.0 | 104 |
| 126CN | 99.6 | 105 | 89.9 | 92.5 | 93.3 | 97.0 | 96.1 | 98.9 | 87.6 | 91.2 | 102 | 104 |
| 3206CN | 107 | 96.0 | 104 | 111 | 91.2 | 97.9 | 95.1 | 107 | 75.1 | 79.9 | 65.0 | 72.4 |
| 3232CN | 99.8 | 91.1 | 99.4 | 104 | 82.9 | 93.9 | 90.3 | 98.7 | 73.5 | 79.9 | 72.3 | 79.9 |
| 3234CN | 92.0 | 94.4 | 102 | 107 | 90.7 | 93.8 | 95.5 | 99.2 | 80.5 | 89.8 | ND | 89.8 |
| 3236CN | ND | ND | ND | ND | ND | ND | ND | ND | ND | ND | 83.7 | ND |
| 3238CN | 91.6 | 101 | 102 | 106 | 85.1 | 97.8 | 93.7 | 97.7 | 86.1 | 90.7 | 90.8 | 95.9 |
| 3240CN | 113 | 106 | 94.9 | 95.6 | 95.8 | 99.4 | 113 | 123 | 94.5 | 98.2 | ND | 97.0 |
| 2940CN | 89.1 | 102 | 98.3 | 104 | 82.9 | 92.9 | 88.9 | 97.3 | 91.7 | 97.1 | 79.4 | 89.7 |
| 3224CN | 94.6 | 112 | 91.7 | 96.0 | 65.1 | 89.8 | 90.0 | 116 | 88.9 | 96.3 | 70.0 | 91.6 |
| 2944CN | 92.1 | 104 | 87.1 | 96.9 | 29.1 | 32.8 | 89.0 | 93.9 | 95.5 | 96.0 | 84.0 | 107 |
| 3226CN | 97.8 | 101 | 94.1 | 97.8 | 86.8 | 96.8 | 109 | 117 | 89.8 | 96.0 | 82.8 | 94.0 |
| 2942CN | 88.1 | 98.2 | 94.9 | 101 | 75.1 | 91.0 | 87.9 | 94.3 | 81.3 | 87.7 | 75.3 | 99.1 |
| 3228CN | 100 | 107 | 91.7 | 98.0 | 85.2 | 101 | 108 | 117 | 92.9 | 97.9 | 86.7 | 96.7 |
| 3328CN | 95.4 | 105 | 87.3 | 92.7 | 82.3 | 93.2 | 104 | 125 | 85.5 | 93.8 | 90.8 | 98.8 |
| 2978CN | 77.5 | 115 | 86.8 | 93.1 | 50.1 | 88.2 | 74.2 | 87.0 | 89.3 | 96.9 | 78.1 | 94.5 |
| 2970CN | 61.2 | 92.0 | 80.8 | 91.9 | 47.0 | 70.5 | 53.4 | 63.7 | 79.8 | 89.4 | 63.3 | 87.8 |
| 3330CN | 93.6 | 102 | 82.4 | 92.9 | 49.7 | 76.8 | 33.7 | 70.6 | 19.0 | 30.4 | 80.4 | 99.4 |
| 3332CN | 94.1 | 104 | 103 | 108 | 87.2 | 101 | 58.3 | 95.3 | 25.0 | 52.0 | 62.5 | 65.6 |
| 3334CN | 96.5 | 105 | 90.0 | 93.2 | 88.6 | 92.8 | 94.4 | 95.9 | 91.2 | 93.6 | 89.1 | 97.7 |
| 3336CN | 89.8 | 98.8 | 107 | 106 | 92.0 | 99.0 | 93.8 | 95.6 | 79.8 | 82.8 | 74.5 | 75.4 |
| 3338CN | 107 | 112 | 93.4 | 94.9 | 87.6 | 94.3 | 101 | 96.9 | 59.4 | 93.3 | 92.2 | 98.8 |
| 3340CN | 97.7 | 96.0 | 90.8 | 95.9 | 86.3 | 101 | 39.9 | 85.6 | 36.4 | 65.7 | 90.8 | 98.9 |
| 3344CN | 57.8 | 103 | 60.3 | 83.7 | 48.0 | 91.6 | 40.1 | 50.2 | 52.6 | 81.9 | 62.7 | 94.1 |
| 3362CN | 88.6 | 105 | 68.6 | 81.6 | 31.4 | 46.8 | 35.1 | 66.7 | 5.6 | 15.3 | 52.5 | 78.5 |
| 3246CN | 3.1 | 91.9 | 0.2 | 66.2 | 0.1 | 3.0 | 0.6 | 67.7 | 0.2 | 59.0 | 0.2 | 53.2 |
| 3248CN | 53.4 | 88.5 | 0.4 | 79.2 | 0.5 | 88.9 | 56.3 | 89.3 | 27.7 | 100 | 73.1 | 109 |
| 3250CN | 0.6 | 87.5 | 0.3 | 0.7 | 0.1 | 0.2 | 0.5 | 67.0 | 0.4 | 30.3 | 0.5 | 71.0 |
| 3252CN | 0.7 | 80.2 | 0.2 | 20.0 | 0.2 | 2.5 | 2.9 | 80.6 | 0.3 | 74.2 | 0.3 | 68.4 |
| 3254CN | 0.3 | 81.4 | 0.2 | 0.4 | 0.2 | 0.3 | 0.3 | 34.2 | 0.3 | 6.3 | 0.2 | 6.9 |
| 3256CN | 85.6 | 91.1 | 2.4 | 55.2 | 0.2 | 3.6 | 29.3 | 78.3 | 13.7 | 61.8 | 56.6 | 82.9 |
| 3258CN | 1.0 | 79.8 | 0.8 | 9.7 | 0.6 | 0.7 | 1.8 | 73.8 | 0.7 | 4.4 | 0.8 | 44.3 |
| 3260CN | 0.9 | 86.7 | 0.4 | 2.2 | 0.3 | 1.2 | 0.7 | 50.7 | 0.3 | 17.5 | 0.4 | 49.1 |
| 3262CN | 0.6 | 98.7 | 0.6 | 74.9 | 0.5 | 2.6 | 0.7 | 67.9 | 0.7 | 42.6 | 0.6 | 70.8 |
| 3264CN | 0.5 | 0.4 | 0.4 | 12.8 | 0.3 | 0.3 | 0.5 | 11.7 | 0.6 | 12.7 | 0.3 | 0.5 |
| 3266CN | 50.3 | 91.4 | 21.1 | 48.1 | 4.7 | 17.7 | 49.1 | 78.0 | 3.8 | 28.1 | 24.9 | 60.6 |
| 3268CN | 77.6 | 91.0 | 11.3 | 61.8 | 22.6 | 73.7 | 64.8 | 94.0 | 80.1 | 109 | 56.0 | 68.6 |
| 3270CN | 1.0 | 33.2 | 31.0 | 49.2 | 6.3 | 47.4 | 32.3 | 79.6 | 34.7 | 52.6 | 24.1 | 37.5 |
| 3272CN | 20.7 | 82.3 | 21.2 | 62.3 | 5.0 | 13.9 | 67.2 | 92.6 | 48.9 | 79.0 | 61.2 | 97.7 |
| 3274CN | 78.2 | 91.3 | 69.2 | 84.7 | 49.5 | 73.3 | 75.0 | 96.2 | 83.4 | 106 | 55.2 | 63.4 |
| 3276CN | 1.0 | 51.9 | 1.0 | 2.9 | 0.9 | 0.9 | 1.0 | 41.2 | 0.9 | 4.5 | 0.9 | 38.5 |
| 3278CN | 88.6 | 96.1 | 45.2 | 90.6 | 7.2 | 85.7 | 51.0 | 95.0 | 68.2 | 90.2 | 53.2 | 87.1 |
| 3282CN | 63.5 | 93.3 | 64.1 | 88.6 | 39.8 | 73.7 | 75.4 | 97.9 | 76.9 | 102 | 40.3 | 58.9 |
| 3284CN | 78.3 | 102 | 64.9 | 88.3 | 27.4 | 83.4 | 79.2 | 95.3 | 61.9 | 89.8 | 68.4 | 90.0 |
| 3286CN | 60.5 | 90.4 | 0.2 | 54.5 | 0.1 | 7.6 | 0.4 | 75.4 | 2.4 | 73.5 | 0.4 | 85.0 |
| 3288CN | 0.4 | 62.8 | 0.3 | 0.5 | 0.2 | 0.5 | 0.3 | 0.6 | 0.3 | 1.9 | 0.3 | 0.6 |
| 3290CN | 7.4 | 76.4 | 0.8 | 57.6 | 0.7 | 43.8 | 1.0 | 80.2 | 2.7 | 74.1 | 0.7 | 75.5 |
| 3292CN | 0.3 | 54.7 | 0.2 | 0.3 | 0.1 | 0.3 | 0.2 | 10.2 | 0.2 | 0.5 | 0.2 | 20.5 |
| 3298CN | 0.5 | 0.3 | 0.3 | 0.3 | 0.3 | 0.3 | 0.6 | 7.1 | 0.5 | 0.5 | 0.4 | 0.3 |
| 3300CN | 0.5 | 70.2 | 0.4 | 47.2 | 0.2 | 13.9 | 0.5 | 63.2 | 0.8 | 60.0 | 0.5 | 62.7 |
| 3302CN | 67.0 | 82.3 | 14.3 | 81.6 | 10.8 | 57.4 | 40.1 | 76.6 | 48.1 | 86.1 | 57.5 | 83.3 |
| 3304CN | 81.0 | 94.2 | 74.4 | 99.5 | 41.6 | 70.6 | 82.8 | 93.3 | 80.7 | 98.9 | 83.4 | 91.2 |

TABLE 10-continued

Example of growth inhibition assay of MOLM14, A375, HCT-166, Huh7, 786-O and HepG2 cell lines (Double screening testing concentrations, 4 and 10 μM)

| | Cell lines, % Cell viability at 10 μM and 4 μM | | | | | | | | | | | |
|---|---|---|---|---|---|---|---|---|---|---|---|---|
| | MOLM-14 | | A375 | | HCT-116 | | Huh7 | | 786-O | | HepG | |
| ID | 10 μM | 4 μM | 10 μM | 4 μM | 10 μM | 4 μM | 10 μM | 4 μM | 10 μM | 4 μM | 10 μM | 4 μM |
| 3306CN | 94.5 | 97.6 | 77.4 | 79.2 | 72.6 | 83.9 | 82.4 | 91.7 | 71.7 | 84.0 | 71.6 | 83.4 |
| 3308CN | 57.1 | 85.8 | 67.7 | 96.3 | 32.9 | 72.8 | 74.2 | 88.6 | 81.1 | 101 | 76.5 | 92.6 |

TABLE 10a

Example of growth inhibition assay of PANC-1 cell line (Double screening testing concentrations, 4 μM and 10 μM)

| | PANC-1, % Cell viability at 10 μM and 4 μM PANC-1 | |
|---|---|---|
| ID | 10 μM | 4 μM |
| 240F | 59.5 | 96.5 |
| 240CN | 30.0 | 98.3 |
| 414CN | 0.8 | 91.0 |
| 416CN | 0.7 | 100 |
| 418CN | 0.4 | 79.8 |
| 3156CN | 0.9 | 102 |
| 3158CN | 53.1 | 107 |
| 3160CN | 1.2 | 96.1 |
| 154CN | 99.0 | 107 |
| 162CN | 0.8 | 75.3 |
| 168CN | 41.5 | 92.0 |
| 3162CN | 0.4 | 51.6 |
| 176CN | 70.6 | 93.2 |
| 178CN | 96.6 | 100 |
| 3168CN | 22.3 | 100 |
| 3164CN | 69.6 | 98.7 |
| 160CN | 75.3 | 99.6 |
| 3170CN | 0.6 | 89.6 |
| 3172CN | 0.5 | 56.4 |
| 3174CN | 0.6 | 84.8 |
| 182CN | 95.3 | 100 |
| 3178CN | 0.8 | 85.8 |
| 3180CN | 58.9 | 94.9 |
| 3182CN | 0.5 | 0.8 |
| 200CN | 60.8 | 98.8 |
| 3188CN | 3.5 | 91.6 |
| 3184CN | 24.1 | 90.7 |
| 184CN | 46.6 | 91.8 |
| 3190CN | 56.1 | 93.7 |
| 3192CN | 1.5 | 77.1 |
| 134CN | 91.7 | 99.4 |
| 136CN | 63.6 | 91.7 |
| 148CN | 100 | 102 |
| 150CN | 101 | 101 |
| 3200CN | 38.4 | 90.2 |
| 3202CN | 81.5 | 96.1 |
| 126CN | 103 | 106 |
| 2944CN | 112 | 111 |
| 3246CN | 38.8 | 88.2 |
| 3250CN | 13.1 | 94.7 |
| 3252CN | 47.9 | 94.7 |
| 3254CN | 3.0 | 78.4 |
| 3256CN | 81.8 | 104 |
| 3260CN | 39.1 | 84.1 |
| 3262CN | 48.0 | 101 |
| 3264CN | 2.4 | 78.1 |
| 3268CN | 43.6 | 95.8 |
| 2940CN | 102 | 103 |
| 3272CN | 65.3 | 84.7 |
| 3274CN | 89.9 | 96.7 |
| 3278CN | 84.2 | 102 |
| 3282CN | 77.3 | 102 |
| 3284CN | 69.4 | 96.3 |
| 3286CN | 54.8 | 101 |
| 3288CN | 0.6 | 63.5 |
| 3290CN | 38.3 | 95.7 |
| 3292CN | 25.0 | 75.6 |
| 3298CN | 34.6 | 70.6 |
| 3300CN | 27.4 | 78.0 |
| 3302CN | 82.3 | 95.8 |
| 3304CN | 98.7 | 99.3 |
| 3306CN | 93.3 | 101 |
| 3308CN | 99.1 | 102 |

These results demonstrate the ability of the compounds of the present invention to effectively inhibit growth of various cancer cell lines.

Taken together, these data demonstrate that the compounds of the present invention have use as antiproliferative agents in particular as anti-neoplastic agents, more particularly as anticancer agents due to their ability to affect cell viability in various cancer cell lines.

The invention claimed is:

1. A compound having a structure represented by formula (I):

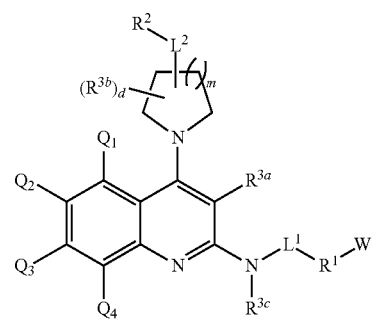

wherein
L¹ is a single bond, or substituted or unsubstituted alkylene, substituted or unsubstituted alkenylene, or substituted or unsubstituted alkynylene;
L² is a single bond or carbonyl;
R¹ is substituted or unsubstituted aryl, substituted or unsubstituted heteroaryl, substituted or unsubstituted arylene, or substituted or unsubstituted heteroarylene;

R² is hydroxyl, substituted or unsubstituted alkoxy, substituted or unsubstituted aryloxy, substituted or unsubstituted heteroaryloxy, substituted or unsubstituted alkoxycarbonylamino, substituted or unsubstituted aryloxycarbonylamino, substituted or unsubstituted heteroaryloxycarbonylamino, substituted or unsubstituted alkylaminocarbonylamino, substituted or unsubstituted arylaminocarbonylamino, substituted or unsubstituted heteroarylaminocarbonylamino, or NR⁵R⁶ wherein each R⁵ and R⁶ is independently H, substituted or unsubstituted alkyl, substituted or unsubstituted cycloalkyl, substituted or unsubstituted aryl, substituted or unsubstituted heteroaryl, or substituted or unsubstituted heterocycloalkyl;

$Q_1$, $Q_2$, $Q_3$ and $Q_4$ are each independently H, hydroxyl, halo, amino, nitro, thiol, carboxyl, cyano, azido, substituted or unsubstituted alkyl, substituted or unsubstituted alkenyl, substituted or unsubstituted alkynyl, substituted or unsubstituted cycloalkyl, substituted or unsubstituted cycloalkenyl, substituted or unsubstituted arylalkyl, substituted or unsubstituted heterocycloalkyl, substituted or unsubstituted aryl, substituted or unsubstituted heteroaryl, substituted or unsubstituted alkoxy, substituted or unsubstituted aryloxy, substituted or unsubstituted heteroaryloxy, substituted or unsubstituted sulfanyl, substituted or unsubstituted alkylamino, substituted or unsubstituted dialkylamino, substituted or unsubstituted arylamino, substituted or unsubstituted heteroarylamino, substituted or unsubstituted acyl, substituted or unsubstituted acylamino, substituted or unsubstituted aminocarbonyl, substituted or unsubstituted alkoxycarbonyl, substituted or unsubstituted aryloxycarbonyl, substituted or unsubstituted heteroaryloxycarbonyl, substituted sulfo, substituted sulfonyl, substituted sulfinyl, substituted or unsubstituted aminosulfonyl, substituted or unsubstituted sulfonylamino, substituted or unsubstituted aminocarbonylamino, substituted or unsubstituted aminocarbonyloxy, substituted or unsubstituted alkoxycarbonylamino, substituted or unsubstituted aryloxycarbonylamino, or substituted or unsubstituted heteroaryloxycarbonylamino;

R³ᵃ is halo, cyano, substituted or unsubstituted alkyl, substituted or unsubstituted aryl, substituted or unsubstituted heteroaryl, substituted or unsubstituted cycloalkyl, substituted or unsubstituted heterocycloalkyl, substituted or unsubstituted alkoxy, substituted or unsubstituted alkoxycarbonyl, substituted or unsubstituted aryloxycarbonyl, substituted or unsubstituted heteroaryloxycarbonyl, or substituted or unsubstituted aminocarbonyl;

each R³ᵇ is independently H, hydroxyl, halo, azido, amino, nitro, thiol, cyano, carboxyl, substituted or unsubstituted alkyl, substituted or unsubstituted alkenyl, substituted or unsubstituted alkynyl, substituted or unsubstituted arylalkyl, substituted or unsubstituted aryl, substituted or unsubstituted heteroaryl, substituted or unsubstituted cycloalkyl, substituted or unsubstituted cycloalkenyl, or substituted or unsubstituted heterocycloalkyl;

R³ᶜ is H;

W is optionally present and if present is H, hydroxyl, halo, azido, amino, nitro, thiol, cyano, carboxyl, substituted or unsubstituted alkyl, substituted or unsubstituted alkenyl, substituted or unsubstituted alkynyl, substituted or unsubstituted arylalkyl, substituted or unsubstituted aryl, substituted or unsubstituted heteroaryl, substituted or unsubstituted cycloalkyl, substituted or unsubstituted cycloalkenyl, substituted or unsubstituted heterocycloalkyl, substituted or unsubstituted alkoxy, substituted or unsubstituted aryloxy, substituted or unsubstituted heteroaryloxy, substituted or unsubstituted sulfanyl, substituted or unsubstituted alkylamino, substituted or unsubstituted dialkylamino, substituted or unsubstituted arylamino, substituted or unsubstituted heteroarylamino, substituted or unsubstituted acyl, substituted or unsubstituted acylamino, substituted or unsubstituted aminocarbonyl, substituted or unsubstituted alkoxycarbonyl, substituted or unsubstituted aryloxycarbonyl, substituted or unsubstituted heteroaryloxycarbonyl, substituted sulfo, substituted sulfonyl, substituted sulfinyl, substituted or unsubstituted aminosulfonyl, substituted or unsubstituted sulfonylamino, substituted or unsubstituted alkylsulfonyl, substituted or unsubstituted arylsulfonyl, substituted or unsubstituted aminocarbonylamino, substituted or unsubstituted aminocarbonyloxy, substituted or unsubstituted alkoxycarbonylamino, substituted or unsubstituted aryloxycarbonylamino, or substituted or unsubstituted heteroaryloxycarbonylamino;

m is 0, 1, 2, 3, or 4;

if in is 0, then d is independently 0, 1 or 2; if m is 1, then d is independently 0, 1, 2 or 3; if m is 2, then d is independently 0, 1, 2, 3 or 4; if in is 3, then d is independently 0, 1, 2, 3, 4 or 5 or if m is 4 then d is independently 0, 1, 2, 3, 4, 5 or 6;

or a pharmaceutically acceptable salt, hydrate or solvate thereof, or an isotopic variant, tautomer, or stereoisomer thereof.

2. The compound according to claim 1, wherein:
L¹ is a single bond, or substituted or unsubstituted alkylene.

3. The compound according to claim 1, wherein m is 0, 1, or 2.

4. The compound according to claim 1, wherein:
L² is a single bond and R² is NR⁵R⁶ wherein R⁵ and R⁶ are as defined in claim 1.

5. The compound according to claim 1 wherein:
L¹ is substituted or unsubstituted alkylene, substituted or unsubstituted alkenylene, or substituted or unsubstituted alkynylene,
R¹ is substituted or unsubstituted arylene, and
W is halo.

6. The compound according to claim 1, wherein:
the substituted or unsubstituted aryl, is substituted or unsubstituted phenylene-1,4-diyl, substituted or unsubstituted phenylene-1,3-diyl, or substituted or unsubstituted naphthalene-1,4-diyl.

7. The compound according to claim 1, wherein:
L¹ is a single bond,
R¹ is substituted or unsubstituted arylene or substituted or unsubstituted heteroarylene.

8. The compound according to claim 1 wherein:
L¹ is a single bond;
R¹ is substituted or unsubstituted arylene or substituted or unsubstituted heteroarylene; and
W is substituted or unsubstituted heteroarylamino.

9. The compound according to claim 1 wherein:
R$^1$ is substituted or unsubstituted phenylene-1,4-diyl, or substituted or unsubstituted phenylene-1,3-diyl, or substituted or unsubstituted naphthalene-1,4-diyl; and
R$^{3a}$ is halo, cyano, substituted or unsubstituted alkyl, or substituted or unsubstituted alkoxycarbonyl.

10. The compound according to claim 1 wherein:
R$^1$ is substituted or unsubstituted pyridindiyl, substituted or unsubstituted pyrimidindiyl, substituted or unsubstituted pyrazindiyl, substituted or unsubstituted 1H-pyrazoldiyl, oxazoldiyl, or substituted or unsubstituted isoxazoldiyl; and R$^{3a}$ is halo, cyano, or a substituted or unsubstituted C$_1$-C$_6$ alkyl, a substituted or unsubstituted alkoxycarbonyl.

11. The compound according to claim 8, wherein:
W is pyrimidin-2-yl-amino, pyrimidin-4-yl-amino, pyrimidin-5-yl-amino, 1H-pyrazol-5-yl-amino, 1H-pyrazol-4-yl-amino, furo[2,3-d]pyrimidin-2-yl-amino, pyridin-2-yl-amino, pyridin-3-yl-amino, or pyridin-4-yl-amino.

12. The compound according to claim 1, wherein the compound is selected from the group consisting of:
2-(4-chlorobenzylamino)-3-fluoro-4-[4-(tert-butylamino) piperidin-1-yl]quinoline,
2-(4-chlorobenzylamino)-3-methyl-4-[4-(tert-butylamino)piperidin-1-yl]quinoline,
methyl 4-(4-(tert-butylamino) piperidin-1-yl)-2-(4-chlorobenzylamino) quinoline-3-carboxylate,
2-[4-(4-methylpyrimidin-2-ylamino)phenylamino]-3-methyl-4-(4-tert-butylaminopiperidin-1-yl)quinoline,
2-[3-(4-trifluoromethylpyrimidin-2-ylamino)phenylamino]-3-methyl-4-(4-tert-butylaminopiperidin-1-yl)quinoline,
2-(4-chlorobenzylamino)-3-cyano-4-[4-(tert-butylamino) piperidin-1-yl]quinoline,
2-[4-(4-(pyridin-3-yl)pyrimidin-2-ylamino)-3-methyl-benzylamino]-3-cyano-4-(4-tert-butylaminopiperidin-1-yl)quinoline,
2-(3-methyl-4-(4-methylpyrimidin-2-ylamino) phenylamino)-3-cyano-4-(4-(tert-butylamino) piperidin-1-yl)-quinoline,
2-[4-(4,6-dimethyl-2-pyrimidinamino)-3-methyl-phenylamino]-3-cyano-4-(4-tert-butylaminopiperidin-1-yl)quinoline,
2-[4-(4-methyl-6-methoxypyrimidin-2-ylamino)-3-methylphenylamino]-3-cyano-4-(4-tert-butylaminopiperidin-1-yl)quinoline,
2-[3-methyl-4-(4,6-dimethylfuro[2,3-d]pyrimidin-2-ylamino)phenylamino]-3-cyano-4-(4-tert-butylaminopiperidin-1-yl)quinoline,
2-{3-methyl-4-[2-(pyridin-3-yl)pyrimidin-4-ylamino]phenylamino}-3-cyano-4-(4-tert-butylaminopiperidin-1-yl)quinoline,
2-{3-methyl-4-[2-(pyridin-3-yl)-5-cyanopyrimidin-4-ylamino]phenylamino}-3-cyano-4-(4-tert-butylaminopiperidin-1-yl)quinoline,
2-[4-(4-methylpyrimidin-2-ylamino)phenylamino]-3-cyano-4-(4-tert-butylaminopiperidin-1-yl)quinoline,
2-[3-methyl-4-(4-trifluoromethylpyrimidin-2-ylamino) phenylamino]-3-cyano-4-(4-tert-butylaminopiperidin-1-yl)quinoline,
2-[3-(4-trifluoromethyl-2-pyrimidinamino)-4-methyl-phenylamino]-3-cyano-4-(4-tert-butylaminopiperidin-1-yl)quinoline,
2-[3-(4-trifluoromethylpyrimidin-2-ylamino)phenylamino]-3-cyano-4-(4-tert-butylaminopiperidin-1-yl)quinoline,
2-[4-(4-(pyridin-3-yl)pyrimidin-2-ylamino)-3-methyl-phenylamino]-3-cyano-4-(4-tert-butylaminopiperidin-1-yl)quinoline,
2-[3-(4-trifluoromethylpyrimidin-2-ylamino)phenylamino]-3-fluoro-4-(4-tert-butylaminopiperidin-1-yl)quinoline,
2-(4-fluorobenzylamino)-3-fluoro-4-[4-(tert-butylamino) piperidin-1-yl]quinoline,
2-(4-fluorobenzylamino)-3-cyano-4-[4-(tert-butylamino) piperidin-1-yl]quinoline,
2-(4-chlorobenzylamino)-3-cyano-4-[4-(tert-butylamino) piperidin-1-yl]-8-methylquinoline,
2-(4-chlorobenzylamino)-3-cyano-4-[4-(tert-butylamino) piperidin-1-yl]-7-methylquinoline,
2-(4-chlorobenzylamino)-3-cyano-4-[4-(tert-butylamino)piperidin-1-yl]-6-methylquinoline,
2-(4-chlorobenzylamino)-3-cyano-4-(3-aminopiperidin-1-yl)quinoline,
2-(4-chlorobenzylamino)-3-cyano-4-[3-(methylamino)piperidin-1-yl]quinoline,
2-(4-chlorobenzylamino)-3-cyano-4-[3-(isopropylamino) piperidin-1-yl]quinoline,
{[(tetrahydro-2H-pyra-4-yl)methyl]amino}-3-fluoro-4-[4-(tert-butylamino)piperidin-1-yl]quinoline,
2-(4-chlorobenzylamino)-3-cyano-4-[3-(cyclopentylamino)piperidin-1-yl]quinoline,
2-(4-chlorobenzylamino)-3-cyano-4-[3-(dimethylamino) piperidin-1-yl]quinoline,
2-(4-chlorobenzylamino)-3-cyano-4-[3-(diethylamino)piperidin-1-yl]quinoline,
2-(4-chlorobenzylamino)-3-cyano-4-(4-aminopiperidin-1-yl)quinoline,
2-(4-chlorobenzylamino)-3-cyano-4-[4-(methylamino)piperidin-1-yl]quinoline,
2-(4-chlorobenzylamino)-3-cyano-4-[4-(iso-propylamino)piperidin-1-yl]quinoline,
2-(4-chlorobenzylamino)-3-cyano-4-[4-(tert-butylamino) piperidin-1-yl]quinoline,
2-(4-chlorobenzylamino)-3-cyano-4-{4-[(tert-butyloxycarbonyl)amino]piperidin-1-yl}quinoline,
2-(4-chlorobenzylamino)-3-cyano-4-[4-(cyclopentylamino)piperidin-1-yl]quinoline,
2-(4-chlorobenzylamino)-3-cyano-4-{4-[(tetrahydro-2H-pyran-4-yl)amino]piperidin-1-yl}quinoline,
2-(4-chlorobenzylamino)-3-cyano-4-{4-[(1-methylpiperidin-4-yl)amino]piperidin-1-yl}quinoline,
2-(4-chlorobenzylamino)-3-cyano-4-[4-(dimethylamino) piperidin-1-yl]quinoline,
2-(4-chlorobenzylamino)-3-cyano-4-[4-(diethylamino)piperidin-1-yl]quinoline,
2-(4-chlorobenzylamino)-3-cyano-4-[3-aminopyrrolidin-1-yl]quinoline,
2-(4-chlorobenzylamino)-3-cyano-4-[3-(methylamino) pyrrolidin-1-yl]quinoline,
2-(4-chlorobenzylamino)-3-cyano-4-[3-(cyclopentylamino)pyrrolidin-1-yl]quinoline,
2-(4-chlorobenzylamino)-3-cyano-4-{3-[(tetrahydro-2H-pyran-4-yl)amino]pyrrolidin-1-yl}quinoline,
2-(4-chlorobenzylamino)-3-cyano-4-[3-(dimethylamino) pyrrolidin-1-yl]quinoline,
2-(4-chlorobenzylamino)-3-cyano-4-[3-(diethylamino) pyrrolidin-1-yl]quinoline,
2-(4-chlorobenzylamino)-3-cyano-4-(3-phenoxypiperidin-1-yl)quinoline,
2-(4-chlorobenzylamino)-3-cyano-4-[3-(4-methoxyphenoxy)piperidin-1-yl]quinoline, 2-(4-chlorobenzylamino)-3-cyano-4-[3-(4-methylphenoxy)piperidin-1-yl]quinoline,
2-(4-chlorobenzylamino)-3-cyano-4-[3-(4-fluorophenoxy)piperidin-1-yl]quinoline,
2-(4-chlorobenzylamino)-3-cyano-4-[3-(3-fluorophenoxy)piperidin-1-yl]quinoline,
2-(4-chlorobenzylamino)-3-cyano-4-{3-[(3-methylpyrazin-2-yl)oxy]piperidin-1-yl}quinoline,
2-(4-chlorobenzylamino)-3-cyano-4-(4-phenoxypiperidin-1-yl)quinoline,
2-(4-chlorobenzylamino)-3-cyano-4-[4-(4-methoxyphenoxy)piperidin-1-yl]quinoline,
2-(4-chlorobenzylamino)-3-cyano-4-[4-(p-tolyloxy)piperidin-1-yl]quinoline,
2-(4-chlorobenzylamino)-3-cyano-4-[4-(4-chlorophenoxy)piperidin-1-yl]quinoline,
2-(4-chlorobenzylamino)-3-cyano-4-[4-(4-fluorophenoxy)piperidin-1-yl]quinoline,
2-(4-chlorobenzylamino)-3-cyano-4-[4-(3-fluorophenoxy)piperidin-1-yl]quinoline,
2-(4-chlorobenzylamino)-3-cyano-4-{4-[(pyridin-4-yl)oxy]piperidin-1-yl}quinoline,
2-(4-chlorobenzylamino)-3-cyano-4-{4-[(5-methylisoxazol-3-yl)oxy]piperidin-1-yl}quinoline,
2-(4-chlorobenzylamino)-3-cyano-4-{4-[(3-methylpyrazin-2-yl)oxy]piperidin-1-yl}quinoline,
2-(4-chlorobenzylamino)-3-cyano-4-(3-phenoxypyrrolidin-1-yl)quinoline,
2-(4-chlorobenzylamino)-3-cyano-4-[3-(4-methylphenoxy)pyrrolidin-1-yl]quinoline,
2-(4-chlorobenzylamino)-3-cyano-4-[3-(4-methoxyphenoxy)pyrrolidin-1-yl]quinoline,
2-(4-chlorobenzylamino)-3-cyano-4-[3-(4-chlorophenoxy)pyrrolidin-1-yl]quinoline,
2-(4-chlorobenzylamino)-3-cyano-4-[3-(4-fluorophenoxy)pyrrolidin-1-yl]quinoline,
2-(4-chlorobenzylamino)-3-cyano-4-[3-(3-fluorophenoxy)pyrrolidin-1-yl]quinoline,
2-(4-chlorobenzylamino)-3-cyano-4-{3-[(3-methylpyrazin-2-yl)oxy]pyrrolidin-1-yl}quinoline,
2-(4-chlorobenzylamino)-3-cyano-4-{3-[(pyridin-4-yl)oxy]pyrrolidin-1-yl}quinoline,
2-(phenylamino)-3-cyano-4-[4-(tert-butylamino)piperidin-1-yl]quinoline,
2-(4-methylphenylamino)-3-cyano-4-[4-(tert-butylamino)piperidin-1-yl]quinoline,
2-(3-methyl-4-fluorophenylamino)-3-cyano-4-[4-(tert-butylamino)piperidin-1-yl]quinoline,
2-(4-methoxyphenylamino)-3-cyano-4-[4-(tert-butylamino)piperidin-1-yl]quinoline,
2-(2-trifluoromethylphenylamino)-3-cyano-4-[4-(tert-butylamino)piperidin-1-yl]quinoline,
2-(3-trifluoromethylphenylamino)-3-cyano-4-[4-(tert-butylamino)piperidin-1-yl]quinoline,
2-(4-chlorophenylamino)-3-cyano-4-[4-(tert-butylamino)piperidin-1-yl]quinoline,
2-(4-fluorophenylamino)-3-cyano-4-[4-(tert-butylamino)piperidin-1-yl]quinoline,
2-(3-fluorophenylamino)-3-cyano-4-[4-(tert-butylamino)piperidin-1-yl]quinoline,
2-(3,4-difluorophenylamino)-3-cyano-4-[4-(tert-butylamino)piperidin-1-yl]quinoline,
2-[4-(trifluoromethyloxy)phenylamino]-3-cyano-4-[4-(tert-butylamino)piperidin-1-yl]quinoline,
2-[(1-methyl-1H-pyrazol-4-yl)amino]-3-cyano-4-[4-(tert-butylamino)piperidin-1-yl]quinoline,
2-[(1l-methyl-1H-1,2,4-triazol-5-yl)amino]-3-cyano-4-[4-(tert-butylamino)piperidin-1-yl]quinoline,
2-[(1,3-dimethyl-1H-1,2,4-triazol-5-yl)amino]-3-cyano-4-[4-(tert-butylamino)piperidin-1-yl]quinoline,
2-{4-[(4,6-dimethylpyrimidin-2-yl)amino]phenylamino}-3-cyano-4-[4-(tert-butylamino)piperidin-1-yl]quinoline,
2-(pyridin-2-ylamino)-3-cyano-4-[4-(tert-butylamino)piperidin-1-yl]quinoline,
2-(pyrimidin-2-ylamino)-3-cyano-4-[4-(tert-butylamino)piperidin-1-yl]quinoline,
2-(pyrimidin-4-ylamino)-3-cyano-4-[4-(tert-butylamino)piperidin-1-yl]quinoline,
2-(pyrazin-2-ylamino)-3-cyano-4-[4-(tert-butylamino)piperidin-1-yl]quinoline,
2-(benzylamino)-3-cyano-4-[4-(tert-butylamino)piperidin-1-yl]quinoline,
2-(4-methylbenzylamino)-3-cyano-4-[4-(tert-butylamino)piperidin-1-yl]quinoline,
2-(4-methoxybenzylamino)-3-cyano-4-[4-(tert-butylamino)piperidin-1-yl]quinoline,
2-[4-(trifluoromethyl)benzylamino]-3-cyano-4-[4-(tert-butylamino)piperidin-1-yl]quinoline,
2-[2-(trifluoromethyl)benzylamino]-3-cyano-4-[4-(tert-butylamino)piperidin-1-yl]quinoline,
2-[(benzo[d][1 1,3]dioxol-5-ylmethyl)amino]-3-cyano-4-[4-(tert-butylamino)piperidin-1-yl]quinoline,
2-[(furan-2-ylmethyl)amino]-3-cyano-4-[4-(tert-butylamino)piperidin-1-yl]quinoline,
2-[(pyridin-3-ylmethyl)amino]-3-cyano-4-[4-(tert-butylamino)piperidin-1-yl]quinoline,
2-[(pyridin-4-ylmethyl)amino]-3-cyano-4-[4-(tert-butylamino)piperidin-1-yl]quinoline,
2-[(pyridin-2-ylmethyl)amino]-3-cyano-4-[4-(tert-butylamino)piperidin-1-yl]quinoline,
or a pharmaceutically acceptable salt, hydrate or solvate thereof, or an isotopic variant, tautomer, or stereoisomer thereof.

13. The compound according to claim 1, wherein the compound having a structure represented by formula (II):

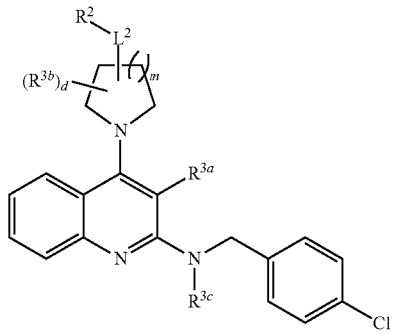

wherein $L^2$, $R^2$, $R^{3a}$, $R^{3b}$, $R^{3c}$ and d and m are as defined in claim 1,
or a pharmaceutically acceptable salt, hydrate or solvate thereof, or an isotopic variant, tautomer, or stereoisomer thereof.

14. The compound according to claim 12, wherein each $R^{3b}$ is independently H and m is 0, 1, or 2.

15. The compound according to claim 1, wherein the compound having a structure represented by formula (IV):

(IV)

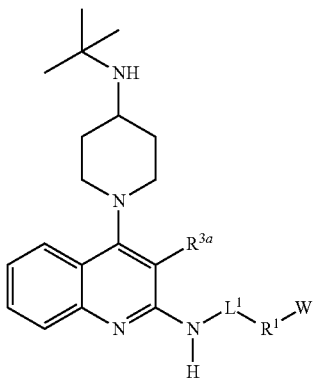

wherein $L^1$, $R^1$, $R^{3a}$ and W are as defined in claim 1,
or a pharmaceutically acceptable salt, hydrate or solvate thereof, or an isotopic variant, tautomer, or stereoisomer thereof.

16. The compound according to claim 15 wherein $R^{3a}$ is halo, cyano or substituted or unsubstituted alkoxycarbonyl;
$L^1$ is a single bond, or substituted or unsubstituted alkylene;
$R^1$ is substituted or unsubstituted aryl, substituted or unsubstituted heteroaryl; and
W is substituted or unsubstituted arylamino, or substituted or unsubstituted heteroarylamino.

17. A compound selected from the group consisting of:
(2S) 2-(4-chlorobenzylamino)-4-[2-(hydroxymethyl)pyrrolidin-1-yl]quinoline,
(2S) 2-(4-chlorobenzylamino)-4-[2-(methoxymethyl)pyrrolidin-1-yl]quinoline,
(2R)-2-(4-chlorobenzylamino)-4-[2-(hydroxymethyl)-pyrrolidin-1-yl]-quinoline,
2-(4-chlorobenzylamino)-4-(4-hydroxypiperidin-1-yl)quinoline,
2-(4-chlorobenzylamino)-4-[4-(iso-propoxy)-piperidin-1-yl]-quinoline,
2-(4-chlorobenzylamino)-4-(4-phenoxypiperidin-1-yl)-quinoline,
2-(4-chlorobenzylamino)-4-[4-(m-tolyloxy)piperidin-1-yl]quinoline,
2-(4-chlorobenzylamino)-4-[4-(pyridin-4-yloxy)piperidin-1-yl]quinoline,
2-(4-chlorobenzylamino)-4-[4-(pyrazin-2-yloxy)piperidin-1-yl]quinoline,
(3R) 2-(4-chlorobenzylamino)-4-(3-hydroxypyrrolidin-1-yl)quinoline,
(3R) 2-(4-chlorobenzylamino)-4-[3-(phenoxy)pyrrolidin-1-yl]quinoline,
(3R) 2-(4-chlorobenzylamino)-4-[3-(pyridin-2-yloxy)pyrrolidin-1-yl]quinoline,
(3S) 2-(4-chlorobenzylamino)-4-(3-hydroxypyrrolidin-1-yl)-quinoline,
(3S) 2-(4-chlorobenzylamino)-4-[3-(pyridin-2-yloxy)pyrrolidin-1-yl]quinoline,
2-(4-fluorobenzylamino)-3-fluoro-4-[4-(tert-butylamino)piperidin-1-yl]quinoline,
or a pharmaceutically acceptable salt, hydrate or solvate thereof, or an isotopic variant, tautomer, or stereoisomer thereof.

18. A pharmaceutical composition comprising the compound according to claim 1, or a pharmaceutically acceptable salt, hydrate or solvate thereof, or an isotopic variant, tautomer, or stereoisomer thereof; and one or more pharmaceutically acceptable carriers.

19. The pharmaceutical composition according to claim 18, further comprising at least one additional therapeutically active agent.

20. The pharmaceutical composition according to claim 19, wherein the additional therapeutically active agent is for the treatment of cancer.

21. A method for treating a malignant neoplastic disease or cancer, comprising administering to a patient in need a therapeutically effective amount of the compound or a pharmaceutically acceptable salt, hydrate or solvate thereof, or an isotopic variant, tautomer, or stereoisomer thereof according to claim 1.

22. The method according to claim 21, wherein the cancer is selected from the group consisting of: malignant tumours, malignant lymphoma, malignant melanoma, malignant astrocytoma, benign tumours, solid tumours, sarcomas, carcinomas, carcinoids, Ewing sarcomas, Kaposi sarcomas, brain tumours, tumours originating from the brain and/or the nervous system and/or the meninges, gliomas, glioblastomas, neuroblastomas, stomach cancer, pancreatic cancer, kidney cancer, kidney cell carcinomas, prostate cancer, prostate carcinomas, connective tissue tumours, soft tissue sarcomas, fibrosarcomas, pancreas tumours, liver cancer, head tumours, neck tumours, laryngeal cancer, nasopharyngeal cancer, oesophageal cancer, colon cancer, thyroid cancer, osteosarcomas, retinoblastomas, thymoma, testicular cancer, lung cancer, lung adenocarcinoma, small cell lung carcinoma, bronchial carcinomas, breast cancer, mamma carcinomas, intestinal cancer, colorectal tumours, colon carcinomas, prostate cancer, rectum carcinomas, gynaecological tumours, ovary tumours/ovarian tumours, uterine cancer, cervical cancer, cervix carcinomas, cancer of body of uterus, corpus carcinomas, endometrial carcinomas, urinary bladder cancer, urogenital tract cancer, bladder cancer, skin cancer, epithelial tumours, squamous epithelial carcinoma, basal cell carcinoma, basaliomas, spinaliomas, melanomas, intraocular melanomas, leukaemias, monocyte leukaemia, chronic leukaemias, chronic myelotic leukaemia, chronic lymphatic leukemia, acute leukaemias, acute myelogenous leukemia, acute promyelocytic leukemia (APL), acute lymphatic leukemia, acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia, stem cell leukemia, germ cell cancer, and metastatic growth.

23. The method according to claim 22, wherein the liver cancer is selected from the group consisting of: hepatocellular carcinoma, cholangiocarcinoma and hepatoblastoma.

24. A method for inhibiting growth or differentiation of a Cancer Stem Cell (CSC), a tumor initiating cell, a mesenchymal-like cell associated with cancer, a mesenchymal cancerous cell, or a mesenchymal cell, comprising contacting at least a Cancer Stem Cell (CSC), a tumor initiating cell, a mesenchymal-like cell associated with cancer, a mesenchymal cancerous cell, or a mesenchymal cell with an amount of a compound or a pharmaceutically acceptable salt, hydrate or solvate thereof, or an isotopic variant, tautomer, or stereoisomer thereof according claim 1.

25. A pharmaceutical composition comprising the compound according to claim 17, or a pharmaceutically acceptable salt, hydrate or solvate thereof, or an isotopic variant, tautomer, or stereoisomer thereof; and one or more pharmaceutically acceptable carriers.

26. The pharmaceutical composition according to claim 25, further comprising at least one additional therapeutically active agent.

27. The pharmaceutical composition according to claim 26, wherein the additional therapeutically active agent is for the treatment of cancer.

28. A method for treating a malignant neoplastic disease or cancer, comprising administering to a patient in need a therapeutically effective amount of the compound or a pharmaceutically acceptable salt, hydrate or solvate thereof, or an isotopic variant, tautomer, or stereoisomer thereof according to claim 17.

29. The method according to claim 28, wherein the cancer is selected from the group consisting of: malignant tumours, malignant lymphoma, malignant melanoma, malignant astrocytoma, benign tumours, solid tumours, sarcomas, carcinomas, carcinoids, Ewing sarcomas, Kaposi sarcomas, brain tumours, tumours originating from the brain and/or the nervous system and/or the meninges, gliomas, glioblastomas, neuroblastomas, stomach cancer, pancreatic cancer, kidney cancer, kidney cell carcinomas, prostate cancer, prostate carcinomas, connective tissue tumours, soft tissue sarcomas, fibrosarcomas, pancreas tumours, liver cancer, head tumours, neck tumours, laryngeal cancer, nasopharyngeal cancer, oesophageal cancer, colon cancer, thyroid cancer, osteosarcomas, retinoblastomas, thymoma, testicular cancer, lung cancer, lung adenocarcinoma, small cell lung carcinoma, bronchial carcinomas, breast cancer, mamma carcinomas, intestinal cancer, colorectal tumours, colon carcinomas, prostate cancer, rectum carcinomas, gynaecological tumours, ovary tumours/ovarian tumours, uterine cancer, cervical cancer, cervix carcinomas, cancer of body of uterus, corpus carcinomas, endometrial carcinomas, urinary bladder cancer, urogenital tract cancer, bladder cancer, skin cancer, epithelial tumours, squamous epithelial carcinoma, basal cell carcinoma, basaliomas, spinaliomas, melanomas, intraocular melanomas, leukaemias, monocyte leukaemia, chronic leukaemias, chronic myelotic leukaemia, chronic lymphatic leukemia, acute leukaemias, acute myelogenous leukemia, acute promyelocytic leukemia (APL), acute lymphatic leukemia, acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lymphoblastic leukemia, lymphocytic leukemia, megakaryocytic leukemia, micromyeloblastic leukemia, monocytic leukemia, neutrophilic leukemia, stem cell leukemia, germ cell cancer, and metastatic growth.

30. The method according to claim 29, wherein the liver cancer is selected from the group consisting of: hepatocellular carcinoma, cholangiocarcinoma and hepatoblastoma.

31. A method for inhibiting growth or differentiation of a Cancer Stem Cell (CSC), a tumor initiating cell, a mesenchymal-like cell associated with cancer, a mesenchymal cancerous cell, or a mesenchymal cell, comprising contacting at least a Cancer Stem Cell (CSC), a tumor initiating cell, a mesenchymal-like cell associated with cancer, a mesenchymal cancerous cell, or a mesenchymal cell with an amount of a compound or a pharmaceutically acceptable salt hydrate or solvate thereof, or an isotopic variant, tautomer, or stereoisomer thereof according claim 17.

* * * * *